United States Patent
Koike et al.

(10) Patent No.: US 9,643,957 B2
(45) Date of Patent: May 9, 2017

(54) HETEROCYCLIC COMPOUNDS HAVING CHOLESTEROL 24-HYDROXYLASE ACTIVITY

(71) Applicant: TAKEDA PHARMACEUTICAL COMPANY LIMITED, Osaka (JP)

(72) Inventors: Tatsuki Koike, Kanagawa (JP); Yuichi Kajita, Kanagawa (JP); Masato Yoshikawa, Kanagawa (JP); Shuhei Ikeda, Kanagawa (JP); Hiromi Fukuda, Kanagawa (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

(21) Appl. No.: 14/650,429

(22) PCT Filed: Dec. 10, 2013

(86) PCT No.: PCT/JP2013/083140
§ 371 (c)(1),
(2) Date: Jun. 8, 2015

(87) PCT Pub. No.: WO2014/092100
PCT Pub. Date: Jun. 19, 2014

(65) Prior Publication Data
US 2015/0315209 A1 Nov. 5, 2015

(30) Foreign Application Priority Data

Dec. 11, 2012 (JP) ................................. 2012-270445
Oct. 7, 2013 (JP) ................................. 2013-210439

(51) Int. Cl.
| C07D 403/12 | (2006.01) |
| C07D 471/08 | (2006.01) |
| C07D 491/08 | (2006.01) |
| C07D 213/12 | (2006.01) |
| C07D 498/08 | (2006.01) |

(Continued)

(52) U.S. Cl.
CPC .......... *C07D 403/12* (2013.01); *A61K 9/2018* (2013.01); *A61K 9/4858* (2013.01); *C07D 213/12* (2013.01); *C07D 213/72* (2013.01); *C07D 239/42* (2013.01); *C07D 401/04* (2013.01); *C07D 401/12* (2013.01); *C07D 401/14* (2013.01); *C07D 403/04* (2013.01); *C07D 403/14* (2013.01); *C07D 405/12* (2013.01); *C07D 405/14* (2013.01); *C07D 413/04* (2013.01); *C07D 413/14* (2013.01); *C07D 417/04* (2013.01); *C07D 417/14* (2013.01); *C07D 451/02* (2013.01); *C07D 451/04* (2013.01); *C07D 471/08* (2013.01); *C07D 471/10* (2013.01); *C07D 487/08* (2013.01); *C07D 487/10* (2013.01); *C07D 487/18* (2013.01); *C07D 491/08* (2013.01); *C07D 491/18* (2013.01); *C07D 498/08* (2013.01); *C12N 9/99* (2013.01)

(58) Field of Classification Search
CPC .. A61K 9/2018; A61K 9/4858; C07D 403/12; C07D 471/08; C07D 471/10; C07D 491/08; C07D 213/12; C07D 403/04; C07D 498/08; C07D 405/12; C07D 403/14; C07D 491/18; C07D 401/14; C07D 239/42; C07D 417/14; C07D 413/14; C07D 451/04; C07D 487/10; C07D 417/04; C07D 487/18; C07D 451/02

See application file for complete search history.

(56) References Cited

U.S. PATENT DOCUMENTS

| 2006/0019962 A1 | 1/2006 | Makings et al. |
| 2007/0219187 A1 | 9/2007 | Bessis et al. |

(Continued)

FOREIGN PATENT DOCUMENTS

| CN | 101005842 | 7/2007 |
| CN | 101432278 | 5/2009 |

(Continued)

OTHER PUBLICATIONS

Burlot et al., Cholesterol 24-hydroxylase defect is implicated in memory impairments associated with Alzheimer-like Tau pathology.*

(Continued)

*Primary Examiner* — Alexander R Pagano
*Assistant Examiner* — Ebenezer O Sackey
(74) *Attorney, Agent, or Firm* — Wenderoth, Lind & Ponack, L.L.P.

(57) ABSTRACT

An object of the present invention is to provide a compound having a superior CH24H inhibitory action, which is useful as an agent for the prophylaxis or treatment of epilepsy, neurodegenerative disease and the like. The present invention relates to a compound represented by the formula:

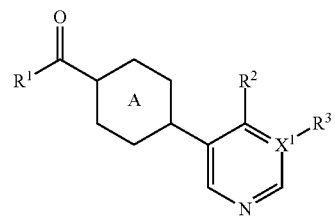

wherein each symbol is as defined in the specification, or a salt thereof.

12 Claims, No Drawings

(51) Int. Cl.
*C07D 405/12* (2006.01)
*C07D 401/14* (2006.01)
*C07D 417/14* (2006.01)
*C07D 451/04* (2006.01)
*C07D 487/10* (2006.01)
*C07D 405/14* (2006.01)
*C07D 413/14* (2006.01)
*C07D 401/04* (2006.01)
*C07D 401/12* (2006.01)
*C07D 239/42* (2006.01)
*C07D 413/04* (2006.01)
*C07D 417/04* (2006.01)
*C07D 451/02* (2006.01)
*C07D 487/18* (2006.01)
*C07D 491/18* (2006.01)
*C07D 403/04* (2006.01)
*C07D 403/14* (2006.01)
*C07D 471/10* (2006.01)
*A61K 9/20* (2006.01)
*A61K 9/48* (2006.01)
*C07D 213/72* (2006.01)
*C07D 487/08* (2006.01)
*C12N 9/99* (2006.01)

(56) References Cited

U.S. PATENT DOCUMENTS

| | | |
|---|---|---|
| 2007/0249579 A1 | 10/2007 | Wang et al. |
| 2007/0299110 A1 | 12/2007 | Gagliardi et al. |
| 2008/0139572 A1 | 6/2008 | Wang et al. |
| 2010/0105693 A1 | 4/2010 | Makings et al. |
| 2011/0112143 A1 | 5/2011 | Bessis et al. |
| 2012/0022108 A1 | 1/2012 | Bessis et al. |
| 2015/0266872 A1 | 9/2015 | Koike et al. |
| 2016/0024049 A1 | 1/2016 | Koike et al. |

FOREIGN PATENT DOCUMENTS

| | | |
|---|---|---|
| CN | 1898206 | 9/2011 |
| JP | 2009-535352 | 10/2009 |
| JP | 2010-248183 | 11/2010 |
| WO | 2005/019200 | 3/2005 |
| WO | 2005/044797 | 5/2005 |
| WO | 2005/117883 | 12/2005 |
| WO | 2007/127635 | 11/2007 |
| WO | 2010/110400 | 9/2010 |
| WO | 2011/016559 | 2/2011 |
| WO | 2013/054822 | 4/2013 |
| WO | 2013/146969 | 10/2013 |
| WO | 2014/061676 | 4/2014 |
| WO | 2014/163161 | 10/2014 |

OTHER PUBLICATIONS

Database Registry, STN Columbus, CAS No. 1367084-18-1, Apr. 12, 2012.

International Search Report issued Mar. 4, 2014 in International (PCT) Application No. PCT/JP2013/083140.

* cited by examiner

```
SEQUENCE LISTING

<160> NUMBER OF SEQ ID NOS: 2

<210> SEQ ID NO 1
<211> LENGTH: 26
<212> TYPE: DNA
<213> ORGANISM: Artificial Sequence
<220> FEATURE:
<223> OTHER INFORMATION: Synthetic PCR primer

<400> SEQUENCE: 1
gccccggagc catgagcccc gggctg                                   26

<210> SEQ ID NO 2
<211> LENGTH: 26
<212> TYPE: DNA
<213> ORGANISM: Artificial Sequence
<220> FEATURE:
<223> OTHER INFORMATION: Synthetic PCR primer

<400> SEQUENCE: 2
gtcctgcctg gaggccccct cagcag                                   26
```

HETEROCYCLIC COMPOUNDS HAVING CHOLESTEROL 24-HYDROXYLASE ACTIVITY

TECHNICAL FIELD

The present invention relates to a heterocyclic compound having a cholesterol 24-hydroxylase (in the present specification, sometimes to be abbreviated as "CH24H") inhibitory action, a pharmaceutical composition comprising same, and the like.

BACKGROUND OF THE INVENTION

Alzheimer's disease is a progressive neurodegenerative disease characterized by the deposition of amyloid β protein (Aβ), accumulation of phosphorylated tau in a nerve cell (neurofibrillary tangle), and nerve cell death. In recent years, the number of patients with Alzheimer's disease is increasing because of aging, but an effective treatment method has not been developed as yet. The therapeutic drugs for Alzheimer's disease which are currently used in the medical practice are mainly acetylcholinesterase (AchE) inhibitors. While AchE inhibitors is confirmed to provide a certain level of usefulness, since they are used with the aim of supplementing decreased acetylcholine, the treatment with AchE inhibitor is merely a symptomatic therapy. Thus, the prompt development of a basic remedy and prophylactic drug has been strongly desired.

It has been clarified that the presence of allele ε4 of apolipoprotein E (ApoE) controlling the cholesterol metabolism is a strong risk factor of Alzheimer's disease [non-patent document 1: Science, vol. 261, 921-923, 1993]. After this finding, the correlation between plural gene polymorphisms playing a role in the expression of protein controlling the cholesterol metabolism and the onset frequency of Alzheimer's disease has been shown, suggesting the correlation between the cholesterol metabolism and Alzheimer's disease [non-patent document 2: Neurobiol. Aging, vol. 24, 421-426, 2003, non-patent document 3: Mol. Psychiatry, vol. 8, 635-638, 2003]. Moreover, it has been reported that Cyp46 (same as "cholesterol 24-hydroxylase (CH24H)"), which is cholesterol oxidase specifically expressed in the brain, is a risk factor of Alzheimer's disease [non-patent document 4: Neurosci. Lett., vol. 328, pages 9-12, 2002]. Furthermore, it has also been reported that Cyp46 (CH24H) is expressed in periphery of deposited amyloid in Alzheimer's disease patients [non-patent document 5: J. Biol. Chem., vol. 279, pages 34674-34681, 2004], 24S-hydroxycholesterol (24-HC), which is a metabolite thereof, increases in the brain spinal cord fluid (CSF) of Alzheimer's disease patients [non-patent document 6: Neurosci. Lett., vol. 324, pages 83-85, 2002, non-patent document 7: Neurosci. Lett., vol. 397, pages 83-87, 2006], 24-HC induces cell death of SH-SY5Y cell, which is a human neuroblast line [non-patent document 8: Brain Res., vol. 818, pages 171-175, 1999], and rats in which 24-HC was injected into the lateral cerebral ventricle showed impaired short-term memory, which is commonly observed in Alzheimer's disease, suggesting that hippocampal neurons were damaged by 24-HC [non-patent document 9: Neuroscience, vol. 164, pages 398-403, 2009]. These findings suggest that Cyp46 (CH24H) is deeply involved in the pathology of Alzheimer's disease. Therefore, a compound that inhibits the Cyp46 (CH24H) activity (i.e., Cyp46 (CH24H) inhibitor) suppresses neuronal cell death, increase in Aβ, intracerebral inflammation and the like observed in Alzheimer's disease, by decreasing intracerebral 24-HC, and is promising as a therapeutic or prophylactic drug showing not only an improvement of symptoms but also a suppression of progression. Moreover, it has been reported that an AchE inhibitor clinically used as a therapeutic drug for Alzheimer's disease shows an improvement effect on memory disorders induced by Aβ in mouse [non-patent document 10: British Journal of Pharmacology, vol. 149, pages 998-1012, 2006]. Thus, a Cyp46 (CH24H) inhibitor showing an improvement effect for memory disorders in Aβ overexpression animal model (APP transgenic mouse, APP/PS1 double transgenic mouse, etc.) is promising as a therapeutic drug for Alzheimer's disease.

As a concept of the preclinical stage of Alzheimer's disease, a mild cognitive impairment has been proposed, and about half of those having this disorder is said to progress into the Alzheimer's disease in the future. In recent years, it has been reported that 24-HC increases not only in patients with Alzheimer's disease but also in CSF of patients with mild cognitive impairment [non-patent document 7: Neurosci. Lett., vol. 397, pages 83-87, 2006]. This finding suggests that Cyp46 (CH24H) is involved in the pathology of mild cognitive impairment, and therefore, a Cyp46 (CH24H) inhibitor is promising as a new therapeutic drug for Alzheimer's disease or a prophylactic drug for the progression into the Alzheimer's disease.

In recent years, moreover, it has been reported that 24-HC in the blood increases before expression of the symptom in an autoimmune encephalomyelitis model, which is an animal model of multiple sclerosis which is one of the demyelination diseases in the central nervous system [non-patent document 11: J. Neurosci. Res., vol. 85, pages 1499-1505, 2007]. Multiple sclerosis is often developed in younger people of about 30 years old, and scarcely developed in the elderly of 60 years or older. It has also been reported that 24-HC in the blood increases in multiple sclerosis patients aged from 21 to 50 [non-patent document 12: Neurosci. Lett., vol. 331, pages 163-166, 2002]. These findings suggest that Cyp46 (CH24H) is involved in the pathology of multiple sclerosis, and therefore, a Cyp46 (CH24H) inhibitor is promising as a new therapeutic or prophylactic drug for multiple sclerosis.

Traumatic brain injury (also referred to as TBI in the present specification) is a condition having an extremely harmful influence on the personal health, for which no effective cure has been established. In the repair process following tissue damage by TBI, reconstruction of neuronal cell membrane and distribution of intracerebral cholesterol along with the growth of glial cell are suggested to be activated [non-patent document 13: Proc. Natl. Acad. Sci. USA, vol. 102, pages 8333-8338, 2005]. In a rat TBI model, an enhanced expression of Cyp46 (CH24H) after trauma has been reported [non-patent document 14: J. Neurotrauma, vol. 25, pages 1087-1098, 2008]. Moreover, it has also been reported that 24-HC is injurious to neuronal cells [non-patent document 8: Brain Res., vol. 818, pages 171-175, 1999]. Therefore, a Cyp46 (CH24H) inhibitor is promising as a new therapeutic or prophylactic drug for TBI.

As a pathological significance of 24-HC in neurodegenerative diseases, an inflammatory gene expression-enhancing action in neuronal cells has been reported [non-patent document 15: NeuroReport, vol. 16, pages 909-913, 2005]. In addition, it is suggested that an intracerebral inflammation reaction accompanied by activation of glial cell is a pathological change characteristic of neurodegenerative diseases [non-patent document 16: Glia, vol. 50, pages 427-434, 2005]. In recent years, an effectiveness of therapy by suppression of intracerebral inflammation has also been reported for neurodegenerative diseases such as Huntington's disease, Parkinson's disease and amyotrophic lateral sclerosis and the like [non-patent document 17: Mol. Neurodegeneration, vol. 4, pages 47-59, 2009]. Therefore, suppression of intracerebral inflammation via decreasing 24-HC by the inhibition of Cyp46 (CH24H) is promising as a new therapeutic or prophylactic drug for neurodegenerative diseases such as Huntington's disease, Parkinson's disease, cerebral infarction, glaucoma, amyotrophic lateral sclerosis and the like.

Glaucoma is the main cause of blindness, and is considered to be a serious social problem. However, there is no effective cure of a normal intraocular pressure type-visual field constriction, which is the major symptom of the disease. In recent years, it has been reported that gene polymorphisms of Cyp46 (CH24H) associated with high value of 24-HC in blood is related to the risk of the onset of glaucoma [non-patent document 18: Invest. Ophthalmol. Vis. Sci., vol. 50, pages 5712-5717, 2009]. Thus, a Cyp46 (CH24H) inhibitor is promising as a therapeutic or prophylactic drug for glaucoma.

Spasm is a disorder that convulsively occurs with abnormal electrical excitation of neuronal cell in the brain. Spasm is one of the characteristic clinical findings of Alzheimer's disease [Non-Patent Document 19: Epilepsia, vol. 47, pages 867-872, 2006], and the relationship between epilepsy and onset of Alzheimer's disease has been indicated [Non-Patent Document 20: Epilepsia, vol. 52, Supplement 1, pages 39-46, 2011]. It has been reported that spasm occurs with high frequency in APP/PS1 double transgenic mouse which is one of the Alzheimer's disease models due to Aβ overexpression [non-patent document 21: J. Neurosci., vol. 29, pages 3453-3462, 2012]. Furthermore, since hippocampus astrocytes induce the expression of Cyp46 (CH24H) in a kainic acid lesion rat model, which is one of the epilepsy models, the relationship between this enzyme and pathology of epilepsy has been indicated [Non-Patent Document 22: J. Neurol., vol. 65, pages 652-663, 2006]. It has been reported that a therapeutic drug for spasm, carbamazepine, shows an improving effect on short-term memory in Y-maze test in an epileptic spasm mouse model [Non-Patent Document 23: J. Neurol. Neurosurg. Psychiatry, vol. 48, pages 459-468, 1985]. Therefore, a CH24H inhibitor, which shows an improving effect on short-term memory in a model animal showing a spasm symptom, is promising as a novel therapeutic drug or prophylaxis drug for spasm, epilepsy, and the like.

Since schizophrenia shows a variety of psychological symptoms such as hallucination, delusion, excitation, manic-depressive state and the like, therapeutic drugs therefor have been developed with various approaches. In recent years, it has been pointed out that changes in the cholesterol metabolism are involved in the abnormality of neural activity seen in schizophrenia [non-patent document 24: J. Psychiatry Neurosci., vol. 36, pages 47-55, 2011]. Since cytotoxic factors such as oxidative stress also contribute to the pathology of schizophrenia, neuronal cell toxicity of 24-HC may aggravate the symptoms [non-patent document 25: Psychoneuroendocrinology, vol. 28, pages 83-96, 2003]. Therefore, a Cyp46 (CH24H) inhibitor that inhibits metabolizing cholesterol to 24-HC in the brain is promising as a therapeutic or prophylactic drug for schizophrenia.

Examples of the compound having a structure similar to the compound described in the present specification include the following compounds.

Patent Document 1 discloses the following compound as an agent for the treatment of HIV, AIDS and the like.

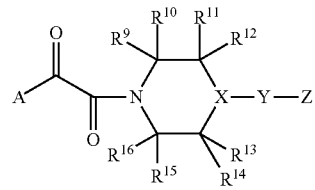

wherein

Ring A is

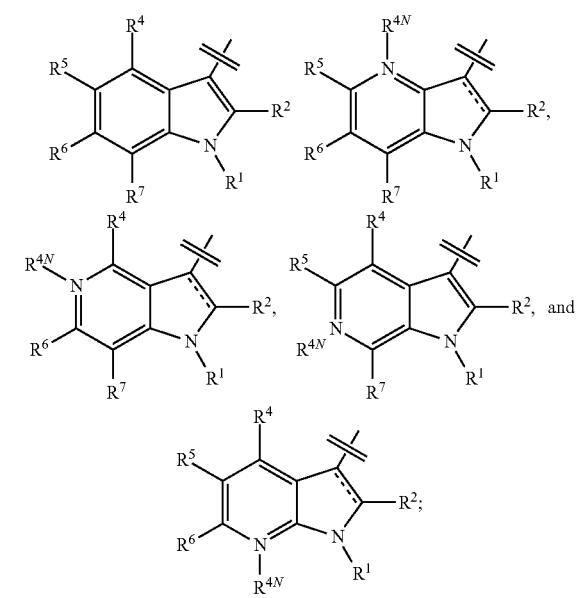

$R^1$ is a hydrogen atom, $C_{1-4}$ alkyl or the like;

$R^2$ is a hydrogen atom;

$R^4$-$R^7$ are independently a hydrogen atom, a halogen atom or the like;

X is N or CH;

Y is a 5- to 7-membered monocyclic aromatic heterocycle or the like;

Z is aryl or an aromatic heterocyclic group; and $R^9$-$R^{16}$ are independently a hydrogen atom, $C_{1-6}$ alkyl or the like.

Patent Document 2 discloses the following compound having a CH24H inhibitory action as an agent for the treatment of neurodegenerative disease (e.g., Alzheimer's disease, mild cognitive disorder, multiple sclerosis and the like).

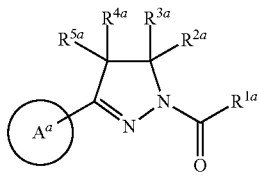
(Ia)

wherein

Ring $A^a$ is an optionally substituted ring;

$R^{1a}$ is (1) a group represented by the formula: $-X^{1a}-R^{6a}$
    wherein $X^{1a}$ is a $C_{1-6}$ alkylene group, a $C_{2-6}$ alkenylene group or a $C_{3-6}$ cycloalkylene group, and $R^{6a}$ is an optionally substituted $C_{6-14}$ aryl group, an optionally substituted $C_{6-14}$ aryloxy group or an optionally substituted heterocyclic group, (2) an optionally substituted $C_{6-14}$ aryl group, (3) an optionally substituted $C_{6-14}$ aryloxy group, or (4) an optionally substituted heterocyclic group;

$R^{2a}$ is a hydrogen atom, an optionally substituted $C_{1-6}$ alkyl group, an optionally substituted $C_{3-6}$ cycloalkyl group or an optionally substituted hydroxy group, $R^{3a}$ is an optionally substituted $C_{1-6}$ alkyl group, an optionally substituted $C_{3-6}$ cycloalkyl group or an optionally substituted hydroxy group, or $R^{2a}$ and $R^{3a}$ in combination optionally form an oxo group, a $C_{1-3}$ alkylidene group or an optionally substituted ring; and $R^{4a}$ and $R^{5a}$ are the same or different and each is a hydrogen atom, a halogen atom, an optionally substituted $C_{1-6}$ alkyl group, an optionally substituted $C_{3-6}$ cycloalkyl group or an optionally substituted hydroxy group, or $R^{4a}$ and $R^{5a}$ in combination optionally form an oxo group, a $C_{1-3}$ alkylidene group or an optionally substituted ring.

Patent Document 3 discloses the following compound having a calcium-sensing receptor (CaSR) antagonistic action as an agent for the treatment of bone disease (e.g., osteoporosis, bone fracture and the like).

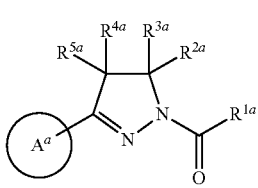

(Ia)

wherein

Ring $A^a$ is an optionally substituted ring;

$R^{1a}$ is (1) a group represented by the formula: $-X^{1a}-R^{6a}$
    wherein $X^{1a}$ is a $C_{1-6}$ alkylene group, a $C_{2-6}$ alkenylene group or a $C_{3-6}$ cycloalkylene group, and $R^{6a}$ is an optionally substituted $C_{3-6}$ cycloalkyl group, an optionally substituted $C_{3-6}$ cycloalkyloxy group, an optionally substituted $C_{6-14}$ aryl group, an optionally substituted $C_{6-14}$ aryloxy group, an optionally substituted $C_{7-14}$ aralkyloxy group, an optionally substituted heterocyclic group, an optionally substituted heterocyclyloxy group or optionally substituted amino group, (2) an optionally substituted $C_{3-6}$ cycloalkyl group, (3) an optionally substituted $C_{3-6}$ cycloalkyloxy group, (4) an optionally substituted $C_{6-14}$ aryl group, (5) an optionally substituted $C_{6-14}$ aryloxy group, (6) an optionally substituted $C_{7-14}$ aralkyloxy group, (7) an optionally substituted heterocyclic group, (8) an optionally substituted heterocyclyloxy group, or (9) an optionally substituted amino group;

$R^{2a}$ is a hydrogen atom, an optionally substituted $C_{1-6}$ alkyl group, an optionally substituted $C_{3-6}$ cycloalkyl group or an optionally substituted hydroxy group, $R^{3a}$ is an optionally substituted $C_{1-6}$ alkyl group, an optionally substituted $C_{3-6}$ cycloalkyl group or an optionally substituted hydroxy group, or $R^{2a}$ and $R^{3a}$ in combination optionally form a $C_{1-3}$ alkylidene group or an optionally substituted ring; and $R^{4a}$ and $R^{5a}$ are the same or different and each is a hydrogen atom, a halogen atom, an optionally substituted $C_{1-6}$ alkyl group, an optionally substituted $C_{3-6}$ cycloalkyl group or an optionally substituted hydroxy group, or $R^{4a}$ and $R^{5a}$ in combination optionally form an oxo group, a $C_{1-3}$ alkylidene group or an optionally substituted ring.

DOCUMENT LIST

Patent Document

Patent Document 1: WO 2007/127635
Patent Document 2: WO 2010/110400
Patent Document 3: JP 2010-248183

Non-Patent Document

Non-Patent Document 1: Science, vol. 261, pages 921-923, 1993
Non-Patent Document 2: Neurobiology of Aging (Neurobiol. Aging), vol. 24, pages 421-426, 2003
Non-Patent Document 3: Molecular Psychiatry (Mol. Psychiatry), vol. 8, pages 635-638, 2003
Non-Patent Document 4: Neuroscience Letters (Neurosci. Lett.), vol. 328, pages 9-12, 2002
Non-Patent Document 5: Journal of the Biological Chemistry (J. Biol. Chem.), vol. 279, pages 34674-34681, 2004
Non-Patent Document 6: Neuroscience Letters (Neurosci. Lett.), vol. 324, pages 83-85, 2002
Non-Patent Document 7: Neuroscience Letters (Neurosci. Lett.), vol. 397, pages 83-87, 2006
Non-Patent Document 8: Brain Research (Brain Res.), vol. 818, pages 171-175, 1999
Non-Patent Document 9: Neuroscience, vol. 164, pages 398-403, 2009
Non-Patent Document 10: British Journal of Pharmacology, vol. 149, pages 998-1012, 2006
Non-Patent Document 11: Journal of Neuroscience Research (J. Neurosci. Res.), vol. 85, pages 1499-1505, 2007
Non-Patent Document 12: Neuroscience Letters (Neurosci. Lett.), vol. 331, pages 163-166, 2002
Non-Patent Document 13: Proceedings of the National Academy of Sciences USA (Proc. Natl. Acad. Sci. USA), vol. 102, pages 8333-8338, 2005
Non-Patent Document 14: Journal of Neurotrauma (J. Neurotrauma), vol. 25, pages 1087-1098, 2008
Non-Patent Document 15: NeuroReport, vol. 16, pages 909-913, 2005
Non-Patent Document 16: Glia, vol. 50, pages 427-434, 2005
Non-Patent Document 17: Molecular Neurodegeneration (Mol. Neurodegeneration), vol. 4, pages 47-59, 2009
Non-Patent Document 18: Investigative Ophthalmology & Visual Science (Invest. Opthalmol. Vis. Sci.), vol. 50, pages 5712-5717, 2009
Non-Patent Document 19: Epilepsia, vol. 47, pages 867-872, 2006
Non-Patent Document 20: Epilepsia, vol. 52, Supplement 1, pages 39-46, 2011
Non-Patent Document 21: Journal of Neuroscience (J. Neurosci.), vol. 29, pages 3453-3462, 2012

Non-Patent Document 22: Journal of Neurology (J. Neural.), vol. 65, pages 652-663, 2006

Non-Patent Document 23: Journal of Neurology Neurosurgery Psychiatry (J. Neurol. Neurosurg. Psychiatry), vol. 48, pages 459-468, 1985

Non-Patent Document 24: Journal of Psychiatry Neuroscience (J. Psychiatry Neurosci.), vol. 36, pages 47-55, 2011

Non-Patent Document 25: Psychoneuroendocrinology, vol. 28, pages 83-96, 2003

SUMMARY OF THE INVENTION

Problems to be Solved by the Invention

An object of the present invention is to provide a compound having a superior CH24H inhibitory action, which is useful as an agent for the prophylaxis or treatment of epilepsy, neurodegenerative disease (e.g., Alzheimer's disease, mild cognitive disorder, Huntington's disease, Parkinson's disease, multiple sclerosis, amyotrophic lateral sclerosis, traumatic brain injury, cerebral infarction, glaucoma and the like), schizophrenia and the like.

Means of Solving the Problems

The present inventors have conducted intensive studies in an attempt to solve the above-mentioned problem and found that a compound (I) represented by the following formula has a superior CH24H inhibitory action, which resulted in the completion of the present invention.

Accordingly, the present invention provides the following.

[1] A compound represented by the formula (I):

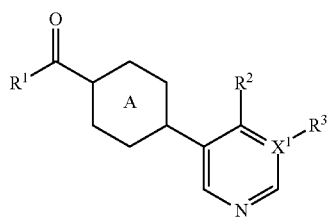

(I)

wherein
$X^1$ is a carbon atom or a nitrogen atom;
Ring A is

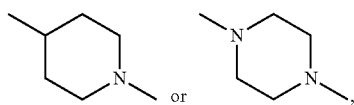

each of which is optionally further substituted and optionally bridged;

$R^1$ is an optionally substituted $C_{1-6}$ alkyl group, an optionally substituted hydroxy group, an optionally substituted amino group, an optionally substituted carbocyclic group, or an optionally substituted heterocyclic group, or $R^1$ is optionally bonded to the atom on Ring A to form, together with Ring A, a spiro ring or a fused ring, each of which is substituted by an oxo group and optionally further substituted;

$R^2$ is an optionally substituted $C_{6-14}$ aryl group, or an optionally substituted aromatic heterocyclic group; and $R^3$ is a hydrogen atom or a substituent when $X^1$ is a carbon atom, or absent when $X^1$ is a nitrogen atom, (hereinafter to be referred to as compound (I)) (tert-butyl 4-(4-phenylpyrimidin-5-yl)piperazine-1-carboxylate is excluded) or a salt thereof.

[2] The compound or salt of [1], wherein $R^1$ is an optionally substituted $C_{1-6}$ alkyl group, an optionally substituted $C_{1-6}$ alkoxy group, an optionally substituted amino group, an optionally substituted $C_{3-8}$ cycloalkyl group, an optionally substituted $C_{6-14}$ aryl group, or an optionally substituted non-aromatic heterocyclic group (tert-butyl 4-(4-phenylpyrimidin-5-yl)piperazine-1-carboxylate is excluded).

[A] The compound or salt of [1], wherein
$R^1$ is
(1) a $C_{1-6}$ alkyl group optionally substituted by 1 to 3 substituents selected from
  (a) a cyano group,
  (b) a $C_{6-14}$ aryl group optionally substituted by 1 to 3 $C_{1-6}$ alkoxy groups,
  (c) a $C_{6-14}$ aryloxy group,
  (d) a $C_{3-8}$ cycloalkyl group,
  (e) a 5- or 6-membered monocyclic aromatic heterocyclic group,
  (f) a 8- to 12-membered fused aromatic heterocyclic group, and
  (g) a 3- to 8-membered monocyclic non-aromatic heterocyclic group optionally substituted by 1 to 3 oxo groups,
(2) a $C_{1-6}$ alkoxy group optionally substituted by 1 to 3 $C_{6-14}$ aryl groups,
(3) an amino group optionally mono- or di-substituted by substituent(s) selected from
  (a) a $C_{1-6}$ alkyl group optionally substituted by 1 to 3 substituents selected from
    (i) a halogen atom,
    (ii) a cyano group,
    (iii) a $C_{3-8}$ cycloalkyl group,
    (iv) a $C_{6-14}$ aryl group optionally substituted by 1 to 3 substituents selected from a halogen atom and a $C_{1-6}$ alkoxy group,
    (v) a 5- or 6-membered monocyclic aromatic heterocyclic group, and
    (vi) a 3- to 8-membered monocyclic non-aromatic heterocyclic group optionally substituted by 1 to 3 $C_{1-6}$ alkyl groups,
  (b) a $C_{3-8}$ cycloalkyl group optionally substituted by 1 to 3 halogen atoms,
  (c) a $C_{6-14}$ aryl group, and
  (d) a 3- to 8-membered monocyclic non-aromatic heterocyclic group optionally substituted by 1 to 3 $C_{1-6}$ alkyl groups,
(4) a $C_{3-8}$ cycloalkyl group optionally substituted by 1 to 3 $C_{6-14}$ aryl groups,
(5) a $C_{6-14}$ aryl group, or
(6) a 3- to 12-membered non-aromatic heterocyclic group optionally substituted by 1 to 5 substituents selected from
  (a) a halogen atom,
  (b) a cyano group,
  (c) a hydroxy group,
  (d) an oxo group,
  (e) a carbamoyl group optionally mono- or di-substituted by $C_{1-6}$ alkyl group(s), (f) a $C_{1-6}$ alkyl group optionally substituted by 1 to 3 substituents selected from
  (i) a hydroxy group, and
  (ii) a $C_{1-6}$ alkoxy group,
(g) a $C_{1-6}$ alkoxy group optionally substituted by 1 to 3 halogen atoms,
(h) a $C_{1-6}$ alkoxy-carbonyl group, and
(i) a $C_{6-14}$ aryl group optionally substituted by 1 to 3 halogen atoms, or $R^1$ is bonded to the atom on Ring A to form, together with Ring A, a spiro ring substituted by oxo and optionally further substituted by 1 to 3 $C_{1-6}$ alkyl groups;

$R^2$ is
(1) a $C_{6-14}$ aryl group optionally substituted by 1 to 3 substituents selected from
  (a) a halogen atom, and
  (b) a $C_{1-6}$ alkyl group optionally substituted by 1 to 3 halogen atoms, or
(2) a 5- to 12-membered aromatic heterocyclic group optionally substituted by 1 to 3 substituents selected from
  (a) a halogen atom,
  (b) a cyano group,
  (c) a $C_{1-6}$ alkyl group optionally substituted by 1 to 3 halogen atoms, and
  (d) a $C_{3-8}$ cycloalkyl group;

$X^1$ is a carbon atom or a nitrogen atom;

$R^3$ is
(1) a hydrogen atom, or
(2) a halogen atom; and

Ring A is

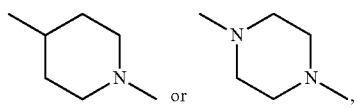

each of which is optionally bridged and optionally further substituted by 1 to 5 substituents selected from
  (a) a halogen atom,
  (b) a $C_{1-6}$ alkyl group, and
  (c) an oxo group,
(tert-butyl 4-(4-phenylpyrimidin-5-yl)piperazine-1-carboxylate is excluded).

[B] The compound or salt of [1] or [A], wherein $R^1$ is
(1) a $C_{1-6}$ alkyl group optionally substituted by 1 to 3 substituents selected from
  (a) a cyano group,
  (b) a $C_{6-14}$ aryl group optionally substituted by 1 to 3 $C_{1-6}$ alkoxy groups,
  (c) a $C_{6-14}$ aryloxy group,
  (d) a $C_{3-8}$ cycloalkyl group,
  (e) a 5- or 6-membered monocyclic aromatic heterocyclic group,
  (f) a 8- to 12-membered fused aromatic heterocyclic group, and
  (g) a 3- to 8-membered monocyclic non-aromatic heterocyclic group optionally substituted by 1 to 3 oxo groups,
(2) a $C_{1-3}$ alkoxy group optionally substituted by 1 to 3 $C_{6-14}$ aryl groups,
(3) an amino group optionally mono- or di-substituted by substituent(s) selected from
  (a) a $C_{1-6}$ alkyl group optionally substituted by 1 to 3 substituents selected from
    (i) a halogen atom,
    (ii) a cyano group,
    (iii) a $C_{3-8}$ cycloalkyl group,
    (iv) a $C_{6-14}$ aryl group optionally substituted by 1 to 3 substituents selected from a halogen atom and a $C_{1-6}$ alkoxy group,
    (v) a 5- or 6-membered monocyclic aromatic heterocyclic group, and
    (vi) a 3- to 8-membered monocyclic non-aromatic heterocyclic group optionally substituted by 1 to 3 $C_{1-6}$ alkyl groups,
  (b) a $C_{3-8}$ cycloalkyl group optionally substituted by 1 to 3 halogen atoms,
  (c) a $C_{6-14}$ aryl group, and
  (d) a 3- to 8-membered monocyclic non-aromatic heterocyclic group optionally substituted by 1 to 3 $C_{1-6}$ alkyl groups,
(4) a $C_{3-8}$ cycloalkyl group optionally substituted by 1 to 3 $C_{6-14}$ aryl groups,
(5) a $C_{6-14}$ aryl group, or
(6) a 3- to 12-membered non-aromatic heterocyclic group optionally substituted by 1 to 5 substituents selected from
  (a) a halogen atom,
  (b) a cyano group,
  (c) a hydroxy group,
  (d) an oxo group,
  (e) a carbamoyl group optionally mono- or di-substituted by $C_{1-6}$ alkyl group(s),
  (f) a $C_{1-6}$ alkyl group optionally substituted by 1 to 3 substituents selected from
    (i) a hydroxy group, and
    (ii) a $C_{1-6}$ alkoxy group,
  (g) a $C_{1-6}$ alkoxy group optionally substituted by 1 to 3 halogen atoms,
  (h) a $C_{1-6}$ alkoxy-carbonyl group, and
  (i) a $C_{6-14}$ aryl group optionally substituted by 1 to 3 halogen atoms, or $R^1$ is bonded to the atom on Ring A to form, together with Ring A, a spiro ring substituted by oxo and optionally further substituted by 1 to 3 $C_{1-6}$ alkyl groups.

[3] The compound or salt of [1] or [A], wherein
$R^1$ is
(1) a $C_{1-6}$ alkyl group optionally substituted by 1 to 3 substituents selected from
  (a) a cyano group,
  (b) a $C_{6-14}$ aryl group optionally substituted by 1 to 3 $C_{1-6}$ alkoxy groups,
  (c) a $C_{6-14}$ aryloxy group,
  (d) a $C_{3-8}$ cycloalkyl group,
  (e) a pyrazolyl group,
  (f) an indazolyl group, and
  (g) a dihydropyridyl group optionally substituted by 1 to 3 oxo groups,
(2) a $C_{1-6}$ alkoxy group optionally substituted by 1 to 3 $C_{6-14}$ aryl groups,
(3) an amino group optionally mono- or di-substituted by substituent(s) selected from
  (a) a $C_{1-6}$ alkyl group optionally substituted by 1 to 3 substituents selected from
    (i) a halogen atom,
    (ii) a cyano group,
    (iii) a $C_{3-8}$ cycloalkyl group,
    (iv) a $C_{6-14}$ aryl group optionally substituted by 1 to 3 substituents selected from a halogen atom and a $C_{1-6}$ alkoxy group, (v) a pyridyl group, and
(vi) an oxetanyl group optionally substituted by 1 to 3 $C_{1-6}$ alkyl groups,
(b) a $C_{3-8}$ cycloalkyl group optionally substituted by 1 to 3 halogen atoms,
(c) a $C_{6-14}$ aryl group, and
(d) a tetrahydropyranyl group, an oxetanyl group, a tetrahydrofuryl group and a pyrrolidinyl group, each of which is optionally substituted by 1 to 3 $C_{1-6}$ alkyl groups,
(4) a $C_{3-8}$ cycloalkyl group optionally substituted by 1 to 3 $C_{6-14}$ aryl groups,
(5) a $C_{6-14}$ aryl group, or
(6) a 3- to 8-membered monocyclic non-aromatic heterocyclic group or a 3,7-dioxa-9-azabicyclo[3.3.1]nonyl group, each of which is optionally substituted by 1 to 5 substituents selected from
(a) a halogen atom,
(b) a cyano group,
(c) a hydroxy group,
(d) an oxo group,
(e) a carbamoyl group optionally mono- or di-substituted by $C_{1-6}$ alkyl group(s),
(f) a $C_{1-6}$ alkyl group optionally substituted by 1 to 3 substituents selected from
(i) a hydroxy group, and
(ii) a $C_{1-6}$ alkoxy group,
(g) a $C_{1-6}$ alkoxy group optionally substituted by 1 to 3 halogen atoms,
(h) a $C_{1-6}$ alkoxy-carbonyl group, and
(i) a $C_{6-14}$ aryl group optionally substituted by 1 to 3 halogen atoms, or
$R^1$ is bonded to the atom on Ring A to form, together with Ring A, a 2,8-diazaspiro[4.5]decane ring substituted by oxo and optionally further substituted by 1 to 3 $C_{1-6}$ alkyl groups;
$R^2$ is
(1) a $C_{6-14}$ aryl group optionally substituted by 1 to 3 substituents selected from
(a) a halogen atom, and
(b) a $C_{1-6}$ alkyl group optionally substituted by 1 to 3 halogen atoms, or
(2) a 5- or 6-membered monocyclic aromatic heterocyclic group or a 8- to 12-membered fused aromatic heterocyclic group, each of which is optionally substituted by 1 to 3 substituents selected from
(a) a halogen atom,
(b) a cyano group,
(c) a $C_{1-6}$ alkyl group optionally substituted by 1 to 3 halogen atoms, and
(d) a $C_{3-8}$ cycloalkyl group;
$X^1$ is a carbon atom or a nitrogen atom;
$R^3$ is
(1) a hydrogen atom, or
(2) a halogen atom; and
Ring A is
(1)

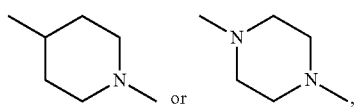

each of which is optionally further substituted by 1 to 3 substituents selected from (a) a halogen atom,
(b) a $C_{1-6}$ alkyl group, and
(c) an oxo group, or
(2) a 8-azabicyclo[3.2.1]octane ring, a 2,5-diazabicyclo[2.2.1]heptane ring or a 3-azabicyclo[3.1.0]hexane ring, (tert-butyl 4-(4-phenylpyrimidin-5-yl)piperazine-1-carboxylate is excluded).
[4] The compound or salt of any of [1], [3], [A] and [B], wherein $R^1$ is
(1) a $C_{1-6}$ alkyl group optionally substituted by 1 to 3 substituents selected from
(a) a cyano group,
(b) a $C_{6-14}$ aryl group optionally substituted by 1 to 3 $C_{1-6}$ alkoxy groups,
(c) a $C_{6-14}$ aryloxy group,
(d) a $C_{3-8}$ cycloalkyl group,
(e) a pyrazolyl group,
(f) an indazolyl group, and
(g) a dihydropyridyl group optionally substituted by 1 to 3 oxo groups,
(2) a $C_{1-3}$ alkoxy group optionally substituted by 1 to 3 $C_{6-14}$ aryl groups,
(3) an amino group optionally mono- or di-substituted by substituent(s) selected from
(a) a $C_{1-6}$ alkyl group optionally substituted by 1 to 3 substituents selected from
(i) a halogen atom,
(ii) a cyano group,
(iii) a $C_{3-8}$ cycloalkyl group,
(iv) a $C_{6-14}$ aryl group optionally substituted by 1 to 3 substituents selected from a halogen atom and a $C_{1-6}$ alkoxy group,
(v) a pyridyl group, and
(vi) an oxetanyl group optionally substituted by 1 to 3 $C_{1-6}$ alkyl groups,
(b) a $C_{3-8}$ cycloalkyl group optionally substituted by 1 to 3 halogen atoms,
(c) a $C_{6-14}$ aryl group, and
(d) a tetrahydropyranyl group, an oxetanyl group, a tetrahydrofuryl group and a pyrrolidinyl group, each of which is optionally substituted by 1 to 3 $C_{1-6}$ alkyl groups,
(4) a $C_{3-8}$ cycloalkyl group optionally substituted by 1 to 3 $C_{6-14}$ aryl groups,
(5) a $C_{6-14}$ aryl group, or
(6) a 3- to 8-membered monocyclic non-aromatic heterocyclic group or a 3,7-dioxa-9-azabicyclo[3.3.1]nonyl group, each of which is optionally substituted by 1 to 5 substituents selected from
(a) a halogen atom,
(b) a cyano group,
(c) a hydroxy group,
(d) an oxo group,
(e) a carbamoyl group optionally mono- or di-substituted by $C_{1-6}$ alkyl group(s),
(f) a $C_{1-6}$ alkyl group optionally substituted by 1 to 3 substituents selected from
(i) a hydroxy group, and
(ii) a $C_{1-6}$ alkoxy group,
(g) a $C_{1-6}$ alkoxy group optionally substituted by 1 to 3 halogen atoms,
(h) a $C_{1-6}$ alkoxy-carbonyl group, and
(i) a $C_{6-14}$ aryl group optionally substituted by 1 to 3 halogen atoms, or
$R^1$ is bonded to the atom on Ring A to form, together with Ring A, a 2,8-diazaspiro[4.5]decane ring substituted by oxo and optionally further substituted by 1 to 3 $C_{1-6}$ alkyl groups.

[C] The compound or salt of [1] or [2], wherein
R¹ is a 3- to 8-membered monocyclic non-aromatic heterocyclic group optionally substituted by 1 to 5 to substituents selected from
(a) a halogen atom,
(b) a cyano group,
(c) a carbamoyl group,
(d) a $C_{1-6}$ alkyl group optionally substituted by 1 to 3 $C_{1-6}$ alkoxy groups, and
(e) a $C_{1-6}$ alkoxy group;
R² is
(1) a $C_{6-14}$ aryl group optionally substituted by 1 to 3 substituents selected from
(a) a halogen atom, and
(b) a $C_{1-6}$ alkyl group optionally substituted by 1 to 3 halogen atoms, or
(2) a 5- or 6-membered monocyclic aromatic heterocyclic group optionally substituted by 1 to 3 substituents selected from
(a) a halogen atom, and
(b) a $C_{1-6}$ alkyl group;
X¹ is a carbon atom;
R³ is a hydrogen atom; and
Ring A is

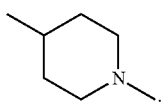

[D] The compound or salt of any of [1], [3] and [A], wherein
R¹ is
(1) a $C_{1-6}$ alkyl group optionally substituted by 1 to 3 substituents selected from
(a) a cyano group,
(b) a phenyl group optionally substituted by 1 to 3 $C_{1-6}$ alkoxy groups,
(c) a phenoxy group,
(d) a cyclopropyl group,
(e) a pyrazolyl group,
(f) an indazolyl group, and
(g) a dihydropyridyl group optionally substituted by 1 to 3 oxo groups,
(2) a $C_{1-6}$ alkoxy group optionally substituted by 1 to 3 phenyl groups,
(3) an amino group optionally mono- or di-substituted by substituent(s) selected from
(a) a $C_{1-6}$ alkyl group optionally substituted by 1 to 3 substituents selected from
(i) a halogen atom,
(ii) a cyano group,
(iii) a cyclopropyl group,
(iv) a cyclobutyl group,
(v) a phenyl group optionally substituted by 1 to 3 substituents selected from a halogen atom and a $C_{1-6}$ alkoxy group,
(vi) a pyridyl group, and
(vii) an oxetanyl group optionally substituted by 1 to 3 $C_{1-6}$ alkyl groups,
(b) a cyclopropyl group, a cyclobutyl group and a cyclopentyl group, each of which is optionally substituted by 1 to 3 halogen atoms,
(c) a phenyl group, and
(d) a tetrahydropyranyl group, an oxetanyl group, a tetrahydrofuryl group and a pyrrolidinyl group, each of which is optionally substituted by 1 to 3 $C_{1-6}$ alkyl groups,
(4) a cyclopropyl group optionally substituted by 1 to 3 phenyl groups,
(5) a phenyl group, or
(6) an azetidinyl group, a pyrrolidinyl group, a piperidyl group, a piperazinyl group, a morpholinyl group, a 1,1-dioxidothiomorpholinyl group, a tetrahydropyranyl group, a 3-oxa-6-azabicyclo[3.1.1]heptyl group, an 8-oxa-3-azabicyclo[3.2.1]octyl group, a 2-oxa-5-azabicyclo[2.2.1]heptyl group, a 3-oxa-8-azabicyclo[3.2.1]octyl group, a 6-oxa-3-azabicyclo[3.1.1]heptyl group or a 3,7-dioxa-9-azabicyclo[3.3.1]nonyl group, each of which is optionally substituted by 1 to 5 substituents selected from
(a) a halogen atom,
(b) a cyano group,
(c) a hydroxy group,
(d) an oxo group,
(e) a carbamoyl group optionally mono- or di-substituted by $C_{1-6}$ alkyl group(s),
(f) a $C_{1-6}$ alkyl group optionally substituted by 1 to 3 substituents selected from
(i) a hydroxy group, and
(ii) a $C_{1-6}$ alkoxy group,
(g) a $C_{1-6}$ alkoxy group optionally substituted by 1 to 3 halogen atoms,
(h) a $C_{1-6}$ alkoxy-carbonyl group, and
(i) a phenyl group optionally substituted by 1 to 3 halogen atoms, or
R¹ is bonded to the atom on Ring A to form, together with Ring A, a 2,8-diazaspiro[4.5]decane ring substituted by oxo and optionally further substituted by 1 to 3 $C_{1-6}$ alkyl groups;
R² is
(1) a phenyl group optionally substituted by 1 to 3 substituents selected from
(a) a halogen atom, and
(b) a $C_{1-6}$ alkyl group optionally substituted by 1 to 3 halogen atoms, or
(2) a pyrazolyl group, an oxazolyl group, a thiazolyl group, a thiadiazolyl group, a pyridyl group, an indazolyl group or a benzothiazolyl group, each of which is optionally substituted by 1 to 3 substituents selected from
(a) a halogen atom,
(b) a cyano group,
(c) a $C_{1-6}$ alkyl group optionally substituted by 1 to 3 halogen atoms, and
(d) a cyclopropyl group;
X¹ is a carbon atom or a nitrogen atom;
R³ is
(1) a hydrogen atom, or
(2) a halogen atom; and
Ring A is
(1)

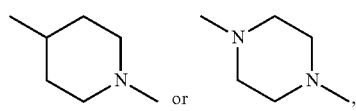

each of which is optionally further substituted by 1 to 3 substituents selected from
- (a) a halogen atom,
- (b) a $C_{1-6}$ alkyl group, and
- (c) an oxo group, or (2) a 8-azabicyclo[3.2.1]octane ring, a 2,5-diazabicyclo[2.2.1]heptane ring or a 3-azabicyclo[3.1.0]hexane ring, (tert-butyl 4-(4-phenylpyrimidin-5-yl)piperazine-1-carboxylate is excluded).

[E] The compound or salt of any of [1], [3], [4], [A], [B] and [D], wherein $R^1$ is (1) a $C_{1-6}$ alkyl group optionally substituted by 1 to 3 substituents selected from
- (a) a cyano group,
- (b) a phenyl group optionally substituted by 1 to 3 $C_{1-6}$ alkoxy groups,
- (c) a phenoxy group,
- (d) a cyclopropyl group,
- (e) a pyrazolyl group,
- (f) an indazolyl group, and
- (g) a dihydropyridyl group optionally substituted by 1 to 3 oxo groups, (2) a $C_{1-3}$ alkoxy group optionally substituted by 1 to 3 phenyl groups, (3) an amino group optionally mono- or di-substituted by substituent(s) selected from
- (a) a $C_{1-6}$ alkyl group optionally substituted by 1 to 3 substituents selected from
  - (i) a halogen atom,
  - (ii) a cyano group,
  - (iii) a cyclopropyl group,
  - (iv) a cyclobutyl group,
  - (v) a phenyl group optionally substituted by 1 to 3 substituents selected from a halogen atom and a $C_{1-6}$ alkoxy group,
  - (vi) a pyridyl group, and
  - (vii) an oxetanyl group optionally substituted by 1 to 3 $C_{1-6}$ alkyl groups,
- (b) a cyclopropyl group, a cyclobutyl group and a cyclopentyl group, each of which is optionally substituted by 1 to 3 halogen atoms,
- (c) a phenyl group, and
- (d) a tetrahydropyranyl group, an oxetanyl group, a tetrahydrofuryl group and a pyrrolidinyl group, each of which is optionally substituted by 1 to 3 $C_{1-6}$ alkyl groups, (4) a cyclopropyl group optionally substituted by 1 to 3 phenyl groups, (5) a phenyl group, or (6) an azetidinyl group, a pyrrolidinyl group, a piperidyl group, a piperazinyl group, a morpholinyl group, a 1,1-dioxidothiomorpholinyl group, a tetrahydropyranyl group, a 3-oxa-6-azabicyclo[3.1.1]heptyl group, an 8-oxa-3-azabicyclo[3.2.1]octyl group, a 2-oxa-5-azabicyclo[2.2.1]heptyl group, a 3-oxa-8-azabicyclo[3.2.1]octyl group, a 6-oxa-3-azabicyclo[3.1.1]heptyl group or a 3,7-dioxa-9-azabicyclo[3.3.1]nonyl group, each of which is optionally substituted by 1 to 5 substituents selected from
- (a) a halogen atom,
- (b) a cyano group,
- (c) a hydroxy group,
- (d) an oxo group,
- (e) a carbamoyl group optionally mono- or di-substituted by $C_{1-6}$ alkyl group(s),
- (f) a $C_{1-6}$ alkyl group optionally substituted by 1 to 3 substituents selected from
  - (i) a hydroxy group, and
  - (ii) a $C_{1-6}$ alkoxy group,
- (g) a $C_{1-6}$ alkoxy group optionally substituted by 1 to 3 halogen atoms,
- (h) a $C_{1-6}$ alkoxy-carbonyl group, and
- (i) a phenyl group optionally substituted by 1 to 3 halogen atoms, or $R^1$ is bonded to the atom on Ring A to form, together with Ring A, a 2,8-diazaspiro[4.5]decane ring substituted by oxo and optionally further substituted by 1 to 3 $C_{1-6}$ alkyl groups.

[5] The compound or salt of any of [1]-[4], [A], [B], [D] and [E], wherein
$R^1$ is (1) an amino group optionally mono- or di-substituted by substituent(s) selected from
- (a) a $C_{1-6}$ alkyl group optionally substituted by 1 to 3 substituents selected from
  - (i) a halogen atom, and
  - (ii) a phenyl group optionally substituted by 1 to 3 halogen atoms,
- (b) a tetrahydropyranyl group, and
- (c) a tetrahydrofuryl group, or (2) an azetidinyl group or a pyrrolidinyl group, each of which is optionally substituted by 1 to 5 substituents selected from
- (a) a halogen atom,
- (b) a cyano group,
- (c) a carbamoyl group,
- (d) a $C_{1-6}$ alkyl group, and
- (e) a $C_{1-6}$ alkoxy group;

$R^2$ is (1) a phenyl group optionally substituted by 1 to 3 halogen atoms, or (2) a pyrazolyl group, a thiazolyl group or a thiadiazolyl group, each of which is optionally substituted by 1 to 3 substituents selected from
- (a) a halogen atom,
- (b) a $C_{1-6}$ alkyl group, and
- (c) a cyclopropyl group;

$X^1$ is a carbon atom or a nitrogen atom;
$R^3$ is a hydrogen atom; and
Ring A is

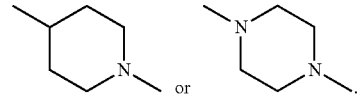

[F] The compound or salt of any of [1]-[5], [A], [B], [D] and [E], wherein
$R^1$ is (1) an amino group optionally mono- or di-substituted by substituent(s) selected from
- (a) a $C_{1-6}$ alkyl group optionally substituted by 1 to 3 substituents selected from
  - (i) a halogen atom, and
  - (ii) a phenyl group optionally substituted by 1 to 3 halogen atoms,
- (b) a tetrahydropyranyl group, and
- (c) a tetrahydrofuryl group, or (2) an azetidinyl group or a pyrrolidinyl group, each of which is optionally substituted by 1 to 5 substituents selected from
- (a) a halogen atom, and
- (b) a cyano group;

R² is
(1) a phenyl group optionally substituted by 1 to 3 halogen atoms, or
(2) a pyrazolyl group or a thiazolyl group, each of which is optionally substituted by 1 to 3 substituents selected from
  (a) a halogen atom,
  (b) a $C_{1-6}$ alkyl group, and
  (c) a cyclopropyl group;
$X^1$ is a carbon atom or a nitrogen atom;
$R^3$ is a hydrogen atom; and
Ring A is

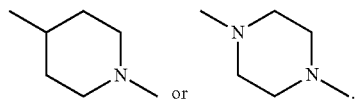

[G] The compound or salt of any of [1]-[5], [A], [B] and [D]-[F], wherein
$R^1$ is
(1) an amino group optionally mono- or di-substituted by substituent(s) selected from
  (a) a $C_{1-6}$ alkyl group optionally substituted by 1 to 3 substituents selected from
    (i) a halogen atom, and
    (ii) a phenyl group optionally substituted by 1 to 3 halogen atoms,
  (b) a tetrahydropyranyl group, and
  (c) a tetrahydrofuryl group, or
(2) an azetidinyl group or a pyrrolidinyl group, each of which is optionally substituted by 1 to 3 halogen atoms;
R² is
(1) a phenyl group optionally substituted by 1 to 3 halogen atoms, or
(2) a pyrazolyl group or a thiazolyl group, each of which is optionally substituted by 1 to 3 substituents selected from
  (a) a halogen atom,
  (b) a $C_{1-6}$ alkyl group, and
  (c) a cyclopropyl group;
$X^1$ is a carbon atom or a nitrogen atom;
$R^3$ is a hydrogen atom; and
Ring A is

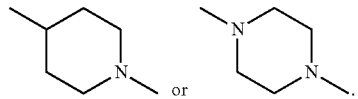

[H] The compound or salt of any of [1], [2] and [C], wherein
$R^1$ is a pyrrolidinyl group optionally substituted by 1 to 5 substituents selected from
  (a) a halogen atom,
  (b) a cyano group,
  (c) a carbamoyl group,
  (d) a $C_{1-6}$ alkyl group optionally substituted by 1 to 3 $C_{1-6}$ alkoxy groups, and
  (e) a $C_{1-6}$ alkoxy group;
R² is
(1) a phenyl group optionally substituted by 1 to 3 substituents selected from
  (a) a halogen atom, and
  (b) a $C_{1-6}$ alkyl group optionally substituted by 1 to 3 halogen atoms, or
(2) a pyrazolyl group, a thiadiazolyl group or a pyridyl group, each of which is optionally substituted by 1 to 3 substituents selected from
  (a) a halogen atom, and
  (b) a $C_{1-6}$ alkyl group;
$X^1$ is a carbon atom;
$R^3$ is a hydrogen atom; and
Ring A is

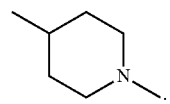

[I] The compound or salt of any of [1]-[5], [A], [B], [D] and [E], wherein
$R^1$ is a pyrrolidinyl group optionally substituted by 1 to 5 substituents selected from
  (a) a halogen atom,
  (b) a cyano group,
  (c) a carbamoyl group,
  (d) a $C_{1-6}$ alkyl group, and
  (e) a $C_{1-6}$ alkoxy group;
R² is a pyrazolyl group or a thiadiazolyl group, each of which is optionally substituted by 1 to 3 substituents selected from
  (a) a halogen atom, and
  (b) a $C_{1-6}$ alkyl group;
$X^1$ is a carbon atom;
$R^3$ is a hydrogen atom; and
Ring A is

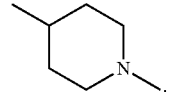

[6] The compound or salt of any of [1]-[5], [A], [B], [D]-[F] and [I], wherein
$R^1$ is a pyrrolidinyl group optionally substituted by 1 to 5 substituents selected from
  (a) a halogen atom, and
  (b) a cyano group;
R² is a pyrazolyl group optionally substituted by 1 to 3 substituents selected from
  (a) a halogen atom, and
  (b) a $C_{1-6}$ alkyl group;
$X^1$ is a carbon atom;
$R^3$ is a hydrogen atom; and
Ring A is

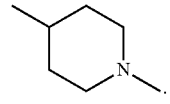

[J] The compound or salt of any of [1], [3], [A] and [D], wherein
$R^1$ is
(1) a $C_{1-6}$ alkyl group optionally substituted by 1 to 3 substituents selected from
  (a) a cyclopropyl group, and
  (b) an indazolyl group, (2) a $C_{1-6}$ alkoxy group optionally substituted by 1 to 3 phenyl groups,
(3) an amino group optionally mono- or di-substituted by substituent(s) selected from
    (a) a $C_{1-6}$ alkyl group optionally substituted by 1 to 3 substituents selected from
        (i) a halogen atom,
        (ii) a phenyl group optionally substituted by 1 to 3 halogen atoms,
        (iii) a pyridyl group, and
        (iv) an oxetanyl group optionally substituted by 1 to 3 $C_{1-6}$ alkyl groups,
    (b) a cyclopropyl group,
    (c) a cyclopentyl group,
    (d) a tetrahydropyranyl group,
    (e) a tetrahydrofuryl group, and
    (f) a phenyl group,
(4) a cyclopropyl group, or
(5) an azetidinyl group, a pyrrolidinyl group, a 1,1-dioxidothiomorpholinyl group or a 3-oxa-6-azabicyclo[3.1.1]heptyl group, each of which is optionally substituted by 1 to 5 substituents selected from
    (a) a halogen atom,
    (b) a cyano group,
    (c) a carbamoyl group,
    (d) a $C_{1-6}$ alkyl group optionally substituted by 1 to 3 $C_{1-6}$ alkoxy groups,
    (e) a $C_{1-6}$ alkoxy group, and
    (f) a phenyl group optionally substituted by 1 to 3 halogen atoms, or
$R^1$ is bonded to the atom on Ring A to form, together with Ring A, a 2,8-diazaspiro[4.5]decane ring substituted by oxo and optionally further substituted by 1 to 3 $C_{1-6}$ alkyl groups;
$R^2$ is
(1) a phenyl group optionally substituted by 1 to 3 substituents selected from
    (a) a halogen atom, and
    (b) a $C_{1-6}$ alkyl group, or
(2) a pyrazolyl group, an oxazolyl group, a thiazolyl group, a thiadiazolyl group, a pyridyl group or a benzothiazolyl group, each of which is optionally substituted by 1 to 3 substituents selected from
    (a) a halogen atom,
    (b) a cyano group,
    (c) a $C_{1-6}$ alkyl group optionally substituted by 1 to 3 halogen atoms, and
    (d) a cyclopropyl group;
$X^1$ is a carbon atom or a nitrogen atom;
$R^3$ is
(1) a hydrogen atom, or
(2) a halogen atom; and
Ring A is
(1)

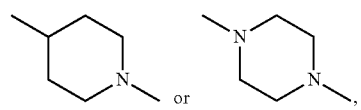

each of which is optionally further substituted by 1 to 3 substituents selected from
    (a) a halogen atom, and
    (b) a $C_{1-6}$ alkyl group, or
(2) a 8-azabicyclo[3.2.1]octane ring or a 2,5-diazabicyclo[2.2.1]heptane ring.

[K] The compound or salt of any of [1]-[4], [A], [B], [D] and [E], wherein
$R^1$ is a pyrrolidinyl group optionally substituted by 1 to 3 substituents selected from
    (a) a halogen atom,
    (b) a cyano group,
    (c) a carbamoyl group, and
    (d) a $C_{1-6}$ alkyl group optionally substituted by 1 to 3 $C_{1-6}$ alkoxy groups;
$R^2$ is a pyrazolyl group, a thiazolyl group, a thiadiazolyl group or a pyridyl group, each of which is optionally substituted by 1 to 3 substituents selected from
    (a) a halogen atom, and
    (b) a $C_{1-6}$ alkyl group;
$X^1$ is a carbon atom;
$R^3$ is a hydrogen atom; and
Ring A is

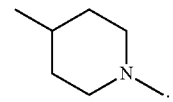

[7] (2R)-1-((1-(4-(4-methyl-1H-pyrazol-1-yl)pyridin-3-yl)piperidin-4-yl)carbonyl)pyrrolidine-2-carbonitrile or a salt thereof,
(2R)-1-((1-(4-(4-chloro-1H-pyrazol-1-yl)pyridin-3-yl)piperidin-4-yl)carbonyl)pyrrolidine-2-carbonitrile or a salt thereof,
(2R)-4,4-difluoro-1-((1-(4-(4-methyl-1H-pyrazol-1-yl)pyridin-3-yl)piperidin-4-yl)carbonyl)pyrrolidine-2-carbonitrile or a salt thereof,
(3-fluoroazetidin-1-yl)(1-(4-(4-fluorophenyl)pyrimidin-5-yl)piperidin-4-yl)methanone or a salt thereof,
(1-(4-(4-chloro-1H-pyrazol-1-yl)pyridin-3-yl)piperidin-4-yl)(3-fluoroazetidin-1-yl)methanone or a salt thereof,
(1-(4-(4-chloro-1H-pyrazol-1-yl)pyridin-3-yl)piperidin-4-yl)((3S)-3-fluoropyrrolidin-1-yl)methanone or a salt thereof,
(1-(4-(4-fluorophenyl)pyrimidin-5-yl)piperidin-4-yl)((3S)-3-fluoropyrrolidin-1-yl)methanone or a salt thereof,
N-benzyl-N-(2-fluoroethyl)-4-(4-phenylpyrimidin-5-yl)piperazine-1-carboxamide or a salt thereof,
N-(4-fluorobenzyl)-N-(2-fluoroethyl)-4-(4-(4-methyl-1H-pyrazol-1-yl)pyridin-3-yl)piperazine-1-carboxamide or a salt thereof,
((3S)-3-fluoropyrrolidin-1-yl)(1-(4-(5-methyl-1,3-thiazol-2-yl)pyridin-3-yl)piperidin-4-yl)methanone or a salt thereof,
(3-fluoroazetidin-1-yl)(1-(4-(5-methyl-1,3-thiazol-2-yl)pyridin-3-yl)piperidin-4-yl)methanone or a salt thereof,
(1-(4-(4-bromo-1H-pyrazol-1-yl)pyridin-3-yl)piperidin-4-yl)(3-fluoroazetidin-1-yl)methanone or a salt thereof, or
(1-(4-(4-cyclopropyl-1H-pyrazol-1-yl)pyridin-3-yl)piperidin-4-yl)(3-fluoroazetidin-1-yl)methanone or a salt thereof.
[8] (2R)-1-((1-(4-(4-methyl-1H-pyrazol-1-yl)pyridin-3-yl)piperidin-4-yl)carbonyl)pyrrolidine-2-carbonitrile or a salt thereof.
[9] (2R)-1-((1-(4-(4-chloro-1H-pyrazol-1-yl)pyridin-3-yl)piperidin-4-yl)carbonyl)pyrrolidine-2-carbonitrile or a salt thereof.
[10] (2R)-4,4-difluoro-1-((1-(4-(4-methyl-1H-pyrazol-1-yl)pyridin-3-yl)piperidin-4-yl)carbonyl)pyrrolidine-2-carbonitrile or a salt thereof.

[11] A medicament comprising the compound or salt of any of [1]-[10].
[12] The medicament of [11], which is a cholesterol 24-hydroxylase inhibitor.
[13] The medicament of [11], which is an agent for the prophylaxis or treatment of epilepsy or neurodegenerative disease.
[14] The medicament of [13], wherein the neurodegenerative disease is Alzheimer's disease, mild cognitive disorder, Huntington's disease, Parkinson's disease or multiple sclerosis.
[15] The compound or salt of any of [1]-[10] for use in the prophylaxis or treatment of epilepsy or neurodegenerative disease.
[16] The compound or salt of [15], wherein the neurodegenerative disease is Alzheimer's disease, mild cognitive disorder, Huntington's disease, Parkinson's disease or multiple sclerosis.
[17] A method of inhibiting cholesterol 24-hydroxylase in a mammal, which comprises administering an effective amount of the compound or salt of any of [1]-[10] to the mammal.
[18] A method for the prophylaxis or treatment of epilepsy or neurodegenerative disease, which comprises administering an effective amount of the compound or salt of any of [1]-[10] to the mammal.
[19] The method of [18], wherein the neurodegenerative disease is Alzheimer's disease, mild cognitive disorder, Huntington's disease, Parkinson's disease or multiple sclerosis.
[20] Use of the compound or salt of any of [1]-[10] for the production of an agent for the prophylaxis or treatment of epilepsy or neurodegenerative disease.
[21] The use of [20], wherein the neurodegenerative disease is Alzheimer's disease, mild cognitive disorder, Huntington's disease, Parkinson's disease or multiple sclerosis.

Effect of the Invention

Compound (I) has a superior CH24H inhibitory action, which is useful as an agent for the prophylaxis or treatment of epilepsy, neurodegenerative disease (e.g., Alzheimer's disease, mild cognitive disorder, Huntington's disease, Parkinson's disease, multiple sclerosis, amyotrophic lateral sclerosis, traumatic brain injury, cerebral infarction, glaucoma and the like), schizophrenia and the like.

DETAILED DESCRIPTION OF THE INVENTION

In the present specification, the "halogen atom" means a fluorine atom, a chlorine atom, a bromine atom or an iodine atom.

In the present specification, the "$C_{1-10}$ alkyl group" means, for example, methyl, ethyl, propyl, isopropyl, butyl, 2-methylpropyl, 1-methylpropyl, tert-butyl, pentyl, isopentyl, neo-pentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl or the like. Among them, a $C_{1-6}$ alkyl group is preferable.

In the present specification, the "$C_{1-6}$ alkyl (group)" means, for example, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl or the like.

In the present specification, the "$C_{2-10}$ alkenyl group" means, for example, vinyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl or the like. Among them, a $C_{2-6}$ alkenyl group is preferable.

In the present specification, the "$C_{2-6}$ alkenyl (group)" means, for example, vinyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl or the like.

In the present specification, the "$C_{2-10}$ alkynyl group" means, for example, ethynyl, 1-propynyl, 2-propynyl, 1-butynyl, 2-butynyl, 3-butynyl, 1-pentynyl, 2-pentynyl, 3-pentynyl, 4-pentynyl, 1,1-dimethylprop-2-yn-1-yl, 1-hexynyl, 2-hexynyl, 3-hexynyl, 4-hexynyl, 5-hexynyl, 1-heptynyl, 1-octynyl or the like. Among them, a $C_{2-6}$ alkynyl group is preferable.

In the present specification, the "$C_{2-6}$ alkynyl (group)" means, for example, ethynyl, 1-propynyl, 2-propynyl, 1-butynyl, 2-butynyl, 3-butynyl, 1-pentynyl, 2-pentynyl, 3-pentynyl, 4-pentynyl, 1,1-dimethylprop-2-yn-1-yl, 1-hexynyl, 2-hexynyl, 3-hexynyl, 4-hexynyl, 5-hexynyl or the like.

In the present specification, the "$C_{1-6}$ alkoxy (group)" means, for example, methoxy, ethoxy, propoxy, isopropoxy, butoxy, isobutoxy, sec-butoxy, tert-butoxy, pentyloxy, isopentyloxy, hexyloxy or the like.

In the present specification, the "$C_{1-3}$ alkoxy group" means, methoxy, ethoxy, propoxy or isopropoxy.

In the present specification, the "$C_{2-6}$ alkenyloxy (group)" means, for example, vinyloxy, 1-propenyloxy, 2-propenyloxy, 2-methyl-1-propenyloxy, 1-butenyloxy, 2-butenyloxy, 3-butenyloxy, 3-methyl-2-butenyloxy, 1-pentenyloxy, 2-pentenyloxy, 3-pentenyloxy, 4-pentenyloxy, 4-methyl-3-pentenyloxy, 1-hexenyloxy, 3-hexenyloxy, 5-hexenyloxy or the like.

In the present specification, the "$C_{2-6}$ alkynyloxy (group)" means, for example, ethynyloxy, 1-propynyloxy, 2-propynyloxy, 1-butynyloxy, 2-butynyloxy, 3-butynyloxy, 1-pentynyloxy, 2-pentynyloxy, 3-pentynyloxy, 4-pentynyloxy, 1,1-dimethylprop-2-yn-1-yloxy, 1-hexynyloxy, 2-hexynyloxy, 3-hexynyloxy, 4-hexynyloxy, 5-hexynyloxy or the like.

In the present specification, the "$C_{1-6}$ alkylenedioxy (group)" means, for example, methylenedioxy, ethylenedioxy or the like.

In the present specification, the "$C_{1-6}$ alkoxy-carbonyl (group)" means, for example, methoxycarbonyl, ethoxycarbonyl, propoxycarbonyl, isopropoxycarbonyl, butoxycarbonyl, isobutoxycarbonyl, tert-butoxycarbonyl or the like.

In the present specification, the "$C_{1-6}$ alkyl-carbonyl (group)" means, for example, acetyl, propanoyl, butanoyl, 2-methylpropanoyl or the like.

In the present specification, the "mono-$C_{1-6}$ alkylamino (group)" means, for example, methylamino, ethylamino, propylamino, isopropylamino, butylamino, isobutylamino, tert-butylamino or the like.

In the present specification, the "di-$C_{1-6}$ alkylamino (group)" means, for example, dimethylamino, diethylamino, dipropylamino, diisopropylamino, dibutylamino, diisobutylamino, ditert-butylamino or the like.

In the present specification, the "$C_{3-10}$ cycloalkyl group" means, for example, cyclopropyl, cyclobutyl, cyclopentyl, cyclohexyl, cycloheptyl, cyclooctyl, cyclononyl, cyclodecyl or the like. Among them, a $C_{3-6}$ cycloalkyl group is preferable.

In the present specification, the "C$_{3-8}$ cycloalkyl (group)" means, for example, cyclopropyl, cyclobutyl, cyclopentyl, cyclohexyl, cycloheptyl, cyclooctyl or the like.

In the present specification, the "C$_{3-6}$ cycloalkyl (group)" means, for example, those having 3 to 6 carbon atoms from among the above-mentioned C$_{3-8}$ cycloalkyl (group).

In the present specification, the "C$_{3-8}$ cycloalkyloxy (group)" means, for example, cyclopropyloxy, cyclobutyloxy, cyclopentyloxy, cyclohexyloxy, cycloheptyloxy, cyclooctyloxy or the like.

In the present specification, the "C$_{3-6}$ cycloalkyloxy (group)" means, for example, cyclopropyloxy, cyclobutyloxy, cyclopentyloxy, cyclohexyloxy or the like.

In the present specification, the "C$_{3-10}$ cycloalkenyl (group)" means, for example, cyclopropenyl (e.g., 2-cyclopropen-1-yl), cyclobutenyl (e.g., 2-cyclobuten-1-yl), cyclopentenyl (e.g., 2-cyclopenten-1-yl, 3-cyclopenten-1-yl), cyclohexenyl (e.g., 1-cyclohexen-1-yl, 2-cyclohexen-1-yl, 3-cyclohexen-1-yl), cycloheptenyl (e.g., 1-cyclohepten-1-yl, 2-cyclohepten-1-yl, 2-cyclohepten-1-yl), cyclooctenyl (e.g., 1-cycloocten-1-yl, 2-cycloocten-1-yl, 3-cycloocten-1-yl), cyclononenyl (e.g., 1-cyclononen-1-yl, 2-cyclononen-1-yl, 3-cyclononen-1-yl) or the like. Among them, a C$_{3-8}$ cycloalkenyl group is preferable.

In the present specification, the "C$_{3-8}$ cycloalkenyl (group)" means, for example, cyclopropenyl (e.g., 2-cyclopropen-1-yl), cyclobutenyl (e.g., 2-cyclobuten-1-yl), cyclopentenyl (e.g., 2-cyclopenten-1-yl, 3-cyclopenten-1-yl), cyclohexenyl (e.g., 2-cyclohexen-1-yl, 3-cyclohexen-1-yl) or the like.

In the present specification, the "C$_{3-8}$ cycloalkenyloxy (group)" means, for example, cyclopropenyloxy (e.g., 2-cyclopropen-1-yloxy), cyclobutenyloxy (e.g., 2-cyclobuten-1-yloxy), cyclopentenyloxy (e.g., 2-cyclopenten-1-yloxy, 3-cyclopenten-1-yloxy), cyclohexenyloxy (e.g., 2-cyclohexen-1-yloxy, 3-cyclohexen-1-yloxy) or the like.

In the present specification, the "C$_{4-10}$ cycloalkadienyl group" means, for example, 1,3-cyclobutadien-1-yl, 1,3-cyclopentadien-1-yl, 1,4-cyclopentadien-1-yl, 2,4-cyclopentadien-1-yl, 1,3-cyclohexadien-1-yl, 1,4-cyclohexadien-1-yl, 1,5-cyclohexadien-1-yl, 2,4-cyclohexadien-1-yl, 2,5-cyclohexadien-1-yl, 1,3-cyclooctadien-1-yl, 1,4-cyclooctadien-1-yl, 1,5-cyclooctadien-1-yl, 1,6-cyclooctadien-1-yl, 1,7-cyclooctadien-1-yl, 2,4-cyclooctadien-1-yl, 2,5-cyclooctadien-1-yl, 2,6-cyclooctadien-1-yl, 2,7-cyclooctadien-1-yl, 3,5-cyclooctadien-1-yl, 3,6-cyclooctadien-1-yl or the like. Among them, a C$_{4-6}$ cycloalkadienyl group is preferable.

In the present specification, the "C$_{4-6}$ cycloalkadienyl group" means, for example, 1,3-cyclobutadien-1-yl, 1,3-cyclopentadien-1-yl, 1,4-cyclopentadien-1-yl, 2,4-cyclopentadien-1-yl, 1,3-cyclohexadien-1-yl, 1,4-cyclohexadien-1-yl, 1,5-cyclohexadien-1-yl, 2,4-cyclohexadien-1-yl, 2,5-cyclohexadien-1-yl or the like.

The above-mentioned C$_{3-10}$ cycloalkyl group, C$_{3-10}$ cycloalkenyl group and C$_{4-10}$ cycloalkadienyl group are each optionally fused with a benzene ring to form a fused ring group, and examples of the fused ring group include indanyl, dihydronaphthyl, tetrahydronaphthyl, fluorenyl and the like.

The above-mentioned C$_{3-10}$ cycloalkyl group, C$_{3-10}$ cycloalkenyl group and C$_{4-10}$ cycloalkadienyl group may be a C$_{7-10}$ bridged hydrocarbon group. Examples of the C$_{7-10}$ bridged hydrocarbon group include bicyclo[2.2.1]heptyl (norbornyl), bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl, adamantyl and the like.

The above-mentioned C$_{3-10}$ cycloalkyl group, C$_{3-10}$ cycloalkenyl group and C$_{4-10}$ cycloalkadienyl group are each optionally form a spiro ring group with a C$_{3-10}$ cycloalkane, a C$_{3-10}$ cycloalkene or a C$_{4-10}$ cycloalkadiene. Examples of the C$_{3-10}$ cycloalkane, C$_{3-10}$ cycloalkene and C$_{4-10}$ cycloalkadiene include rings corresponding to the above-mentioned C$_{3-10}$ cycloalkyl group, C$_{3-10}$ cycloalkenyl group and C$_{4-10}$ cycloalkadienyl group. Examples of the spiro ring group include spiro[4.5]decan-8-yl and the like.

In the present specification, the "C$_{6-14}$ aryl (group)" means, for example, phenyl, 1-naphthyl, 2-naphthyl or the like.

In the present specification, the "C$_{6-14}$ aryloxy (group)" means, for example, phenoxy, 1-naphthyloxy, 2-naphthyloxy or the like.

In the present specification, the "C$_{7-14}$ aralkyl (group)" means, for example, benzyl, phenethyl or the like.

In the present specification, the "C$_{7-14}$ aralkyloxy (group)" means, for example, benzyloxy, phenethyloxy or the like.

In the present specification, the "C$_{8-13}$ arylalkenyl (group)" means, for example, styryl or the like.

In the present specification, the "hydrocarbon group" means, for example, a C$_{1-10}$ alkyl group, a C$_{2-10}$ alkenyl group, a C$_{2-10}$ alkynyl group, a C$_{3-10}$ cycloalkyl group, a C$_{3-10}$ cycloalkenyl group, a C$_{4-10}$ cycloalkadienyl group, a C$_{6-14}$ aryl group, a C$_{7-14}$ aralkyl group, a C$_{8-13}$ arylalkenyl group or the like.

In the present specification, the "heterocyclic group" means an aromatic heterocyclic group or a non-aromatic heterocyclic group.

In the present specification, the "aromatic heterocyclic group" means a monocyclic aromatic heterocyclic group or a fused aromatic heterocyclic group, for example, a 5- to 12-membered aromatic heterocyclic group, specifically a 5- to 7-membered monocyclic aromatic heterocyclic group or a 8- to 12-membered fused aromatic heterocyclic group.

In the present specification, examples of the "monocyclic aromatic heterocyclic group" include a 5- to 7-membered (preferably 5- or 6-membered) monocyclic aromatic heterocyclic group containing, as a ring-constituting atom besides carbon atoms, 1 to 4 hetero atoms selected from an oxygen atom, a sulfur atom (optionally oxidized) and a nitrogen atom (optionally oxidized). Examples thereof include furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl) and the like.

In the present specification, examples of the "fused aromatic heterocyclic group" include an 8- to 12-membered fused aromatic heterocyclic group, specifically, a group derived from a fused ring wherein a ring corresponding to the above-mentioned 5- to 7-membered monocyclic aromatic heterocyclic group is fused with a C$_{6-14}$ aromatic hydrocarbon; and a group derived from a fused ring wherein rings corresponding to the above-mentioned 5- to 7-membered monocyclic aromatic heterocyclic groups are fused. Examples thereof include quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuranyl (e.g., 2-benzofuranyl, 3-benzofuranyl), benzothienyl (e.g., 2-benzothienyl, 3-benzothienyl), benzoxazolyl (e.g., 2-benzoxazolyl), benzisoxazolyl (e.g., 7-benzisoxazolyl), benzothiazolyl (e.g., 2-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridyl (e.g., 1H-imidazo[4,5-b]pyridin-2-yl, 1H-imidazo[4,5-c]pyridin-2-yl, 2H-imidazo[1,2-a]pyridin-3-yl), thienopyridyl (e.g., thieno[2,3-b]pyridin-3-yl), imidazopyrazinyl (e.g., 1H-imidazo[4,5-b]pyrazin-2-yl), pyrazolopyridyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl) and the like.

In the present specification, the "non-aromatic heterocyclic group" means a monocyclic non-aromatic heterocyclic group or a fused non-aromatic heterocyclic group, for example, a 3- to 12-membered non-aromatic heterocyclic group, specifically a 3- to 8-membered monocyclic non-aromatic heterocyclic group or a 8- to 12-membered fused non-aromatic heterocyclic group.

In the present specification, examples of the "monocyclic non-aromatic heterocyclic group" include a 3- to 8-membered (preferably 5- or 6-membered) monocyclic non-aromatic heterocyclic group containing, as a ring-constituting atom besides carbon atoms, 1 to 4 hetero atoms selected from an oxygen atom, a sulfur atom (optionally oxidized) and a nitrogen atom (optionally oxidized). Examples thereof include azetidinyl (e.g., 1-azetidinyl, 2-azetidinyl), pyrrolidinyl (e.g., 1-pyrrolidinyl, 2-pyrrolidinyl), piperidyl (e.g., piperidino, 2-piperidyl, 3-piperidyl, 4-piperidyl), morpholinyl (e.g., morpholino), thiomorpholinyl (e.g., thiomorpholino), piperazinyl (e.g., 1-piperazinyl, 2-piperazinyl, 3-piperazinyl), oxazolidinyl (e.g., oxazolidin-2-yl), thiazolidinyl (e.g., thiazolidin-2-yl), dihydrothiopyranyl (e.g., dihydrothiopyran-3-yl, dihydrothiopyran-4-yl), imidazolidinyl (e.g., imidazolidin-2-yl, imidazolidin-3-yl), oxazolinyl (e.g., oxazolin-2-yl), thiazolinyl (e.g., thiazolin-2-yl), imidazolinyl (e.g., imidazolin-2-yl, imidazolin-3-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), pyranyl (e.g., 2-pyranyl, 4-pyranyl), tetrahydropyranyl (e.g., 2-tetrahydropyranyl, 3-tetrahydropyranyl, 4-tetrahydropyranyl), thiopyranyl (e.g., 4-thiopyranyl), tetrahydrothiopyranyl (e.g., 2-tetrahydrothiopyranyl, 3-tetrahydrothiopyranyl, 4-tetrahydrothiopyranyl), 1-oxidotetrahydrothiopyranyl (e.g., 1-oxidotetrahydrothiopyran-4-yl), 1,1-dioxidotetrahydrothiopyranyl (e.g., 1,1-dioxidotetrahydrothiopyran-4-yl), tetrahydrofuryl (e.g., tetrahydrofuran-3-yl, tetrahydrofuran-2-yl), oxetanyl (e.g., oxetan-2-yl, oxetan-3-yl), pyrazolidinyl (e.g., pyrazolidin-1-yl, pyrazolidin-3-yl), pyrazolinyl (e.g., pyrazolin-1-yl), tetrahydropyrimidinyl (e.g., tetrahydropyrimidin-1-yl), dihydrotriazolyl (e.g., 2,3-dihydro-1H-1,2,3-triazol-1-yl), tetrahydrotriazolyl (e.g., 2,3,4,5-tetrahydro-1H-1,2,3-triazol-1-yl), azepanyl (e.g., 1-azepanyl, 2-azepanyl, 3-azepanyl, 4-azepanyl), dihydropyridyl (e.g., dihydropyridin-1-yl, dihydropyridin-2-yl, dihydropyridin-3-yl, dihydropyridin-4-yl), tetrahydropyridyl (e.g., 1,2,3,4-tetrahydropyridin-1-yl, 1,2,3,4-tetrahydropyridin-2-yl, 1,2,3,4-tetrahydropyridin-3-yl, 1,2,3,4-tetrahydropyridin-4-yl) and the like.

In the present specification, examples of the "fused non-aromatic heterocyclic group" include an 8- to 12-membered fused non-aromatic heterocyclic group, specifically, a group derived from a fused ring wherein a ring corresponding to the above-mentioned 3- to 8-membered monocyclic non-aromatic heterocyclic group is fused with a $C_{6-14}$ aromatic hydrocarbon; a group derived from a fused ring wherein rings corresponding to the above-mentioned 3- to 8-membered monocyclic non-aromatic heterocyclic groups are fused; a group derived from a fused ring wherein a ring corresponding to the above-mentioned 3- to 8-membered monocyclic non-aromatic heterocyclic group is fused with a ring corresponding to the above-mentioned 5- to 7-membered monocyclic aromatic heterocyclic group; and a group wherein the above-mentioned group is partially saturated. Examples thereof include dihydroindolyl (e.g., 2,3-dihydro-1H-indol-1-yl), dihydroisoindolyl (e.g., 1,3-dihydro-2H-isoindol-2-yl), dihydrobenzofuranyl (e.g., 2,3-dihydro-1-benzofuran-5-yl), tetrahydrobenzofuranyl (e.g., 4,5,6,7-tetrahydro-1-benzofuran-3-yl), dihydrobenzodioxinyl (e.g., 2,3-dihydro-1,4-benzodioxin-2-yl), dihydrobenzodioxepinyl (e.g., 3,4-dihydro-2H-1,5-benzodioxepin-2-yl), chromenyl (e.g., 4H-chromen-2-yl, 2H-chromen-3-yl), dihydrochromenyl (e.g., 3,4-dihydro-2H-chromen-2-yl), dihydroquinolyl (e.g., 1,2-dihydroquinolin-4-yl), tetrahydroquinolyl (e.g., 1,2,3,4-tetrahydroquinolin-4-yl), dihydroisoquinolyl (e.g., 1,2-dihydroisoquinolin-4-yl), tetrahydroisoquinolyl (e.g., 1,2,3,4-tetrahydroisoquinolin-4-yl), dihydrophthalazinyl (e.g., 1,4-dihydrophthalazin-4-yl) and the like.

The above-mentioned "monocyclic non-aromatic heterocyclic group" and "fused non-aromatic heterocyclic group" may be bridged, and examples thereof include 3-oxa-6-azabicyclo[3.1.1]heptyl, 8-oxa-3-azabicyclo[3.2.1]octyl, 2-oxa-5-azabicyclo[2.2.1]heptyl, 3-oxa-8-azabicyclo[3.2.1]octyl, 6-oxa-3-azabicyclo[3.1.1]heptyl and the like.

In the present specification, the "carbocyclic group" means a $C_{6-14}$ aryl group, a $C_{3-10}$ cycloalkyl group, a $C_{3-10}$ cycloalkenyl group or a $C_{4-10}$ cycloalkadienyl group. The "carbocyclic group" is optionally fused with a $C_{6-14}$ aromatic hydrocarbon, a $C_{3-10}$ cycloalkane, a $C_{3-10}$ cycloalkene or a $C_{4-10}$ cycloalkadiene, or optionally form a spiro ring with a $C_{3-10}$ cycloalkane, a $C_{3-10}$ cycloalkene or a $C_{4-10}$ cycloalkadiene, or optionally bridged.

In the present specification, the "$C_{6-14}$ aromatic hydrocarbon" means, for example, benzene or naphthalene.

In the present specification, the "$C_{3-10}$ cycloalkane" means, for example, cyclopropane, cyclobutane, cyclopentane, cyclohexane, cycloheptane, cyclooctane, cyclononane, cyclodecane or the like.

In the present specification, the "$C_{3-10}$ cycloalkene" means, for example, cyclopropene, cyclobutene, cyclopentene, cyclohexene, cyclooctene, cyclononene, cyclodecene or the like.

In the present specification, the "$C_{4-10}$ cycloalkadiene" means, for example, 1,3-cyclobutadiene, 1,3-cyclopentadiene, 1,4-cyclopentadiene, 2,4-cyclopentadiene, 1,3-cyclohexadiene, 1,4-cyclohexadiene, 1,5-cyclohexadiene, 2,4-cyclohexadiene, 2,5-cyclohexadiene, 1,3-cyclooctadiene, 1,4-cyclooctadiene, 1,5-cyclooctadiene, 1,6-cyclooctadiene, 1,7-cyclooctadiene, 2,4-cyclooctadiene, 2,5-cyclooctadiene, 2,6-cyclooctadiene, 2,7-cyclooctadiene, 3,5-cyclooctadiene, 3,6-cyclooctadiene or the like.

Each symbol of the formula (I) is explained below.

In the formula (I), $R^1$ is an optionally substituted $C_{1-6}$ alkyl group, an optionally substituted hydroxy group, an optionally substituted amino group, an optionally substituted carbocyclic group, or an optionally substituted heterocyclic group, or $R^1$ is optionally bonded to the atom on Ring A to form, together with Ring A, a spiro ring or a fused ring, each of which is substituted by an oxo group and optionally further substituted.

The "$C_{1-6}$ alkyl group" of the "optionally substituted $C_{1-6}$ alkyl group" for $R^1$ optionally has 1 to 5 (preferably 1 to 3) substituents at substitutable position(s). Examples of the substituent include substituents selected from the following Substituent Group A. When the number of the substituents is plural, the respective substituents may be the same or different.

Substituent Group A:
(1) a halogen atom;
(2) a cyano group;
(3) a nitro group;
(4) a hydroxy group;
(5) a $C_{3-8}$ cycloalkyl group optionally substituted by 1 to 3 substituents selected from
  (a) a halogen atom,
  (b) a cyano group,
  (c) a $C_{1-6}$ alkyl group optionally substituted by 1 to 3 halogen atoms, and
  (d) a $C_{1-6}$ alkoxy group optionally substituted by 1 to 3 halogen atoms;
(6) a $C_{6-14}$ aryl group optionally substituted by 1 to 3 substituents selected from
  (a) a halogen atom,
  (b) a cyano group,
  (c) a $C_{1-6}$ alkyl group optionally substituted by 1 to 3 halogen atoms, and
  (d) a $C_{1-6}$ alkoxy group optionally substituted by 1 to 3 halogen atoms;
(7) a $C_{1-6}$ alkoxy group optionally substituted by 1 to 3 substituents selected from
  (a) a halogen atom,
  (b) a cyano group,
  (c) a $C_{3-8}$ cycloalkyl group optionally having 1 to 3 halogen atoms,
  (d) a $C_{3-8}$ cycloalkenyl group optionally having 1 to 3 halogen atoms,
  (e) a $C_{6-14}$ aryl group optionally having 1 to 3 halogen atoms, and
  (f) a 5- or 6-membered monocyclic aromatic heterocyclic group;
(8) a $C_{2-6}$ alkenyloxy group (e.g., vinyloxy, propenyloxy, butenyloxy, pentenyloxy, hexenyloxy) optionally having 1 to 3 halogen atoms;
(9) a $C_{2-6}$ alkynyloxy group (e.g., ethynyloxy, propynyloxy, butynyloxy, pentynyloxy, hexynyloxy) optionally having 1 to 3 halogen atoms;
(10) a $C_{3-8}$ cycloalkyloxy group (e.g., cyclopropyloxy, cyclobutyloxy, cyclopentyloxy, cyclohexyloxy) optionally having 1 to 3 halogen atoms;
(11) a $C_{3-8}$ cycloalkenyloxy group (e.g., cyclopropenyloxy, cyclobutenyloxy, cyclopentenyloxy, cyclohexenyloxy) optionally having 1 to 3 halogen atoms;
(12) a $C_{6-14}$ aryloxy group optionally having 1 to 3 halogen atoms;
(13) a $C_{7-14}$ aralkyloxy group optionally having 1 to 3 halogen atoms;
(14) a carbamoyl group optionally mono- or di-substituted by substituent(s) selected from
  (a) a $C_{1-6}$ alkyl group,
  (b) a $C_{3-6}$ cycloalkyl group,
  (c) a $C_{6-14}$ aryl group,
  (d) a $C_{1-6}$ alkoxy group,
  (e) a 5- or 6-membered monocyclic aromatic heterocyclic group,
  (f) an 8- to 12-membered fused aromatic heterocyclic group,
  (g) a 3- to 8-membered monocyclic non-aromatic heterocyclic group, and
  (h) an 8- to 12-membered fused non-aromatic heterocyclic group;
(15) a sulfamoyl group optionally mono- or di-substituted by substituent(s) selected from
  (a) a $C_{1-6}$ alkyl group,
  (b) a $C_{3-6}$ cycloalkyl group,
  (c) a $C_{6-14}$ aryl group,
  (d) a $C_{1-6}$ alkoxy group,
  (e) a 5- or 6-membered monocyclic aromatic heterocyclic group,
  (f) an 8- to 12-membered fused aromatic heterocyclic group,
  (g) a 3- to 8-membered monocyclic non-aromatic heterocyclic group, and
  (h) an 8- to 12-membered fused non-aromatic heterocyclic group;
(16) a formyl group;
(17) a $C_{1-6}$ alkyl-carbonyl group;
(18) a $C_{2-6}$ alkenyl-carbonyl group (e.g., acryloyl, butenoyl, pentenoyl, hexenoyl, heptenoyl);
(19) a $C_{2-6}$ alkynyl-carbonyl group (e.g., propioloyl, propynylcarbonyl, butynylcarbonyl, pentynylcarbonyl, hexynylcarbonyl);
(20) a $C_{3-8}$ cycloalkyl-carbonyl group (e.g., cyclopropylcarbonyl, cyclobutylcarbonyl, cyclopentylcarbonyl, cyclohexylcarbonyl);
(21) a $C_{3-8}$ cycloalkenyl-carbonyl group (e.g., cyclopropenylcarbonyl, cyclobutenylcarbonyl, cyclopentenylcarbonyl, cyclohexenylcarbonyl);
(22) a $C_{6-14}$ aryl-carbonyl group (e.g., benzoyl, 1-naphthylcarbonyl, 2-naphthylcarbonyl);
(23) a $C_{3-8}$ cycloalkyl-$C_{1-6}$ alkyl-carbonyl group (e.g., cyclopropylacetyl, 3-cyclopropylpropionyl, cyclobutylacetyl, cyclopentylacetyl, cyclohexylacetyl, cyclohexylpropionyl);
(24) a $C_{3-8}$ cycloalkenyl-$C_{1-6}$ alkyl-carbonyl group (e.g., cyclopentenylacetyl, cyclohexenylacetyl, 3-cyclohexenylpropionyl, 3-cyclohexenylpropionyl);
(25) a $C_{7-14}$ aralkyl-carbonyl group (e.g., phenylacetyl, 3-phenylpropionyl);
(26) a 5- or 6-membered monocyclic aromatic heterocyclylcarbonyl group (e.g., furylcarbonyl, thienylcarbonyl, pyrrolylcarbonyl, oxazolylcarbonyl, isoxazolylcarbonyl, thiazolylcarbonyl, isothiazolylcarbonyl, imidazolylcarbonyl, pyridylcarbonyl, pyrazolylcarbonyl);
(27) an 8- to 12-membered fused aromatic heterocyclylcarbonyl group (e.g., benzofuranylcarbonyl, isobenzofuranylcarbonyl, benzothienylcarbonyl, isobenzothienylcarbonyl, indolylcarbonyl, isoindolylcarbonyl, indazolylcarbonyl, benzimidazolylcarbonyl, benzoxazolylcarbonyl);
(28) a 3- to 8-membered monocyclic non-aromatic heterocyclylcarbonyl group (e.g., oxetanylcarbonyl, azetidinylcarbonyl, oxetanylcarbonyl, thietanylcarbonyl, pyrrolidinylcarbonyl, tetrahydrofurylcarbonyl, thiolanylcarbonyl, piperidylcarbonyl);
(29) an 8- to 12-membered fused non-aromatic heterocyclylcarbonyl group (e.g., dihydrobenzofuranyl);

(30) an amino group optionally mono- or di-substituted by substituent(s) selected from
  (a) a $C_{1-6}$ alkyl group optionally having 1 to 3 halogen atoms,
  (b) a $C_{1-6}$ alkyl-carbonyl group optionally having 1 to 3 halogen atoms,
  (c) a $C_{3-13}$ cycloalkyl-carbonyl group,
  (d) a $C_{6-14}$ aryl-carbonyl group optionally having 1 to 3 halogen atoms,
  (e) a 5- or 6-membered monocyclic aromatic heterocyclylcarbonyl group,
  (f) an 8- to 12-membered fused aromatic heterocyclylcarbonyl group,
  (g) a 3- to 8-membered monocyclic non-aromatic heterocyclylcarbonyl group, and
  (h) an 8- to 12-membered fused non-aromatic heterocyclylcarbonyl group;
(31) a sulfanyl group;
(32) a $C_{1-6}$ alkylsulfanyl group (e.g., methylsulfanyl, ethylsulfanyl);
(33) a $C_{2-6}$ alkenylsulfanyl group (e.g., vinylsulfanyl, propenylsulfanyl);
(34) a $C_{2-6}$ alkynylsulfanyl group (e.g., ethynylsulfanyl, propynylsulfanyl);
(35) a $C_{3-8}$ cycloalkylsulfanyl group (e.g., cyclopropylsulfanyl, cyclobutylsulfanyl);
(36) a $C_{3-8}$ cycloalkenylsulfanyl group (e.g., cyclopropenylsulfanyl, cyclobutenylsulfanyl);
(37) a $C_{6-14}$ arylsulfanyl group (e.g., phenylsulfanyl);
(38) a $C_{3-8}$ cycloalkyl-$C_{1-6}$ alkylsulfanyl group (e.g., cyclopropylmethylsulfanyl);
(39) a $C_{3-8}$ cycloalkenyl-$C_{1-6}$ alkylsulfanyl group (e.g., cyclopentenylmethylsulfanyl);
(40) a $C_{1-6}$ alkylsulfinyl group (e.g., methylsulfinyl, ethylsulfinyl);
(41) a $C_{2-6}$ alkenylsulfinyl group (e.g., vinylsulfinyl, propenylsulfinyl);
(42) a $C_{2-6}$ alkynylsulfinyl group (e.g., ethynylsulfinyl, propynylsulfinyl);
(43) a $C_{3-8}$ cycloalkylsulfinyl group (e.g., cyclopropylsulfinyl, cyclobutylsulfinyl);
(44) a $C_{3-8}$ cycloalkenylsulfinyl group (e.g., cyclopropenylsulfinyl, cyclobutenylsulfinyl);
(45) a $C_{6-14}$ arylsulfinyl group (e.g., phenylsulfinyl);
(46) a $C_{3-8}$ cycloalkyl-$C_{1-6}$ alkylsulfinyl group (e.g., cyclopropylmethylsulfinyl);
(47) a $C_{3-8}$ cycloalkenyl-$C_{1-6}$ alkylsulfinyl group (e.g., cyclopentenylmethylsulfinyl);
(48) a $C_{1-6}$ alkylsulfonyl group (e.g., methylsulfonyl, ethylsulfonyl);
(49) a $C_{2-6}$ alkenylsulfonyl group (e.g., vinylsulfonyl, propenylsulfonyl);
(50) a $C_{2-6}$ alkynylsulfonyl group (e.g., ethynylsulfonyl, propynylsulfonyl);
(51) a $C_{3-8}$ cycloalkylsulfonyl group (e.g., cyclopropylsulfonyl, cyclobutylsulfonyl);
(52) a $C_{3-8}$ cycloalkenylsulfonyl group (e.g., cyclopropenylsulfonyl, cyclobutenylsulfonyl);
(53) a $C_{6-14}$ arylsulfonyl group (e.g., phenylsulfonyl);
(54) a $C_{3-8}$ cycloalkyl-$C_{1-5}$ alkylsulfonyl group (e.g., cyclopropylmethylsulfonyl);
(55) a $C_{3-8}$ cycloalkenyl-$C_{1-6}$ alkylsulfonyl group (e.g., cyclopentenylmethylsulfonyl);
(56) a $C_{6-14}$ aryl-$C_{1-6}$ alkylsulfonyl group (e.g., benzylsulfonyl);
(57) a 5- or 6-membered monocyclic aromatic heterocyclylsulfonyl group (e.g., furylsulfonyl, thienylsulfonyl, pyridylsulfonyl);
(58) an 8- to 12-membered fused aromatic heterocyclylsulfonyl group (e.g., benzofuranylsulfonyl, isobenzofuranylsulfonyl);
(59) a 3- to 8-membered monocyclic non-aromatic heterocyclylsulfonyl group (e.g., oxiranylsulfonyl, azetidinylsulfonyl);
(60) an 8- to 12-membered fused non-aromatic heterocyclylsulfonyl group (e.g., dihydrobenzofuranylsulfonyl);
(61) a 5- or 6-membered monocyclic aromatic heterocyclic group (e.g., furyl, thienyl, pyrrolyl, oxazolyl, isoxazolyl, thiazolyl, isothiazolyl, imidazolyl, pyridyl, pyrazolyl, morpholinyl) optionally substituted by 1 to 3 substituents selected from
  (a) a halogen atom,
  (b) a $C_{1-6}$ alkyl group optionally substituted by 1 to 3 halogen atoms, and
  (c) a $C_{1-6}$ alkoxy group optionally substituted by 1 to 3 halogen atoms;
(62) an 8- to 12-membered fused aromatic heterocyclic group (e.g., benzofuranyl, isobenzofuranyl, benzothienyl, isobenzothienyl, indolyl, isoindolyl, indazolyl, benzimidazolyl, benzoxazolyl) optionally substituted by 1 to 3 substituents selected from
  (a) a halogen atom,
  (b) a $C_{1-6}$ alkyl group optionally substituted by 1 to 3 halogen atoms, and
  (c) a $C_{1-6}$ alkoxy group optionally substituted by 1 to 3 halogen atoms;
(63) a 3- to 8-membered monocyclic non-aromatic heterocyclic group (e.g., oxiranyl, azetidinyl, oxetanyl, thietanyl, pyrrolidinyl, tetrahydrofuryl, thiolanyl, piperidyl, piperazinyl, dihydrooxadiazolyl, thiazolinyl) optionally substituted by 1 to 3 substituents selected from
  (a) a halogen atom,
  (b) a $C_{1-6}$ alkyl group optionally substituted by 1 to 3 halogen atoms,
  (c) a $C_{1-6}$ alkoxy group optionally substituted by 1 to 3 halogen atoms, and
  (d) an oxo group;
(64) an 8- to 12-membered fused non-aromatic heterocyclic group (e.g., dihydrobenzofuranyl) optionally substituted by 1 to 3 substituents selected from
  (a) a halogen atom,
  (b) a $C_{1-6}$ alkyl group optionally substituted by 1 to 3 halogen atoms,
  (c) a $C_{1-6}$ alkoxy group optionally substituted by 1 to 3 halogen atoms, and
  (d) an oxo group;
(65) a 5- or 6-membered monocyclic aromatic heterocyclyloxy group (e.g., furyloxy, thienyloxy, pyrrolyloxy, oxazolyloxy, isoxazolyloxy, thiazolyloxy, isothiazolyloxy, imidazolyloxy, pyridyloxy, pyrazolyloxy);
(66) an 8- to 12-membered fused aromatic heterocyclyloxy group (e.g., benzofuranyloxy, isobenzofuranyloxy, benzothienyloxy, isobenzothienyloxy, indolyloxy, isoindolyloxy, indazolyloxy, benzimidazolyloxy, benzoxazolyloxy);
(67) a 3- to 8-membered monocyclic non-aromatic heterocyclyloxy group (e.g., oxiranyloxy, azetidinyloxy, oxetanyloxy, thietanyloxy, pyrrolidinyloxy, tetrahydrofuryloxy, thiolanyloxy, piperidyloxy);
(68) an 8- to 12-membered fused non-aromatic heterocyclyloxy group (e.g., dihydrobenzofuranyloxy);
(69) a carboxy group;
(70) a $C_{1-6}$ alkoxy-carbonyl group;

(71) a $C_{2-6}$ alkenyloxy-carbonyl group (e.g., vinyloxycarbonyl, propenyloxycarbonyl, butenyloxycarbonyl, pentenyloxycarbonyl, hexenyloxycarbonyl);
(72) a $C_{2-6}$ alkynyloxy-carbonyl group (e.g., ethynyloxycarbonyl, propynyloxycarbonyl, butynyloxycarbonyl, pentynyloxycarbonyl, hexynyloxycarbonyl);
(73) a $C_{3-8}$ cycloalkyloxy-carbonyl group (e.g., cyclopropyloxycarbonyl, cyclobutyloxycarbonyl, cyclopentyloxycarbonyl, cyclohexyloxycarbonyl);
(74) a $C_{3-8}$ cycloalkenyloxy-carbonyl group (e.g., cyclopropenyloxycarbonyl, cyclobutenyloxycarbonyl, cyclopentenyloxycarbonyl, cyclohexenyloxycarbonyl);
(75) a $C_{6-14}$ aryloxy-carbonyl group (e.g., phenoxycarbonyl, 1-naphthyloxycarbonyl, 2-naphthyloxycarbonyl);
(76) a $C_{3-8}$ cycloalkyl-$C_{1-6}$ alkoxy-carbonyl group (e.g., cyclopropylmethyloxycarbonyl, cyclopropylethyloxycarbonyl, cyclobutylmethyloxycarbonyl, cyclopentylmethyloxycarbonyl, cyclohexylmethyloxycarbonyl, cyclohexylethyloxycarbonyl);
(77) a $C_{3-8}$ cycloalkenyl-$C_{1-6}$ alkoxy-carbonyl group (e.g., cyclopentenylmethyloxycarbonyl, cyclohexenylmethyloxycarbonyl, cyclohexenylethyloxycarbonyl, cyclohexenylpropyloxycarbonyl);
(78) a $C_{7-14}$ aralkyloxy-carbonyl group (e.g., benzyloxycarbonyl, phenethyloxycarbonyl);
(79) a mono-$C_{1-6}$ alkylthio-carbamoyl group (e.g., methylthiocarbamoyl, ethylthiocarbamoyl, propylthiocarbamoyl);
(80) a di-$C_{1-6}$ alkylthio-carbamoyl group (e.g., dimethylthiocarbamoyl, diethylthiocarbamoyl, dipropylthiocarbamoyl);
(81) a $C_{1-6}$ alkyl-carbonyloxy group (e.g., acetyloxy, propanoyloxy, butanoyloxy, 2-methylpropanoyloxy);
(82) an imino group optionally substituted by a hydroxy group; and
(83) a $C_{1-6}$ alkylenedioxy group (e.g., methylenedioxy, ethylenedioxy).

Examples of the "optionally substituted hydroxy group" for $R^1$ include a hydroxy group optionally substituted by a substituent selected from a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-14}$ aralkyl group, a $C_{8-13}$ arylalkenyl group, a $C_{1-6}$ alkyl-carbonyl group, a heterocyclic group (e.g., an aromatic heterocyclic group, a non-aromatic heterocyclic group) and the like, each of which is optionally substituted.

The $C_{1-10}$ alkyl group, $C_{2-10}$ alkenyl group and $C_{1-6}$ alkyl-carbonyl group optionally have 1 to 5 (preferably 1 to 3) substituents at substitutable position(s). Examples of the substituent include substituents selected from the above-mentioned Substituent Group A. When the number of the substituents is plural, the respective substituents may be the same or different.

The $C_{3-10}$ cycloalkyl group, $C_{3-10}$ cycloalkenyl group and non-aromatic heterocyclic group optionally have 1 to 5 (preferably 1 to 3) substituents at substitutable position(s). Examples of the substituent include substituents selected from the following Substituent Group B. When the number of the substituents is plural, the respective substituents may be the same or different.

Substituent Group B:
(1) the above-mentioned Substituent Group A;
(2) a $C_{1-6}$ alkyl group optionally substituted by 1 to 3 substituents selected from
  (a) a halogen atom,
  (b) a cyano group,
  (c) a hydroxy group,
  (d) a $C_{3-8}$ cycloalkyl group optionally substituted by 1 to 3 substituents selected from
    (i) a halogen atom,
    (ii) a cyano group, and
    (iii) a $C_{1-6}$ alkyl group optionally substituted by 1 to 3 halogen atoms;
  (e) a $C_{6-14}$ aryl group optionally substituted by 1 to 3 substituents selected from
    (i) a halogen atom,
    (ii) a cyano group, and
    (iii) a $C_{1-6}$ alkyl group optionally substituted by 1 to 3 halogen atoms,
  (f) a $C_{1-6}$ alkoxy group optionally substituted by 1 to 3 halogen atoms,
  (g) an amino group optionally mono- or di-substituted by $C_{1-6}$ alkyl group(s),
  (h) a 5- or 6-membered monocyclic aromatic heterocyclic group,
  (i) a 8- to 12-membered fused aromatic heterocyclic group,
  (j) a 3- to 8-membered monocyclic non-aromatic heterocyclic group,
  (k) a 8- to 12-membered fused non-aromatic heterocyclic group,
  (l) a carboxy group, and
  (m) a $C_{1-6}$ alkoxy-carbonyl group optionally substituted by 1 to 3 halogen atoms;
(3) a $C_{2-6}$ alkenyl group optionally substituted by 1 to 3 substituents selected from
  (a) a halogen atom,
  (b) a hydroxy group,
  (c) a $C_{1-6}$ alkoxy group,
  (d) an amino group optionally mono- or di-substituted by $C_{1-6}$ alkyl group(s),
  (e) a carboxy group, and
  (f) a $C_{1-6}$ alkoxy-carbonyl group;
(4) a $C_{7-14}$ aralkyl group optionally substituted by 1 to 3 substituents selected from
  (a) a halogen atom,
  (b) a hydroxy group,
  (c) a $C_{1-6}$ alkoxy group, and
  (d) a $C_{1-6}$ alkyl group optionally substituted by 1 to 3 halogen atoms; and
(5) an oxo group.

The $C_{6-14}$ aryl group, $C_{7-14}$ aralkyl group, $C_{8-13}$ arylalkenyl group and aromatic heterocyclic group have 1 to 5 (preferably 1 to 3) substituents at substitutable position(s). Examples of the substituent include substituents selected from the above-mentioned Substituent Group B excluding oxo. When the number of the substituents is plural, the respective substituents may be the same or different.

Examples of the "optionally substituted amino group" for $R^1$ include an amino group optionally mono- or di-substituted by substituent(s) selected from a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-14}$ aralkyl group, a $C_{8-13}$ arylalkenyl group, a heterocyclic group (e.g., an aromatic heterocyclic group, a non-aromatic heterocyclic group) and the like, each of which is optionally substituted; and an acyl group. When the amino group is di-substituted, the two substituent in combination optionally form an optionally substituted heterocyclic group.

The $C_{1-10}$ alkyl group and $C_{2-10}$ alkenyl group optionally have 1 to 5 (preferably 1 to 3) substituents at substitutable position(s). Examples of the substituent include substituents selected from the above-mentioned Substituent Group A.

When the number of the substituents is plural, the respective substituents may be the same or different.

The $C_{3-10}$ cycloalkyl group, $C_{3-10}$ cycloalkenyl group and non-aromatic heterocyclic group optionally have 1 to 5 (preferably 1 to 3) substituents at substitutable position(s). Examples of the substituent include substituents selected from the above-mentioned Substituent Group B. When the number of the substituents is plural, the respective substituents may be the same or different.

The $C_{6-14}$ aryl group, $C_{7-14}$ aralkyl group, $C_{8-13}$ arylalkenyl group and aromatic heterocyclic group optionally have 1 to 5 (preferably 1 to 3) substituents at substitutable position(s). Examples of the substituent include substituents selected from the above-mentioned Substituent Group B excluding oxo. When the number of the substituents is plural, the respective substituents may be the same or different.

Examples of the "acyl group" exemplified as the substituent for the "amino group" include a group represented by the formula: —$COR^A$, —CO—$OR^A$, —$SO_3R^A$, —$S(O)_2R^A$, —$SOR^A$, —CO—$NR^{A'}R^{B'}$, —CS—$NR^{A'}R^{B'}$ or —$S(O)_2NR^{A'}R^{B'}$ wherein $R^A$ is a hydrogen atom, an optionally substituted hydrocarbon group, or an optionally substituted heterocyclic group, and $R^{A'}$ and $R^{B'}$ are the same or different and each is a hydrogen atom, an optionally substituted hydrocarbon group, or an optionally substituted heterocyclic group, or $R^{A'}$ and $R^{B'}$ in combination optionally form, together with the adjacent nitrogen atom, an optionally substituted nitrogen-containing heterocycle, and the like.

Examples of the "hydrocarbon group" of the "optionally substituted hydrocarbon group" for $R^A$, $R^{A'}$ or $R^{B'}$ include a $C_{1-10}$ alkyl group, a $C_{2-10}$ alkenyl group, a $C_{2-10}$ alkynyl group, a $C_{3-10}$ cycloalkyl group, a $C_{3-10}$ cycloalkenyl group, a $C_{4-10}$ cycloalkadienyl group, a $C_{6-14}$ aryl group, a $C_{7-14}$ aralkyl group, a $C_{8-13}$ arylalkenyl group and the like.

The $C_{1-10}$ alkyl group, $C_{2-10}$ alkenyl group and $C_{2-10}$ alkynyl group, which are exemplified as the above-mentioned "hydrocarbon group", optionally have 1 to 5 (preferably 1 to 3) substituents at substitutable position(s). Examples of the substituent include substituents selected from the above-mentioned Substituent Group A. When the number of the substituents is plural, the respective substituents may be the same or different.

The $C_{3-10}$ cycloalkyl group, $C_{3-10}$ cycloalkenyl group and $C_{4-10}$ cycloalkadienyl group, which are exemplified as the above-mentioned "hydrocarbon group", optionally have 1 to 5 (preferably 1 to 3) substituents at substitutable position(s). Examples of the substituent include substituents selected from the above-mentioned Substituent Group B. When the number of the substituents is plural, the respective substituents may be the same or different.

The $C_{6-14}$ aryl group, $C_{7-14}$ aralkyl group and $C_{8-13}$ arylalkenyl group, which are exemplified as the above-mentioned "hydrocarbon group", optionally have 1 to 5 (preferably 1 to 3) substituents at substitutable position(s). Examples of the substituent include substituents selected from the above-mentioned Substituent Group B excluding an oxo group. When the number of the substituents is plural, the respective substituents may be the same or different.

The "heterocyclic group" of the "optionally substituted heterocyclic group" for $R^A$, $R^{A'}$ or $R^{B'}$ optionally has 1 to 5 (preferably 1 to 3) substituents at substitutable position(s). Examples of the substituent for the aromatic heterocyclic group include the above-mentioned Substituent Group B excluding an oxo group, and examples of the substituent for the non-aromatic heterocyclic group include the above-mentioned Substituent Group B. When the number of the substituents is plural, the respective substituents may be the same or different.

Examples of the "nitrogen-containing heterocycle" of the "optionally substituted nitrogen-containing heterocycle" formed by $R^{A'}$ and $R^{B'}$ together with the adjacent nitrogen atom include a 5- to 7-membered nitrogen-containing heterocycle containing, as a ring-constituting atom besides carbon atoms, at least one nitrogen atom and optionally further containing one or two hetero atoms selected from an oxygen atom, a sulfur atom and a nitrogen atom. Preferable examples of the nitrogen-containing heterocycle include pyrrolidine, imidazolidine, pyrazolidine, piperidine, piperazine, morpholine, thiomorpholine and the like.

The nitrogen-containing heterocycle optionally has 1 to 5 (preferably 1 to 3) substituents at substitutable position(s). Examples of the substituent include substituents selected from the above-mentioned Substituent Group B. When the number of the substituents is plural, the respective substituents may be the same or different.

Preferable examples of the "acyl group" include
(1) a formyl group;
(2) a carboxy group;
(3) a $C_{1-6}$ alkyl-carbonyl group (e.g., acetyl) optionally substituted by 1 to 3 halogen atoms;
(4) a $C_{1-6}$ alkoxy-carbonyl group (e.g., methoxycarbonyl, ethoxycarbonyl, propoxycarbonyl, tert-butoxycarbonyl) optionally substituted by 1 to 3 halogen atoms;
(5) a $C_{3-10}$ cycloalkyl-carbonyl group (e.g., cyclopropylcarbonyl, cyclopentylcarbonyl, cyclohexylcarbonyl);
(6) a $C_{6-14}$ aryl-carbonyl group (e.g., benzoyl, 1-naphthoyl, 2-naphthoyl) optionally substituted by 1 to 3 halogen atoms;
(7) a carbamoyl group optionally mono- or di-substituted by substituent(s) selected from
 (a) a $C_{1-6}$ alkyl group optionally substituted by 1 to 3 substituents selected from a halogen atom, a $C_{1-6}$ alkoxy group, a $C_{1-6}$ alkoxy-carbonyl group and a carboxy group, and
 (b) an amino group optionally mono- or di-substituted by $C_{1-6}$ alkoxy-carbonyl group(s);
(8) a $C_{1-6}$ alkylsulfonyl group (e.g., methylsulfonyl, ethylsulfonyl, isopropylsulfonyl) optionally substituted by 1 to 3 halogen atoms;
(9) a $C_{6-14}$ arylsulfonyl group (e.g., benzenesulfonyl);
(10) a sulfamoyl group;
(11) a thiocarbamoyl group;
(12) an aromatic heterocyclylcarbonyl group (e.g., furylcarbonyl, thienylcarbonyl) optionally substituted by 1 to 3 substituents selected from a $C_{1-6}$ alkyl group optionally substituted by 1 to 3 halogen atoms;
(13) a non-aromatic heterocyclylcarbonyl group (e.g., tetrahydrofurylcarbonyl, pyrrolidinylcarbonyl) optionally substituted by 1 to 3 substituents selected from a $C_{1-6}$ alkyl group optionally substituted by 1 to 3 halogen atoms; and the like.

The "carbocyclic group" of the "optionally substituted carbocyclic group" for $R^1$ optionally has 1 to 5 (preferably 1 to 3) substituents at substitutable position(s). Examples of the substituent for the $C_{6-14}$ aryl group include the above-mentioned Substituent Group B excluding an oxo group, and examples of the substituent for the $C_{3-10}$ cycloalkyl group, $C_{3-10}$ cycloalkenyl group and $C_{4-10}$ cycloalkadienyl group include the above-mentioned Substituent Group B. When the number of the substituents is plural, the respective substituents may be the same or different.

The "heterocyclic group" of the "optionally substituted heterocyclic group" for $R^1$ optionally has 1 to 5 (preferably 1 to 3) substituents at substitutable position(s). Examples of the substituent for the aromatic heterocyclic group include the above-mentioned Substituent Group B excluding an oxo group, and examples of the substituent for the non-aromatic heterocyclic group include the above-mentioned Substituent Group B. When the number of the substituents is plural, the respective substituents may be the same or different.

Examples of the "spiro ring or fused ring, each of which is substituted by an oxo group and optionally further substituted" formed by $R^1$ and the atom on Ring A in combination, together with Ring A, include Spiro rings such as 2,8-diazaspiro[4.5]decane, 2,7-diazaspiro[3.5]nonane and the like, and fused rings such as hexahydroimidazo[1,5-a]pyrazine, hexahydropyrrolo[1,2-a]pyrazine and the like.

The "spiro ring or fused ring" of the "spiro ring or fused ring, each of which is substituted by an oxo group and optionally further substituted" formed by $R^1$ and the atom on Ring A in combination, together with Ring A, optionally has 1 to 5 (preferably 1 to 3) substituents at substitutable position(s). Examples of the substituent include substituents selected from the above-mentioned Substituent Group B. When the number of the substituents is plural, the respective substituents may be the same or different.

$R^1$ is preferably an optionally substituted $C_{1-6}$ alkyl group, an optionally substituted $C_{1-6}$ alkoxy group, an optionally substituted amino group, an optionally substituted $C_{3-8}$ cycloalkyl group, an optionally substituted $C_{6-14}$ aryl group, or an optionally substituted non-aromatic heterocyclic group, or $R^1$ is bonded to the atom on Ring A to form, together with Ring A, a spiro ring substituted by oxo and optionally further substituted.

$R^1$ is more preferably
(1) a $C_{1-6}$ alkyl group (e.g., methyl, ethyl) optionally substituted by 1 to 3 substituents selected from
  (a) a cyano group,
  (b) a $C_{6-14}$ aryl group (e.g., phenyl) optionally substituted by 1 to 3 $C_{1-6}$ alkoxy groups (e.g., methoxy),
  (c) a $C_{6-14}$ aryloxy group (e.g., phenoxy),
  (d) a $C_{3-8}$ cycloalkyl group (e.g., cyclopropyl),
  (e) a 5- or 6-membered monocyclic aromatic heterocyclic group (e.g., pyrazolyl),
  (f) a 8- to 12-membered fused aromatic heterocyclic group (e.g., indazolyl), and
  (g) a 3- to 8-membered monocyclic non-aromatic heterocyclic group (e.g., dihydropyridyl) optionally substituted by 1 to 3 oxo groups,
(2) a $C_{1-6}$ alkoxy group (e.g., methoxy, tert-butoxy, preferably a $C_{1-3}$ alkoxy group (e.g., methoxy)) optionally substituted by 1 to 3 $C_{6-14}$ aryl groups (e.g., phenyl),
(3) an amino group optionally mono- or di-substituted by substituent(s) selected from
  (a) a $C_{1-6}$ alkyl group (e.g., methyl, ethyl) optionally substituted by 1 to 3 substituents selected from
    (i) a halogen atom (e.g., a fluorine atom),
    (ii) a cyano group,
    (iii) a $C_{3-8}$ cycloalkyl group (e.g., cyclopropyl, cyclobutyl),
    (iv) a $C_{6-14}$ aryl group (e.g., phenyl) optionally substituted by 1 to 3 halogen atoms (e.g., a fluorine atom),
    (v) a 5- or 6-membered monocyclic aromatic heterocyclic group (e.g., pyridyl), and
    (vi) a 3- to 8-membered monocyclic non-aromatic heterocyclic group (e.g., oxetanyl) optionally substituted by 1 to 3 $C_{1-6}$ alkyl groups (e.g., methyl),
  (b) a $C_{3-8}$ cycloalkyl group (e.g., cyclopropyl, cyclobutyl, cyclopentyl) optionally substituted by 1 to 3 halogen atoms (e.g., a fluorine atom),
  (c) a $C_{6-14}$ aryl group (e.g., phenyl), and
  (d) a 3- to 8-membered monocyclic non-aromatic heterocyclic group (e.g., tetrahydropyranyl, oxetanyl, tetrahydrofuryl, pyrrolidinyl) optionally substituted by 1 to 3 $C_{1-6}$ alkyl groups (e.g., methyl),
(4) a $C_{3-8}$ cycloalkyl group (e.g., cyclopropyl) optionally substituted by 1 to 3 $C_{6-14}$ aryl groups (e.g., phenyl),
(5) a $C_{6-14}$ aryl group (e.g., phenyl), or
(6) a 3- to 12-membered non-aromatic heterocyclic group (preferably a 3- to 8-membered monocyclic non-aromatic heterocyclic group (e.g., azetidinyl, pyrrolidinyl, piperidyl, piperazinyl, morpholinyl, 1,1-dioxidothiomorpholinyl, tetrahydropyranyl, 3-oxa-6-azabicyclo[3.1.1]heptyl, 8-oxa-3-azabicyclo[3.2.1]octyl, 2-oxa-5-azabicyclo[2.2.1]heptyl, 3-oxa-8-azabicyclo[3.2.1]octyl, 6-oxa-3-azabicyclo[3.1.1]heptyl)) optionally substituted by 1 to 5 substituents selected from
  (a) a halogen atom (e.g., a fluorine atom),
  (b) a cyano group,
  (c) a hydroxy group,
  (d) an oxo group,
  (e) a carbamoyl group,
  (f) a $C_{1-6}$ alkyl group (e.g., methyl, ethyl, isopropyl) optionally substituted by 1 to 3 substituents selected from
    (i) a hydroxy group, and
    (ii) a $C_{1-6}$ alkoxy group (e.g., methoxy),
  (g) a $C_{1-6}$ alkoxy group (e.g., methoxy, ethoxy, isopropoxy),
  (h) a $C_{1-6}$ alkoxy-carbonyl group (e.g., methoxycarbonyl), and
  (i) a $C_{6-14}$ aryl group (e.g., phenyl) optionally substituted by 1 to 3 halogen atoms (e.g., a fluorine atom), or
$R^1$ is bonded to the atom on Ring A to form, together with Ring A, a spiro ring (e.g., 2,8-diazaspiro[4.5]decane) substituted by oxo and optionally further substituted by 1 to 3 $C_{1-6}$ alkyl groups (e.g., methyl).

In another embodiment, $R^1$ is more preferably
(1) a $C_{1-6}$ alkyl group (e.g., methyl, ethyl) optionally substituted by 1 to 3 substituents selected from
  (a) a cyano group,
  (b) a $C_{6-14}$ aryl group (e.g., phenyl) optionally substituted by 1 to 3 $C_{1-6}$ alkoxy groups (e.g., methoxy),
  (c) a $C_{6-14}$ aryloxy group (e.g., phenoxy),
  (d) a $C_{3-8}$ cycloalkyl group (e.g., cyclopropyl),
  (e) a 5- or 6-membered monocyclic aromatic heterocyclic group (e.g., pyrazolyl),
  (f) a 8- to 12-membered fused aromatic heterocyclic group (e.g., indazolyl), and
  (g) a 3- to 8-membered monocyclic non-aromatic heterocyclic group (e.g., dihydropyridyl) optionally substituted by 1 to 3 oxo groups,
(2) a $C_{1-6}$ alkoxy group (e.g., methoxy, tert-butoxy, preferably a $C_{1-3}$ alkoxy group (e.g., methoxy)) optionally substituted by 1 to 3 $C_{6-14}$ aryl groups (e.g., phenyl),
(3) an amino group optionally mono- or di-substituted by substituent(s) selected from
  (a) a $C_{1-6}$ alkyl group (e.g., methyl, ethyl) optionally substituted by 1 to 3 substituents selected from
    (i) a halogen atom (e.g., a fluorine atom),
    (ii) a cyano group,
    (iii) a $C_{3-8}$ cycloalkyl group (e.g., cyclopropyl, cyclobutyl),
    (iv) a $C_{6-14}$ aryl group (e.g., phenyl) optionally substituted by 1 to 3 substituents selected from a halogen atom (e.g., a fluorine atom) and a $C_{1-6}$ alkoxy group (e.g., methoxy), (v) a 5- or 6-membered monocyclic aromatic heterocyclic group (e.g., pyridyl), and
(vi) a 3- to 8-membered monocyclic non-aromatic heterocyclic group (e.g., oxetanyl) optionally substituted by 1 to 3 $C_{1-6}$ alkyl groups (e.g., methyl),
(b) a $C_{3-8}$ cycloalkyl group (e.g., cyclopropyl, cyclobutyl, cyclopentyl) optionally substituted by 1 to 3 halogen atoms (e.g., a fluorine atom),
(c) a $C_{6-14}$ aryl group (e.g., phenyl), and
(d) a 3- to 8-membered monocyclic non-aromatic heterocyclic group (e.g., tetrahydropyranyl, oxetanyl, tetrahydrofuryl, pyrrolidinyl) optionally substituted by 1 to 3 $C_{1-6}$ alkyl groups (e.g., methyl),
(4) a $C_{3-8}$ cycloalkyl group (e.g., cyclopropyl) optionally substituted by 1 to 3 $C_{6-14}$ aryl groups (e.g., phenyl),
(5) a $C_{6-14}$ aryl group (e.g., phenyl), or
(6) a 3- to 12-membered non-aromatic heterocyclic group (preferably a 3- to 8-membered monocyclic non-aromatic heterocyclic group (e.g., azetidinyl, pyrrolidinyl, piperidyl, piperazinyl, morpholinyl, 1,1-dioxidothiomorpholinyl, tetrahydropyranyl, 3-oxa-6-azabicyclo[3.1.1]heptyl, 8-oxa-3-azabicyclo[3.2.1]octyl, 2-oxa-5-azabicyclo[2.2.1]heptyl, 3-oxa-8-azabicyclo[3.2.1]octyl, 6-oxa-3-azabicyclo[3.1.1]heptyl), 3,7-dioxa-9-azabicyclo[3.3.1]nonyl)) optionally substituted by 1 to 5 substituents selected from
(a) a halogen atom (e.g., a fluorine atom),
(b) a cyano group,
(c) a hydroxy group,
(d) an oxo group,
(e) a carbamoyl group optionally mono- or di-substituted by $C_{1-6}$ alkyl group(s) (e.g., methyl),
(f) a $C_{1-6}$ alkyl group (e.g., methyl, ethyl, isopropyl) optionally substituted by 1 to 3 substituents selected from
(i) a hydroxy group, and
(ii) a $C_{1-6}$ alkoxy group (e.g., methoxy),
(g) a $C_{1-6}$ alkoxy group (e.g., methoxy, ethoxy, isopropoxy) optionally substituted by 1 to 3 halogen atoms (e.g., a fluorine atom),
(h) a $C_{1-6}$ alkoxy-carbonyl group (e.g., methoxycarbonyl), and
(i) a $C_{6-14}$ aryl group (e.g., phenyl) optionally substituted by 1 to 3 halogen atoms (e.g., a fluorine atom), or
$R^1$ is bonded to the atom on Ring A to form, together with Ring A, a spiro ring (e.g., 2,8-diazaspiro[4.5]decane) substituted by oxo and optionally further substituted by 1 to 3 $C_{1-6}$ alkyl groups (e.g., methyl).

$R^1$ is still more preferably
(1) a $C_{1-6}$ alkyl group (e.g., methyl, ethyl) optionally substituted by 1 to 3 substituents selected from
(a) a $C_{3-8}$ cycloalkyl group (e.g., cyclopropyl), and
(b) a 8- to 12-membered fused aromatic heterocyclic group (e.g., indazolyl),
(2) a $C_{1-6}$ alkoxy group (preferably a $C_{1-3}$ alkoxy group (e.g., methoxy)) optionally substituted by 1 to 3 $C_{6-14}$ aryl groups (e.g., phenyl),
(3) an amino group optionally mono- or di-substituted by substituent(s) selected from
(a) a $C_{1-6}$ alkyl group (e.g., methyl, ethyl) optionally substituted by 1 to 3 substituents selected from
(i) a halogen atom (e.g., a fluorine atom),
(ii) a $C_{6-14}$ aryl group (e.g., phenyl) optionally substituted by 1 to 3 halogen atoms (e.g., a fluorine atom),
(iii) a 5- or 6-membered monocyclic aromatic heterocyclic group (e.g., pyridyl), and
(iv) a 3- to 8-membered monocyclic non-aromatic heterocyclic group (e.g., oxetanyl) optionally substituted by 1 to 3 $C_{1-6}$ alkyl groups (e.g., methyl),
(b) a $C_{3-8}$ cycloalkyl group (e.g., cyclopropyl, cyclopentyl),
(c) a 3- to 8-membered monocyclic non-aromatic heterocyclic group (e.g., tetrahydropyranyl, tetrahydrofuryl), and
(d) a $C_{6-14}$ aryl group (e.g., phenyl),
(4) a $C_{3-8}$ cycloalkyl group (e.g., cyclopropyl), or
(5) a 3- to 8-membered monocyclic non-aromatic heterocyclic group (e.g., azetidinyl, pyrrolidinyl, 1,1-dioxidothiomorpholinyl, 3-oxa-6-azabicyclo[3.1.1]heptyl) optionally substituted by 1 to 5 substituents selected from
(a) a halogen atom (e.g., a fluorine atom),
(b) a cyano group,
(c) a carbamoyl group,
(d) a $C_{1-6}$ alkyl group (e.g., methyl, isopropyl) optionally substituted by 1 to 3 $C_{1-6}$ alkoxy groups (e.g., methoxy),
(e) a $C_{1-6}$ alkoxy group (e.g., methoxy), and
(f) a $C_{6-14}$ aryl group (e.g., phenyl) optionally substituted by 1 to 3 halogen atoms (e.g., a fluorine atom), or
$R^1$ is bonded to the atom on Ring A to form, together with Ring A, a spiro ring (e.g., 2,8-diazaspiro[4.5]decane) substituted by oxo and optionally further substituted by 1 to 3 $C_{1-6}$ alkyl groups (e.g., methyl).

In another embodiment, $R^1$ is preferably an optionally substituted $C_{1-6}$ alkyl group, an optionally substituted $C_{1-6}$ alkoxy group, an optionally substituted amino group, an optionally substituted $C_{3-8}$ cycloalkyl group, an optionally substituted $C_{6-14}$ aryl group, or an optionally substituted non-aromatic heterocyclic group.

$R^1$ is more preferably
(1) a $C_{1-6}$ alkyl group (e.g., methyl, ethyl) optionally substituted by 1 to 3 substituents selected from
(a) a cyano group,
(b) a $C_{6-14}$ aryl group (e.g., phenyl) optionally substituted by 1 to 3 $C_{1-6}$ alkoxy groups (e.g., methoxy),
(c) a $C_{6-14}$ aryloxy group (e.g., phenoxy),
(d) a $C_{3-8}$ cycloalkyl group (e.g., cyclopropyl),
(e) a 5- or 6-membered monocyclic aromatic heterocyclic group (e.g., pyrazolyl),
(f) a 8- to 12-membered fused aromatic heterocyclic group (e.g., indazolyl), and
(g) a 3- to 8-membered monocyclic non-aromatic heterocyclic group (e.g., dihydropyridyl) optionally substituted by 1 to 3 oxo groups,
(2) a $C_{1-6}$ alkoxy group (e.g., methoxy, tert-butoxy, preferably a $C_{1-3}$ alkoxy group (e.g., methoxy)) optionally substituted by 1 to 3 $C_{6-14}$ aryl groups (e.g., phenyl),
(3) an amino group optionally mono- or di-substituted by substituent(s) selected from
(a) a $C_{1-6}$ alkyl group (e.g., methyl, ethyl) optionally substituted by 1 to 3 substituents selected from
(i) a halogen atom (e.g., a fluorine atom),
(ii) a cyano group,
(iii) a $C_{3-8}$ cycloalkyl group (e.g., cyclopropyl, cyclobutyl),
(iv) a $C_{6-14}$ aryl group (e.g., phenyl) optionally substituted by 1 to 3 substituents selected from a halogen atom (e.g., a fluorine atom) and a $C_{1-6}$ alkoxy group (e.g., methoxy),
(v) a 5- or 6-membered monocyclic aromatic heterocyclic group (e.g., pyridyl), and (vi) a 3- to 8-membered monocyclic non-aromatic heterocyclic group (e.g., oxetanyl) optionally substituted by 1 to 3 $C_{4-6}$ alkyl groups (e.g., methyl),
(b) a $C_{3-8}$ cycloalkyl group (e.g., cyclopropyl, cyclobutyl, cyclopentyl) optionally substituted by 1 to 3 halogen atoms (e.g., a fluorine atom),
(c) a $C_{6-14}$ aryl group (e.g., phenyl), and
(d) a 3- to 8-membered monocyclic non-aromatic heterocyclic group (e.g., tetrahydropyranyl, oxetanyl, tetrahydrofuryl, pyrrolidinyl) optionally substituted by 1 to 3 $C_{1-6}$ alkyl groups (e.g., methyl),
(4) a $C_{3-8}$ cycloalkyl group (e.g., cyclopropyl) optionally substituted by 1 to 3 $C_{6-14}$ aryl groups (e.g., phenyl),
(5) a $C_{6-14}$ aryl group (e.g., phenyl), or
(6) a 3- to 12-membered non-aromatic heterocyclic group (preferably a 3- to 8-membered monocyclic non-aromatic heterocyclic group (e.g., azetidinyl, pyrrolidinyl, piperidyl, piperazinyl, morpholinyl, 1,1-dioxidothiomorpholinyl, tetrahydropyranyl, 3-oxa-6-azabicyclo[3.1.1]heptyl, 8-oxa-3-azabicyclo[3.2.1]octyl, 2-oxa-5-azabicyclo[2.2.1]heptyl, 3-oxa-8-azabicyclo[3.2.1]octyl, 6-oxa-3-azabicyclo[3.1.1]heptyl), 3,7-dioxa-9-azabicyclo[3.3.1]nonyl)) optionally substituted by 1 to 5 substituents selected from
    (a) a halogen atom (e.g., a fluorine atom),
    (b) a cyano group,
    (c) a hydroxy group,
    (d) an oxo group,
    (e) a carbamoyl group optionally mono- or di-substituted by $C_{1-6}$ alkyl group(s) (e.g., methyl),
    (f) a $C_{1-6}$ alkyl group (e.g., methyl, ethyl, isopropyl) optionally substituted by 1 to 3 substituents selected from
        (i) a hydroxy group, and
        (ii) a $C_{1-6}$ alkoxy group (e.g., methoxy),
    (g) a $C_{1-6}$ alkoxy group (e.g., methoxy, ethoxy, isopropoxy) optionally substituted by 1 to 3 halogen atoms (e.g., a fluorine atom),
    (h) a $C_{1-6}$ alkoxy-carbonyl group (e.g., methoxycarbonyl), and
    (i) a $C_{6-14}$ aryl group (e.g., phenyl) optionally substituted by 1 to 3 halogen atoms (e.g., a fluorine atom).
$R^1$ is further more preferably a 3- to 8-membered monocyclic non-aromatic heterocyclic group (e.g., pyrrolidinyl) optionally substituted by 1 to 5 substituents selected from
    (a) a halogen atom (e.g., a fluorine atom),
    (b) a cyano group,
    (c) a carbamoyl group,
    (d) a $C_{1-6}$ alkyl group (e.g., methyl) optionally substituted by 1 to 3 $C_{1-6}$ alkoxy groups (e.g., methoxy), and
    (e) a $C_{1-6}$ alkoxy group (e.g., methoxy).
$R^1$ is still more preferably a 3- to 8-membered monocyclic non-aromatic heterocyclic group (e.g., pyrrolidinyl) optionally substituted by 1 to 5 (preferably 1 to 3) substituents selected from
    (a) a halogen atom (e.g., a fluorine atom),
    (b) a cyano group,
    (c) a carbamoyl group, and
    (d) a $C_{1-6}$ alkyl group (e.g., methyl) optionally substituted by 1 to 3 $C_{1-6}$ alkoxy groups (e.g., methoxy).
In another embodiment, $R^1$ is further more preferably
(1) an amino group optionally mono- or di-substituted by substituent(s) selected from
    (a) a $C_{1-6}$ alkyl group (e.g., methyl, ethyl) optionally substituted by 1 to 3 substituents selected from
        (i) a halogen atom (e.g., a fluorine atom), and
        (ii) a $C_{6-14}$ aryl group (e.g., phenyl) optionally substituted by 1 to 3 halogen atoms (e.g., a fluorine atom), and
    (b) a 3- to 8-membered monocyclic non-aromatic heterocyclic group (e.g., tetrahydropyranyl, tetrahydrofuryl), or
(2) a 3- to 8-membered monocyclic non-aromatic heterocyclic group (e.g., azetidinyl, pyrrolidinyl) optionally substituted by 1 to 5 substituents selected from
    (a) a halogen atom (e.g., a fluorine atom),
    (b) a cyano group,
    (c) a carbamoyl group,
    (d) a $C_{1-6}$ alkyl group (e.g., methyl), and
    (e) a $C_{1-6}$ alkoxy group (e.g., methoxy).
$R^1$ is still more preferably
(1) an amino group optionally mono- or di-substituted by substituent(s) selected from
    (a) a $C_{1-6}$ alkyl group (e.g., methyl, ethyl) optionally substituted by 1 to 3 substituents selected from
        (i) a halogen atom (e.g., a fluorine atom), and
        (ii) a $C_{6-14}$ aryl group (e.g., phenyl) optionally substituted by 1 to 3 halogen atoms (e.g., a fluorine atom), and
    (b) a 3- to 8-membered monocyclic non-aromatic heterocyclic group (e.g., tetrahydropyranyl, tetrahydrofuryl), or
(2) a 3- to 8-membered monocyclic non-aromatic heterocyclic group (e.g., azetidinyl, pyrrolidinyl) optionally substituted by 1 to 5 substituents selected from
    (a) a halogen atom (e.g., a fluorine atom), and
    (b) a cyano group.
$R^1$ is particularly preferably
(1) an amino group optionally mono- or di-substituted by substituent(s) selected from
    (a) a $C_{1-6}$ alkyl group (e.g., methyl, ethyl) optionally substituted by 1 to 3 substituents selected from
        (i) a halogen atom (e.g., a fluorine atom), and
        (ii) a $C_{6-14}$ aryl group (e.g., phenyl) optionally substituted by 1 to 3 halogen atoms (e.g., a fluorine atom), and
    (b) a 3- to 8-membered monocyclic non-aromatic heterocyclic group (e.g., tetrahydropyranyl, tetrahydrofuryl), or
(2) a 3- to 8-membered monocyclic non-aromatic heterocyclic group (e.g., azetidinyl, pyrrolidinyl) optionally substituted by 1 to 3 halogen atoms (e.g., a fluorine atom).
In another embodiment, $R^1$ is further more preferably a 3- to 8-membered monocyclic non-aromatic heterocyclic group (e.g., pyrrolidinyl) optionally substituted by 1 to 5 substituents selected from
    (a) a halogen atom (e.g., a fluorine atom),
    (b) a cyano group,
    (c) a carbamoyl group,
    (d) a $C_{1-6}$ alkyl group (e.g., methyl), and
    (e) a $C_{1-6}$ alkoxy group (e.g., methoxy).
$R^1$ is still more preferably a 3- to 8-membered monocyclic non-aromatic heterocyclic group (e.g., pyrrolidinyl) optionally substituted by 1 to 5 substituents selected from
    (a) a halogen atom (e.g., a fluorine atom), and
    (b) a cyano group.
In the formula (I), $R^2$ is an optionally substituted $C_{6-14}$ aryl group, or an optionally substituted aromatic heterocyclic group.
The "$C_{6-14}$ aryl group" of the "optionally substituted $C_{6-14}$ aryl group" for $R^2$ optionally has 1 to 5 (preferably 1 to 3) substituents at substitutable position(s). Examples of the substituent include substituents selected from the above-mentioned Substituent Group B excluding an oxo group. When the number of the substituents is plural, the respective substituents may be the same or different.

The "aromatic heterocyclic group" of the "optionally substituted aromatic heterocyclic group" for $R^2$ optionally has 1 to 5 (preferably 1 to 3) substituents at substitutable position(s). Examples of the substituent include substituents selected from the above-mentioned Substituent Group B excluding an oxo group. When the number of the substituents is plural, the respective substituents may be the same or different.

$R^2$ is preferably
(1) a $C_{6-14}$ aryl group (e.g., phenyl) optionally substituted by 1 to 3 substituents selected from
  (a) a halogen atom (e.g., a fluorine atom, a chlorine atom), and
  (b) a $C_{1-6}$ alkyl group (e.g., methyl) optionally substituted by 1 to 3 halogen atoms (e.g., a fluorine atom), or
(2) a 5- to 12-membered aromatic heterocyclic group (preferably a 5- or 6-membered monocyclic aromatic heterocyclic group (e.g., pyrazolyl, oxazolyl, thiazolyl, thiadiazolyl, pyridyl), a 8- to 12-membered fused aromatic heterocyclic group (e.g., indazolyl, benzothiazolyl)) optionally substituted by 1 to 3 substituents selected from
  (a) a halogen atom (e.g., a chlorine atom, a bromine atom),
  (b) a cyano group,
  (c) a $C_{1-6}$ alkyl group (e.g., methyl, ethyl) optionally substituted by 1 to 3 halogen atoms (e.g., a fluorine atom), and
  (d) a $C_{3-8}$ cycloalkyl group (e.g., cyclopropyl).

$R^2$ is more preferably
(1) a $C_{6-14}$ aryl group (e.g., phenyl) optionally substituted by 1 to 3 substituents selected from
  (a) a halogen atom (e.g., a fluorine atom, a chlorine atom), and
  (b) a $C_{1-6}$ alkyl group (e.g., methyl) optionally substituted by 1 to 3 halogen atoms (e.g., a fluorine atom), or
(2) a 5- or 6-membered monocyclic aromatic heterocyclic group (e.g., pyrazolyl, thiadiazolyl, pyridyl) optionally substituted by 1 to 3 substituents selected from
  (a) a halogen atom (e.g., a chlorine atom), and
  (b) a $C_{1-6}$ alkyl group (e.g., methyl).

In another embodiment, $R^2$ is more preferably
(1) a $C_{6-14}$ aryl group (e.g., phenyl) optionally substituted by 1 to 3 substituents selected from
  (a) a halogen atom (e.g., a fluorine atom), and
  (b) a $C_{1-6}$ alkyl group (e.g., methyl), or
(2) a 5- to 12-membered aromatic heterocyclic group (preferably a 5- or 6-membered monocyclic aromatic heterocyclic group (e.g., pyrazolyl, oxazolyl, thiazolyl, thiadiazolyl, pyridyl), a 8- to 12-membered fused aromatic heterocyclic group (e.g., benzothiazolyl)) optionally substituted by 1 to 3 substituents selected from
  (a) a halogen atom (e.g., a chlorine atom, a bromine atom),
  (b) a cyano group,
  (c) a $C_{1-6}$ alkyl group (e.g., methyl) optionally substituted by 1 to 3 halogen atoms (e.g., a fluorine atom), and
  (d) a $C_{3-8}$ cycloalkyl group (e.g., cyclopropyl).

$R^2$ is still more preferably a 5- or 6-membered monocyclic aromatic heterocyclic group (e.g., pyrazolyl, thiazolyl, thiadiazolyl, pyridyl (preferably pyrazolyl, thiadiazolyl, more preferably pyrazolyl)) optionally substituted by 1 to 3 substituents selected from
  (a) a halogen atom (e.g., a chlorine atom), and
  (b) a $C_{1-6}$ alkyl group (e.g., methyl).

In another embodiment, $R^2$ is more preferably
(1) a $C_{6-14}$ aryl group (e.g., phenyl) optionally substituted by 1 to 3 halogen atoms (e.g., a fluorine atom), or
(2) a 5- or 6-membered monocyclic aromatic heterocyclic group (e.g., pyrazolyl, thiazolyl, thiadiazolyl (preferably pyrazolyl, thiazolyl)) optionally substituted by 1 to 3 substituents selected from
  (a) a halogen atom (e.g., a chlorine atom, a bromine atom),
  (b) a $C_{1-6}$ alkyl group (e.g., methyl), and
  (c) a $C_{3-8}$ cycloalkyl group (e.g., cyclopropyl).

In the formula (I), X is a carbon atom or a nitrogen atom. $X^1$ is preferably a carbon atom.

In the formula (I), $R^3$ is a hydrogen atom or a substituent when $X^1$ is a carbon atom, or absent when $X^1$ is a nitrogen atom.

The "substituent" for $R^3$ means an optionally substituted hydrocarbon group, an optionally substituted heterocyclic group, an optionally substituted hydroxy group, an optionally substituted sulfanyl group, an optionally substituted amino group, an acyl group, a nitro group, a cyano group or a halogen atom.

The $C_{1-10}$ alkyl group, $C_{2-10}$ alkenyl group and $C_{2-10}$ alkynyl group, which are exemplified as the above-mentioned "hydrocarbon group", optionally have 1 to 5 (preferably 1 to 3) substituents at substitutable position(s). Examples of the substituent include substituents selected from the above-mentioned Substituent Group A. When the number of the substituents is plural, the respective substituents may be the same or different.

The $C_{3-10}$ cycloalkyl group, $C_{3-10}$ cycloalkenyl group and $C_{4-10}$ cycloalkadienyl group, which are exemplified as the above-mentioned "hydrocarbon group", optionally have 1 to 5 (preferably 1 to 3) substituents at substitutable position(s). Examples of the substituent include substituents selected from the above-mentioned Substituent Group B. When the number of the substituents is plural, the respective substituents may be the same or different.

The $C_{6-14}$ aryl group, $C_{7-14}$ aralkyl group and $C_{8-13}$ arylalkenyl group, which are exemplified as the above-mentioned "hydrocarbon group", optionally have 1 to 5 (preferably 1 to 3) substituents at substitutable position(s). Examples of the substituent include substituents selected from the above-mentioned Substituent Group B excluding an oxo group. When the number of the substituents is plural, the respective substituents may be the same or different.

Examples of the "optionally substituted heterocyclic group" exemplified as the "substituent" for $R^3$ include those similar to the "optionally substituted heterocyclic group" for $R^1$.

Examples of the "optionally substituted hydroxy group" exemplified as the "substituent" for $R^3$ include those similar to the "optionally substituted hydroxy group" for $R^1$.

Examples of the "optionally substituted sulfanyl group" exemplified as the "substituent" for $R^3$ include a sulfanyl group optionally substituted by a substituent selected from a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-14}$ aralkyl group, a $C_{8-13}$ arylalkenyl group, a $C_{1-6}$ alkyl-carbonyl group, a heterocyclic group (e.g., an aromatic heterocyclic group, a non-aromatic heterocyclic group) and the like, each of which is optionally substituted.

The $C_{1-10}$ alkyl group, $C_{2-10}$ alkenyl group and $C_{1-6}$ alkyl-carbonyl group optionally have 1 to 5 (preferably 1 to 3) substituents at substitutable position(s). Examples of the substituent include substituents selected from the above-mentioned Substituent Group A. When the number of the substituents is plural, the respective substituents may be the same or different.

The $C_{3-10}$ cycloalkyl group, $C_{3-10}$ cycloalkenyl group and non-aromatic heterocyclic group optionally have 1 to 5 (preferably 1 to 3) substituents at substitutable position(s). Examples of the substituent include substituents selected from the above-mentioned Substituent Group B. When the number of the substituents is plural, the respective substituents may be the same or different.

The $C_{6-14}$ aryl group, $C_{7-14}$ aralkyl group, $C_{8-13}$ arylalkenyl group and aromatic heterocyclic group optionally have 1 to 5 (preferably 1 to 3) substituents at substitutable position(s). Examples of the substituent include substituents selected from the above-mentioned Substituent Group B excluding oxo. When the number of the substituents is plural, the respective substituents may be the same or different.

Examples of the "optionally substituted amino group" exemplified as the "substituent" for $R^3$ include those similar to the "optionally substituted amino group" for $R^1$.

Examples of the "acyl group" exemplified as the "substituent" for $R^3$ include those similar to the "acyl group" exemplified as the substituent of the "optionally substituted amino group" for $R^1$.

$R^3$ is preferably (1) a hydrogen atom, or (2) a halogen atom (e.g., a fluorine atom).

$R^3$ is more preferably a hydrogen atom.

In the formula (I), Ring A is

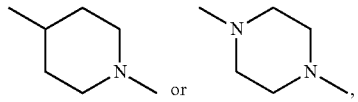

each of which is optionally further substituted and optionally bridged.

Examples of the

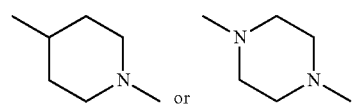

in Ring A, each of which is optionally bridged, include 8-azabicyclo[3.2.1]octane, 2,5-diazabicyclo[2.2.1]heptane, 3-azabicyclo[3.1.0]hexane and the like. 8-Azabicyclo[3.2.1]octane and 2,5-diazabicyclo[2.2.1]heptane are preferable.

The

in Ring A, each of which is optionally bridged, is preferably optionally bridged

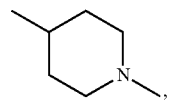

particularly preferably

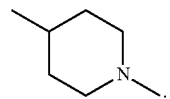

The

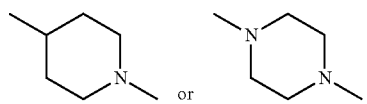

in Ring A, each of which is optionally bridged, optionally has 1 to 5 (preferably 1 to 3) substituents at substitutable position(s). Examples of the substituent include substituents selected from the above-mentioned Substituent Group B. When the number of the substituents is plural, the respective substituents may be the same or different.

Ring A is preferably

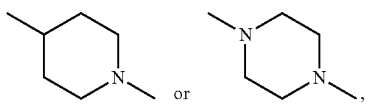

each of which is optionally bridged (e.g., the ring represented by the above-mentioned formula, 8-azabicyclo[3.2.1]octane, 2,5-diazabicyclo[2.2.1]heptane, 3-azabicyclo[3.1.0]hexane), each of which is optionally further substituted by 1 to 5 (preferably 1 to 3) substituents selected from (a) a halogen atom (e.g., a fluorine atom), (b) a $C_{1-6}$ alkyl group (e.g., methyl), and (c) an oxo group.

Ring A is more preferably (1)

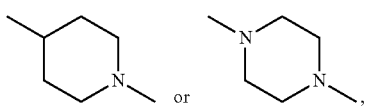

each of which is optionally further substituted by 1 to 3 substituents selected from (a) a halogen atom (e.g., a fluorine atom), (b) a $C_{1-6}$ alkyl group (e.g., methyl), and (c) an oxo group, or (2) a 8-azabicyclo[3.2.1]octane ring, a 2,5-diazabicyclo[2.2.1]heptane ring or a 3-azabicyclo[3.1.0]hexane ring.

Ring A is further more preferably
(1)

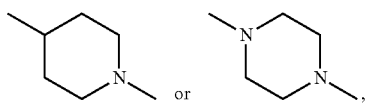

each of which is optionally further substituted by 1 to 3 substituents selected from
(a) a halogen atom (e.g., a fluorine atom), and
(b) a $C_{1-6}$ alkyl group (e.g., methyl), or
(2) a 8-azabicyclo[3.2.1]octane ring or a 2,5-diazabicyclo[2.2.1]heptane ring.

Ring A is still more preferably

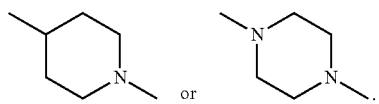

Ring A is particularly preferably

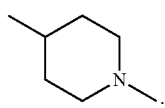

Preferable examples of compound (I) include the following compounds.

[Compound A-1]
Compound (I) wherein
$R^1$ is an optionally substituted $C_{1-6}$ alkyl group, an optionally substituted $C_{1-6}$ alkoxy group, an optionally substituted amino group, an optionally substituted $C_{3-8}$ cycloalkyl group, an optionally substituted $C_{6-14}$ aryl group, or an optionally substituted non-aromatic heterocyclic group, or $R^1$ is bonded to the atom on Ring A to form, together with Ring A, a spiro ring substituted by an oxo group and optionally further substituted;
$R^2$ is an optionally substituted $C_{6-14}$ aryl group, or an optionally substituted aromatic heterocyclic group;
$X^1$ is a carbon atom or a nitrogen atom;
$R^3$ is a hydrogen atom or a substituent when $X^1$ is a carbon atom, or absent when $X^1$ is a nitrogen atom; and
Ring A is

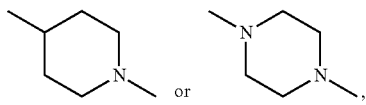

each of which is optionally further substituted and optionally bridged.

[Compound A-2]
Compound (I) wherein
$R^1$ is an optionally substituted $C_{1-6}$ alkyl group, an optionally substituted $C_{1-6}$ alkoxy group, an optionally substituted amino group, an optionally substituted $C_{3-8}$ cycloalkyl group, an optionally substituted $C_{6-14}$ aryl group, or an optionally substituted non-aromatic heterocyclic group;
$R^2$ is an optionally substituted $C_{6-14}$ aryl group, or an optionally substituted aromatic heterocyclic group;
$X^1$ is a carbon atom or a nitrogen atom;
$R^3$ is a hydrogen atom or a substituent when $X^1$ is a carbon atom, or absent when $X^1$ is a nitrogen atom; and
Ring A is

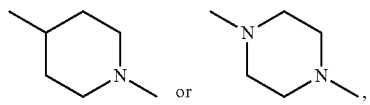

each of which is optionally further substituted and optionally bridged.

[Compound B-1]
Compound (I) wherein
$R^1$ is
(1) a $C_{1-6}$ alkyl group (e.g., methyl, ethyl) optionally substituted by 1 to 3 substituents selected from
    (a) a cyano group,
    (b) a $C_{6-14}$ aryl group (e.g., phenyl) optionally substituted by 1 to 3 $C_{1-6}$ alkoxy groups (e.g., methoxy),
    (c) a $C_{6-14}$ aryloxy group (e.g., phenoxy),
    (d) a $C_{3-8}$ cycloalkyl group (e.g., cyclopropyl),
    (e) a 5- or 6-membered monocyclic aromatic heterocyclic group (e.g., pyrazolyl),
    (f) a 8- to 12-membered fused aromatic heterocyclic group (e.g., indazolyl), and
    (g) a 3- to 8-membered monocyclic non-aromatic heterocyclic group (e.g., dihydropyridyl) optionally substituted by 1 to 3 oxo groups,
(2) a $C_{1-6}$ alkoxy group (e.g., methoxy, tert-butoxy, preferably a $C_{1-3}$ alkoxy group (e.g., methoxy)) optionally substituted by 1 to 3 $C_{6-14}$ aryl groups (e.g., phenyl),
(3) an amino group optionally mono- or di-substituted by substituent(s) selected from
    (a) a $C_{1-6}$ alkyl group (e.g., methyl, ethyl) optionally substituted by 1 to 3 substituents selected from
        (i) a halogen atom (e.g., a fluorine atom),
        (ii) a cyano group,
        (iii) a $C_{3-8}$ cycloalkyl group (e.g., cyclopropyl, cyclobutyl),
        (iv) a $C_{6-14}$ aryl group (e.g., phenyl) optionally substituted by 1 to 3 halogen atoms (e.g., a fluorine atom),
        (v) a 5- or 6-membered monocyclic aromatic heterocyclic group (e.g., pyridyl), and
        (vi) a 3- to 8-membered monocyclic non-aromatic heterocyclic group (e.g., oxetanyl) optionally substituted by 1 to 3 $C_{1-6}$ alkyl groups (e.g., methyl),
    (b) a $C_{3-8}$ cycloalkyl group (e.g., cyclopropyl, cyclobutyl, cyclopentyl) optionally substituted by 1 to 3 halogen atoms (e.g., a fluorine atom),
    (c) a $C_{6-14}$ aryl group (e.g., phenyl), and
    (d) a 3- to 8-membered monocyclic non-aromatic heterocyclic group (e.g., tetrahydropyranyl, oxetanyl, tetrahydrofuryl, pyrrolidinyl) optionally substituted by 1 to 3 $C_{1-6}$ alkyl groups (e.g., methyl),
(4) a $C_{3-8}$ cycloalkyl group (e.g., cyclopropyl) optionally substituted by 1 to 3 $C_{6-14}$ aryl groups (e.g., phenyl),
(5) a $C_{6-14}$ aryl group (e.g., phenyl), or
(6) a 3- to 12-membered non-aromatic heterocyclic group (preferably a 3- to 8-membered monocyclic non-aromatic heterocyclic group (e.g., azetidinyl, pyrrolidinyl, piperidyl, piperazinyl, morpholinyl, 1,1-dioxidothiomorpholinyl, tetrahydropyranyl, 3-oxa-6-azabicyclo[3.1.1]heptyl, 8-oxa-3- azabicyclo[3.2.1]octyl, 2-oxa-5-azabicyclo[2.2.1]heptyl, 3-oxa-8-azabicyclo[3.2.1]octyl, 6-oxa-3-azabicyclo[3.1.1]heptyl)) optionally substituted by 1 to 5 substituents selected from
  (a) a halogen atom (e.g., a fluorine atom),
  (b) a cyano group,
  (c) a hydroxy group,
  (d) an oxo group,
  (e) a carbamoyl group,
  (f) a $C_{1-6}$ alkyl group (e.g., methyl, ethyl, isopropyl) optionally substituted by 1 to 3 substituents selected from
    (i) a hydroxy group, and
    (ii) a $C_{1-6}$ alkoxy group (e.g., methoxy),
  (g) a $C_{1-6}$ alkoxy group (e.g., methoxy, ethoxy, isopropoxy),
  (h) a $C_{1-6}$ alkoxy-carbonyl group (e.g., methoxycarbonyl), and
  (i) a $C_{6-14}$ aryl group (e.g., phenyl) optionally substituted by 1 to 3 halogen atoms (e.g., a fluorine atom), or
$R^1$ is bonded to the atom on Ring A to form, together with Ring A, a spiro ring (e.g., 2,8-diazaspiro[4.5]decane) substituted by oxo and optionally further substituted by 1 to 3 $C_{1-6}$ alkyl groups (e.g., methyl);
$R^2$ is
(1) a $C_{6-14}$ aryl group (e.g., phenyl) optionally substituted by 1 to 3 substituents selected from
  (a) a halogen atom (e.g., a fluorine atom, a chlorine atom), and
  (b) a $C_{1-6}$ alkyl group (e.g., methyl) optionally substituted by 1 to 3 halogen atoms (e.g., a fluorine atom), or
(2) a 5- to 12-membered aromatic heterocyclic group (preferably a 5- or 6-membered monocyclic aromatic heterocyclic group (e.g., pyrazolyl, oxazolyl, thiazolyl, thiadiazolyl, pyridyl), a 8- to 12-membered fused aromatic heterocyclic group (e.g., indazolyl, benzothiazolyl)) optionally substituted by 1 to 3 substituents selected from
  (a) a halogen atom (e.g., a chlorine atom, a bromine atom),
  (b) a cyano group,
  (c) a $C_{1-6}$ alkyl group (e.g., methyl, ethyl) optionally substituted by 1 to 3 halogen atoms (e.g., a fluorine atom), and
  (d) a $C_{3-8}$ cycloalkyl group (e.g., cyclopropyl);
$X^1$ is a carbon atom or a nitrogen atom;
$R^3$ is
(1) a hydrogen atom, or
(2) a halogen atom (e.g., a fluorine atom); and
Ring A is

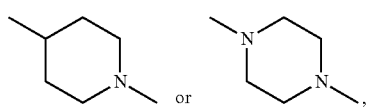

each of which is optionally bridged (e.g., the ring represented by the above-mentioned formula, 8-azabicyclo[3.2.1]octane, 2,5-diazabicyclo[2.2.1]heptane, 3-azabicyclo[3.1.0]hexane), each of which is optionally further substituted by 1 to 5 (preferably 1 to 3) substituents selected from
  (a) a halogen atom (e.g., a fluorine atom),
  (b) a $C_{1-6}$ alkyl group (e.g., methyl), and
  (c) an oxo group.

[Compound B-2]
Compound (I) wherein
$R^1$ is
(1) a $C_{1-6}$ alkyl group (e.g., methyl, ethyl) optionally substituted by 1 to 3 substituents selected from
  (a) a cyano group,
  (b) a $C_{6-14}$ aryl group (e.g., phenyl) optionally substituted by 1 to 3 $C_{1-6}$ alkoxy groups (e.g., methoxy),
  (c) a $C_{6-14}$ aryloxy group (e.g., phenoxy),
  (d) a $C_{3-8}$ cycloalkyl group (e.g., cyclopropyl),
  (e) a 5- or 6-membered monocyclic aromatic heterocyclic group (e.g., pyrazolyl),
  (f) a 8- to 12-membered fused aromatic heterocyclic group (e.g., indazolyl), and
  (g) a 3- to 8-membered monocyclic non-aromatic heterocyclic group (e.g., dihydropyridyl) optionally substituted by 1 to 3 oxo groups,
(2) a $C_{1-6}$ alkoxy group (e.g., methoxy, tert-butoxy, preferably a $C_{1-3}$ alkoxy group (e.g., methoxy)) optionally substituted by 1 to 3 $C_{6-14}$ aryl groups (e.g., phenyl),
(3) an amino group optionally mono- or di-substituted by substituent(s) selected from
  (a) a $C_{1-6}$ alkyl group (e.g., methyl, ethyl) optionally substituted by 1 to 3 substituents selected from
    (i) a halogen atom (e.g., a fluorine atom),
    (ii) a cyano group,
    (iii) a $C_{3-8}$ cycloalkyl group (e.g., cyclopropyl, cyclobutyl),
    (iv) a $C_{6-14}$ aryl group (e.g., phenyl) optionally substituted by 1 to 3 substituents selected from a halogen atom (e.g., a fluorine atom) and a $C_{1-6}$ alkoxy group (e.g., methoxy),
    (v) a 5- or 6-membered monocyclic aromatic heterocyclic group (e.g., pyridyl), and
    (vi) a 3- to 8-membered monocyclic non-aromatic heterocyclic group (e.g., oxetanyl) optionally substituted by 1 to 3 $C_{1-6}$ alkyl groups (e.g., methyl),
  (b) a $C_{3-8}$ cycloalkyl group (e.g., cyclopropyl, cyclobutyl, cyclopentyl) optionally substituted by 1 to 3 halogen atoms (e.g., a fluorine atom),
  (c) a $C_{6-14}$ aryl group (e.g., phenyl), and
  (d) a 3- to 8-membered monocyclic non-aromatic heterocyclic group (e.g., tetrahydropyranyl, oxetanyl, tetrahydrofuryl, pyrrolidinyl) optionally substituted by 1 to 3 $C_{1-6}$ alkyl groups (e.g., methyl),
(4) a $C_{3-8}$ cycloalkyl group (e.g., cyclopropyl) optionally substituted by 1 to 3 $C_{6-14}$ aryl groups (e.g., phenyl),
(5) a $C_{6-14}$ aryl group (e.g., phenyl), or
(6) a 3- to 12-membered non-aromatic heterocyclic group (preferably a 3- to 8-membered monocyclic non-aromatic heterocyclic group (e.g., azetidinyl, pyrrolidinyl, piperidyl, piperazinyl, morpholinyl, 1,1-dioxidothiomorpholinyl, tetrahydropyranyl, 3-oxa-6-azabicyclo[3.1.1]heptyl, 8-oxa-3-azabicyclo[3.2.1]octyl, 2-oxa-5-azabicyclo[2.2.1]heptyl, 3-oxa-8-azabicyclo[3.2.1]octyl, 6-oxa-3-azabicyclo[3.1.1]heptyl), 3,7-dioxa-9-azabicyclo[3.3.1]nonyl)) optionally substituted by 1 to 5 substituents selected from
  (a) a halogen atom (e.g., a fluorine atom),
  (b) a cyano group,
  (c) a hydroxy group,
  (d) an oxo group,
  (e) a carbamoyl group optionally mono- or di-substituted by $C_{1-6}$ alkyl group(s) (e.g., methyl),
  (f) a $C_{1-6}$ alkyl group (e.g., methyl, ethyl, isopropyl) optionally substituted by 1 to 3 substituents selected from (i) a hydroxy group, and
(ii) a $C_{1-6}$ alkoxy group (e.g., methoxy),
(g) a $C_{1-6}$ alkoxy group (e.g., methoxy, ethoxy, isopropoxy) optionally substituted by 1 to 3 halogen atoms (e.g., a fluorine atom),
(h) a $C_{1-6}$ alkoxy-carbonyl group (e.g., methoxycarbonyl), and
(i) a $C_{6-14}$ aryl group (e.g., phenyl) optionally substituted by 1 to 3 halogen atoms (e.g., a fluorine atom), or
$R^1$ is bonded to the atom on Ring A to form, together with Ring A, a spiro ring (e.g., 2,8-diazaspiro[4.5]decane) substituted by oxo and optionally further substituted by 1 to 3 $C_{1-6}$ alkyl groups (e.g., methyl);
$R^2$ is
(1) a $C_{6-14}$ aryl group (e.g., phenyl) optionally substituted by 1 to 3 substituents selected from
  (a) a halogen atom (e.g., a fluorine atom, a chlorine atom), and
  (b) a $C_{1-6}$ alkyl group (e.g., methyl) optionally substituted by 1 to 3 halogen atoms (e.g., a fluorine atom), or
(2) a 5- to 12-membered aromatic heterocyclic group (preferably a 5- or 6-membered monocyclic aromatic heterocyclic group (e.g., pyrazolyl, oxazolyl, thiazolyl, thiadiazolyl, pyridyl), a 8- to 12-membered fused aromatic heterocyclic group (e.g., indazolyl, benzothiazolyl)) optionally substituted by 1 to 3 substituents selected from
  (a) a halogen atom (e.g., a chlorine atom, a bromine atom),
  (b) a cyano group,
  (c) a $C_{1-6}$ alkyl group (e.g., methyl, ethyl) optionally substituted by 1 to 3 halogen atoms (e.g., a fluorine atom), and
  (d) a $C_{3-8}$ cycloalkyl group (e.g., cyclopropyl);
$X^1$ is a carbon atom or a nitrogen atom;
$R^3$ is
(1) a hydrogen atom, or
(2) a halogen atom (e.g., a fluorine atom); and
Ring A is

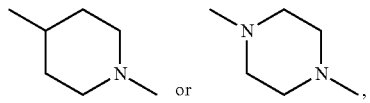

each of which is optionally bridged (e.g., the ring represented by the above-mentioned formula, 8-azabicyclo[3.2.1]octane, 2,5-diazabicyclo[2.2.1]heptane, 3-azabicyclo[3.1.0]hexane), each of which is optionally further substituted by 1 to 5 (preferably 1 to 3) substituents selected from
  (a) a halogen atom (e.g., a fluorine atom),
  (b) a $C_{1-6}$ alkyl group (e.g., methyl), and
  (c) an oxo group.
[Compound B-3]
Compound (I) wherein
$R^1$ is
(1) a $C_{1-6}$ alkyl group (e.g., methyl, ethyl) optionally substituted by 1 to 3 substituents selected from
  (a) a cyano group,
  (b) a $C_{6-14}$ aryl group (e.g., phenyl) optionally substituted by 1 to 3 $C_{1-6}$ alkoxy groups (e.g., methoxy),
  (c) a $C_{6-14}$ aryloxy group (e.g., phenoxy),
  (d) a $C_{3-8}$ cycloalkyl group (e.g., cyclopropyl),
  (e) a 5- or 6-membered monocyclic aromatic heterocyclic group (e.g., pyrazolyl),
  (f) a 8- to 12-membered fused aromatic heterocyclic group (e.g., indazolyl), and
  (g) a 3- to 8-membered monocyclic non-aromatic heterocyclic group (e.g., dihydropyridyl) optionally substituted by 1 to 3 oxo groups,
(2) a $C_{1-3}$ alkoxy group (e.g., methoxy) optionally substituted by 1 to 3 $C_{6-14}$ aryl groups (e.g., phenyl),
(3) an amino group optionally mono- or di-substituted by substituent(s) selected from
  (a) a $C_{1-6}$ alkyl group (e.g., methyl, ethyl) optionally substituted by 1 to 3 substituents selected from
    (i) a halogen atom (e.g., a fluorine atom),
    (ii) a cyano group,
    (iii) a $C_{3-8}$ cycloalkyl group (e.g., cyclopropyl, cyclobutyl),
    (iv) a $C_{6-14}$ aryl group (e.g., phenyl) optionally substituted by 1 to 3 substituents selected from a halogen atom (e.g., a fluorine atom) and a $C_{1-6}$ alkoxy group (e.g., methoxy),
    (v) a 5- or 6-membered monocyclic aromatic heterocyclic group (e.g., pyridyl), and
    (vi) a 3- to 8-membered monocyclic non-aromatic heterocyclic group (e.g., oxetanyl) optionally substituted by 1 to 3 $C_{1-6}$ alkyl groups (e.g., methyl),
  (b) a $C_{3-8}$ cycloalkyl group (e.g., cyclopropyl, cyclobutyl, cyclopentyl) optionally substituted by 1 to 3 halogen atoms (e.g., a fluorine atom),
  (c) a $C_{6-14}$ aryl group (e.g., phenyl), and
  (d) a 3- to 8-membered monocyclic non-aromatic heterocyclic group (e.g., tetrahydropyranyl, oxetanyl, tetrahydrofuryl, pyrrolidinyl) optionally substituted by 1 to 3 $C_{1-6}$ alkyl groups (e.g., methyl),
(4) a $C_{3-8}$ cycloalkyl group (e.g., cyclopropyl) optionally substituted by 1 to 3 $C_{6-14}$ aryl groups (e.g., phenyl),
(5) a $C_{6-14}$ aryl group (e.g., phenyl), or
(6) a 3- to 12-membered non-aromatic heterocyclic group (preferably a 3- to 8-membered monocyclic non-aromatic heterocyclic group (e.g., azetidinyl, pyrrolidinyl, piperidyl, piperazinyl, morpholinyl, 1,1-dioxidothiomorpholinyl, tetrahydropyranyl, 3-oxa-6-azabicyclo[3.1.1]heptyl, 8-oxa-3-azabicyclo[3.2.1]octyl, 2-oxa-5-azabicyclo[2.2.1]heptyl, 3-oxa-8-azabicyclo[3.2.1]octyl, 6-oxa-3-azabicyclo[3.1.1]heptyl), 3,7-dioxa-9-azabicyclo[3.3.1]nonyl)) optionally substituted by 1 to 5 substituents selected from
  (a) a halogen atom (e.g., a fluorine atom),
  (b) a cyano group,
  (c) a hydroxy group,
  (d) an oxo group,
  (e) a carbamoyl group optionally mono- or di-substituted by $C_{1-6}$ alkyl group(s) (e.g., methyl),
  (f) a $C_{1-6}$ alkyl group (e.g., methyl, ethyl, isopropyl) optionally substituted by 1 to 3 substituents selected from
    (i) a hydroxy group, and
    (ii) a $C_{1-6}$ alkoxy group (e.g., methoxy),
  (g) a $C_{1-6}$ alkoxy group (e.g., methoxy, ethoxy, isopropoxy) optionally substituted by 1 to 3 halogen atoms (e.g., a fluorine atom),
  (h) a $C_{1-6}$ alkoxy-carbonyl group (e.g., methoxycarbonyl), and
  (i) a $C_{6-14}$ aryl group (e.g., phenyl) optionally substituted by 1 to 3 halogen atoms (e.g., a fluorine atom), or
$R^1$ is bonded to the atom on Ring A to form, together with Ring A, a spiro ring (e.g., 2,8-diazaspiro[4.5]decane) substituted by oxo and optionally further substituted by 1 to 3 $C_{1-6}$ alkyl groups (e.g., methyl);

$R^2$ is
(1) a $C_{6-14}$ aryl group (e.g., phenyl) optionally substituted by 1 to 3 substituents selected from
  (a) a halogen atom (e.g., a fluorine atom, a chlorine atom), and
  (b) a $C_{1-6}$ alkyl group (e.g., methyl) optionally substituted by 1 to 3 halogen atoms (e.g., a fluorine atom), or
(2) a 5- to 12-membered aromatic heterocyclic group (preferably a 5- or 6-membered monocyclic aromatic heterocyclic group (e.g., pyrazolyl, oxazolyl, thiazolyl, thiadiazolyl, pyridyl), a 8- to 12-membered fused aromatic heterocyclic group (e.g., indazolyl, benzothiazolyl)) optionally substituted by 1 to 3 substituents selected from
  (a) a halogen atom (e.g., a chlorine atom, a bromine atom),
  (b) a cyano group,
  (c) a $C_{1-6}$ alkyl group (e.g., methyl, ethyl) optionally substituted by 1 to 3 halogen atoms (e.g., a fluorine atom), and
  (d) a $C_{3-8}$ cycloalkyl group (e.g., cyclopropyl);
$X^1$ is a carbon atom or a nitrogen atom;
$R^3$ is
(1) a hydrogen atom, or
(2) a halogen atom (e.g., a fluorine atom); and
Ring A is

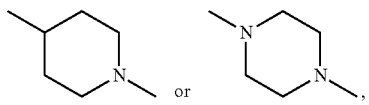

each of which is optionally bridged (e.g., the ring represented by the above-mentioned formula, 8-azabicyclo[3.2.1]octane, 2,5-diazabicyclo[2.2.1]heptane, 3-azabicyclo[3.1.0]hexane), each of which is optionally further substituted by 1 to 5 (preferably 1 to 3) substituents selected from
  (a) a halogen atom (e.g., a fluorine atom),
  (b) a $C_{1-6}$ alkyl group (e.g., methyl), and
  (c) an oxo group.
[Compound B-4]
Compound (I) wherein
$R^1$ is
(1) a $C_{1-6}$ alkyl group (e.g., methyl, ethyl) optionally substituted by 1 to 3 substituents selected from
  (a) a cyano group,
  (b) a $C_{6-14}$ aryl group (e.g., phenyl) optionally substituted by 1 to 3 $C_{1-6}$ alkoxy groups (e.g., methoxy),
  (c) a $C_{6-14}$ aryloxy group (e.g., phenoxy),
  (d) a $C_{3-8}$ cycloalkyl group (e.g., cyclopropyl),
  (e) a pyrazolyl group,
  (f) an indazolyl group, and
  (g) a dihydropyridyl group optionally substituted by 1 to 3 oxo groups,
(2) a $C_{1-6}$ alkoxy group (e.g., methoxy, tert-butoxy, preferably a $C_{1-3}$ alkoxy group (e.g., methoxy)) optionally substituted by 1 to 3 $C_{6-14}$ aryl groups (e.g., phenyl),
(3) an amino group optionally mono- or di-substituted by substituent(s) selected from
  (a) a $C_{1-6}$ alkyl group (e.g., methyl, ethyl) optionally substituted by 1 to 3 substituents selected from
    (i) a halogen atom (e.g., a fluorine atom),
    (ii) a cyano group,
    (iii) a $C_{3-8}$ cycloalkyl group (e.g., cyclopropyl, cyclobutyl),
    (iv) a $C_{6-14}$ aryl group (e.g., phenyl) optionally substituted by 1 to 3 substituents selected from a halogen atom (e.g., a fluorine atom) and a $C_{1-6}$ alkoxy group (e.g., methoxy),
    (v) a pyridyl group, and
    (vi) an oxetanyl group optionally substituted by 1 to 3 $C_{1-6}$ alkyl groups (e.g., methyl),
  (b) a $C_{3-8}$ cycloalkyl group (e.g., cyclopropyl, cyclobutyl, cyclopentyl) optionally substituted by 1 to 3 halogen atoms (e.g., a fluorine atom),
  (c) a $C_{6-14}$ aryl group (e.g., phenyl), and
  (d) a tetrahydropyranyl group, an oxetanyl group, a tetrahydrofuryl group and a pyrrolidinyl group, each of which is optionally substituted by 1 to 3 $C_{1-6}$ alkyl groups (e.g., methyl),
(4) a $C_{3-8}$ cycloalkyl group (e.g., cyclopropyl) optionally substituted by 1 to 3 $C_{6-14}$ aryl groups (e.g., phenyl),
(5) a $C_{6-14}$ aryl group (e.g., phenyl), or
(6) a 3- to 8-membered monocyclic non-aromatic heterocyclic group (e.g., azetidinyl, pyrrolidinyl, piperidyl, piperazinyl, morpholinyl, 1,1-dioxidothiomorpholinyl, tetrahydropyranyl, 3-oxa-6-azabicyclo[3.1.1]heptyl, 8-oxa-3-azabicyclo[3.2.1]octyl, 2-oxa-5-azabicyclo[2.2.1]heptyl, 3-oxa-8-azabicyclo[3.2.1]octyl, 6-oxa-3-azabicyclo[3.1.1]heptyl) or a 3,7-dioxa-9-azabicyclo[3.3.1]nonyl group, each of which is optionally substituted by 1 to 5 substituents selected from
  (a) a halogen atom (e.g., a fluorine atom),
  (b) a cyano group,
  (c) a hydroxy group,
  (d) an oxo group,
  (e) a carbamoyl group optionally mono- or di-substituted by $C_{1-6}$ alkyl group(s) (e.g., methyl),
  (f) a $C_{1-6}$ alkyl group (e.g., methyl, ethyl, isopropyl) optionally substituted by 1 to 3 substituents selected from
    (i) a hydroxy group, and
    (ii) a $C_{1-6}$ alkoxy group (e.g., methoxy),
  (g) a $C_{1-6}$ alkoxy group (e.g., methoxy, ethoxy, isopropoxy) optionally substituted by 1 to 3 halogen atoms (e.g., a fluorine atom),
  (h) a $C_{1-6}$ alkoxy-carbonyl group (e.g., methoxycarbonyl), and
  (i) a $C_{6-14}$ aryl group (e.g., phenyl) optionally substituted by 1 to 3 halogen atoms (e.g., a fluorine atom), or
$R^1$ is bonded to the atom on Ring A to form, together with Ring A, a 2,8-diazaspiro[4.5]decane ring substituted by oxo and optionally further substituted by 1 to 3 $C_{1-6}$ alkyl groups (e.g., methyl);
$R^2$ is
(1) a $C_{6-14}$ aryl group (e.g., phenyl) optionally substituted by 1 to 3 substituents selected from
  (a) a halogen atom (e.g., a fluorine atom, a chlorine atom), and
  (b) a $C_{1-6}$ alkyl group (e.g., methyl) optionally substituted by 1 to 3 halogen atoms (e.g., a fluorine atom), or
(2) a 5- or 6-membered monocyclic aromatic heterocyclic group (e.g., pyrazolyl, oxazolyl, thiazolyl, thiadiazolyl, pyridyl) or a 8- to 12-membered fused aromatic heterocyclic group (e.g., indazolyl, benzothiazolyl), each of which is optionally substituted by 1 to 3 substituents selected from
  (a) a halogen atom (e.g., a chlorine atom, a bromine atom),
  (b) a cyano group,
  (c) a $C_{1-6}$ alkyl group (e.g., methyl, ethyl) optionally substituted by 1 to 3 halogen atoms (e.g., a fluorine atom), and (d) a $C_{3-8}$ cycloalkyl group (e.g., cyclopropyl);
$X^1$ is a carbon atom or a nitrogen atom;
$R^3$ is
(1) a hydrogen atom, or
(2) a halogen atom (e.g., a fluorine atom); and
Ring A is
(1)

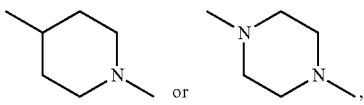

each of which is optionally further substituted by 1 to 3 substituents selected from
  (a) a halogen atom (e.g., a fluorine atom),
  (b) a $C_{1-6}$ alkyl group (e.g., methyl), and
  (c) an oxo group, or
(2) a 8-azabicyclo[3.2.1]octane ring, a 2,5-diazabicyclo[2.2.1]heptane ring or a 3-azabicyclo[3.1.0]hexane ring.

[Compound B-5]
Compound (I) wherein
$R^1$ is
(1) a $C_{1-6}$ alkyl group (e.g., methyl, ethyl) optionally substituted by 1 to 3 substituents selected from
  (a) a cyano group,
  (b) a $C_{6-14}$ aryl group (e.g., phenyl) optionally substituted by 1 to 3 $C_{1-6}$ alkoxy groups (e.g., methoxy),
  (c) a $C_{6-14}$ aryloxy group (e.g., phenoxy),
  (d) a $C_{3-8}$ cycloalkyl group (e.g., cyclopropyl),
  (e) a pyrazolyl group,
  (f) an indazolyl group, and
  (g) a dihydropyridyl group optionally substituted by 1 to 3 oxo groups,
(2) a $C_{1-3}$ alkoxy group (e.g., methoxy) optionally substituted by 1 to 3 $C_{6-14}$ aryl groups (e.g., phenyl),
(3) an amino group optionally mono- or di-substituted by substituent(s) selected from
  (a) a $C_{1-6}$ alkyl group (e.g., methyl, ethyl) optionally substituted by 1 to 3 substituents selected from
    (i) a halogen atom (e.g., a fluorine atom),
    (ii) a cyano group,
    (iii) a $C_{3-8}$ cycloalkyl group (e.g., cyclopropyl, cyclobutyl),
    (iv) a $C_{6-14}$ aryl group (e.g., phenyl) optionally substituted by 1 to 3 substituents selected from a halogen atom (e.g., a fluorine atom) and a $C_{1-6}$ alkoxy group (e.g., methoxy),
    (v) a pyridyl group, and
    (vi) an oxetanyl group optionally substituted by 1 to 3 $C_{1-6}$ alkyl groups (e.g., methyl),
  (b) a $C_{3-8}$ cycloalkyl group (e.g., cyclopropyl, cyclobutyl, cyclopentyl) optionally substituted by 1 to 3 halogen atoms (e.g., a fluorine atom),
  (c) a $C_{6-14}$ aryl group (e.g., phenyl), and
  (d) a tetrahydropyranyl group, an oxetanyl group, a tetrahydrofuryl group and a pyrrolidinyl group, each of which is optionally substituted by 1 to 3 $C_{1-6}$ alkyl groups (e.g., methyl),
(4) a $C_{3-8}$ cycloalkyl group (e.g., cyclopropyl) optionally substituted by 1 to 3 $C_{6-14}$ aryl groups (e.g., phenyl),
(5) a $C_{6-14}$ aryl group (e.g., phenyl), or
(6) a 3- to 8-membered monocyclic non-aromatic heterocyclic group (e.g., azetidinyl, pyrrolidinyl, piperidyl, piperazinyl, morpholinyl, 1,1-dioxidothiomorpholinyl, tetrahydropyranyl, 3-oxa-6-azabicyclo[3.1.1]heptyl, 8-oxa-3-azabicyclo[3.2.1]octyl, 2-oxa-5-azabicyclo[2.2.1]heptyl, 3-oxa-8-azabicyclo[3.2.1]octyl, 6-oxa-3-azabicyclo[3.1.1]heptyl or a 3,7-dioxa-9-azabicyclo[3.3.1]nonyl group, each of which is optionally substituted by 1 to 5 substituents selected from
  (a) a halogen atom (e.g., a fluorine atom),
  (b) a cyano group,
  (c) a hydroxy group,
  (d) an oxo group,
  (e) a carbamoyl group optionally mono- or di-substituted by $C_{1-6}$ alkyl group(s) (e.g., methyl),
  (f) a $C_{1-6}$ alkyl group (e.g., methyl, ethyl, isopropyl) optionally substituted by 1 to 3 substituents selected from
    (i) a hydroxy group, and
    (ii) a $C_{1-6}$ alkoxy group (e.g., methoxy),
  (g) a $C_{1-6}$ alkoxy group (e.g., methoxy, ethoxy, isopropoxy) optionally substituted by 1 to 3 halogen atoms (e.g., a fluorine atom),
  (h) a $C_{1-6}$ alkoxy-carbonyl group (e.g., methoxycarbonyl), and
  (i) a $C_{6-14}$ aryl group (e.g., phenyl) optionally substituted by 1 to 3 halogen atoms (e.g., a fluorine atom), or
$R^1$ is bonded to the atom on Ring A to form, together with Ring A, a 2,8-diazaspiro[4.5]decane ring substituted by oxo and optionally further substituted by 1 to 3 $C_{1-6}$ alkyl groups (e.g., methyl);
$R^2$ is
(1) a $C_{6-14}$ aryl group (e.g., phenyl) optionally substituted by 1 to 3 substituents selected from
  (a) a halogen atom (e.g., a fluorine atom, a chlorine atom), and
  (b) a $C_{1-6}$ alkyl group (e.g., methyl) optionally substituted by 1 to 3 halogen atoms (e.g., a fluorine atom), or
(2) a 5- or 6-membered monocyclic aromatic heterocyclic group (e.g., pyrazolyl, oxazolyl, thiazolyl, thiadiazolyl, pyridyl) or a 8- to 12-membered fused aromatic heterocyclic group (e.g., indazolyl, benzothiazolyl), each of which is optionally substituted by 1 to 3 substituents selected from
  (a) a halogen atom (e.g., a chlorine atom, a bromine atom),
  (b) a cyano group,
  (c) a $C_{1-6}$ alkyl group (e.g., methyl, ethyl) optionally substituted by 1 to 3 halogen atoms (e.g., a fluorine atom), and
  (d) a $C_{3-8}$ cycloalkyl group (e.g., cyclopropyl);
$X^1$ is a carbon atom or a nitrogen atom;
$R^3$ is
(1) a hydrogen atom, or
(2) a halogen atom (e.g., a fluorine atom); and
Ring A is
(1)

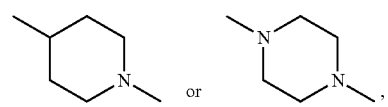

each of which is optionally further substituted by 1 to 3 substituents selected from
  (a) a halogen atom (e.g., a fluorine atom),
  (b) a $C_{1-6}$ alkyl group (e.g., methyl), and
  (c) an oxo group, or
(2) a 8-azabicyclo[3.2.1]octane ring, a 2,5-diazabicyclo[2.2.1]heptane ring or a 3-azabicyclo[3.1.0]hexane ring.

[Compound B-6]
Compound (I) wherein
R¹ is
(1) a $C_{1-6}$ alkyl group (e.g., methyl, ethyl) optionally substituted by 1 to 3 substituents selected from
(a) a cyano group,
(b) a phenyl group optionally substituted by 1 to 3 $C_{1-6}$ alkoxy groups (e.g., methoxy),
(c) a phenoxy group,
(d) a cyclopropyl group,
(e) a pyrazolyl group,
(f) an indazolyl group, and
(g) a dihydropyridyl group optionally substituted by 1 to 3 oxo groups,
(2) a $C_{1-6}$ alkoxy group (e.g., methoxy, tert-butoxy, preferably a $C_{1-3}$ alkoxy group (e.g., methoxy)) optionally substituted by 1 to 3 phenyl groups,
(3) an amino group optionally mono- or di-substituted by substituent(s) selected from
(a) a $C_{1-6}$ alkyl group (e.g., methyl, ethyl) optionally substituted by 1 to 3 substituents selected from
(i) a halogen atom (e.g., a fluorine atom),
(ii) a cyano group,
(iii) a cyclopropyl group,
(iv) a cyclobutyl group,
(v) a phenyl group optionally substituted by 1 to 3 substituents selected from a halogen atom (e.g., a fluorine atom) and a $C_{1-6}$ alkoxy group (e.g., methoxy),
(vi) a pyridyl group, and
(vii) an oxetanyl group optionally substituted by 1 to 3 $C_{1-6}$ alkyl groups (e.g., methyl),
(b) a cyclopropyl group, a cyclobutyl group and a cyclopentyl group, each of which is optionally substituted by 1 to 3 halogen atoms (e.g., a fluorine atom),
(c) a phenyl group, and
(d) a tetrahydropyranyl group, an oxetanyl group, a tetrahydrofuryl group and a pyrrolidinyl group, each of which is optionally substituted by 1 to 3 $C_{1-6}$ alkyl groups (e.g., methyl),
(4) a cyclopropyl group optionally substituted by 1 to 3 phenyl groups,
(5) a phenyl group, or
(6) an azetidinyl group, a pyrrolidinyl group, a piperidyl group, a piperazinyl group, a morpholinyl group, a 1,1-dioxidothiomorpholinyl group, a tetrahydropyranyl group, a 3-oxa-6-azabicyclo[3.1.1]heptyl group, an 8-oxa-3-azabicyclo[3.2.1]octyl group, a 2-oxa-5-azabicyclo[2.2.1]heptyl group, a 3-oxa-8-azabicyclo[3.2.1]octyl group, a 6-oxa-3-azabicyclo[3.1.1]heptyl group or a 3,7-dioxa-9-azabicyclo[3.3.1]nonyl group, each of which is optionally substituted by 1 to 5 substituents selected from
(a) a halogen atom (e.g., a fluorine atom),
(b) a cyano group,
(c) a hydroxy group,
(d) an oxo group,
(e) a carbamoyl group optionally mono- or di-substituted by $C_{1-6}$ alkyl group(s) (e.g., methyl),
(f) a $C_{1-6}$ alkyl group (e.g., methyl, ethyl, isopropyl) optionally substituted by 1 to 3 substituents selected from
(i) a hydroxy group, and
(ii) a $C_{1-6}$ alkoxy group (e.g., methoxy),
(g) a $C_{1-6}$ alkoxy group (e.g., methoxy, ethoxy, isopropoxy) optionally substituted by 1 to 3 halogen atoms (e.g., a fluorine atom),
(h) a $C_{1-6}$ alkoxy-carbonyl group (e.g., methoxycarbonyl), and
(i) a phenyl group optionally substituted by 1 to 3 halogen atoms (e.g., a fluorine atom), or
R¹ is bonded to the atom on Ring A to form, together with Ring A, a 2,8-diazaspiro[4.5]decane ring substituted by oxo and optionally further substituted by 1 to 3 $C_{1-6}$ alkyl groups (e.g., methyl);
R² is
(1) a phenyl group optionally substituted by 1 to 3 substituents selected from
(a) a halogen atom (e.g., a fluorine atom, a chlorine atom), and
(b) a $C_{1-6}$ alkyl group (e.g., methyl) optionally substituted by 1 to 3 halogen atoms (e.g., a fluorine atom), or
(2) a pyrazolyl group, an oxazolyl group, a thiazolyl group, a thiadiazolyl group, a pyridyl group, an indazolyl group or a benzothiazolyl group, each of which is optionally substituted by 1 to 3 substituents selected from
(a) a halogen atom (e.g., a chlorine atom, a bromine atom),
(b) a cyano group,
(c) a $C_{1-6}$ alkyl group (e.g., methyl, ethyl) optionally substituted by 1 to 3 halogen atoms (e.g., a fluorine atom), and
(d) a cyclopropyl group;
X¹ is a carbon atom or a nitrogen atom;
R³ is
(1) a hydrogen atom, or
(2) a halogen atom (e.g., a fluorine atom); and
Ring A is
(1)

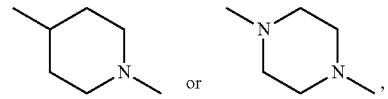

each of which is optionally further substituted by 1 to 3 substituents selected from
(a) a halogen atom (e.g., a fluorine atom),
(b) a $C_{1-6}$ alkyl group (e.g., methyl), and
(c) an oxo group, or
(2) a 8-azabicyclo[3.2.1]octane ring, a 2,5-diazabicyclo[2.2.1]heptane ring or a 3-azabicyclo[3.1.0]hexane ring.

[Compound B-7]
Compound (I) wherein
R¹ is
(1) a $C_{1-6}$ alkyl group (e.g., methyl, ethyl) optionally substituted by 1 to 3 substituents selected from
(a) a cyano group,
(b) a phenyl group optionally substituted by 1 to 3 $C_{1-6}$ alkoxy groups (e.g., methoxy),
(c) a phenoxy group,
(d) a cyclopropyl group,
(e) a pyrazolyl group,
(f) an indazolyl group, and
(g) a dihydropyridyl group optionally substituted by 1 to 3 oxo groups,
(2) a $C_{1-3}$ alkoxy group optionally substituted by 1 to 3 phenyl groups (e.g., methoxy),
(3) an amino group optionally mono- or di-substituted by substituent(s) selected from
(a) a $C_{1-6}$ alkyl group (e.g., methyl, ethyl) optionally substituted by 1 to 3 substituents selected from (i) a halogen atom (e.g., a fluorine atom),
(ii) a cyano group,
(iii) a cyclopropyl group,
(iv) a cyclobutyl group,
(v) a phenyl group optionally substituted by 1 to 3 substituents selected from a halogen atom (e.g., a fluorine atom) and a $C_{1-6}$ alkoxy group (e.g., methoxy),
(vi) a pyridyl group, and
(vii) an oxetanyl group optionally substituted by 1 to 3 $C_{1-6}$ alkyl groups (e.g., methyl),
(b) a cyclopropyl group, a cyclobutyl group and a cyclopentyl group, each of which is optionally substituted by 1 to 3 halogen atoms (e.g., a fluorine atom),
(c) a phenyl group, and
(d) a tetrahydropyranyl group, an oxetanyl group, a tetrahydrofuryl group and a pyrrolidinyl group, each of which is optionally substituted by 1 to 3 $C_{1-6}$ alkyl groups (e.g., methyl),
(4) a cyclopropyl group optionally substituted by 1 to 3 phenyl groups,
(5) a phenyl group, or
(6) an azetidinyl group, a pyrrolidinyl group, a piperidyl group, a piperazinyl group, a morpholinyl group, a 1,1-dioxidothiomorpholinyl group, a tetrahydropyranyl group, a 3-oxa-6-azabicyclo[3.1.1]heptyl group, an 8-oxa-3-azabicyclo[3.2.1]octyl group, a 2-oxa-5-azabicyclo[2.2.1]heptyl group, a 3-oxa-8-azabicyclo[3.2.1]octyl group, a 6-oxa-3-azabicyclo[3.1.1]heptyl group or a 3,7-dioxa-9-azabicyclo[3.3.1]nonyl group, each of which is optionally substituted by 1 to 5 substituents selected from
(a) a halogen atom (e.g., a fluorine atom),
(b) a cyano group,
(c) a hydroxy group,
(d) an oxo group,
(e) a carbamoyl group optionally mono- or di-substituted by $C_{1-6}$ alkyl group(s) (e.g., methyl),
(f) a $C_{1-6}$ alkyl group (e.g., methyl, ethyl, isopropyl) optionally substituted by 1 to 3 substituents selected from
(i) a hydroxy group, and
(ii) a $C_{1-6}$ alkoxy group (e.g., methoxy),
(g) a $C_{1-6}$ alkoxy group (e.g., methoxy, ethoxy, isopropoxy) optionally substituted by 1 to 3 halogen atoms (e.g., a fluorine atom),
(h) a $C_{1-6}$ alkoxy-carbonyl group (e.g., methoxycarbonyl), and
(i) a phenyl group optionally substituted by 1 to 3 halogen atoms (e.g., a fluorine atom), or
$R^1$ is bonded to the atom on Ring A to form, together with Ring A, a 2,8-diazaspiro[4.5]decane ring substituted by oxo and optionally further substituted by 1 to 3 $C_{1-6}$ alkyl groups (e.g., methyl);
$R^2$ is
(1) a phenyl group optionally substituted by 1 to 3 substituents selected from
(a) a halogen atom (e.g., a fluorine atom, a chlorine atom), and
(b) a $C_{1-6}$ alkyl group (e.g., methyl) optionally substituted by 1 to 3 halogen atoms (e.g., a fluorine atom), or
(2) a pyrazolyl group, an oxazolyl group, a thiazolyl group, a thiadiazolyl group, a pyridyl group, an indazolyl group or a benzothiazolyl group, each of which is optionally substituted by 1 to 3 substituents selected from
(a) a halogen atom (e.g., a chlorine atom, a bromine atom),
(b) a cyano group,
(c) a $C_{1-6}$ alkyl group (e.g., methyl, ethyl) optionally substituted by 1 to 3 halogen atoms (e.g., a fluorine atom), and
(d) a cyclopropyl group;
$X^1$ is a carbon atom or a nitrogen atom;
$R^3$ is
(1) a hydrogen atom, or
(2) a halogen atom (e.g., a fluorine atom); and
Ring A is
(1)

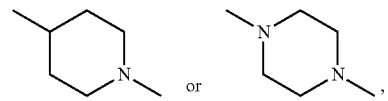

each of which is optionally further substituted by 1 to 3 substituents selected from
(a) a halogen atom (e.g., a fluorine atom),
(b) a $C_{1-6}$ alkyl group (e.g., methyl), and
(c) an oxo group, or
(2) a 8-azabicyclo[3.2.1]octane ring, a 2,5-diazabicyclo[2.2.1]heptane ring or a 3-azabicyclo[3.1.0]hexane ring.
[Compound C-1]
Compound (I) wherein
$R^1$ is
(1) an amino group optionally mono- or di-substituted by substituent(s) selected from
(a) a $C_{1-6}$ alkyl group (e.g., methyl, ethyl) optionally substituted by 1 to 3 substituents selected from
(i) a halogen atom (e.g., a fluorine atom), and
(ii) a $C_{6-14}$ aryl group (e.g., phenyl) optionally substituted by 1 to 3 halogen atoms (e.g., a fluorine atom), and
(b) a 3- to 8-membered monocyclic non-aromatic heterocyclic group (e.g., tetrahydropyranyl, tetrahydrofuryl), or
(2) a 3- to 8-membered monocyclic non-aromatic heterocyclic group (e.g., azetidinyl, pyrrolidinyl) optionally substituted by 1 to 5 substituents selected from
(a) a halogen atom (e.g., a fluorine atom),
(b) a cyano group,
(c) a carbamoyl group,
(d) a $C_{1-6}$ alkyl group (e.g., methyl), and
(e) a $C_{1-6}$ alkoxy group (e.g., methoxy);
$R^2$ is
(1) a $C_{6-14}$ aryl group (e.g. phenyl) optionally substituted by 1 to 3 halogen atoms (e.g., a fluorine atom), or
(2) a 5- or 6-membered monocyclic aromatic heterocyclic group (e.g., pyrazolyl, thiazolyl, thiadiazolyl (preferably pyrazolyl, thiazolyl)) optionally substituted by 1 to 3 substituents selected from
(a) a halogen atom (e.g., a chlorine atom, a bromine atom),
(b) a $C_{1-6}$ alkyl group (e.g., methyl), and
(c) a $C_{3-8}$ cycloalkyl group (e.g., cyclopropyl);
$X^1$ is a carbon atom or a nitrogen atom;
$R^3$ is a hydrogen atom; and
Ring A is

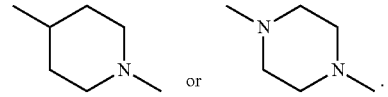

[Compound C-2]
Compound (I) wherein
R¹ is
(1) an amino group optionally mono- or di-substituted by substituent(s) selected from
  (a) a $C_{1-6}$ alkyl group (e.g., methyl, ethyl) optionally substituted by 1 to 3 substituents selected from
    (i) a halogen atom (e.g., a fluorine atom), and
    (ii) a phenyl group optionally substituted by 1 to 3 halogen atoms (e.g., a fluorine atom),
  (b) a tetrahydropyranyl group, and
  (c) a tetrahydrofuryl group, or
(2) an azetidinyl group or a pyrrolidinyl group, each of which is optionally substituted by 1 to 5 substituents selected from
  (a) a halogen atom (e.g., a fluorine atom),
  (b) a cyano group,
  (c) a carbamoyl group,
  (d) a $C_{1-6}$ alkyl group (e.g., methyl), and
  (e) a $C_{1-6}$ alkoxy group (e.g., methoxy);
R² is
(1) a phenyl group optionally substituted by 1 to 3 halogen atoms (e.g., a fluorine atom), or
(2) a pyrazolyl group, a thiazolyl group or a thiadiazolyl group, each of which is optionally substituted by 1 to 3 substituents selected from
  (a) a halogen atom (e.g., a chlorine atom, a bromine atom),
  (b) a $C_{1-6}$ alkyl group (e.g., methyl), and
  (c) a cyclopropyl group;
$X^1$ is a carbon atom or a nitrogen atom;
R³ is a hydrogen atom; and
Ring A is

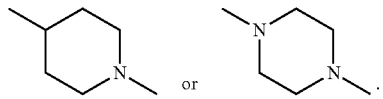

[Compound D-1]
Compound (I) wherein
R¹ is
(1) an amino group optionally mono- or di-substituted by substituent(s) selected from
  (a) a $C_{1-6}$ alkyl group (e.g., methyl, ethyl) optionally substituted by 1 to 3 substituents selected from
    (i) a halogen atom (e.g., a fluorine atom), and
    (ii) a $C_{6-14}$ aryl group (e.g., phenyl) optionally substituted by 1 to 3 halogen atoms (e.g., a fluorine atom), and
  (b) a 3- to 8-membered monocyclic non-aromatic heterocyclic group (e.g., tetrahydropyranyl, tetrahydrofuryl), or
(2) a 3- to 8-membered monocyclic non-aromatic heterocyclic group (e.g., azetidinyl, pyrrolidinyl) optionally substituted by 1 to 5 substituents selected from
  (a) a halogen atom (e.g., a fluorine atom), and
  (b) a cyano group;
R² is
(1) a $C_{6-14}$ aryl group (e.g., phenyl) optionally substituted by 1 to 3 halogen atoms (e.g., a fluorine atom), or
(2) a 5- or 6-membered monocyclic aromatic heterocyclic group (e.g., pyrazolyl, thiazolyl, thiadiazolyl (preferably pyrazolyl, thiazolyl)) optionally substituted by 1 to 3 substituents selected from
  (a) a halogen atom (e.g., a chlorine atom, a bromine atom),
  (b) a $C_{1-6}$ alkyl group (e.g., methyl), and
  (c) a $C_{3-8}$ cycloalkyl group (e.g., cyclopropyl);
$X^1$ is a carbon atom or a nitrogen atom;
R³ is a hydrogen atom; and
Ring A is

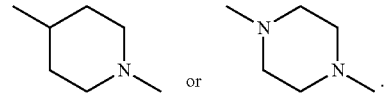

[Compound D-2]
Compound (I) wherein
R¹ is
(1) an amino group optionally mono- or di-substituted by substituent(s) selected from
  (a) a $C_{1-6}$ alkyl group (e.g., methyl, ethyl) optionally substituted by 1 to 3 substituents selected from
    (i) a halogen atom (e.g., a fluorine atom), and
    (ii) a phenyl group optionally substituted by 1 to 3 halogen atoms (e.g., a fluorine atom),
  (b) a tetrahydropyranyl group, and
  (c) a tetrahydrofuryl group, or
(2) an azetidinyl group or a pyrrolidinyl group, each of which is optionally substituted by 1 to 5 substituents selected from
  (a) a halogen atom (e.g., a fluorine atom), and
  (b) a cyano group;
R² is
(1) a phenyl group optionally substituted by 1 to 3 halogen atoms (e.g., a fluorine atom), or
(2) a pyrazolyl group or a thiazolyl group, each of which is optionally substituted by 1 to 3 substituents selected from
  (a) a halogen atom (e.g., a chlorine atom, a bromine atom),
  (b) a $C_{1-6}$ alkyl group (e.g., methyl), and
  (c) a cyclopropyl group;
$X^1$ is a carbon atom or a nitrogen atom;
R³ is a hydrogen atom; and
Ring A is

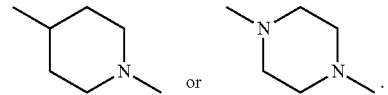

[Compound E-1]
Compound (I) wherein
R¹ is
(1) an amino group optionally mono- or di-substituted by substituent(s) selected from
  (a) a $C_{1-6}$ alkyl group (e.g., methyl, ethyl) optionally substituted by 1 to 3 substituents selected from
    (i) a halogen atom (e.g., a fluorine atom), and
    (ii) a $C_{6-14}$ aryl group (e.g., phenyl) optionally substituted by 1 to 3 halogen atoms (e.g., a fluorine atom), and
  (b) a 3- to 8-membered monocyclic non-aromatic heterocyclic group (e.g., tetrahydropyranyl, tetrahydrofuryl), or
(2) a 3- to 8-membered monocyclic non-aromatic heterocyclic group (e.g., azetidinyl, pyrrolidinyl) optionally substituted by 1 to 3 halogen atoms (e.g., a fluorine atom);

R² is
(1) a $C_{6-14}$ aryl group (e.g., phenyl) optionally substituted by 1 to 3 halogen atoms (e.g., a fluorine atom), or
(2) a 5- or 6-membered monocyclic aromatic heterocyclic group (e.g., pyrazolyl, thiazolyl, thiadiazolyl (preferably pyrazolyl, thiazolyl)) optionally substituted by 1 to 3 substituents selected from
  (a) a halogen atom (e.g., a chlorine atom, a bromine atom),
  (b) a $C_{1-6}$ alkyl group (e.g., methyl), and
  (c) a $C_{3-8}$ cycloalkyl group (e.g., cyclopropyl);
$X^1$ is a carbon atom or a nitrogen atom;
$R^3$ is a hydrogen atom; and
Ring A is

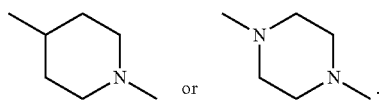

[Compound E-2]
Compound (I) wherein
R¹ is
(1) an amino group optionally mono- or di-substituted by substituent(s) selected from
  (a) a $C_{1-6}$ alkyl group (e.g., methyl, ethyl) optionally substituted by 1 to 3 substituents selected from
    (i) a halogen atom (e.g., a fluorine atom), and
    (ii) a phenyl group optionally substituted by 1 to 3 halogen atoms (e.g., a fluorine atom),
  (b) a tetrahydropyranyl group, and
  (c) a tetrahydrofuryl group, or
(2) an azetidinyl group or a pyrrolidinyl group, each of which is optionally substituted by 1 to 3 halogen atoms (e.g., a fluorine atom);
R² is
(1) a phenyl group optionally substituted by 1 to 3 halogen atoms (e.g., a fluorine atom), or
(2) a pyrazolyl group or a thiazolyl group, each of which is optionally substituted by 1 to 3 substituents selected from
  (a) a halogen atom (e.g., a chlorine atom, a bromine atom),
  (b) a $C_{1-6}$ alkyl group (e.g., methyl), and
  (c) a cyclopropyl group;
$X^1$ is a carbon atom or a nitrogen atom;
$R^3$ is a hydrogen atom; and
Ring A is

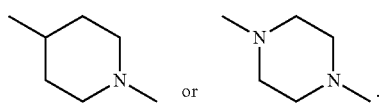

[Compound F-1]
Compound (I) wherein
R¹ is a 3- to 8-membered monocyclic non-aromatic heterocyclic group (e.g., pyrrolidinyl) optionally substituted by 1 to 5 substituents selected from
  (a) a halogen atom (e.g., a fluorine atom),
  (b) a cyano group,
  (c) a carbamoyl group,
  (d) a $C_{1-6}$ alkyl group (e.g., methyl), and
  (e) a $C_{1-6}$ alkoxy group (e.g., methoxy);
R² is a 5- or 6-membered monocyclic aromatic heterocyclic group (e.g., pyrazolyl, thiazolyl, thiadiazolyl, pyridyl (preferably pyrazolyl, thiadiazolyl, more preferably pyrazolyl)) optionally substituted by 1 to 3 substituents selected from
  (a) a halogen atom (e.g., a chlorine atom), and
  (b) a $C_{1-6}$ alkyl group (e.g., methyl);
$X^1$ is a carbon atom;
$R^3$ is a hydrogen atom; and
Ring A is

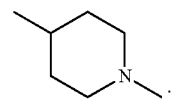

[Compound F-2]
Compound (I) wherein
R¹ is a pyrrolidinyl group optionally substituted by 1 to 5 substituents selected from
  (a) a halogen atom (e.g., a fluorine atom),
  (b) a cyano group,
  (c) a carbamoyl group,
  (d) a $C_{1-6}$ alkyl group (e.g., methyl), and
  (e) a $C_{1-6}$ alkoxy group (e.g., methoxy);
R² is a pyrazolyl group or a thiadiazolyl group, each of which is optionally substituted by 1 to 3 substituents selected from
  (a) a halogen atom (e.g., a chlorine atom), and
  (b) a $C_{1-6}$ alkyl group (e.g., methyl);
$X^1$ is a carbon atom;
$R^3$ is a hydrogen atom; and
Ring A is

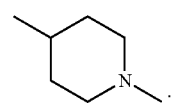

[Compound G-1]
Compound (I) wherein
R¹ is a 3- to 8-membered monocyclic non-aromatic heterocyclic group (e.g., pyrrolidinyl) optionally substituted by 1 to 5 substituents selected from
  (a) a halogen atom (e.g., a fluorine atom), and
  (b) a cyano group;
R² is a 5- or 6-membered monocyclic aromatic heterocyclic group (e.g., pyrazolyl, thiazolyl, thiadiazolyl, pyridyl (preferably pyrazolyl, thiadiazolyl, more preferably pyrazolyl)) optionally substituted by 1 to 3 substituents selected from
  (a) a halogen atom (e.g., a chlorine atom), and
  (b) a $C_{1-6}$ alkyl group (e.g., methyl);
$X^1$ is a carbon atom;
$R^3$ is a hydrogen atom; and
Ring A is

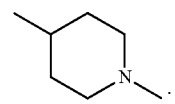

[Compound G-2]
Compound (I) wherein
R¹ is a pyrrolidinyl group optionally substituted by 1 to 5 substituents selected from (a) a halogen atom (e.g., a fluorine atom), and
(b) a cyano group;
R² is a pyrazolyl group optionally substituted by 1 to 3 substituents selected from
(a) a halogen atom (e.g., a chlorine atom), and
(b) a C₁₋₆ alkyl group (e.g., methyl);
X¹ is a carbon atom;
R³ is a hydrogen atom; and
Ring A is

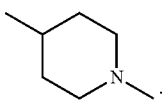

[Compound H-1]
Compound (I) wherein
R¹ is
(1) a C₁₋₆ alkyl group (e.g., methyl, ethyl) optionally substituted by 1 to 3 substituents selected from
   (a) a C₃₋₈ cycloalkyl group (e.g., cyclopropyl), and
   (b) a 8- to 12-membered fused aromatic heterocyclic group (e.g., indazolyl),
(2) a C₁₋₆ alkoxy group (preferably a C₁₋₃ alkoxy group (e.g., methoxy)) optionally substituted by 1 to 3 C₆₋₁₄ aryl groups (e.g., phenyl),
(3) an amino group optionally mono- or di-substituted by substituent(s) selected from
   (a) a C₁₋₆ alkyl group (e.g., methyl, ethyl) optionally substituted by 1 to 3 substituents selected from
      (i) a halogen atom (e.g., a fluorine atom),
      (ii) a C₆₋₁₄ aryl group (e.g., phenyl) optionally substituted by 1 to 3 halogen atoms (e.g., a fluorine atom),
      (iii) a 5- or 6-membered monocyclic aromatic heterocyclic group (e.g., pyridyl), and
      (iv) a 3- to 8-membered monocyclic non-aromatic heterocyclic group (e.g., oxetanyl) optionally substituted by 1 to 3 C₁₋₆ alkyl groups (e.g., methyl),
   (b) a C₃₋₈ cycloalkyl group (e.g., cyclopropyl, cyclopentyl),
   (c) a 3- to 8-membered monocyclic non-aromatic heterocyclic group (e.g., tetrahydropyranyl, tetrahydrofuryl), and
   (d) a C₆₋₁₄ aryl group (e.g., phenyl),
(4) a C₃₋₈ cycloalkyl group (e.g., cyclopropyl), or
(5) a 3- to 8-membered monocyclic non-aromatic heterocyclic group (e.g., azetidinyl, pyrrolidinyl, 1,1-dioxidothiomorpholinyl, 3-oxa-6-azabicyclo[3.1.1]heptyl) optionally substituted by 1 to 5 substituents selected from
   (a) a halogen atom (e.g., a fluorine atom),
   (b) a cyano group,
   (c) a carbamoyl group,
   (d) a C₁₋₆ alkyl group (e.g., methyl, isopropyl) optionally substituted by 1 to 3 C₁₋₆ alkoxy groups (e.g., methoxy),
   (e) a C₁₋₆ alkoxy group (e.g., methoxy), and
   (f) a C₆₋₁₄ aryl group (e.g., phenyl) optionally substituted by 1 to 3 halogen atoms (e.g., a fluorine atom), or
R¹ is bonded to the atom on Ring A to form, together with Ring A, a spiro ring (e.g., 2,8-diazaspiro[4.5]decane) substituted by oxo and optionally further substituted by 1 to 3 C₁₋₆ alkyl groups (e.g., methyl);
R² is
(1) a C₆₋₁₄ aryl group (e.g., phenyl) optionally substituted by 1 to 3 substituents selected from (a) a halogen atom (e.g., a fluorine atom), and
(b) a C₁₋₆ alkyl group (e.g., methyl), or
(2) a 5- to 12-membered aromatic heterocyclic group (preferably a 5- or 6-membered monocyclic aromatic heterocyclic group (e.g., pyrazolyl, oxazolyl, thiazolyl, thiadiazolyl, pyridyl), a 8- to 12-membered fused aromatic heterocyclic group (e.g., benzothiazolyl)) optionally substituted by 1 to 3 substituents selected from
   (a) a halogen atom (e.g., a chlorine atom, a bromine atom),
   (b) a cyano group,
   (c) a C₁₋₆ alkyl group (e.g., methyl) optionally substituted by 1 to 3 halogen atoms (e.g., a fluorine atom), and
   (d) a C₃₋₈ cycloalkyl group (e.g., cyclopropyl);
X¹ is a carbon atom or a nitrogen atom;
R³ is
(1) a hydrogen atom, or
(2) a halogen atom (e.g., a fluorine atom); and
Ring A is
(1)

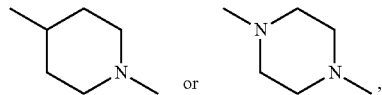

each of which is optionally further substituted by 1 to 3 substituents selected from
   (a) a halogen atom (e.g., a fluorine atom), and
   (b) a C₁₋₆ alkyl group (e.g., methyl), or
(2) a 8-azabicyclo[3.2.1]octane ring or a 2,5-diazabicyclo[2.2.1]heptane ring.
[Compound H-2]
Compound (I) wherein
R¹ is
(1) a C₁₋₆ alkyl group (e.g., methyl, ethyl) optionally substituted by 1 to 3 substituents selected from
   (a) a cyclopropyl group, and
   (b) an indazolyl group,
(2) a C₁₋₆ alkoxy group optionally substituted by 1 to 3 phenyl groups (preferably C₁₋₃ alkoxy group (e.g., methoxy)),
(3) an amino group optionally mono- or di-substituted by substituent(s) selected from
   (a) a C₁₋₆ alkyl group (e.g., methyl, ethyl) optionally substituted by 1 to 3 substituents selected from
      (i) a halogen atom (e.g., a fluorine atom),
      (ii) a phenyl group optionally substituted by 1 to 3 halogen atoms (e.g., a fluorine atom),
      (iii) a pyridyl group, and
      (iv) an oxetanyl group optionally substituted by 1 to 3 C₁₋₆ alkyl groups (e.g., methyl),
   (b) a cyclopropyl group,
   (c) a cyclopentyl group,
   (d) a tetrahydropyranyl group,
   (e) a tetrahydrofuryl group, and
   (f) a phenyl group,
(4) a cyclopropyl group, or
(5) an azetidinyl group, a pyrrolidinyl group, a 1,1-dioxidothiomorpholinyl group or a 3-oxa-6-azabicyclo[3.1.1]heptyl group, each of which is optionally substituted by 1 to 5 substituents selected from
   (a) a halogen atom (e.g., a fluorine atom),
   (b) a cyano group,
   (c) a carbamoyl group, (d) a $C_{1-6}$ alkyl group (e.g., methyl, isopropyl) optionally substituted by 1 to 3 $C_{1-6}$ alkoxy groups (e.g., methoxy),
(e) a $C_{1-6}$ alkoxy group (e.g., methoxy), and
(f) a phenyl group optionally substituted by 1 to 3 halogen atoms (e.g., a fluorine atom), or $R^1$ is bonded to the atom on Ring A to form, together with Ring A, a 2,8-diazaspiro[4.5]decane ring substituted by oxo and optionally further substituted by 1 to 3 $C_{1-6}$ alkyl groups (e.g., methyl);

$R^2$ is
(1) a phenyl group optionally substituted by 1 to 3 substituents selected from
    (a) a halogen atom (e.g., a fluorine atom), and
    (b) a $C_{1-6}$ alkyl group (e.g., methyl), or
(2) a pyrazolyl group, an oxazolyl group, a thiazolyl group, a thiadiazolyl group, a pyridyl group or a benzothiazolyl group, each of which is optionally substituted by 1 to 3 substituents selected from
    (a) a halogen atom (e.g., a chlorine atom, a bromine atom),
    (b) a cyano group,
    (c) a $C_{1-6}$ alkyl group (e.g., methyl) optionally substituted by 1 to 3 halogen atoms (e.g., a fluorine atom), and
    (d) a cyclopropyl group;

$X^1$ is a carbon atom or a nitrogen atom;

$R^3$ is
(1) a hydrogen atom, or
(2) a halogen atom (e.g., a fluorine atom); and Ring A is
(1)

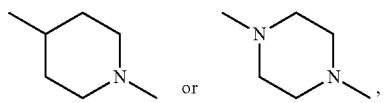

each of which is optionally further substituted by 1 to 3 substituents selected from
    (a) a halogen atom (e.g., a fluorine atom), and
    (b) a $C_{1-6}$ alkyl group (e.g., methyl), or
(2) a 8-azabicyclo[3.2.1]octane ring or a 2,5-diazabicyclo[2.2.1]heptane ring.

[Compound I-1]
Compound (I) wherein
$R^1$ is a 3- to 8-membered monocyclic non-aromatic heterocyclic group (e.g., pyrrolidinyl) optionally substituted by 1 to 5 (preferably 1 to 3) substituents selected from
    (a) a halogen atom (e.g., a fluorine atom),
    (b) a cyano group,
    (c) a carbamoyl group, and
    (d) a $C_{1-6}$ alkyl group (e.g., methyl) optionally substituted by 1 to 3 $C_{1-6}$ alkoxy groups (e.g., methoxy);

$R^2$ is a 5- or 6-membered monocyclic aromatic heterocyclic group (e.g., pyrazolyl, thiazolyl, thiadiazolyl, pyridyl (preferably pyrazolyl, thiadiazolyl, more preferably pyrazolyl)) optionally substituted by 1 to 3 substituents selected from
    (a) a halogen atom (e.g., a chlorine atom), and
    (b) a $C_{1-6}$ alkyl group (e.g., methyl);

$X^1$ is a carbon atom;

$R^3$ is a hydrogen atom; and

Ring A is

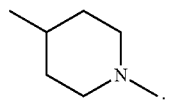

[Compound I-2]
Compound (I) wherein
$R^1$ is a pyrrolidinyl group optionally substituted by 1 to 3 substituents selected from
    (a) a halogen atom (e.g., a fluorine atom),
    (b) a cyano group,
    (c) a carbamoyl group, and
    (d) a $C_{1-6}$ alkyl group (e.g., methyl) optionally substituted by 1 to 3 $C_{1-6}$ alkoxy groups (e.g., methoxy);

$R^2$ is a pyrazolyl group, a thiazolyl group, a thiadiazolyl group or a pyridyl group, each of which is optionally substituted by 1 to 3 substituents selected from
    (a) a halogen atom (e.g., a chlorine atom), and
    (b) a $C_{1-6}$ alkyl group (e.g., methyl);

$X^1$ is a carbon atom;

$R^3$ is a hydrogen atom; and

Ring A is

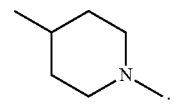

[Compound J-1]
Compound (I) wherein
$R^1$ is a 3- to 8-membered monocyclic non-aromatic heterocyclic group (e.g., pyrrolidinyl) optionally substituted by 1 to 5 substituents selected from
    (a) a halogen atom (e.g., a fluorine atom),
    (b) a cyano group,
    (c) a carbamoyl group,
    (d) a $C_{1-6}$ alkyl group (e.g., methyl) optionally substituted by 1 to 3 $C_{1-6}$ alkoxy groups (e.g., methoxy), and
    (e) a $C_{1-6}$ alkoxy group (e.g., methoxy);

$R^2$ is
(1) a $C_{6-14}$ aryl group (e.g., phenyl) optionally substituted by 1 to 3 substituents selected from
    (a) a halogen atom (e.g., a fluorine atom, a chlorine atom), and
    (b) a $C_{1-6}$ alkyl group (e.g., methyl) optionally substituted by 1 to 3 halogen atoms (e.g., a fluorine atom), or
(2) a 5- or 6-membered monocyclic aromatic heterocyclic group (e.g., pyrazolyl, thiadiazolyl, pyridyl) optionally substituted by 1 to 3 substituents selected from
    (a) a halogen atom (e.g., a chlorine atom), and
    (b) a $C_{1-6}$ alkyl group (e.g., methyl);

$X^1$ is a carbon atom;

$R^3$ is a hydrogen atom; and

Ring A is

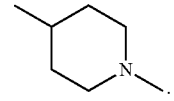

[Compound J-2]
Compound (I) wherein
R¹ is a pyrrolidinyl group optionally substituted by 1 to 5 substituents selected from
(a) a halogen atom (e.g., a fluorine atom),
(b) a cyano group,
(c) a carbamoyl group,
(d) a $C_{1-6}$ alkyl group (e.g., methyl) optionally substituted by 1 to 3 $C_{1-6}$ alkoxy groups (e.g., methoxy), and
(e) a $C_{1-6}$ alkoxy group (e.g., methoxy);
R² is
(1) a phenyl group optionally substituted by 1 to 3 substituents selected from
(a) a halogen atom (e.g., a fluorine atom, a chlorine atom), and
(b) a $C_{1-6}$ alkyl group (e.g., methyl) optionally substituted by 1 to 3 halogen atoms (e.g., a fluorine atom), or
(2) a pyrazolyl group, a thiadiazolyl group or a pyridyl group, each of which is optionally substituted by 1 to 3 substituents selected from
(a) a halogen atom (e.g., a chlorine atom), and
(b) a $C_{1-6}$ alkyl group (e.g., methyl);
X¹ is a carbon atom;
R³ is a hydrogen atom; and
Ring A is

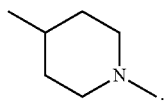

[Compound K-1]
Compound (I) which is selected from
(2R)-1-((1-(4-(4-methyl-1H-pyrazol-1-yl)pyridin-3-yl)piperidin-4-yl)carbonyl)pyrrolidine-2-carbonitrile,
(2R)-1-((1-(4-(4-chloro-1H-pyrazol-1-yl)pyridin-3-yl)piperidin-4-yl)carbonyl)pyrrolidine-2-carbonitrile,
(2R)-4,4-difluoro-1-((1-(4-(4-methyl-1H-pyrazol-1-yl)pyridin-3-yl)piperidin-4-yl)carbonyl)pyrrolidine-2-carbonitrile,
(3-fluoroazetidin-1-yl)(1-(4-(4-fluorophenyl)pyrimidin-5-yl)piperidin-4-yl)methanone,
(1-(4-(4-chloro-1H-pyrazol-1-yl)pyridin-3-yl)piperidin-4-yl)(3-fluoroazetidin-1-yl)methanone,
(1-(4-(4-chloro-1H-pyrazol-1-yl)pyridin-3-yl)piperidin-4-yl)((3S)-3-fluoropyrrolidin-1-yl)methanone,
(1-(4-(4-fluorophenyl)pyrimidin-5-yl)piperidin-4-yl)((3S)-3-fluoropyrrolidin-1-yl)methanone,
N-benzyl-N-(2-fluoroethyl)-4-(4-phenylpyrimidin-5-yl)piperazine-1-carboxamide,
N-(4-fluorobenzyl)-N-(2-fluoroethyl)-4-(4-(4-methyl-1H-pyrazol-1-yl)pyridin-3-yl)piperazine-1-carboxamide,
((3S)-3-fluoropyrrolidin-1-yl)(1-(4-(5-methyl-1,3-thiazol-2-yl)pyridin-3-yl)piperidin-4-yl)methanone,
(3-fluoroazetidin-1-yl)(1-(4-(5-methyl-1,3-thiazol-2-yl)pyridin-3-yl)piperidin-4-yl)methanone,
(1-(4-(4-bromo-1H-pyrazol-1-yl)pyridin-3-yl)piperidin-4-yl)(3-fluoroazetidin-1-yl)methanone, and
(1-(4-(4-cyclopropyl-1H-pyrazol-1-yl)pyridin-3-yl)piperidin-4-yl)(3-fluoroazetidin-1-yl)methanone.
[Compound K-2]
(2R)-1-((1-(4-(4-methyl-1H-pyrazol-1-yl)pyridin-3-yl)piperidin-4-yl)carbonyl)pyrrolidine-2-carbonitrile
[Compound K-3]
(2R)-1-((1-(4-(4-chloro-1H-pyrazol-1-yl)pyridin-3-yl)piperidin-4-yl)carbonyl)pyrrolidine-2-carbonitrile
[Compound K-4]
(2R)-4,4-difluoro-1-((1-(4-(4-methyl-1H-pyrazol-1-yl)pyridin-3-yl)piperidin-4-yl)carbonyl)pyrrolidine-2-carbonitrile When compound (I) is in a form of a salt, examples thereof include metal salts, an ammonium salt, salts with organic base, salts with inorganic acid, salts with organic acid, salts with basic or acidic amino acid, and the like. Preferable examples of the metal salt include alkali metal salts such as sodium salt, potassium salt and the like; alkaline earth metal salts such as calcium salt, magnesium salt, barium salt and the like; an aluminum salt, and the like. Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include salts with hydrochloric acid, hydrobromic acid, nitric acid, sulfuric acid, phosphoric acid and the like. Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include salts with arginine, lysine, ornithine and the like. Preferable examples of the salt with acidic amino acid include salts with aspartic acid, glutamic acid and the like.

Among them, a pharmaceutically acceptable salt is preferable. For example, when a compound has an acidic functional group, examples thereof include inorganic salts such as alkali metal salts (e.g., sodium salt, potassium salt etc.), alkaline earth metal salts (e.g., calcium salt, magnesium salt etc.) and the like, ammonium salt etc., and when a compound has a basic functional group, examples thereof include salts with inorganic acid such as hydrochloric acid, hydrobromic acid, nitric acid, sulfuric acid, phosphoric acid and the like, and salts with organic acid such as acetic acid, phthalic acid, fumaric acid, oxalic acid, tartaric acid, maleic acid, citric acid, succinic acid, methanesulfonic acid, benzenesulfonic acid, p-toluenesulfonic acid and the like.

[Production Method]

The compound of the present invention and the starting compounds can be produced by a method known per se, for example, by method shown in the following scheme and the like. In the following, the "room temperature" generally means 0-40° C. and, unless otherwise specified, each symbol in the chemical formulas described in the schemes is as defined above. In the formulas, each compound includes salts, and examples of such salt include those similar to the salts of the compound of the present invention and the like. The compound obtained in each step can be used directly as the reaction mixture or as a crude product for the next reaction. It can also be isolated from a reaction mixture by a conventional method, and can be easily purified by a separation means such as recrystallization, distillation, chromatography and the like. When the compound in the formula is commercially available, a commercially available product can also be used directly. When each ring in the formula (I) has a substituent, the corresponding precursor also has a similar substituent.

When the starting compound has an amino group, a carboxyl group, a hydroxy group or a heterocyclic group, these groups may be protected by a protecting group generally used in peptide chemistry and the like. By removing the protecting group as necessary after the reaction, the objective compound can be obtained. The protection and deprotection can be performed according to a method known per se, for example, the method described in "Protective Groups in Organic Synthesis, 3rd Ed", John Wiley and Sons, Inc. (1999) (Theodora W. Greene, Peter G. M. Wuts). Preferable examples of the protecting group include a tert-butylcarbamate group, a benzylcarbamate group, a benzyl group, a methyl group, an ethyl group, a tert-butyl and the like.

Examples of the "leaving group" for $LG^1$ to $LG^3$ include a halogen atom (e.g., a fluorine atom, a chlorine atom, a bromine atom, an iodine atom etc.), $C_{1-6}$ alkylsulfonyloxy (e.g., methanesulfonyloxy, ethanesulfonyloxy, trifluoromethanesulfonyloxy etc.), $C_{1-6}$ alkylsulfonyl (e.g., methanesulfonyl, ethanesulfonyl etc.) and the like. In addition, a substituent capable of converting to a leaving group is encompassed in $LG^1$-$LG^3$, and it can be converted to a leaving group according to a reaction known per se in a desired step. For example, when $LG^1$-$LG^3$ is a methylsulfanyl group, it is converted to a methanesulfonyl group by oxidation reaction.

The following each step can be performed without solvent, or by dissolving or suspending starting material compound in a suitable solvent prior to the reaction. In this case, solvent may be used alone, or two or more kinds of these solvents may be mixed in an appropriate ratio and used. Specific examples of the solvent used for the production method of the compound of the present invention include the followings.

alcohols: methanol, ethanol, 1-propanol, 2-propanol, tert-butyl alcohol, tert-amyl alcohol, 2-methoxyethanol etc.
ethers: diethyl ether, diisopropyl ether, diphenyl ether, tetrahydrofuran, 1,4-dioxane, 1,2-dimethoxyethane etc.
aromatic hydrocarbons: benzene, chlorobenzene, toluene, xylene etc.
saturated hydrocarbons: cyclohexane, hexane etc.
amides: N,N-dimethylformamide, N,N-dimethylacetamide, hexamethylphosphoric triamide, N-methylpyrrolidone etc.
halogenated hydrocarbons: dichloromethane, chloroform, carbon tetrachloride, 1,2-dichloroethane etc.
nitriles: acetonitrile, propionitrile etc.
sulfoxides: dimethylsulfoxide etc.
organic bases: triethylamine, pyridine, lutidine etc.
acid anhydrides: acetic anhydride etc.
organic acids: formic acid, acetic acid, propionic acid, trifluoroacetic acid, methanesulfonic acid etc.
inorganic acids: hydrochloric acid, sulfuric acid etc.
esters: methyl acetate, ethyl acetate, butyl acetate etc.
ketones: acetone, methyl ethyl ketone etc.
water Specific examples of the base or acid scavenger used for the production method of the compound of the present invention include the followings.

inorganic bases: sodium hydroxide, potassium hydroxide, magnesium hydroxide etc.
basic salts: sodium carbonate, potassium carbonate, cesium carbonate, calcium carbonate, sodium hydrogen carbonate etc.
organic bases: triethylamine, diisopropylethylamine, tributylamine, cyclohexyldimethylamine, pyridine, lutidine, 4-dimethylaminopyridine, N,N-dimethylaniline, N-methylpiperidine, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene, imidazole etc.
metal alkoxides: sodium methoxide, sodium ethoxide, potassium tert-butoxide etc.
alkali metal hydrides: sodium hydride, potassium hydride etc.
metal amides: sodium amide, lithiumdiisopropylamide, lithiumhexamethyldisilazide etc.
organic lithium reagents: methyllithium, n-butyllithium, sec-butyllithium, tert-butyllithium etc.

Specific examples of the acid or acid catalyst used for the production method of the compound of the present invention include the followings.

inorganic acids: hydrochloric acid, sulfuric acid, nitric acid, hydrobromic acid, phosphoric acid etc.
organic acids: acetic acid, trifluoroacetic acid, oxalic acid, phthalic acid, fumaric acid, tartaric acid, maleic acid, citric acid, succinic acid, methanesulfonic acid, p-toluenesulfonic acid, 10-camphorsulfonic acid etc.
Lewis acid: boron trifluoride ether complex, zinc iodide, anhydrous aluminum chloride, anhydrous zinc chloride, anhydrous iron chloride etc.

Compound (I) can be produced according to Production Method A.

Unless otherwise specified, each symbol in the general formulas in the schemes is as defined above. Each $R^a$ is a hydrogen atom or an optionally substituted $C_{1-6}$ alkyl group. When each $R^a$ is an optionally substituted $C_{1-6}$ alkyl group, two $R^a$ in combination optionally form a ring such as 4,4,5,5-tetramethyl-1,3,2-dioxaborolane and the like. $R^4$ is an optionally substituted hydrocarbon group, an optionally substituted heterocyclic group or a hydrogen atom. $X^2$ is an optionally substituted carbon atom or a nitrogen atom.

$X^3$ is an oxygen atom or a sulfur atom.

Examples of the "optionally substituted $C_{1-6}$ alkyl group" for $R^a$ include those similar to the "optionally substituted $C_{1-6}$ alkyl group" for $R^1$.

Examples of the "optionally substituted hydrocarbon group" and the "optionally substituted heterocyclic group" for $R^4$ include those similar to the "optionally substituted hydrocarbon group" and "optionally substituted heterocyclic group" for $R^A$, $R^{A\prime}$ or $R^{B\prime}$.

Examples of the substituent of the "optionally substituted carbon atom" for $X^2$ include those similar to the substituent of the "optionally substituted aromatic heterocyclic group" for $R^2$.

[Production Method A]

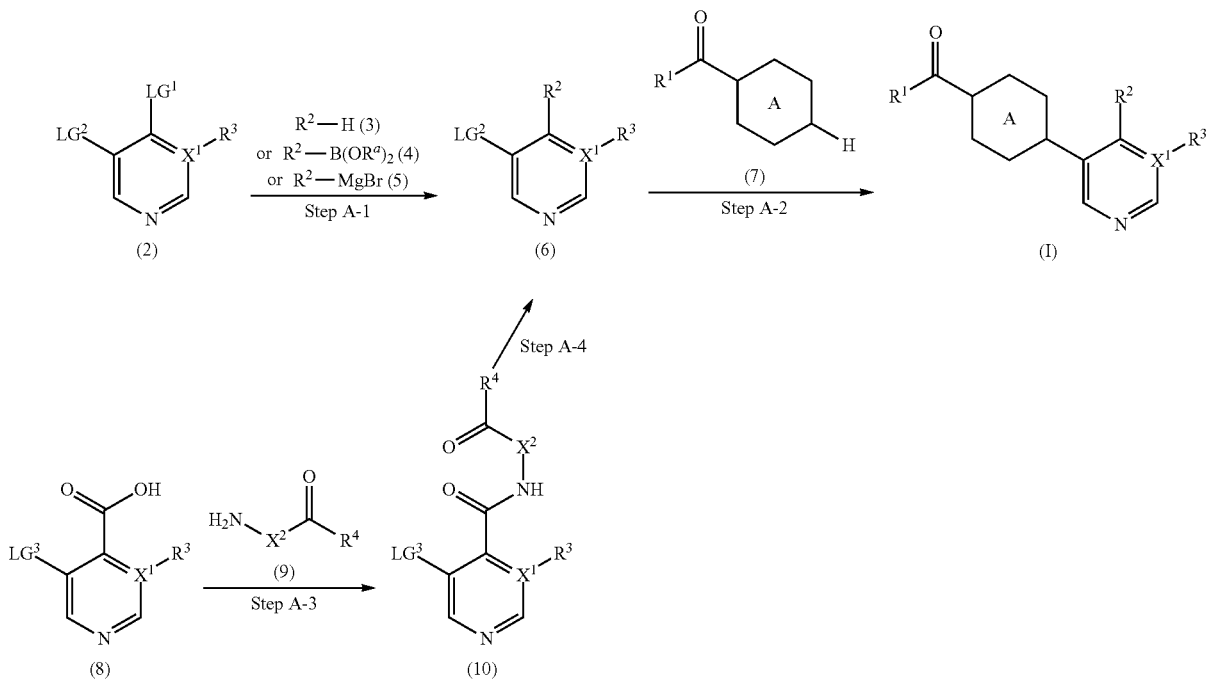

(Step A-1)

Compound (6) can be produced by reacting compound (2) with compound (3), or compound (2) with compound (4), or compound (2) with compound (5). The reaction is carried out using compound (2) and compound (3), or compound (2) and compound (4), or compound (2) and compound (5) in the presence of an acid catalyst, a base or a metal catalyst. Examples of the acid catalyst include organic acids and the like. The acid catalyst is used in an amount of about 0.05 to 2 mol per 1 mol of compound (2). Examples of the base include basic salts, organic bases, alkali metal hydrides, organic lithium reagents and the like. The base is used in an amount of about 1 to 20 mol per 1 mol of compound (2). Examples of the metal catalyst include palladium compounds [e.g.: palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), [1,1-bis(diphenylphosphino)ferrocene]dichloropalladium(II), a complex of palladium(II) acetate and 1,1'-bis(diphenylphosphino)ferrocene, and the like], copper compounds [e.g.: copper(I) iodide, copper(I) bromide and the like] and the like. The metal catalyst is used in an amount of about 0.000001 to 10 mol per 1 mol of compound (2). The metal catalyst can be used together with a phosphine ligand [e.g.: triphenylphosphine, 4,5-bis(diphenylphosphino)-9,9-dimethylxanthene, tri-tert-butylphosphine, tri-tert-butylphosphine tetrafluoroborate and the like] or an amine ligand [e.g.: 8-methylquinolin-1-ol, 1,10-phenanthroline, 1,2-diaminocyclohexane, N,N'-dimethyl-1,2-ethanediamine and the like]. The phosphine ligand or amine ligand is used in an amount of about 0.01 to 5 mol per 1 mol of compound (2). Compound (3), compound (4) or compound (5) is used in an amount of about 0.8 to 10 mol per 1 mol of compound (2). When the reaction is carried out using a metal catalyst, the reaction is preferably carried out in the presence of a base. Examples of the base include inorganic bases, basic salts and the like. The base is used in an amount of about 1 to 20 mol per 1 mol of compound (2). When the reaction is carried out using a metal catalyst unstable to oxygen, for example, the reaction is preferably carried out under inert gas such as argon gas, nitrogen gas and the like. This reaction is advantageously carried out in a solvent inert to the reaction. The solvent is not particularly limited as long as the reaction proceeds. Preferable examples thereof include alcohols, ethers, aromatic hydrocarbons, saturated hydrocarbons, amides, halogenated hydrocarbons, nitriles, esters, sulfoxides, water, mixed solvents thereof and the like. While the reaction time varies depending on the kind of the reagent and solvent to be used, it is generally 1 min to 200 hr. The reaction temperature is preferably 0 to 200° C. In addition, microwave may be irradiated to promote the reaction. Compound (2), compound (3), compound (4) and compound (5) may be a commercially available product, or can also be produced according to a method known per se or a method analogous thereto.

(Step A-2)

Compound (I) can be produced by reacting compound (6) with compound (7). The reaction is carried out in the same manner as in the method in Step A-1. Compound (7) may be a commercially available product, or can also be produced according to a method known per se or a method analogous thereto.

Compound (6) wherein $R^2$ is

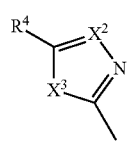

can also be produced from compound (B) according to a sequence reaction step of Step A-3 to Step A-4.

(Step A-3)

Compound (10) can be produced by subjecting compound (8) to condensation with compound (9). The condensation reaction is carried out by reacting compound (8) or a reactive derivative thereof with compound (9). Examples of the reactive derivative include acid halides such as acid chlorides, acid bromides and the like; acid amides with pyrazole, imidazole, benzotriazole and the like; mixed anhydride with acetic acid, propionic acid, butyric acid and the like; acid azides; activated esters such as diethoxyphosphoric acid ester, diphenoxyphosphoric acid ester, p-nitrophenyl ester, 2,4-dinitrophenyl ester, cyanomethyl ester, pentachlorophenyl ester, an ester with N-hydroxysuccinimide, an ester with N-hydroxyphthalimide, an ester with 1-hydroxybenzotriazole, an ester with 6-chloro-1-hydroxybenzotriazole, an ester with 1-hydroxy-1H-2-pyridone, and the like; activated thio esters such as 2-pyridylthio ester, 2-benzothiazolylthio ester and the like, and the like. Alternatively, instead of use of the reactive derivative, compound (8) may be directly reacted with compound (9) in the presence of a suitable condensing agent. Examples of the condensing agent include N,N'-disubstituted carbodiimides such as N,N'-dicyclohexyl carbodiimide, 1-ethyl-3-(3-dimethylaminopropyl)carbodiimide (WSC) hydrochloride and the like; azolides such as N,N'-carbonyldiimidazole and the like; dehydrating agents such as N-ethoxycarbonyl-2-ethoxy-1,2-dihydroquinoline, phosphorus oxychloride, alkoxy acetylene and the like; 2-halogeno pyridinium salts such as 2-chloromethylpyridinium iodide, 2-fluoro-1-methylpyridinium iodide and the like; phosphorylcyanides such as diethylphosphorylcyanide and the like; 2-(7-azabenzotriazol-1-yl)-1,1,3,3-tetramethyluroniumhexafluorophosphate (HATU), O-(7-azabenzotriazole-1-yl)-N,N,N',N'-tetramethyluroniumtetrafluoroborate (TATU) and the like. The reaction is considered to proceed via a reactive derivative of compound (8) by using a condensing agent. Compound (9) is generally used in an amount of about 0.8 to 5 mol per 1 mol of compound (8) or a reactive derivative thereof. This reaction is advantageously carried out in a solvent inert to the reaction. The solvent is not particularly limited as long as the reaction proceeds. Preferable examples thereof include ethers, aromatic hydrocarbons, saturated hydrocarbons, amides, halogenated hydrocarbons, nitriles, sulfoxides, aromatic organic bases, mixed solvent thereof and the like. In addition, when an acidic substance is generated due to the reaction, the reaction can be carried out in the presence of an acid scavenger to remove the acidic substance from the reaction system. Examples of the acid scavenger include basic salts, organic bases and the like. In addition, for example, basic salts, organic bases and the like can also be used to promote the reaction. While the reaction time varies depending on the kind of the reagent and solvent to be used, it is generally 1 min to 72 hr. The reaction temperature is preferably 0 to 100° C. Compound (8) and compound (9) may be a commercially available product, or can also be produced according to a method known per se or a method analogous thereto.

(Step A-4)

Compound (6) can be produced by treating compound (10) with an acid or a dehydrating agent. Examples of the acid include organic acids, inorganic acids and the like. The acid is used in an amount of about 1 to 50 mol per 1 mol of compound (10). Examples of the dehydrating agent include phosphorus oxychloride, methyl carbamate-N-(triethylammonium sulfonyl) (Burgess reagent) and the like. The dehydrating agent is used in an amount of about 1 to 10 mol per 1 mol of compound (10). Where desired, the reaction can also be carried out in the presence of a sulfidizing agent. Examples of the sulfidizing agent include 2,4-bis(4-methoxyphenyl)-1,3,2,4-dithiadiphosphetane-2,4-disulfide (Lawesson's reagent) and the like. The sulfidizing agent is used in an amount of about 1 to 10 mol per 1 mol of compound (10). This reaction is advantageously carried out in a solvent inert to the reaction. The solvent is not particularly limited as long as the reaction proceeds. Preferable examples thereof include ethers, aromatic hydrocarbons, saturated hydrocarbons, amides, halogenated hydrocarbons, nitriles, sulfoxides, aromatic organic bases, mixed solvent thereof and the like. In addition, when an acidic substance is generated due to the reaction, the reaction can be carried out in the presence of an acid scavenger to remove the acidic substance from the reaction system. Examples of the acid scavenger include basic salts, organic bases and the like. In addition, for example, basic salts, organic bases and the like can also be used to promote the reaction. While the reaction time varies depending on the kind of the reagent and solvent to be used, it is generally 1 min to 72 hr. The reaction temperature is preferably 0 to 150° C.

In compound (I), for example, compound (Ic) can also be produced from compound (Ia) according to Production Method B explained below. In addition, in compound (I), for example, compound (Ie) can also be produced from compound (Id) according to Production Method B explained below.

$R^5$ and $R^8$ are each an optionally substituted hydrocarbon group.

$R^6$ and $R^7$ are each a hydrogen atom, a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-14}$ aralkyl group, a $C_{8-13}$ arylalkenyl group or a heterocyclic group (e.g., an aromatic heterocyclic group, a non-aromatic heterocyclic group), each of which is optionally substituted, or acyl group, or $R^6$ and $R^7$ in combination an optionally form an optionally substituted heterocyclic group.

$A^1$ is an optionally further substituted and optionally bridged piperidine ring, and $A^2$ is an optionally further substituted and optionally bridged piperazine ring.

Ring $A^1$ and Ring $A^2$ optionally have 1 to 5 (preferably 1 to 3) substituents at substitutable position(s). Examples of the substituent include substituents selected from the above-mentioned Substituent Group B. When the number of the substituents is plural, the respective substituents may be the same or different.

Examples of the "bridged piperidine ring and bridged piperazine ring" include 8-azabicyclo[3.2.1]octane, 2,5-diazabicyclo[2.2.1]heptane, 3-azabicyclo[3.1.0]hexane and the like.

Examples of the "optionally substituted hydrocarbon group" for $R^5$ or $R^8$ include those similar to the "optionally substituted hydrocarbon group" for $R^A$, $R^{A'}$ or $R^{B'}$.

Examples of the "optionally substituted hydrocarbon group" and "optionally substituted heterocyclic group" for $R^6$ or $R^7$ include those similar to the "optionally substituted hydrocarbon group" and "optionally substituted heterocyclic group" for $R^A$, $R^{A'}$ or $R^{B'}$.

Examples of the "optionally substituted heterocyclic group" formed by $R^6$ and $R^7$ in combination include those similar to the "optionally substituted heterocyclic group" for $R^A$, $R^{A'}$ or $R^{B'}$.

[Production Method B]

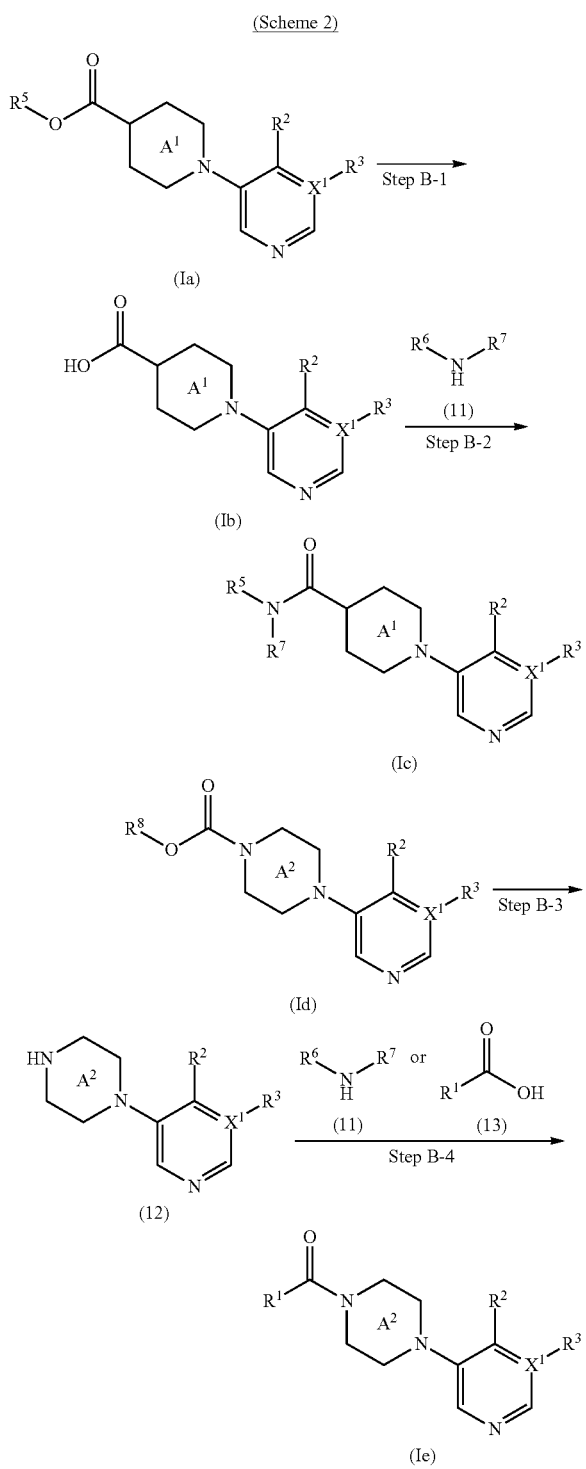

(Scheme 2)

(Step B-1)

Compound (Ib) can be produced by subjecting compound (Ia) to hydrolysis. The hydrolysis reaction can be carried out using an inorganic base or an inorganic acid, under a reaction condition generally used for a hydrolysis reaction. It can be carried out according to a method known per se, for example, the method described in "Protective Groups in Organic Synthesis, 3rd Ed", Wiley-Interscience (1999) (Theodora W. Greene, Peter G. M. Wuts), or the like.

(Step B-2)

Compound (Ic) can be produced by subjecting compound (Ib) to condensation with compound (11). The reaction is carried out in the same manner as in the method in Step A-3. Compound (11) may be a commercially available product, or can also be produced according to a method known per se or a method analogous thereto.

(Step B-3)

Compound (12) can be produced by removing the carbamate group of compound (Id). The removal of the carbamate group can be carried out according to a method known per se, for example, the method described in "Protective Groups in Organic Synthesis, 3rd Ed", Wiley-Interscience (1999) (Theodora W. Greene, Peter G. M. Wuts), or the like.

(Step B-4)

Compound (Ie) can be produced by subjecting compound (12) to condensation with compound (11) ($R^1$=N($R^6$)($R^7$)) or compound (13).

When compound (12) is condensed with compound (13), the reaction is carried out in the same manner as in the method in Step A-3.

When compound (12) is condensed with compound (11), the reaction is carried out by reacting the reactive derivative of compound (12) with compound (11), by directly reacting compound (12) with compound (11) in the presence of a suitable condensing agent, or the like. Examples of the reactive derivative include carboxamide with imidazole and the like, and the like. Examples of the condensing agent include phosgenes such as phosgene, triphosgene and the like, azolides such as N,N'-carbonyldiimidazole and the like, and the like. The reaction is considered to proceed via a reactive derivative of compound (12) by using a condensing agent. Compound (11) is generally used in an amount of about 0.8 to 5 mol per 1 mol of compound (12) or a reactive derivative thereof. This reaction is advantageously carried out in a solvent inert to the reaction. The solvent is not particularly limited as long as the reaction proceeds. Preferable examples thereof include ethers, aromatic hydrocarbons, saturated hydrocarbons, amides, halogenated hydrocarbons, nitriles, sulfoxides, aromatic organic bases, mixed solvent thereof and the like. In addition, when an acidic substance is generated due to the reaction, the reaction can be carried out in the presence of an acid scavenger to remove the acidic substance from the reaction system. Examples of the acid scavenger include basic salts, organic bases and the like. In addition, for example, basic salts, organic bases and the like can also be used to promote the reaction. While the reaction time varies depending on the kind of the reagent and solvent to be used, it is generally 1 min to 72 hr. The reaction temperature is preferably 0 to 100° C. Compound (13) may be a commercially available product, or can also be produced according to a method known per se or a method analogous thereto.

The starting compound and/or the production intermediate for the compound (I) may form a salt. While the salt is not particularly limited as long as the reaction can be performed, examples thereof include those similar to the salts optionally formed by the compound (I) and the like, and the like.

As for the configuration isomers (E, Z forms) of compound (I), they can be isolated and purified when isomerization occurs, for example, according to a conventional separation means such as extraction, recrystallization, distillation, chromatography and the like to obtain a pure compound. In addition, the corresponding pure isomer can be obtained by isomerizing a double bond using heating, an acid catalyst, a transition metal complex, a metal catalyst, a radical catalyst, light irradiation or a strong base catalyst and the like, according to the method described in Jikken Kagaku Kouza (Courses in Experimental Chemistry) 14 (The Chemical Society of Japan ed.), pages 251 to 253, 4th Edition Jikken Kagaku Kouza 19 (The Chemical Society of Japan ed.), pages 273 to 274 or a method analogous thereto.

Compound (I) contains a stereoisomer depending to the kind of a substituent, and each stereoisomer and a mixture thereof are encompassed in the present invention.

Compound (I) may be a hydrate or a non-hydrate.

When desired, compound (I) can be synthesized by performing deprotection reaction, acylation reaction, alkylation reaction, hydrogenation reaction, oxidation reaction, reduction reaction, reaction of carbon chain extension, substituent exchange reaction singly or two or more thereof in combination.

When the objective product is obtained as a free form by the above-mentioned reaction, it can be converted to a salt according to a conventional method, or when the objective product is obtained as a salt, it can be converted to a free form or other salt according to a conventional method. The thus-obtained compound (I) can also be isolated and purified from a reaction mixture according to a known method such as phase transfer, concentration, solvent extraction, distillation, crystallization, recrystallization, chromatography and the like.

When compound (I) contains a configurational isomer, a diastereomer, a conformer and the like, each can be isolated according to the above-mentioned separation and purification methods, if desired. In addition, when compound (I) is recemic, d-form and l-form can be isolated according to a conventional optical resolution.

In each of the above-mentioned reactions, when the compound has a functional group such as an amino group, a hydroxy group or a carboxyl group, the reaction can be carried out after a protecting group generally used in peptide chemistry and the like is introduced into these groups. By removing the protecting group as necessary after the reaction, the objective compound can be obtained.

Examples of the protecting group include formyl, $C_{1-6}$ alkyl-carbonyl (e.g., acetyl, propionyl etc.), phenylcarbonyl, $C_{1-6}$ alkoxy-carbonyl (e.g., methoxycarbonyl, ethoxycarbonyl etc.), phenyloxycarbonyl, $C_{7-10}$ aralkyloxy-carbonyl (e.g., benzyloxycarbonyl etc.), trityl, phthaloyl and the like, each of which is optionally substituted. Examples of the substituent include a halogen atom (e.g., fluorine, chlorine, bromine, iodine etc.), $C_{1-6}$ alkyl-carbonyl (e.g., acetyl, propionyl, valeryl etc.), nitro and the like. The number of substituents is, for example, 1 to 3.

The removal method of the protecting group can be carried out according to a method known per se, and for example, a method using acid, base, ultraviolet rays, hydrazine, phenylhydrazine, sodium N-methyldithiocarbamate, tetrabutylammonium fluoride, palladium acetate and the like, a reduction method, and the like can be employed.

The thus-obtained compound (I), other reaction intermediate therefor and starting compounds thereof can be isolated and purified from a reaction mixture according to a method known per se, for example, extraction, concentration, neutralization, filtration, distillation, recrystallization, column chromatography, thin layer chromatography, preparative high performance liquid chromatography (preparative HPLC), moderate-pressure preparative liquid chromatography (moderate-pressure preparative LC) and the like.

A salt of compound (I) can be produced according to a method known per se. For example, when compound (I) is a basic compound, it can be produced by adding an inorganic acid or organic acid, or when compound (I) is an acidic compound, by adding an organic base or inorganic base.

When compound (I) contains an optical isomer, each optical isomer and a mixture thereof are encompassed in the scope of the present invention, and these isomers can be subjected to optical resolution or can be produced respectively, according to a method known per se, if desired.

When compound (I) contains a configurational isomer, a diastereomer, a conformer and the like, each can be isolated according to the above-mentioned separation and purification methods, if desired. In addition, when compound (I) is recemic, S-form and R-form can be isolated according to a conventional optical resolution.

When compound (I) contains a stereoisomer, each isomer and a mixture thereof are encompassed in the present invention.

Compound (I) may be a prodrug, and the prodrug of compound (I) refers to a compound which is converted to compound (I) as a result of a reaction with an enzyme, gastric acid, etc. under physiological conditions in vivo, thus a compound that undergoes enzymatic oxidation, reduction, hydrolysis etc. to convert to compound (I) and a compound that undergoes hydrolysis and the like by gastric acid, etc. to convert to compound (I).

Examples of the prodrug for compound (I) include
(1) a compound obtained by subjecting an amino group in compound (I) to acylation, alkylation or phosphorylation (e.g., a compound obtained by subjecting an amino group in compound (I) to eicosanoylation, alanylation, pentylaminocarbonylation, (5-methyl-2-oxo-1,3-dioxolen-4-yl)methoxycarbonylation, tetrahydrofurylation, pyrrolidylmethylation, pivaloyloxymethylation, tert-butylation, ethoxycarbonylation, tert-butoxycarbonylation, acetylation, cyclopropylcarbonylation and the like);
(2) a compound obtained by subjecting a hydroxy group in compound (I) to acylation, alkylation, phosphorylation or boration (e.g., a compound obtained by subjecting a hydroxy group in compound (I) to acetylation, palmitoylation, propanoylation, pivaloylation, succinylation, fumarylation, alanylation or dimethylaminomethylcarbonylation and the like);
(3) a compound obtained by subjecting a carboxyl group in compound (I) to esterification or amidation (e.g., a compound obtained by subjecting a carboxyl group in compound (I) to ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation and the like) and the like. Any of these compounds can be produced from compound (I) according to a method known per se.

A prodrug of compound (I) may also be one which is converted to compound (I) under physiological conditions as described in "IYAKUHIN no KAIHATSU (Development of Pharmaceuticals)", Vol. 7, Design of Molecules, p. 163-198, Published by HIROKAWA SHOTEN (1990).

In the present specification, compound (I) and a prodrug thereof are sometimes collectively abbreviated as "the compound of the present invention".

When compound (I) has isomers such as optical isomer, stereoisomer, positional isomer, rotamer and the like, such isomers and a mixture thereof are also encompassed in compound (I). For example, when compound (I) has optical isomers, an optical isomer resolved from this compound is also encompassed in compound (I). These isomers can be obtained as a single product according to synthesis methods or separation methods known per se (e.g., concentration, solvent extraction, column chromatography, recrystallization, etc.).

Compound (I) may be a crystal, and a single crystal form and a mixture of crystal forms are both encompassed in compound (I). The crystal can be produced by crystallizing according to a crystallization method known per se.

Compound (I) may be a hydrate, a non-hydrate, a solvate or a non-solvate.

Compound (I) may be labeled with an isotope (e.g., $^{3}$H, $^{11}$C, $^{14}$C, $^{18}$F, $^{35}$S, $^{125}$I etc.) and the like.

Compound (I) also encompasses a deuterium conversion form wherein $^{1}$H is converted to $^{2}$H(D).

Compound (I) may be a pharmaceutically acceptable cocrystal or a salt thereof. The cocrystal or a salt thereof means a crystalline substance constituted with two or more special solids at room temperature, each having different physical properties (e.g., structure, melting point, melting heat, hygroscopicity, solubility and stability etc.). The cocrystal or a salt thereof can be produced according to a cocrystallization a method known per se.

Compound (I) may also be used as a PET tracer.

The compound of the present invention has low toxicity, and can be used as it is or in the form of a pharmaceutical composition by mixing with a pharmacologically acceptable carrier etc. to mammals (e.g., human, mouse, rat, rabbit, dog, cat, bovine, horse, swine, monkey) as an agent for the prophylaxis or treatment of various diseases mentioned below.

As pharmacologically acceptable carriers, various organic or inorganic carrier substances conventionally used as preparation materials can be used. These are incorporated as excipient, lubricant, binder and disintegrant for solid preparations, or solvent, solubilizing agent, suspending agent, isotonicity agent, buffer and soothing agent for liquid preparations, and the like, and preparation additives such as preservative, antioxidant, colorant, sweetening agent and the like can be added as necessary.

Preferable examples of the excipient include lactose, sucrose, D-mannitol, D-sorbitol, starch, gelatinated starch, dextrin, crystalline cellulose, low-substituted hydroxypropylcellulose, sodium carboxymethylcellulose, gum arabic, pullulan, light anhydrous silicic acid, synthesis aluminum silicate and magnesium alumino metasilicate.

Preferable examples of the lubricant include magnesium stearate, calcium stearate, talc and colloidal silica.

Preferable examples of the binder include gelatinated starch, sucrose, gelatin, gum arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose and polyvinylpyrrolidone.

Preferable examples of the disintegrant include lactose, sucrose, starch, carboxymethylcellulose, calcium carboxymethylcellulose, croscarmellose sodium, sodium carboxymethyl starch, light anhydrous silicic acid and low-substituted hydroxypropylcellulose.

Preferable examples of the solvent include water for injection, physiological brine, Ringer's solution, alcohol, propylene glycol, polyethylene glycol, sesame oil, corn oil, olive oil and cottonseed oil.

Preferable examples of the solubilizing agents include polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate.

Preferable examples of the suspending agent include surfactants such as stearyltriethanolamine, sodium lauryl sulfate, lauryl aminopropionate, lecithin, benzalkonium chloride, benzethonium chloride, glycerol monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like; polysorbates, and polyoxyethylene hydrogenated castor oil.

Preferable examples of the isotonicity agent include sodium chloride, glycerol, D-mannitol, D-sorbitol and glucose.

Preferable examples of the buffer include buffers such as phosphate, acetate, carbonate, citrate and the like.

Preferable examples of the soothing agent include benzyl alcohol.

Preferable examples of the preservative include p-oxybenzoates, chlorobutanol, benzyl alcohol, phenethyl alcohol, dehydroacetic acid and sorbic acid.

Preferable examples of the antioxidant include sulfite and ascorbate.

Preferable examples of the colorant include aqueous water-soluble food tar colors (e.g., food colors such as Food Color Red Nos. 2 and 3, Food Color Yellow Nos. 4 and 5, Food Color Blue Nos. 1 and 2 and the like), water insoluble lake dyes (e.g., aluminum salt of the above-mentioned water-soluble food tar color) and natural dyes (e.g., β-carotene, chlorophyll, ferric oxide red).

Preferable examples of the sweetening agent include saccharin sodium, dipotassium glycyrrhizinate, aspartame and stevia.

Examples of the dosage form of the pharmaceutical composition include oral preparations such as tablet (including sugar-coated tablet, film-coated tablet, sublingual tablet, orally disintegrating tablet), capsules (including soft capsule, microcapsule), granule, powder, troche, syrup, emulsion, suspension, films (e.g., orally disintegrable films) and the like; and parenteral agents such as injection (e.g., subcutaneous injection, intravenous injection, intramuscular injection, intraperitoneal injection, drip infusion), external preparations (e.g., dermal preparation, ointment), suppository (e.g., rectal suppository, vaginal suppository), pellet, nasal preparation, pulmonary preparation (inhalant), eye drop and the like.

These can be respectively safely administered orally or parenterally (e.g., topically, rectally, intravenously administered).

These preparations may be a release control preparation (e.g., sustained-release microcapsule) such as an immediate-release preparation, a sustained-release preparation and the like.

The pharmaceutical composition can be produced according to a method conventionally used in the field of pharmaceutical formulation, for example, the method described in the Japanese Pharmacopoeia, and the like.

While the content of the compound of the present invention in the pharmaceutical composition varies depending on the dosage form, dose of the compound of the present invention and the like, it is for example, about 0.1 to 100 wt %.

During production of an oral preparation, coating may be applied as necessary for the purpose of masking of taste, enteric property or durability.

Examples of the coating base to be used for coating include sugar coating base, water-soluble film coating base, enteric film coating base and sustained-release film coating base.

As the sugar coating base, sucrose is used. Moreover, one or more kinds selected from talc, precipitated calcium carbonate, gelatin, gum arabic, pullulan, carnauba wax and the like may be used in combination.

Examples of the water-soluble film coating base include cellulose polymers such as hydroxypropyl cellulose, hydroxypropylmethyl cellulose, hydroxyethyl cellulose, methylhydroxyethyl cellulose etc.; synthetic polymers such as polyvinylacetal diethylaminoacetate, aminoalkyl methacrylate copolymer E [Eudragit E (trade name)], polyvinylpyrrolidone etc.; and polysaccharides such as pullulan etc.

Examples of the enteric film coating base include cellulose polymers such as hydroxypropylmethyl cellulose phthalate, hydroxypropylmethyl cellulose acetate succinate, carboxymethylethyl cellulose, cellulose acetate phthalate etc.; acrylic polymers such as methacrylic acid copolymer L [Eudragit L (trade name)], methacrylic acid copolymer LD [Eudragit L-30D55 (trade name)], methacrylic acid copolymer S [Eudragit S (trade name)] etc.; and naturally occurring substances such as shellac etc.

Examples of the sustained-release film coating base include cellulose polymers such as ethyl cellulose etc.; and acrylic polymers such as aminoalkyl methacrylate copolymer RS [Eudragit RS (trade name)], ethyl acrylate-methyl methacrylate copolymer suspension [Eudragit NE (trade name)] etc.

The above-mentioned coating bases may be used after mixing with two or more kinds thereof at appropriate ratios. For coating, for example, a light shielding agent such as titanium oxide, red ferric oxide and the like can be used.

The compound of the present invention shows low toxicity (e.g., acute toxicity, chronic toxicity, genetic toxicity, reproductive toxicity, cardiotoxicity, carcinogenicity) and a few side effects. Therefore, it can be used as an agent for the prophylaxis or treatment or a diagnostic of various diseases in a mammal (e.g., human, bovine, horse, dog, cat, monkey, mouse, rat).

The compound of the present invention has a superior CH24H inhibitory action and can suppress nerve cell death, Aβ increase, intracerebral inflammation and the like.

Accordingly, the compound of the present invention is useful for the prophylaxis, improvement of symptoms, suppression of progression or treatment of diseases involving enhanced function of CH24H, for example, neurodegenerative disease.

In the present specification, the "neurodegenerative disease" means a disease associated with denaturation of neural tissues.

Specific examples of the neurodegenerative disease include Alzheimer's disease, mild cognitive impairment, Huntington's disease, Parkinson's disease, multiple sclerosis, amyotrophic lateral sclerosis, traumatic brain injury, cerebral infarction, glaucoma and the like.

In addition, the compound of the present invention is useful for the prophylaxis, improvement of symptoms, suppression of progression or treatment of diseases involving enhanced function of CH24H, for example, epilepsy, schizophrenia, spasm and the like.

The dose of the compound of the present invention varies depending on the administration subject, route of administration, target disease, symptoms, etc. For example, when it is administered orally to an adult patient (body weight 60 kg), its dose is about 0.01 to 100 mg/kg body weight per dose, preferably 0.05 to 30 mg/kg body weight per dose, more preferably 0.1 to 10 mg/kg body weight per dose and this amount is desirably administered in 1 to 3 portions daily.

When the compound of the present invention is applied to each of the above-mentioned diseases, it can be used in an appropriate combination with a medicament or a treatment method generally employed for the disease.

Examples of the medicament (hereinafter to be abbreviated as "concomitant drug") to be used in combination with the compound of the present invention include acetylcholine esterase inhibitors (e.g., donepezil, rivastigmine, galanthamine, zanapezil etc.), antidementia agents (e.g., memantine), inhibitors of β amyloid protein production, secretion, accumulation, coagulation and/or deposition, β secretase inhibitors (e.g., 6-(4-biphenyl)methoxy-2-[2-(N,N-dimethylamino)ethyl]tetralin, 6-(4-biphenyl)methoxy-2-(N,N-dimethylamino)methyltetralin, 6-(4-biphenyl)methoxy-2-(N,N-dipropylamino)methyltetralin, 2-(N,N-dimethylamino)methyl-6-(4'-methoxybiphenyl-4-yl)methoxytetralin, 6-(4-biphenyl)methoxy-2-[2-(N,N-diethylamino)ethyl]tetralin, 2-[2-(N,N-dimethylamino)ethyl]-6-(4'-methylbiphenyl-4-yl)methoxytetralin, 2-[2-(N,N-dimethylamino)ethyl]-6-(4'-methoxybiphenyl-4-yl)methoxytetralin, 6-(2',4'-dimethoxybiphenyl-4-yl)methoxy-2-[2-(N,N-dimethylamino)ethyl] tetralin, 6-[4-(1,3-benzodioxol-5-yl)phenyl]methoxy-2-[2-(N,N-dimethylamino)ethyl]tetralin, 6-(3',4'-dimethoxybiphenyl-4-yl)methoxy-2-[2-(N,N-dimethylamino)ethyl]tetralin, an optically active form thereof, a salt thereof and a hydrate thereof, OM99-2 (WO01/00663)), γ secretase inhibitory agent, β amyloid protein coagulation inhibitory agent (e.g., PTI-00703, ALZHEMED (NC-531), PPI-368 (JP-A-11-514333), PPI-558 (JP-A-2001-500852), SKF-74652 (Biochem. J. (1999), 340(1), 283-289)), β amyloid vaccine, β amyloid degrading enzyme and the like, cerebral function activators (e.g., aniracetam, nicergoline), other therapeutic drug for Parkinson's disease [(e.g., dopamine receptor agonists (e.g., L-DOPA, bromocriptine, pergolide, talipexole, pramipexole, cabergoline, amantadine), a monoamine oxidase (MAO) inhibitors (e.g., deprenyl, Selgiline (selegiline), remacemide, riluzole), anticholinergic agents (e.g., trihexyphenidyl, biperiden), COMT inhibitors (e.g., entacapone)], therapeutic drug for amyotropic lateral sclerosis (e.g., riluzole etc., neurotrophic factor), therapeutic drug for abnormal behavior wandering and the like due to the progress of dementia (e.g., sedative drug, antianxiety drug), apoptosis inhibitors (e.g., CPI-1189, IDN-6556, CEP-1347), neuronal differentiation or regeneration promoters (e.g., leteprinim, xaliproden (SR-57746-A), SB-216763, Y-128, VX-853, prosaptide, 5,6-dimethoxy-2-[2,2,4,6,7-pentamethyl-3-(4-methylphenyl)-2,3-dihydro-1-benzofuran-5-yl]isoindoline, 5,6-dimethoxy-2-[3-(4-isopropylphenyl)-2,2,4,6,7-pentamethyl-2,3-dihydro-1-benzofuran-5-yl]isoindoline, 6-[3-(4-isopropylphenyl)-2,2,4,6,7-pentamethyl-2,3-dihydro-1-benzofuran-5-yl]-6,7-dihydro-5H-[1,3]dioxolo[4,5-f]isoindole and optically active forms, salts and hydrates thereof), antidepressants (e.g., desipramine, amitriptyline, imipramine, tramadol), antiepilepsy drug (e.g., lamotrigine), antianxiety drugs (e.g., benzodiazepine), non-steroidal anti-inflammatory drugs (e.g., meloxicam, tenoxicam, indomethacin, ibuprofen, celecoxib, rofecoxib, aspirin, indomethacin), disease-modifying anti-rheumatic drugs (DMARDs), anti-cytokine drugs (e.g., TNF inhibitor MAP kinase inhibitor), steroidal drugs (e.g., dexamethasone, hexestrol, cortisone acetate), therapeutic agents for incontinence or frequent urination (e.g., flavoxate hydrochloride, oxybutynin hydrochloride, propiverine hydrochloride), phosphodiesterase inhibitors (e.g., sildenafil (citrate)), dopamine agonists (e.g., apomorphine etc.), antiarrhythmics (e.g., mexiletine), sex hormones or derivatives thereof (e.g., progesterone, estradiol, estradiol benzoate), therapeutic agents for osteoporosis (e.g., alfacalcidol, calcitriol, elcatonin, calcitonin salmon, estriol, ipriflavone, disodium pamidronate, sodium alendronate hydrate, disodium incadronate), parathyroid hormone (PTH), calcium receptor antagonists, therapeutic drugs for insomnia (e.g., benzodiazepine medicament, non-benzodiazepine medicament, melatonin agonist), therapeutic drugs for schizophrenia (e.g., typical antipsychotic agents such as haloperidol and the like; atypical antipsychotic agents such as clozapine, olanzapine, risperidone, aripiprazole and the like; medicament acted on metabotropic glutamate receptor or ionic channel-conjugated glutamate receptor; phosphodiesterase inhibitor) and the like.

In addition, a combined use with a transplantation method of neural stem cell or neural precursor cell prepared from embryonic stem cell or nervous tissue, or fetal neural tissue, and a combined use with a pharmaceutical agent such as an immunosuppressant after the transplantation and the like.

Furthermore, the compound of the present invention may be used in combination with the following concomitant drugs.

(1) Therapeutic Agent for Diabetes

For example, insulin preparations (e.g., animal insulin preparation extracted from the pancreas of bovine, swine; human insulin preparation genetically synthesized using *Escherichia coli*, yeast; zinc insulin; protamine zinc insulin; insulin fragment or derivatives (e.g., INS-1), oral insulin preparation), insulin sensitizer (e.g., pioglitazone or a salt thereof (preferably hydrochloride), rosiglitazone or a salt thereof (preferably maleate), Tesaglitazar, Ragaglitazar, Muraglitazar, Edaglitazone, Metaglidasen, Naveglitazar, AMG-131, THR-0921), α-glucosidase inhibitor (e.g., voglibose, acarbose, miglitol, emiglitate), biguanide (e.g., metformin, buformin or a salt thereof (e.g., hydrochloride, fumarate, succinate)), insulin secretagogue [sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or calcium salt hydrate thereof, glucose-dependent insulin secretagogue (e.g., [(3S)-6-({2',6'-dimethyl-4'-[3-(methylsulfonyl)propoxy]biphenyl-3-yl}methoxy)-2,3-dihydro-1-benzofuran-3-yl]acetic acid or a salt thereof)], dipeptidyl peptidase IV inhibitor (e.g., Alogliptin, Vildagliptin, Sitagliptin, Saxagliptin, T-6666, TS-021), β3 agonist (e.g., AJ-9677), GPR40 agonist, GLP-1 receptor agonist [e.g., GLP-1, GLP-1MR agent, NN-2211, AC-2993 (exendin-4), BIM-51077, Aib(8,35)hGLP-1(7,37)NH$_2$, CJC-1131], amylin agonist (e.g., pramlintide), phosphotyrosine phosphatase inhibitors (e.g., sodium vanadate), gluconeogenesis inhibitor (e.g., glycogen phosphorylase inhibitor glucose-6-phosphatase inhibitors, glucagon antagonists), SGLUT (sodium-glucose cotransporter) inhibitor (e.g., T-1095), 11β-hydroxysteroid dehydrogenase inhibitor (e.g., BVT-3498), adiponectin or an agonist thereof, IKK inhibitor (e.g., AS-2868), leptin resistance improving drugs, somatostatin receptor agonists, glucokinase activators (e.g., Ro-28-1675), GIP (Glucose-dependent insulinotropic peptide) and the like.

(2) Therapeutic Agents for Diabetic Complications

For example, aldose reductase inhibitors (e.g., tolrestat, epalrestat, zenarestat, zopolrestat, minalrestat, fidarestat, CT-112), neurotrophic factor and an increasing agent thereof (e.g., NGF, NT-3, BDNF, neurotrophic factors and increasing drugs described in WO01/14372 (e.g., 4-(4-chlorophenyl)-2-(2-methyl-1-imidazolyl)-5-[3-(2-methylphenoxyl)propyl]oxazole)), nerve regeneration promoting agent (e.g., Y-128), PKC inhibitor (e.g., ruboxistaurin mesylate), AGE inhibitor (e.g., ALT946, pimagedine, pyratoxanthine, N-phenacylthiazolium bromide (ALT766), ALT-711, EXO-226, Pyridorin, pyridoxamine), active oxygen scavengers (e.g., thioctic acid), cerebral vasodilator (e.g., tiapuride, mexiletine), somatostatin receptor agonists (e.g., BIM23190), apoptosis signal regulating kinase-1 (ASK-1) inhibitor and the like can be mentioned.

(3) Therapeutic Agent for Hyperlipidemia

For example, statin compound (e.g., pravastatin, simvastatin, lovastatin, atorvastatin, fluvastatin, rosuvastatin, pitavastatin, or a salt thereof (e.g., sodium salt, calcium salt)), squalene synthase inhibitors (e.g., lapaquistat acetate or a salt thereof), fibrate compound (e.g., bezafibrate, clofibrate, simfibrate, clinofibrate), ACAT inhibitor (e.g., Avasimibe, Eflucimibe), anion exchange resin (e.g., colestyramine), probucol, nicotinic acid drug (e.g., nicomol, niceritrol), ethyl icosapentate, phytosterol (e.g., soysterol, gamma oryzanol) and the like.

(4) Antihypertensive Agent

For example, angiotensin converting enzyme inhibitor (e.g., captopril, enalapril, delapril), angiotensin II antagonist (e.g., candesartan cilexetil, losartan, eprosartan, valsartan, telmisartan, irbesartan, tasosartan, 1-[[2'-(2,5-dihydro-5-oxo-4H-1,2,4-oxadiazol-3-yl)biphenyl-4-yl]methyl]-2-ethoxy-1H-benzimidazole-7-carboxylic acid, Azilsartan, Azilsartan medoxomil), calcium antagonist (e.g., manidipine, nifedipine, amlodipine, efonidipine, nicardipine), potassium channel opener (e.g., levcromakalim, L-27152, AL 0671, NIP-121), clonidine and the like.

(5) Antiobesity Agent

For example, central-acting antiobesity agent (e.g., dexfenfluramine, fenfluramine, phentermine, sibutramine, amfepramone, dexamphetamine, mazindol, phenylpropanolamine, clobenzorex; MCH receptor antagonists (e.g., SB-568849; SNAP-7941; compounds described in WO01/82925 and WO01/87834); neuropeptide Y antagonist (e.g., CP-422935); cannabinoid receptor antagonists (e.g., SR-141716, SR-147778); ghrelin antagonist; 11β-hydroxysteroid dehydrogenase inhibitor (e.g., BVT-3498)), pancreatic lipase inhibitors (e.g., orlistat, cetilistat), β3 agonist (e.g., AJ-9677, AZ40140), anorectic peptides (e.g., leptin, CNTF (ciliary neurotrophic factor)), cholecystokinin agonist (e.g., lintitript, FPL-15849), anorexigenic agent (e.g., P-57) and the like.

(6) Diuretic

For example, xanthine derivative (e.g., theobromine sodium salicylate, theobromine calcium salicylate), thiazide preparation (e.g., ethiazide, cyclopenthiazide, trichloromethyazide, hydrochlorothiazide, hydroflumethiazide, benzylhydrochlorothiazide, penflutizide, polythiazide, methyclothiazide), antialdosterone preparation (e.g., spironolactone, triamterene), carbonic anhydrase inhibitors (e.g., acetazolamide), chlorobenzenesulfonamide agent (e.g., chlortalidone, mefruside, indapamide), azosemide, isosorbide, ethacrynic acid, piretanide, bumetanide, furosemide and the like.

(7) Chemotherapeutic Agent

For example, alkylating agents (e.g., cyclophosphamide, ifosfamide), metabolic antagonists (e.g., methotrexate, 5-fluorouracil or derivative thereof), antitumor antibiotics (e.g., mitomycin, adriamycin), plant-derived antitumor agents (e.g., vincristine, vindesine, Taxol), cisplatin, carboplatin, etoposide and the like. Of these, Furtulon and Neo-Furtulon, which are 5-fluorouracil derivatives, and the like are preferable.

(8) Immunotherapeutic Agent

For example, microorganism or bacterial components (e.g., muramyl dipeptide derivative, Picibanil), polysaccharides having immunity potentiating activity (e.g., lentinan, schizophyllan, krestin), cytokines obtained by genetic engineering techniques (e.g., interferon, interleukin (IL)), colony stimulating factors (e.g., granulocyte colony stimulating factor erythropoietin) and the like, with preference given to interleukins such as IL-1, IL-2, IL-12 and the like.

(9) Antithrombotic Agent

For example, heparin (e.g., heparin sodium, heparin calcium, dalteparin sodium), warfarin (e.g., warfarin potassium), anti-thrombin drug (e.g., argatroban), thrombolytic agent (e.g., urokinase, tisokinase, alteplase, nateplase, monteplase, pamiteplase), platelet aggregation inhibitor (e.g., ticlopidine hydrochloride, cilostazol, ethyl icosapentate, beraprost sodium, sarpogrelate hydrochloride) and the like.

(10) Cachexia Improving Medicament

For example, cyclooxygenase inhibitors (e.g., indomethacin etc.) [Cancer Research, Vol. 49, pages 5935-5939, 1989], progesterone derivatives (e.g., megestrol acetate) [Journal of Clinical Oncology, Vol. 12, pages 213-225, 1994], glucosteroids (e.g., dexamethasone etc.), metoclopramide agents, tetrahydrocannabinol agents (publications are all as mentioned above), fat metabolism improving agents (e.g., eicosapentanoic acid etc.) [British Journal of Cancer, Vol. 68, pages 314-318, 1993], growth hormones, IGF-1, or antibodies to a cachexia-inducing factor such as TNF-α, LIF, IL-6, oncostatin M and the like.

Two or more kinds of the above-mentioned concomitant drugs may be used in combination at an appropriate ratio.

It is also possible to apply compound of the present invention to each of the above-mentioned diseases in combination with a biologic (e.g., antibody, vaccine preparation etc.), or as a combination therapy in combination with gene therapy method and the like.

Examples of the antibody and vaccine preparation include vaccine preparation to angiotensin II, vaccine preparation to CETP, CETP antibody, TNFα antibody and antibody to other cytokine, amyloid β vaccine preparation, type 1 diabetes vaccine (e.g., DIAPEP-277 manufactured by Peptor Ltd.), anti-HIV antibody, HIV vaccine preparation and the like, antibody or vaccine preparation to cytokine, renin-angiotensin enzyme and a product thereof, antibody or vaccine preparation to enzyme or protein involved in blood lipid metabolism, antibody or vaccine to enzyme or protein involved in blood coagulation or fibrinolytic system, antibody or vaccine preparation to protein involved in saccharometabolism or insulin resistance and the like.

In addition, a combined use with a biological preparation involved in a growth factor such as GH, IGF and the like is possible.

Examples of the gene therapy method include a treatment method using a gene relating to cytokine, renin-angiotensin enzyme and a product thereof, G protein, G protein conjugated receptor and its phosphorylation enzyme, a treatment method using a DNA decoy such as NFκB decoy and the like, a treatment method using an antisense, a treatment method using a gene relating to an enzyme or protein involved in blood lipid metabolism (e.g., gene relating to metabolism, excretion or absorption of cholesterol or triglyceride or HDL-cholesterol or blood phospholipid), a treatment method using a gene relating to an enzyme or protein involved in angiogenesis therapy targeting obstruction of peripheral vessel and the like (e.g., growth factors such as HGF, VEGF etc.), a treatment method using a gene relating to a protein involved in saccharometabolism or insulin resistance, an antisense to cytokine such as TNF and the like, and the like.

In addition, it is possible to use in combination with various organ regeneration methods such as heart regeneration, kidney regeneration, pancreas regeneration, blood vessel regeneration and the like or cell transplantation therapy utilizing bone marrow cell (myelomonocytic cell, myeloid stem cell) or an artificial organ utilizing tissue engineering (e.g., artificial blood vessel and cardiac muscle cell sheet).

The time of administration of the compound of the present invention and that of the concomitant drug are not limited, and they may be administered simultaneously or in a staggered manner to the administration subject. Furthermore, the compound of the present invention and the concomitant drug may be administered as two kinds of preparations containing each active ingredient, or a single preparation containing both active ingredients.

The dose of the concomitant drug can be appropriately determined based on the dose employed in clinical situations. The mixing ratio of the compound of the present invention and a concomitant drug can be appropriately determined depending on the administration subject, administration route, target disease, symptom, combination and the like. When the subject of administration is human, for example, a concomitant drug can be used in 0.01-100 parts by weight relative to 1 part by weight of the compound of the present invention.

EXAMPLES

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

In silica gel column chromatography, NH means use of aminopropylsilane-bound silica gel. In HPLC (high performance liquid chromatography), C18 means use of octadecyl-bound silica gel. The ratios of elution solvents are volume mixing ratios, unless otherwise specified.

The abbreviations used in the specification mean the following.

THF: tetrahydrofuran
DME: 1,2-dimethoxyethane
DMF: N,N-dimethylformamide
DMA: N,N-dimethylacetamide
DMSO: dimethyl sulfoxide
ESI: electrospray method
APCI: atmospheric chemical ionization
$[M+H]^+$: molecular ion peak
M: mol concentration
IPE: diisopropyl ether
WSC: 1-[3-(dimethylamino)propyl]-3-ethylcarbodiimide
HATU: 2-(7-azabenzotriazol-1-yl)-1,1,3,3-tetramethyluronium hexafluorophosphate
HOBt: 1-hydroxybenzotriazole
HPLC: high-performance liquid chromatography
DIPEA: N,N-diisopropylethylamine
NMP: N-methyl-2-pyrrolidone DPPF: 1,1'-bis(diphenylphosphino)ferrocene
Pd$_2$(dba)$_3$: tris(dibenzylideneacetone)dipalladium(0)
Xantphos: 4,5-bis(diphenylphosphino)-9,9-dimethylxanthene $^1$H NMR (protone nuclear magnetic resonance spectrum) was measured by Fourier-transform type NMR. For the analysis, ACD/SpecManager (trade name) and the like were used. Peaks with very mild protons such as a hydroxy group, an amino group and the like are not described.

MS (mass spectrum) was measured by LC/MS (liquid chromatography mass spectrometer). As API (Atmospheric Pressure Ionization), ESI (Electro Spray Ionization) method, or APCI (Atmospheric Pressure Chemical Ionization) method was used. The data indicates those found. Generally, a molecular ion peak is observed. In the case of a compound having a tert-butoxycarbonyl group (-Boc), a peak after elimination of a tert-butoxycarbonyl group or tert-butyl group may be observed as a fragment ion. In the case of a compound having a hydroxy group (—OH), a peak after elimination of H$_2$O may be observed as a fragment ion. In the case of a salt, a molecular ion peak or fragment ion peak of free form is generally observed.

The elemental analysis value (Anal.) shows Calculated value (Calcd) and Found value (Found).

Example 1

1-(4-(4-chloro-1H-pyrazol-1-yl)pyridin-3-yl)-N,N-dimethylpiperidine-4-carboxamide A) 4-(4-chloro-1H-pyrazol-1-yl)-3-fluoropyridine A mixture of p-toluenesulfonic acid monohydrate (0.58 g), 4-chloro-3-fluoropyridine (2.0 g), 4-chloro-1H-pyrazole (1.7 g) and 2-propanol (10 mL) was irradiated with microwave at 130° C. for 2 hr. The mixture was allowed to be cooled to room temperature, saturated aqueous sodium bicarbonate solution was added thereto, and the mixture was extracted with ethyl acetate. The organic layer was washed with saturated brine, and dried over anhydrous sodium sulfate, and the solvent was evaporated under reduced pressure. The residue was purified by silica gel column chromatography (ethyl acetate/hexane) to give the title compound (2.2 g).

MS (API+), found: 198.2, 200.0.

B) benzyl 4-(dimethylcarbamoyl)piperidine-1-carboxylate

To a mixture of 1-((benzyloxy)carbonyl)piperidine-4-carboxylic acid (1.2 g) and DMF (12 mL) were added HATU (2.1 g), triethylamine (0.83 mL) and dimethylamine THF solution (2M, 2.73 mL) at room temperature. The mixture was stirred at room temperature for 4 hr, saturated aqueous ammonium chloride solution was added thereto, and the mixture was extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane) to give the title compound (960 mg).

MS (API+): [M+H]$^+$ 291.2.

C) N,N-dimethylpiperidine-4-carboxamide

Benzyl 4-(dimethylcarbamoyl)piperidine-1-carboxylate (960 mg) was dissolved in ethanol (15 mL) and ethyl acetate (15 mL), 10% palladium carbon (96 mg) was added thereto, and the mixture was stirred at room temperature for 5 hr under hydrogen atmosphere. The insoluble substance was removed by filtration, and the filtrate was concentrated under reduced pressure to give the title compound (530 mg).

$^1$H NMR (300 MHz, DMSO-d$_6$) δ 1.31-1.57 (4H, m), 2.45 (1H, d, J=3.0 Hz), 2.63 (1H, tt, J=11.1, 4.0 Hz), 2.79 (3H, s), 2.91 (2H, dt, J=12.1, 3.0 Hz), 2.99 (3H, s), 3.29 (2H, brs).

D) 1-(4-(4-chloro-1H-pyrazol-1-yl)pyridin-3-yl)-N,N-dimethylpiperidine-4-carboxamide A mixture of 4-(4-chloro-1H-pyrazol-1-yl)-3-fluoropyridine (98 mg), N,N-dimethylpiperidine-4-carboxamide (160 mg), potassium carbonate (140 mg) and DMA (0.50 mL) was irradiated with microwave at 200° C. for 10 hr. Water was added thereto, and the mixture was extracted with ethyl acetate. The organic layer was washed with saturated brine, and dried over anhydrous sodium sulfate, and the solvent was evaporated under reduced pressure. The residue was purified by silica gel column chromatography (NH, ethyl acetate/hexane), and the obtained solid was crystallized from ethyl acetate/hexane to give the title compound (39 mg).

$^1$H NMR (300 MHz, DMSO-d$_6$) δ 1.57-1.74 (4H, m), 2.67-2.79 (3H, m), 2.82 (3H, s), 2.86-2.96 (2H, m), 3.02 (3H, s), 7.52 (1H, d, J=5.3 Hz), 7.96 (1H, s), 8.36 (1H, d, J=5.3 Hz), 8.48 (1H, s), 8.77 (1H, s).

Example 13

(3-exo)-N,N-dimethyl-8-(4-(4-methyl-1H-pyrazol-1-yl)pyridin-3-yl)-8-azabicyclo[3.2.1]octane-3-carboxamide A) tert-butyl 3-(dimethylcarbamoyl)-8-azabicyclo[3.2.1]octane-8-carboxylate A mixture of 8-(tert-butoxycarbonyl)-8-azabicyclo[3.2.1]octane-3-carboxylic acid (400 mg), dimethylamine hydrochloride (260 mg), HATU (770 mg), DIPEA (0.96 mL) and DMF (5.0 mL) was stirred at room temperature for 16 hr. The mixture was diluted with ethyl acetate/water, and extracted with ethyl acetate. The organic layer was separated, washed with water and saturated brine, and dried over sodium sulfate, and the solvent was evaporated under reduced pressure. The residue was purified by silica gel column chromatography (ethyl acetate/hexane and methanol/ethyl acetate) to give the title compound (440 mg).

$^1$H NMR (300 MHz, CDCl$_3$) δ 1.45-1.56 (11H, m), 1.60-1.70 (2H, m), 1.95-2.07 (4H, m), 2.93 (3H, s), 3.00-3.13 (4H, m), 4.20-4.35 (2H, m).

B) N,N-dimethyl-8-azabicyclo[3.2.1]octane-3-carboxamide hydrochloride

To a mixture of tert-butyl 3-(dimethylcarbamoyl)-8-azabicyclo[3.2.1]octane-8-carboxylate (440 mg) and ethyl acetate (4.0 mL) was added 4M hydrogen chloride/ethyl acetate (10 mL), and the mixture was stirred at room temperature for 16 hr, and concentrated under reduced pressure to give the title compound (340 mg).

$^1$H NMR (300 MHz, DMSO-d$_6$) δ 1.59-1.71 (2H, m), 1.86-2.06 (6H, m), 2.81 (3H, s), 2.99-3.15 (4H, m), 3.86-4.00 (2H, m), 8.68 (1H, brs), 9.39 (1H, brs).

C) 3-fluoro-4-(4-methyl-1H-pyrazol-1-yl)pyridine

A mixture of p-toluenesulfonic acid monohydrate (0.83 g), 4-chloro-3-fluoropyridine (2.9 g), 4-methyl-1H-pyrazole (1.9 mL) and 2-propanol (14 mL) was irradiated with microwave at 130° C. for 2 hr. To the mixture was added saturated aqueous sodium bicarbonate solution, and the mixture was extracted with ethyl acetate. The organic layer was washed with water and saturated brine, and dried over anhydrous sodium sulfate, and the solvent was evaporated under reduced pressure. The residue was purified by silica gel column chromatography (ethyl acetate/hexane) to give the title compound (3.3 g).
$^1$H NMR (300 MHz, DMSO-$d_6$) δ 2.12 (3H, s), 7.76 (1H, s), 7.93 (1H, dd, J=7.0, 5.5 Hz), 8.18 (1H, dd, J=1.9, 0.8 Hz), 8.49 (1H, d, J=5.3 Hz), 8.74 (1H, d, J=4.2 Hz).

D) (3-exo)-N,N-dimethyl-8-(4-(4-methyl-1H-pyrazol-1-yl)pyridin-3-yl)-8-azabicyclo[3.2.1]octane-3-carboxamide A mixture of N,N-dimethyl-8-azabicyclo[3.2.1]octane-3-carboxamide hydrochloride (170 mg), 3-fluoro-4-(4-methyl-1H-pyrazol-1-yl)pyridine (260 mg), potassium carbonate (320 mg) and NMP (2.0 mL) was stirred with microwave irradiation at 200° C. for 16 hr. The mixture was diluted with ethyl acetate/water, and extracted with ethyl acetate. The organic layer was separated, washed with water and saturated brine, and dried over sodium sulfate, and the solvent was evaporated under reduced pressure. The residue was purified by silica gel column chromatography (NH, ethyl acetate/hexane), and the obtained solid was recrystallized from ethyl acetate/hexane to give the title compound (25 mg).
$^1$H NMR (300 MHz, CDCl$_3$) δ 1.45-1.55 (2H, m), 1.63-1.72 (2H, m), 1.98-2.13 (4H, m), 2.18 (3H, s), 2.90-3.03 (4H, m), 3.05 (3H, s), 3.59-3.67 (2H, m), 7.36 (1H, d, J=5.3 Hz), 7.52 (1H, s), 8.03-8.07 (1H, m), 8.20 (1H, d, J=4.9 Hz), 8.32 (1H, s).

Example 21

1-(4-(1,3-benzothiazol-2-yl)pyridin-3-yl)-N,N-dimethylpiperidine-4-carboxamide

A) 2-(3-fluoropyridin-4-yl)benzo[d]thiazole

To a mixture of 3-fluoroisonicotinic acid (1.0 g) and DIPEA (1.9 mL) were added 2,4,6-tripropyl-1,3,5,2,4,6-trioxatriphosphorinane-2,4,6-trioxide (1.9 mL, 50% ethyl acetate solution) and 2-aminobenzenethiol (0.76 mL) at room temperature, and the mixture was stirred overnight at 70° C. The mixture was diluted with water and ethyl acetate, and heated to 60° C. The insoluble substance was removed by filtration, and the filtrate was extracted with ethyl acetate. The organic layer was washed with saturated brine, and dried over anhydrous magnesium sulfate, and the solvent was evaporated under reduced pressure. The residue was purified by silica gel column chromatography (ethyl acetate/hexane) to give the title compound (460 mg).
MS (API+): [M+H]$^+$ 231.1.

B) 1-(4-(1,3-benzothiazol-2-yl)pyridin-3-yl)-N,N-dimethylpiperidine-4-carboxamide A mixture of 2-(3-fluoropyridin-4-yl)benzo[d]thiazole (100 mg), N,N-dimethylpiperidine-4-carboxamide (81 mg), potassium carbonate (90 mg) and NMP (0.50 mL) was stirred overnight at 150° C. The mixture was allowed to be cooled to room temperature, diluted with water, and extracted with ethyl acetate. The organic layer was washed with saturated brine, and dried over anhydrous magnesium sulfate, and the solvent was evaporated under reduced pressure. The residue was purified by silica gel column chromatography (NH, ethyl acetate/hexane), and the obtained solid was recrystallized from ethyl acetate/hexane to give the title compound (79 mg).
$^1$H NMR (400 MHz, CDCl$_3$) δ 1.86 (2H, d, J=13.0 Hz), 2.24-2.37 (2H, m), 2.72 (1H, tt, J=11.6, 3.6 Hz), 2.93-3.04 (5H, m), 3.12 (3H, s), 3.29 (2H, d, J=11.7 Hz), 7.41-7.48 (1H, m), 7.52 (1H, td, J=7.6, 1.2 Hz), 8.00 (1H, d, J=7.8 Hz), 8.11 (1H, d, J=8.1 Hz), 8.25 (1H, d, J=5.1 Hz), 8.52 (1H, d, J=5.1 Hz), 8.66 (1H, s).

Example 33

(2R)-1-((1-(4-(4-chloro-1H-pyrazol-1-yl)pyridin-3-yl)piperidin-4-yl)carbonyl)pyrrolidine-2-carbonitrile

A) ethyl 1-(4-(4-chloro-1H-pyrazol-1-yl)pyridin-3-yl)piperidine-4-carboxylate A mixture of 4-(4-chloro-1H-pyrazol-1-yl)-3-fluoropyridine (3.4 g), ethyl piperidine-4-carboxylate (13 mL), potassium carbonate (7.1 g) and NMP (15 mL) was stirred at 180° C. for 4 hr. To the mixture was added water at 0° C., and the mixture was extracted with ethyl acetate. The organic layer was washed with water and saturated brine, and dried over anhydrous sodium sulfate, and the solvent was evaporated under reduced pressure. The residue was purified by silica gel column chromatography (ethyl acetate/hexane) to give the title compound (5.3 g).
$^1$H NMR (300 MHz, DMSO-$d_6$) δ 1.16-1.23 (3H, m), 1.56-1.74 (2H, m), 1.80-1.93 (2H, m), 2.37-2.46 (1H, m), 2.66-2.79 (2H, m), 2.89 (2H, dt, J=12.1, 3.2 Hz), 4.09 (2H, q, J=7.2 Hz), 7.52 (1H, d, J=4.9 Hz), 7.96 (1H, s), 8.36 (1H, d, J=4.9 Hz), 8.48 (1H, s), 8.77 (1H, s).

B) 1-(4-(4-chloro-1H-pyrazol-1-yl)pyridin-3-yl)piperidine-4-carboxylic acid Ethyl 1-(4-(4-chloro-1H-pyrazol-1-yl)pyridin-3-yl)piperidine-4-carboxylate (5.3 g) was dissolved in THF (55 mL) and ethanol (20 mL), to the mixture was added 2M aqueous sodium hydroxide solution (12 mL), and the mixture was stirred overnight at room temperature. The mixture was neutralized with 1M hydrochloric acid (24 mL), and the precipitated solid was collected by filtration to give the title compound (4.0 g).
$^1$H NMR (300 MHz, DMSO-$d_6$) δ 1.55-1.71 (2H, m), 1.84 (2H, dd, J=13.3, 3.0 Hz), 2.25-2.39 (1H, m), 2.64-2.76 (2H, m), 2.89 (2H, dt, J=12.0, 3.3 Hz), 7.52 (1H, d, J=5.3 Hz), 7.96 (1H, s), 8.36 (1H, d, J=5.3 Hz), 8.48 (1H, s), 8.77 (1H, s), 12.27 (1H, brs).

C) (2R)-1-((1-(4-(4-chloro-1H-pyrazol-1-yl)pyridin-3-yl)piperidin-4-yl)carbonyl)pyrrolidine-2-carbonitrile To a mixture of 1-(4-(4-chloro-1H-pyrazol-1-yl)pyridin-3-yl)piperidine-4-carboxylic acid (300 mg) and DMF (6.0 mL) were added HATU (480 mg), triethylamine (0.30 mL) and (R)-pyrrolidine-2-carbonitrile hydrochloride (160 mg) at room temperature, and the mixture was stirred for 2 hr. To the mixture was added water, and the mixture was extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane), and the obtained solid was crystallized from ethyl acetate/hexane to give the title compound (290 mg).

$^1$H NMR (300 MHz, DMSO-$d_6$) δ 1.60-1.84 (4H, m), 1.95-2.31 (4H, m), 2.66-3.04 (5H, m), 3.36-3.59 (1H, m), 3.60-3.75 (1H, m), 4.72 (1H, dd, J=7.6, 3.8 Hz), 7.52 (1H, d, J=4.9 Hz), 7.97 (1H, s), 8.36 (1H, d, J=4.9 Hz), 8.49 (1H, s), 8.78 (1H, s).

Example 43

1-(4-(4-bromo-1H-pyrazol-1-yl)pyridin-3-yl)-N,N-dimethylpiperidine-4-carboxamide A) 4-(4-bromo-1H-pyrazol-1-yl)-3-fluoropyridine A mixture of p-toluenesulfonic acid monohydrate (0.30 g), 4-chloro-3-fluoropyridine (1.0 g), 4-bromo-1H-pyrazole (1.3 g) and 2-propanol (5.0 mL) was irradiated with microwave at 130° C. for 2 hr. The mixture was allowed to be cooled to room temperature, saturated aqueous sodium bicarbonate solution was added thereto, and the mixture was extracted with ethyl acetate. The organic layer was washed with saturated brine, and dried over anhydrous sodium sulfate, and the solvent was evaporated under reduced pressure. The residue was purified by silica gel column chromatography (ethyl acetate/hexane) to give the title compound (1.5 g).

MS (API+), found: 242.0, 244.0.

B) 1-(4-(4-bromo-1H-pyrazol-1-yl)pyridin-3-yl)-N,N-dimethylpiperidine-4-carboxamide A mixture of 4-(4-bromo-1H-pyrazol-1-yl)-3-fluoropyridine (700 mg), N,N-dimethylpiperidine-4-carboxamide (680 mg), potassium carbonate (800 mg) and NMP (2.5 mL) was heated at 180° C. for 5 hr. The mixture was allowed to be cooled to room temperature, water was added thereto, and the mixture was extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane), and the obtained solid was crystallized from ethyl acetate/hexane/IPE to give the title compound (410 mg).

$^1$H NMR (300 MHz, DMSO-$d_6$) δ 1.49-1.78 (4H, m), 2.64-2.84 (6H, m), 2.86-2.96 (2H, m), 3.02 (3H, s), 7.52 (1H, d, J=4.9 Hz), 7.96 (1H, s), 8.36 (1H, d, J=5.3 Hz), 8.48 (1H, s), 8.77 (1H, d, J=0.8 Hz).

Example 54

1-(4-(4-chloro-1H-pyrazol-1-yl)pyridin-3-yl)-N-methyl-N-(tetrahydro-2H-pyran-4-yl)piperidine-4-carboxamide A mixture of 1-(4-(4-chloro-1H-pyrazol-1-yl)pyridin-3-yl)piperidine-4-carboxylic acid (0.50 g), N-methyltetrahydro-2H-pyran-4-amine (0.16 g), HATU (0.81 g), triethylamine (0.91 mL) and DMF (8.2 mL) was stirred at room temperature for 3 hr. To the mixture was added water, and the mixture was extracted with ethyl acetate. The organic layer was washed with water and saturated brine, and dried over anhydrous magnesium sulfate, and the solvent was evaporated under reduced pressure. The residue was purified by silica gel column chromatography (NH, ethyl acetate/hexane), and the obtained solid was crystallized from ethyl acetate/hexane to give the title compound (0.43 g).

$^1$H NMR (300 MHz, CDCl$_3$) δ1.45-1.65 (2H, m), 1.65-2.11 (6H, m), 2.61 (1H, brs), 2.71-2.97 (5H, m), 3.13 (2H, d, J=11.7 Hz), 3.37-3.59 (2H, m), 3.94-4.16 (2H, m), 4.66-4.84 (1H, m), 7.59 (1H, s), 7.66 (1H, s), 8.40 (1H, s), 8.46 (1H, s), 8.59 (1H, s).

Example 58

1-(4-(4-chloro-1H-pyrazol-1-yl)pyridin-3-yl)-N-cyclopropyl-N-methylpiperidine-4-carboxamide To a mixture of 1-(4-(4-chloro-1H-pyrazol-1-yl)pyridin-3-yl)piperidine-4-carboxylic acid (0.5 g) and DMF (8.2 mL) were added HATU (0.81 g), triethylamine (0.91 mL) and N-methylcyclopropanamine (0.14 g), and the mixture was stirred at room temperature for 3 hr. To the mixture was added water, and the mixture was extracted with ethyl acetate. The organic layer was washed with water and saturated brine, and dried over anhydrous magnesium sulfate, and the solvent was evaporated under reduced pressure. The residue was purified by silica gel column chromatography (NH, ethyl acetate/hexane), and the obtained solid was crystallized from ethyl acetate/hexane to give the title compound (0.40 g).

$^1$H NMR (300 MHz, CDCl$_3$) δ 0.71-0.99 (4H, m), 1.71-1.83 (2H, m), 1.96 (2H, dd, J=12.3, 2.8 Hz), 2.64-2.85 (3H, m), 2.94 (3H, s), 3.06-3.22 (3H, m), 7.60 (1H, d, J=4.9 Hz), 7.66 (1H, s), 8.37 (1H, s), 8.46 (1H, s), 8.62 (1H, s).

Example 59

1-(4-(4-cyclopropyl-1H-pyrazol-1-yl)pyridin-3-yl)-N,N-dimethylpiperidine-4-carboxamide A mixture of 1-(4-(4-bromo-1H-pyrazol-1-yl)pyridin-3-yl)-N,N-dimethylpiperidine-4-carboxamide (80 mg), cyclopropylboronic acid (36 mg), 1,1'-bis(diphenylphosphino)ferrocene-palladium(II) dichloride dichloromethane complex (17 mg), cesium carbonate (210 mg), DME (1.5 mL) and water (0.30 mg) was irradiated with microwave at 100° C. for 30 min. 1,1'-Bis(diphenylphosphino)ferrocene-palladium(II) dichloride dichloromethane complex (17 mg) and cyclopropylboronic acid (36 mg) were added thereto, and the mixture was irradiated with microwave at 100° C. for 1 hr. Saturated aqueous sodium bicarbonate solution was added thereto, and the mixture was extracted with ethyl acetate. The organic layer was washed with saturated brine, and dried over anhydrous sodium sulfate, and the solvent was evaporated under reduced pressure. The residue was purified by silica gel column chromatography (NH, ethyl acetate/hexane), and then purified by HPLC (C18, mobile phase: water/acetonitrile (containing 0.1% TFA)). To the obtained fractions was added saturated aqueous sodium hydrogen carbonate solution, and the mixture was extracted with ethyl acetate. The organic layer was dried over anhydrous sodium sulfate, and concentrated under reduced pressure, and the obtained solid was crystallized from ethyl acetate/hexane to give the title compound (15 mg).

$^1$H NMR (300 MHz, CDCl$_3$) δ 0.56-0.63 (2H, m), 0.88-0.96 (2H, m), 1.73-1.83 (3H, m), 1.86-2.02 (2H, m), 2.56-2.67 (1H, m), 2.73 (2H, td, J=11.9, 2.3 Hz), 2.98 (3H, s), 3.08 (3H, s), 3.09-3.17 (2H, m), 7.49 (1H, s), 7.60 (1H, d, J=5.3 Hz), 8.34 (1H, d, J=5.3 Hz), 8.36 (1H, s), 8.40 (1H, s).

Example 68

1-(4-(4-methyl-1H-pyrazol-1-yl)pyridin-3-yl)-N-(tetrahydro-2H-pyran-4-yl)piperidine-4-carboxamide A mixture of 1-(4-(4-methyl-1H-pyrazol-1-yl)pyridin-3-yl)piperidine-4-carboxylic acid (1.0 g), tetrahydro-2H-pyran-4-amine (0.36 mL), HATU (1.7 g), triethylamine (1.9 mL) and DMF (12 mL) was stirred at room temperature for 3 hr. To the mixture was added water, and the mixture was extracted with ethyl acetate. The organic layer was washed with water and saturated brine, and dried over anhydrous magnesium sulfate, and the solvent was evaporated under reduced pressure. The residue was purified by silica gel column chromatography (NH, ethyl acetate/hexane), and the obtained solid was crystallized from ethyl acetate/hexane to give the title compound (0.78 g).
$^1$H NMR (300 MHz, CDCl$_3$) δ 1.35-1.54 (2H, m), 1.78-1.98 (6H, m), 2.06-2.21 (4H, m), 2.70 (2H, dt, J=11.7, 7.2 Hz), 3.12 (2H, d, J=12.1 Hz), 3.48 (2H, td, J=11.7, 2.3 Hz), 3.88-4.09 (3H, m), 5.37 (1H, d, J=7.6 Hz), 7.54 (1H, s), 7.60 (1H, d, J=5.3 Hz), 8.30-8.36 (2H, m), 8.39 (1H, s).

Example 70

(2R)-1-((1-(4-(4-methyl-1H-pyrazol-1-yl)pyridin-3-yl)piperidin-4-yl)carbonyl)pyrrolidine-2-carbonitrile A) ethyl 1-(4-(4-methyl-1H-pyrazol-1-yl)pyridin-3-yl)piperidine-4-carboxylate A mixture of 3-fluoro-4-(4-methyl-1H-pyrazol-1-yl)pyridine (2.5 g), ethyl piperidine-4-carboxylate (4.3 mL), potassium carbonate (5.8 g) and NMP (0.12 mL) was stirred at 180° C. for 7 hr. To the mixture was added ethyl piperidine-4-carboxylate (2.0 mL) at room temperature, and the mixture was stirred at 180° C. for 2 hr, and then overnight at room temperature. To the mixture was added water at 0° C., and the mixture was extracted with ethyl acetate. The organic layer was washed with water and saturated brine, and dried over anhydrous sodium sulfate, and the solvent was evaporated under reduced pressure. The residue was purified by silica gel column chromatography (ethyl acetate/hexane) to give the title compound (2.8 g).
MS (API+): [M+H]$^+$ 315.2.

B) 1-(4-(4-methyl-1H-pyrazol-1-yl)pyridin-3-yl)piperidine-4-carboxylic acid

To a solution of ethyl 1-(4-(4-methyl-1H-pyrazol-1-yl)pyridin-3-yl)piperidine-4-carboxylate (1.2 g), THF (15 mL) and ethanol (5.0 mL) was added 2M aqueous sodium hydroxide solution (3.0 mL), and the mixture was stirred overnight at room temperature. The mixture was cooled to 0° C., and neutralized with 1M hydrochloric acid (6.0 mL). The precipitated solid was collected by filtration, and washed with water to give the title compound (0.84 g).
MS (API+): [M+H]$^+$ 287.2.

C) (2R)-1-((1-(4-(4-methyl-1H-pyrazol-1-yl)pyridin-3-yl)piperidin-4-yl)carbonyl)pyrrolidine-2-carbonitrile To a solution of 1-(4-(4-methyl-1H-pyrazol-1-yl)pyridin-3-yl)piperidine-4-carboxylic acid (0.25 g) and DMF (6.0 mL) were added HATU (0.43 g), triethylamine (0.27 mL) and (R)-pyrrolidine-2-carbonitrile hydrochloride (0.14 g) at room temperature, and the mixture was stirred for 2 hr. To the mixture was added water, and the mixture was extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane), and the obtained solid was crystallized from ethyl acetate/hexane to give the title compound (0.22 g).
$^1$H NMR (300 MHz, DMSO-d$_6$) δ 1.64-1.83 (4H, m), 1.97-2.07 (2H, m), 2.10-2.21 (5H, m), 2.54-2.61 (1H, m), 2.69-2.81 (2H, m), 2.89-3.04 (2H, m), 3.49-3.59 (1H, m), 3.63-3.73 (1H, m), 4.72 (1H, dd, J=7.6, 3.8 Hz), 7.54 (1H, d, J=5.3 Hz), 7.63 (1H, s), 8.31 (1H, d, J=5.3 Hz), 8.42 (1H, s), 8.44 (1H, s).

Example 70

Another Production Method (2R)-1-((1-(4-(4-methyl-1H-pyrazol-1-yl)pyridin-3-yl)piperidin-4-yl)carbonyl)pyrrolidine-2-carbonitrile A) ethyl 1-(4-(4-methyl-1H-pyrazol-1-yl)pyridin-3-yl)piperidine-4-carboxylate A mixture of 3-fluoro-4-(4-methyl-1H-pyrazol-1-yl)pyridine (0.80 g), ethyl piperidine-4-carboxylate (1.5 mL) and NMP (4.5 mL) was stirred at 185° C. for 8.5 hr. The mixture was purified by silica gel column chromatography (ethyl acetate/hexane) to give the title compound (1.0 g).
$^1$H NMR (300 MHz, DMSO-d$_6$) δ 1.19 (3H, t, J=7.2 Hz), 1.60-1.76 (2H, m), 1.81-1.93 (2H, m), 2.12 (3H, s), 2.37-2.48 (1H, m), 2.65-2.77 (2H, m), 2.88-2.99 (2H, m), 4.09 (2H, q, J=7.2 Hz), 7.53 (1H, d, J=4.9 Hz), 7.63 (1H, s), 8.31 (1H, d, J=5.3 Hz), 8.41 (1H, s), 8.42 (1H, s).

B) 1-(4-(4-methyl-1H-pyrazol-1-yl)pyridin-3-yl)piperidine-4-carboxylic acid

To a solution of ethyl 1-(4-(4-methyl-1H-pyrazol-1-yl)pyridin-3-yl)piperidine-4-carboxylate (2.8 g), THF (30 mL) and ethanol (10 mL) was added 2M aqueous sodium hydroxide solution (7.0 mL), and the mixture was stirred overnight at room temperature. The mixture was neutralized with 1M hydrochloric acid (14 mL) at 0° C. The obtained solid was, collected by filtration, and washed with water to give the title compound (2.2 g).
$^1$H NMR (300 MHz, DMSO-d$_6$) δ 1.54-1.75 (2H, m), 1.78-1.92 (2H, m), 2.12 (3H, s), 2.25-2.41 (1H, m), 2.63-2.75 (2H, m), 2.86-2.98 (2H, m), 7.53 (1H, d, J=4.9 Hz), 7.63 (1H, s), 8.30 (1H, d, J=5.3 Hz), 8.39-8.45 (2H, m), 12.33 (1H, brs).

C) (2R)-1-((1-(4-(4-methyl-1H-pyrazol-1-yl)pyridin-3-yl)piperidin-4-yl)carbonyl)pyrrolidine-2-carbonitrile (crude crystals)

To a suspension of 1-(4-(4-methyl-1H-pyrazol-1-yl)pyridin-3-yl)piperidine-4-carboxylic acid (80 g) and acetonitrile (0.32 L) were added DIPEA (0.21 L), (R)-prolinamide (40 g) and 2,4,6-tripropyl-1,3,5,2,4,6-trioxatriphosphorinane-2,4,6-trioxide (1.7M ethyl acetate solution, 0.28 L) at 0° C. The mixture was stirred at room temperature for 1 hr, to the mixture was added 2,4,6-tripropyl-1,3,5,2,4,6-trioxatriphosphorinane-2,4,6-trioxide (1.7M ethyl acetate solution, 0.35 L), and the mixture was stirred overnight at 70° C. To the mixture was added saturated aqueous sodium hydrogen carbonate solution (1600 mL) at 0° C., and the mixture was extracted with a mixed solvent of ethyl acetate and THF. The organic layer was washed with saturated brine, and dried over anhydrous magnesium sulfate, and the solution was purified by silica gel column chromatography (ethyl acetate). The solvent was evaporated under reduced pressure, to the residue was added diisopropyl ether, and the mixture was stirred overnight at room temperature. The solid was collected by filtration, and washed with diisopropyl ether to give the title compound (93 g).

$^1$H NMR (300 MHz, DMSO-$d_6$) δ 1.57-1.82 (4H, m), 1.89-2.30 (7H, m), 2.53-2.83 (3H, m), 2.86-3.06 (2H, m), 3.41-3.58 (1H, m), 3.62-3.75 (1H, m), 4.72 (1H, dd, J=7.4, 4.0 Hz), 7.53 (1H, d, J=5.3 Hz), 7.63 (1H, s), 8.31 (1H, d, J=5.3 Hz), 8.41 (1H, s), 8.43 (1H, s).

D) (2R)-1-((1-(4-(4-methyl-1H-pyrazol-1-yl)pyridin-3-yl)piperidin-4-yl)carbonyl)pyrrolidine-2-carbonitrile The crystals (103 g) of (2R)-1-((1-(4-(4-methyl-1H-pyrazol-1-yl)pyridin-3-yl)piperidin-4-yl)carbonyl)pyrrolidine-2-carbonitrile were dissolved in ethanol (620 mL) at 70° C., heptane (620 mL) was added dropwise thereto at the same temperature, and the mixture was stirred for 1 hr. Heptane (820 mL) was added again thereto over 1 hr, and the mixture was stirred overnight at room temperature. The crystals were collected by filtration, and washed with heptane (1.0 L) to give the title compound (92 g).

$^1$H NMR (300 MHz, DMSO-$d_6$) δ 1.59-1.83 (4H, m), 1.89-2.29 (7H, m), 2.53-2.82 (3H, m), 2.88-3.07 (2H, m), 3.43-3.58 (1H, m), 3.66-3.72 (1H, m), 4.72 (1H, dd, J=7.6, 3.8 Hz), 7.53 (1H, d, J=4.9 Hz), 7.63 (1H, s), 8.31 (1H, d, J=5.3 Hz), 8.41 (1H, s), 8.43 (1H, s).

mp: 178° C.

Example 79

1-(4-(4-chloro-1H-pyrazol-1-yl)pyridin-3-yl)-3,3-difluoro-N-(tetrahydro-2H-pyran-4-yl)piperidine-4-carboxamide A) 3-(4-((benzyloxy)methyl)-3,3-difluoropiperidin-1-yl)-4-chloropyridine A mixture of 4-((benzyloxy)methyl)-3,3-difluoropiperidine (560 mg), 3-bromo-4-chloropyridine (490 mg), palladium acetate (26 mg), Xantphos (140 mg), sodium tert-butoxide (340 mg) and toluene (12 mL) was stirred with microwave irradiation at 120° C. for 3 hr. The mixture was filtered through NH-silica gel pad (ethyl acetate), and the filtrate was concentrated under reduced pressure. The residue was purified by silica gel column chromatography (ethyl acetate/hexane), and then silica gel column chromatography (NH, ethyl acetate/hexane) to give the title compound (550 mg).

$^1$H NMR (300 MHz, CDCl$_3$) δ 1.74-1.92 (1H, m), 2.13-2.37 (2H, m), 2.83-2.94 (1H, m), 2.98-3.15 (1H, m), 3.44-3.56 (2H, m), 3.59-3.71 (1H, m), 3.94 (1H, dd, J=9.3, 4.0 Hz), 4.53 (1H, d, J=12.0 Hz), 4.59 (1H, d, J=12.0 Hz), 7.27-7.40 (6H, m), 8.21 (1H, d, J=4.9 Hz), 8.29 (1H, s).

B) 3-(4-((benzyloxy)methyl)-3,3-difluoropiperidin-1-yl)-4-(4-chloro-1H-pyrazol-1-yl)pyridine A mixture of 3-(4-((benzyloxy)methyl)-3,3-difluoropiperidin-1-yl)-4-chloropyridine (1.9 g), 4-chloro-1H-pyrazole (0.72 g), p-toluenesulfonic acid monohydrate (0.21 g) and 2-propanol (12 mL) was stirred with microwave irradiation at 150° C. for 6 hr. The mixture was diluted with ethyl acetate/saturated aqueous sodium bicarbonate solution, and extracted with ethyl acetate. The organic layer was separated, washed with water and saturated brine, and dried over sodium sulfate, and the solvent was evaporated under reduced pressure. The residue was purified by silica gel column chromatography (NH, ethyl acetate/hexane) to give the title compound (1.5 g).

$^1$H NMR (300 MHz, CDCl$_3$) δ 1.59-1.74 (1H, m), 2.05-2.33 (2H, m), 2.65-2.79 (1H, m), 2.94-3.16 (2H, m), 3.27-3.40 (1H, m), 3.52 (1H, t, J=8.9 Hz), 3.92 (1H, dd, J=9.3, 4.0 Hz), 4.53 (1H, d, J=12.0 Hz), 4.57 (1H, d, J=12.0 Hz), 7.27-7.40 (5H, m), 7.63 (1H, d, J=5.3 Hz), 7.67 (1H, s), 8.42 (1H, s), 8.44 (1H, d, J=4.9 Hz), 8.52 (1H, s).

C) (1-(4-(4-chloro-1H-pyrazol-1-yl)pyridin-3-yl)-3,3-difluoropiperidin-4-yl)methanol To a mixture of 3-(4-((benzyloxy)methyl)-3,3-difluoropiperidin-1-yl)-4-(4-chloro-1H-pyrazol-1-yl)pyridine (1.5 g) and acetonitrile (30 mL) was added trimethylsilyl iodide (5.0 mL) under ice-cooling, and the mixture was stirred at room temperature for 20 hr. To the mixture was added water under ice-cooling, and the mixture was stirred at the same temperature for 10 min. To the mixture were added pyridine (15 mL), aqueous sodium thiosulfate solution and saturated aqueous sodium bicarbonate solution, and the mixture was extracted with ethyl acetate. The organic layer was separated, washed with water and saturated brine, and dried over sodium sulfate, and the solvent was evaporated under reduced pressure. The residue was purified by silica gel column chromatography (NH, ethyl acetate/hexane and methanol/ethyl acetate) to give the title compound (0.91 g).

$^1$H NMR (300 MHz, CDCl$_3$) δ 1.57-1.78 (2H, m), 1.90-2.21 (2H, m), 2.70-2.83 (1H, m), 2.95-3.17 (2H, m), 3.29-3.42 (1H, m), 3.70-3.81 (1H, m), 4.03-4.12 (1H, m), 7.64 (1H, d, J=5.3 Hz), 7.68 (1H, s), 8.43 (1H, s), 8.46 (1H, d, J=5.3 Hz), 8.51 (1H, s).

D) (1r,3s,5R,7S)-1-methyl-2-oxo-2-azaadamantan-2-ium tetrafluoroborate

To a mixture of 1-methyl-2-azaadamantane N-oxyl (1.5 g) and water (5.0 mL) was added dropwise 42% aqueous tetrafluoroboric acid solution (1.9 mL) over 30 min at room temperature. After confirming that the reaction solution became golden brown, aqueous sodium hypochlorite solution (6.1 mL) was added thereto over 1 hr under ice-cooling, and the mixture was stirred at the same temperature for an additional 1 hr. The precipitate was collected by filtration, washed with ice-cooled 5% aqueous sodium bicarbonate (15 mL), water (15 mL) and ice-cooled diethyl ether (75 mL), and dried at 50° C. for 24 hr to give the title compound (850 mg).

Anal. Calcd for C$_{10}$H$_{16}$BF$_4$NO: C, 47.46; H, 6.37; N, 5.49. Found: C, 47.47; H, 6.40; N, 5.50.

E) 1-(4-(4-chloro-1H-pyrazol-1-yl)pyridin-3-yl)-3,3-difluoropiperidine-4-carboxylic acid To a mixture of (1-(4-(4-chloro-1H-pyrazol-1-yl)pyridin-3-yl)-3,3-difluoropiperidin-4-yl)methanol (0.91 g) and acetonitrile (20 mL)/pH 6.8 phosphoric acid buffer solution (10 mL) were added successively sodium chlorite (1.3 g) and (1r,3s,5R,7S)-1-methyl-2-oxo-2-azaadamantan-2-ium tetrafluoroborate (42 mg). The mixture was stirred at room temperature for 1.5 hr, 2-methylbut-2-ene (6.0 mL) was added thereto, and the mixture was stirred for an additional 15 min. The large part of the solvent was evaporated, water was added thereto, and the mixture was stirred under ice-cooling for 30 min. The resulting precipitate was collected by filtration, washed with water and diethyl ether, and dried to give the title compound (0.85 g).

$^1$H NMR (400 MHz, DMSO-$d_6$) δ 1.82-2.00 (2H, m), 2.79-2.94 (2H, m), 3.00-3.13 (1H, m), 3.19-3.34 (2H, m), 7.58 (1H, d, J=5.1 Hz), 7.99 (1H, d, J=0.5 Hz), 8.43 (1H, d, J=5.4 Hz), 8.57 (1H, s), 8.63 (1H, d, J=0.5 Hz), 12.90 (1H, brs).

F) 1-(4-(4-chloro-1H-pyrazol-1-yl)pyridin-3-yl)-3,3-difluoro-N-(tetrahydro-2H-pyran-4-yl)piperidine-4-carboxamide A mixture of 1-(4-(4-chloro-1H-pyrazol-1-yl)pyridin-3-yl)-3,3-difluoropiperidine-4-carboxylic acid (30 mg), tetrahydropyran-4-ylamine (12 mg), HATU (43 mg), DIPEA (20 μL) and DMF (1.0 mL) was stirred at room temperature for 1 hr. The mixture was diluted with ethyl acetate/water, and extracted with ethyl acetate. The organic layer was separated, washed with water and saturated brine, and dried over sodium sulfate, and the solvent was evaporated under reduced pressure. The residue was purified by silica gel column chromatography (NH, ethyl acetate/hexane and methanol/ethyl acetate) to give the title compound (30 mg).

$^1$H NMR (300 MHz, CDCl$_3$) δ 1.43-1.59 (2H, m), 1.87-2.01 (2H, m), 2.05-2.15 (2H, m), 2.64-2.83 (2H, m), 3.02-3.25 (2H, m), 3.41-3.56 (3H, m), 3.90-4.11 (3H, m), 5.80 (1H, d, J=5.7 Hz), 7.63 (1H, d, J=5.3 Hz), 7.68 (1H, s), 8.43-8.50 (3H, m).

Example 82

2-methyl-8-(4-(4-methyl-1H-pyrazol-1-yl)pyridin-3-yl)-2,8-diazaspiro[4.5]decan-1-one A) 1-tert-butyl 4-ethyl 4-(cyanomethyl)piperidine-1,4-dicarboxylate To a mixture of diisopropylamine (4.7 g) and THF (75 mL) was added n-butyllithium hexane solution (1.6 M, 29 mL) under ice-cooling, and the mixture was stirred for 30 min. To the mixture was added a mixture of 1-tert-butyl 4-ethyl piperidine-1,4-dicarboxylate (6.0 g) and THF (10 mL) under ice-cooling, the mixture was stirred under ice-cooling for 3 hr, and 2-bromoacetonitrile (5.6 g) was added thereto under ice-cooling. The mixture was stirred for 12 hr, and the solvent was evaporated under reduced pressure. Water was added thereto, and the mixture was extracted with ethyl acetate. The organic layer was dried over anhydrous magnesium sulfate, and the solvent was evaporated under reduced pressure. The residue was purified by silica gel column chromatography (ethyl acetate/hexane) to give the title compound (2.6 g).

$^1$H NMR (300 MHz, DMSO-$d_6$) δ 1.21 (3H, t, J=7.0 Hz), 1.39 (9H, s), 1.43-1.54 (2H, m), 1.90-2.00 (2H, m), 2.87 (2H, s), 2.96-3.12 (2H, m), 3.57-3.67 (2H, m), 4.11-4.22 (2H, m).

B) tert-butyl 1-oxo-2,8-diazaspiro[4.5]decane-8-carboxylate

To a mixture of 1-tert-butyl 4-ethyl 4-(cyanomethyl)piperidine-1,4-dicarboxylate (2.5 g), cobalt(II) chloride hexahydrate (1.0 g) and methanol (50 mL) was added sodium borohydride (1.6 g) under ice-cooling, and the mixture was stirred under ice-cooling for 2 hr, and then at room temperature for 2 days, and then 60° C. for 1 hr. 28% Aqueous ammonia was added thereto, the precipitate was removed by filtration, and the filtrate was extract with ethyl acetate. The organic layer was dried over anhydrous magnesium sulfate, and the solvent was evaporated under reduced pressure. The residue was purified by silica gel column chromatography (ethyl acetate) to give the title compound (1.1 g).

$^1$H NMR (300 MHz, DMSO-$d_6$) δ 1.25-1.35 (2H, m), 1.40 (9H, s), 1.45-1.58 (2H, m), 1.90-1.98 (2H, m), 2.90 (2H, brs), 3.16 (2H, t, J=7.2 Hz), 3.76-3.86 (2H, m), 7.56 (1H, brs).

C) 2,8-diazaspiro[4.5]decan-1-one hydrochloride

To a mixture of text-butyl 1-oxo-2,8-diazaspiro[4.5]decane-8-carboxylate (400 mg), ethyl acetate (10 mL) and ethanol (2.0 mL) was added 4 M hydrogen chloride/ethyl acetate solution (5.0 mL) at room temperature, the mixture was stirred at 60° C. for 2 hr, and the solvent was evaporated under reduced pressure. The residue was diluted with ethyl acetate, and the obtained solid was collected by filtration to give the title compound (240 mg).

$^1$H NMR (300 MHz, CDCl$_3$) δ 1.47-1.64 (2H, m), 1.77-1.92 (2H, m), 1.93-2.03 (2H, m), 2.81-3.03 (2H, m), 3.11-3.34 (4H, m), 7.72 (1H, brs), 8.62-9.33 (2H, m).

D) 8-(4-(4-methyl-1H-pyrazol-1-yl)pyridin-3-yl)-2,8-diazaspiro[4.5]decan-1-one

A mixture of 3-fluoro-4-(4-methyl-1H-pyrazol-1-yl)pyridine (50 mg), 2,8-diazaspiro[4.5]decan-1-one hydrochloride (54 mg), potassium carbonate (120 mg) and NMP (0.20 mL) was stirred at 160° C. for 1 day, and then at 180° C. for 7 hr. The mixture was allowed to be cooled to room temperature, diluted with water, and extracted with ethyl acetate. The organic layer was washed with saturated brine, and dried over anhydrous magnesium sulfate, and the solvent was evaporated under reduced pressure. The residue was purified by silica gel column chromatography (NH, methanol/ethyl acetate) to give the title compound (36 mg).

MS (API+): [M+H]$^+$ 312.2.

E) 2-methyl-8-(4-(4-methyl-1H-pyrazol-1-yl)pyridin-3-yl)-2,8-diazaspiro[4.5]decan-1-one To a mixture of 8-(4-(4-methyl-1H-pyrazol-1-yl)pyridin-3-yl)-2,8-diazaspiro[4.5]decan-1-one (35 mg) and DMF (0.50 mL) was added sodium hydride (60%, 6.7 mg) under ice-cooling. The mixture was stirred at room temperature for 30 min under nitrogen atmosphere, to the mixture was added a mixture of methyl iodide (7.0 μL) and DMF (0.50 mL), and the mixture was stirred at room temperature for 1 hr. To the mixture was added water, and the mixture was extracted with ethyl acetate. The organic layer was separated, washed with saturated brine, and dried over anhydrous magnesium sulfate, and the solvent was evaporated under reduced pressure. The residue was purified by silica gel column chromatography (NH, ethyl acetate/hexane), and the obtained solid was recrystallized from ethyl acetate/hexane to give the title compound (18 mg).

$^1$H NMR (300 MHz, CDCl$_3$) δ 1.46 (2H, d, J=13.6 Hz), 1.95-2.12 (4H, m), 2.17 (3H, s), 2.76 (2H, td, J=12.0, 2.5 Hz), 2.87 (3H, s), 3.08 (2H, dt, J=12.1, 3.4 Hz), 3.27-3.37

(2H, m), 7.53 (1H, s), 7.60 (1H, d, J=5.3 Hz), 8.34 (1H, d, J=5.3 Hz), 8.40 (2H, d, J=4.9 Hz).

Example 83

1-(4-(4-cyano-1H-pyrazol-1-yl)pyridin-3-yl)-N,N-dimethylpiperidine-4-carboxamide A mixture of 1-(4-(4-bromo-1H-pyrazol-1-yl)pyridin-3-yl)-N,N-dimethylpiperidine-4-carboxamide (60 mg), Pd$_2$(dba)$_3$ (15 mg), zinc cyanide (56 mg), DPPF (18 mg) and anhydrous DMF (1.5 mL) was heated at 100° C. for 7 hr under argon atmosphere. The mixture was allowed to be cooled to room temperature, to the mixture was added again Pd$_2$(dba)$_3$ (7.0 mg), and the mixture was heated at 100° C. for 5 hr under argon atmosphere. The mixture was allowed to be cooled to room temperature, and the insoluble substance was removed by filtration. To the filtrate were added ethyl acetate and water, and the organic layer was washed with water and saturated brine, dried over anhydrous sodium sulfate, and concentrated under reduced pressure. The residue was purified by silica gel column chromatography (NH, ethyl acetate/hexane), and then purified by HPLC (C18, mobile phase: water/acetonitrile (containing 0.1% TFA)). To the obtained fractions was added saturated aqueous sodium hydrogen carbonate solution, and the mixture was extracted with ethyl acetate. The organic layer was dried over anhydrous sodium sulfate, and concentrated under reduced pressure, and the obtained solid was crystallized from ethyl acetate/THF/hexane to give the title compound (17 mg).
$^1$H NMR (300 MHz, DMSO-d$_6$) δ 1.58-1.69 (4H, m), 2.65-2.91 (8H, m), 3.01 (3H, s), 7.54 (1H, d, J=5.3 Hz), 8.39 (1H, d, J=4.9 Hz), 8.44 (1H, s), 8.53 (1H, s), 9.32 (1H, s).

Example 86

N-cyclopropyl-N-methyl-1-(4-(4-methyl-1H-pyrazol-1-yl)pyridin-3-yl)piperidine-4-carboxamide To a mixture of 1-(4-(4-methyl-1H-pyrazol-1-yl)pyridin-3-yl)piperidine-4-carboxylic acid (0.5 g) and DMF (8.2 mL) were added HATU (0.86 g), triethylamine (0.97 mL) and N-methylcyclopropanamine (0.15 g), and the mixture was stirred at room temperature for 3 hr. To the mixture was added water, and the mixture was extracted with ethyl acetate. The organic layer was washed with water and saturated brine, and dried over anhydrous magnesium sulfate, and the solvent was evaporated under reduced pressure. The residue was purified by silica gel column chromatography (NH, ethyl acetate/hexane), and the obtained solid was crystallized from ethyl acetate/hexane to give the title compound (0.25 g).
$^1$H NMR (300 MHz, CDCl$_3$) δ 0.68-1.00 (4H, m), 1.77 (2H, s), 1.96 (2H, dd, J=12.3, 2.8 Hz), 2.17 (3H, s), 2.65-2.83 (3H, m), 2.94 (3H, s), 3.14 (3H, d, J=11.7 Hz), 7.54 (1H, s), 7.62 (1H, d, J=5.3 Hz), 8.25-8.50 (3H, m).

Example 87

(2R)-1-((1-(4-(5-methyl-1,3,4-thiadiazol-2-yl)pyridin-3-yl)piperidin-4-yl)carbonyl)pyrrolidine-2-carbonitrile A) N'-acetyl-3-fluoroisonicotinohydrazide A mixture of 3-fluoroisonicotine acid (4.5 g) and thionyl chloride (20 mL) was heated with reflux under nitrogen atmosphere for 4 hr. The solvent was evaporated under reduced pressure. The residue was suspended in toluene, and the solvent was evaporated under reduced pressure. The residue was suspended in THF (20 mL), the suspension was added dropwise to a mixture of acetohydrazide (2.8 g), triethylamine (9.8 mL) and THF (20 mL) under ice-cooling, and the mixture was stirred at room temperature for 30 min. The insoluble substance was removed by filtration, and the solvent was evaporated under reduced pressure. The residue was purified by silica gel column chromatography (methanol/ethyl acetate) to give the title compound (3.9 g).
MS (API+): [M+H]$^+$ 198.1.

B) 2-(3-fluoropyridin-4-yl)-5-methyl-1,3,4-thiadiazole

To a mixture of N'-acetyl-3-fluoroisonicotinohydrazide (3.8 g) and toluene (100 mL) was added 2,4-bis(4-methoxyphenyl)-1,3-dithia-2,4-diphosphetane 2,4-disulfide (7.8 g), and the mixture was stirred at 110° C. for 5 hr. The solvent was evaporated under reduced pressure. The residue was purified by silica gel column chromatography (NH, ethyl acetate/hexane) to give the title compound (2.6 g).
MS (API+): [M+H]$^+$ 196.1.

C) ethyl 1-(4-(5-methyl-1,3,4-thiadiazol-2-yl)pyridin-3-yl)piperidine-4-carboxylate A mixture of 2-(3-fluoropyridin-4-yl)-5-methyl-1,3,4-thiadiazole (1.5 g), ethyl piperidine-4-carboxylate (1.8 g), potassium carbonate (1.6 g) and NMP (8.0 mL) was stirred at 150° C. for 2 hr. The mixture was allowed to be cooled to room temperature, diluted with water, and extracted with ethyl acetate. The organic layer was washed with saturated brine, and dried over anhydrous magnesium sulfate, and the solvent was evaporated under reduced pressure. The residue was purified by silica gel column chromatography (NH, ethyl acetate/hexane), and the obtained solid was washed with ethyl acetate/hexane to give the title compound (1.5 g).
MS (API+): [M+H]$^+$ 333.2.

D) 1-(4-(5-methyl-1,3,4-thiadiazol-2-yl)pyridin-3-yl)piperidine-4-carboxylic acid To a mixture of ethyl 1-(4-(5-methyl-1,3,4-thiadiazol-2-yl)pyridin-3-yl)piperidine-4-carboxylate (1.5 g), THF (10 mL) and methanol (3.0 mL) was added 2M aqueous sodium hydroxide solution (2.2 mL) at room temperature, and the mixture was stirred overnight. To the mixture was added again 2M aqueous sodium hydroxide solution (2.2 mL), and the mixture was stirred at room temperature for 15 min. The mixture was neutralized with 1M hydrochloric acid, and the obtained solid was collected by filtration to give the title compound (1.3 g).
MS (API+): [M+H]$^+$ 305.2.

E) (2R)-1-((1-(4-(5-methyl-1,3,4-thiadiazol-2-yl)pyridin-3-yl)piperidin-4-yl)carbonyl)pyrrolidine-2-carbonitrile To a mixture of 1-(4-(5-methyl-1,3,4-thiadiazol-2-yl)pyridin-3-yl)piperidine-4-carboxylic acid (80 mg), DIPEA (0.23 mL) and DMF (0.50 mL) was added HATU (150 mg), and a mixture of (R)-pyrrolidine-2-carbonitrile hydrochloride (52 mg) and DMF (0.50 mL) was added thereto, and the mixture was stirred overnight at room temperature. The mixture was diluted with water, and extracted with ethyl acetate. The organic layer was washed with saturated brine, and dried over anhydrous magnesium sulfate, and the solvent was evaporated under reduced pressure. The residue was purified by silica gel column chromatography (NH, ethyl acetate/hexane), and the obtained solid was recrystallized from ethyl acetate/hexane to give the title compound (59 mg).

$^1$H NMR (300 MHz, CDCl$_3$) δ 1.77-2.01 (2H, m), 2.07-2.41 (6H, m), 2.45-2.63 (1H, m), 2.80-2.88 (3H, m), 2.89-3.08 (2H, m), 3.18 (2H, d, J=3.4 Hz), 3.44-3.65 (1H, m), 3.68-3.81 (1H, m), 4.66-4.85 (1H, m), 8.20 (1H, d, J=5.7 Hz), 8.53 (1H, d, J=4.9 Hz), 8.60-8.68 (1H, m).

Example 114

1-((1-(4-(4-methyl-1H-pyrazol-1-yl)pyridin-3-yl)piperidin-4-yl)carbonyl)-L-prolinamide To a mixture of 1-(4-(4-methyl-1H-pyrazol-1-yl)pyridin-3-yl)piperidine-4-carboxylic acid (100 mg), DIPEA (0.31 mL) and DMF (2.0 mL) were added HATU (200 mg) and (S)-pyrrolidine-2-carboxamide (48 mg), and the mixture was stirred at room temperature for 30 min. The mixture was diluted with water and saturated brine, and extracted with ethyl acetate/THF. The organic layer was washed with saturated brine, and dried over anhydrous magnesium sulfate, and the solvent was evaporated under reduced pressure. The residue was purified by silica gel column chromatography (NH, methanol/ethyl acetate) to give the title compound (92 mg).

$^1$H NMR (300 MHz, CDCl$_3$) δ 1.74-2.23 (10H, m), 2.36-2.58 (2H, m), 2.65-2.82 (2H, m), 3.05-3.23 (2H, m), 3.49-3.72 (2H, m), 4.61 (1H, dd, J=8.1, 2.1 Hz), 5.28 (1H, brs), 6.88 (1H, brs), 7.54 (1H, s), 7.58-7.63 (1H, m), 8.30-8.37 (2H, m), 8.37-8.42 (1H, m).

Example 118

4,4-difluoro-1-((1-(4-(4-methyl-1H-pyrazol-1-yl)pyridin-3-yl)piperidin-4-yl)carbonyl)-L-prolinamide To a mixture of 1-(4-(4-methyl-1H-pyrazol-1-yl)pyridin-3-yl)piperidine-4-carboxylic acid (300 mg) and DMF (6.0 mL) were added HATU (520 mg), triethylamine (0.32 mL) and (S)-4,4-difluoropyrrolidine-2-carboxamide (240 mg) at room temperature, and the mixture was stirred for 1 hr. To the mixture was added water, and the mixture was extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane), and a part (53 mg) of the obtained solid was washed with ether to give the title compound (39 mg).

$^1$H NMR (300 MHz, DMSO-d$_6$) δ 1.56-1.85 (4H, m), 2.12 (3H, s), 2.25-2.37 (1H, m), 2.62-2.80 (3H, m), 2.88-3.04 (3H, m), 3.86-4.24 (2H, m), 4.44 (1H, dd, J=9.5, 4.9 Hz), 7.07 (1H, s), 7.38 (1H, brs), 7.53 (1H, d, J=5.3 Hz), 7.63 (1H, s), 8.31 (1H, d, J=4.9 Hz), 8.40 (1H, s), 8.43 (1H, s).

Example 120

(2S)-1-((1-(4-(4-methyl-1H-pyrazol-1-yl)pyridin-3-yl)piperidin-4-yl)carbonyl)pyrrolidine-2-carbonitrile To a mixture of 1-(4-(4-methyl-1H-pyrazol-1-yl)pyridin-3-yl)piperidine-4-carboxylic acid (100 mg), DIPEA (0.31 mL) and DMF (2.0 mL) were added HATU (200 mg) and (S)-pyrrolidine-2-carbonitrile hydrochloride (56 mg), and the mixture was stirred at room temperature for 30 min. The mixture was diluted with water and saturated brine, and extracted with ethyl acetate/THF. The organic layer was washed with saturated brine, and dried over anhydrous magnesium sulfate, and the solvent was evaporated under reduced pressure. The residue was purified by silica gel column chromatography (NH, ethyl acetate/hexane), and the obtained solid was recrystallized from ethyl acetate/hexane to give the title compound (86 mg).

$^1$H NMR (300 MHz, CDCl$_3$) δ 1.70-2.05 (4H, m), 2.10-2.60 (8H, m), 2.62-2.88 (2H, m), 3.02-3.27 (2H, m), 3.44-3.60 (1H, m), 3.64-3.77 (1H, m), 4.59-4.88 (1H, m), 7.54 (1H, s), 7.61 (1H, d, J=5.3 Hz), 8.30-8.38 (2H, m), 8.40 (1H, s).

Example 121

(2S)-4,4-difluoro-1-((1-(4-(4-methyl-1H-pyrazol-1-yl)pyridin-3-yl)piperidin-4-yl)carbonyl)pyrrolidine-2-carbonitrile To a mixture of 4,4-difluoro-1-((1-(4-(4-methyl-1H-pyrazol-1-yl)pyridin-3-yl)piperidin-4-yl)carbonyl)-L-prolinamide (380 mg), imidazole (62 mg) and pyridine (4.5 mL) was added phosphorus oxychloride (0.17 mL) at −40° C., and the mixture was stirred at −20° C. for 1 hr. To the mixture was added 1M hydrochloric acid (30 mL), and the mixture was extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane) to give the title compound (290 mg).

$^1$H NMR (300 MHz, DMSO-d$_6$) δ 1.52-1.85 (4H, m), 2.12 (3H, s), 2.61-3.06 (6H, m), 3.92-4.32 (3H, m), 5.04 (1H, dd, J=9.1, 3.0 Hz), 7.53 (1H, d, J=5.3 Hz), 7.63 (1H, s), 8.31 (1H, d, J=4.9 Hz), 8.42 (2H, d, J=6.8 Hz).

Example 124

1-((1-(4-(4-methyl-1H-pyrazol-1-yl)pyridin-3-yl)piperidin-4-yl)carbonyl)-D-prolinamide To a mixture of 1-(4-(4-methyl-1H-pyrazol-1-yl)pyridin-3-yl)piperidine-4-carboxylic acid (52 mg) and DMF (1.0 mL) were added HATU (90 mg), triethylamine (0.056 mL) and (R)-prolinamide (25 mg) at room temperature, and the mixture was stirred for 2 hr. To the mixture was added water, and the mixture was extracted with ethyl acetate. The organic layer was washed with saturated brine, and dried over anhydrous sodium sulfate, and the solvent was evaporated under reduced pressure. The residue was purified by silica gel column chromatography (NH, ethyl acetate/hexane and methanol/ethyl acetate) to give the title compound (62 mg).

$^1$H NMR (300 MHz, DMSO-d$_6$) δ 1.58-1.98 (8H, m), 2.12 (3H, s), 2.62-2.81 (2H, m), 2.87-3.04 (2H, m), 3.40-3.67 (2H, m), 4.15-4.39 (1H, m), 5.74 (1H, s), 6.84 (1H, s), 7.12-7.23 (1H, m), 7.50-7.56 (1H, m), 7.63 (1H, s), 8.30 (1H, d, J=5.3 Hz), 8.39-8.46 (2H, m).

Example 125

2-methyl-1-((1-(4-(4-methyl-1H-pyrazol-1-yl)pyridin-3-yl)piperidin-4-yl)carbonyl)-D-prolinamide

A) (R)-methyl 2-methylpyrrolidine-2-carboxylate hydrochloride

To a mixture of (R)-2-methylpyrrolidine-2-carboxylic acid (400 mg) and methanol (10 mL) was added dropwise thionyl chloride (0.68 mL) under ice-cooling, and the mixture was stirred overnight at room temperature. The solvent was evaporated under reduced pressure. The residue was suspended in ethyl acetate, and the obtained solid was collected by filtration to give the title compound (400 mg).
$^1$H NMR (300 MHz, CDCl$_3$) δ 1.86 (3H, s), 1.93-2.25 (3H, m), 2.33-2.53 (1H, m), 3.48-3.69 (2H, m), 3.86 (3H, s), 9.47 (1H, brs), 10.48 (1H, brs).

B) (R)-methyl 2-methyl-1-(1-(4-(4-methyl-1H-pyrazol-1-yl)pyridin-3-yl)piperidine-4-carbonyl)pyrrolidine-2-carboxylate To a mixture of 1-(4-(4-methyl-1H-pyrazol-1-yl)pyridin-3-yl)piperidine-4-carboxylic acid (200 mg), (R)-methyl 2-methylpyrrolidine-2-carboxylate hydrochloride (150 mg) and DMF (3.0 mL) were added HATU (400 mg) and DIPEA (0.61 mL), and the mixture was stirred overnight at room temperature. The mixture was diluted with water, and extracted with ethyl acetate. The organic layer was washed with saturated brine, and dried over anhydrous magnesium sulfate, and the solvent was evaporated under reduced pressure. The residue was purified by silica gel column chromatography (NH, ethyl acetate/hexane) to give the title compound (190 mg).
MS (API+): [M+H]$^+$ 412.3.

C) (R)-2-methyl-1-(1-(4-(4-methyl-1H-pyrazol-1-yl)pyridin-3-yl)piperidine-4-carbonyl)pyrrolidine-2-carboxylic acid To a mixture of (R)-methyl 2-methyl-1-(1-(4-(4-methyl-1H-pyrazol-1-yl)pyridin-3-yl)piperidine-4-carbonyl)pyrrolidine-2-carboxylate (160 mg), THF (1.0 mL) and methanol (0.30 mL) was added 2M aqueous sodium hydroxide solution (0.39 mL), and the mixture was stirred at room temperature for 3 hr, and then overnight at 50° C. The mixture was acidified (pH=4) with 1M hydrochloric acid, diluted with saturated brine, and extracted with ethyl acetate/THF. The organic layer was washed with saturated brine, and dried over anhydrous magnesium sulfate, and the solvent was evaporated under reduced pressure to give the title compound (160 mg).
MS (API+): [M+H]$^+$ 398.2.

D) 2-methyl-1-((1-(4-(4-methyl-1H-pyrazol-1-yl)pyridin-3-yl)piperidin-4-yl)carbonyl)-D-prolinamide To a mixture of (R)-2-methyl-1-(1-(4-(4-methyl-1H-pyrazol-1-yl)pyridin-3-yl)piperidine-4-carbonyl)pyrrolidine-2-carboxylic acid (160 mg), DIPEA (0.11 mL) and DMF (2.0 mL) was added HATU (230 mg), and the mixture was stirred at room temperature for 30 min. To the mixture was added 0.4M ammonia/THF solution (1.5 mL), and the mixture was stirred overnight at room temperature. The mixture was diluted with water, saturated aqueous sodium bicarbonate solution and saturated brine, and extracted with ethyl acetate. The organic layer was washed with saturated brine, and dried over anhydrous magnesium sulfate, and the solvent was evaporated under reduced pressure. The residue was purified by silica gel column chromatography (NH, methanol/ethyl acetate) to give the title compound (110 mg).
$^1$H NMR (300 MHz, CDCl$_3$) δ 1.68 (3H, s), 1.70-2.03 (7H, m), 2.17 (3H, s), 2.43-2.79 (4H, m), 3.09-3.21 (2H, m), 3.55-3.77 (2H, m), 5.25 (1H, brs), 6.91 (1H, s), 7.54 (1H, s), 7.61 (1H, d, J=5.3 Hz), 8.31-8.38 (2H, m), 8.40 (1H, s).

Example 126

2-methyl-1-((1-(4-(5-methyl-1,3,4-thiadiazol-2-yl)pyridin-3-yl)piperidin-4-yl)carbonyl)-D-prolinamide

A) (R)-methyl 2-methyl-1-(1-(4-(5-methyl-1,3,4-thiadiazol-2-yl)pyridin-3-yl)piperidine-4-carbonyl)pyrrolidine-2-carboxylate To a mixture of 1-(4-(5-methyl-1,3,4-thiadiazol-2-yl)pyridin-3-yl)piperidine-4-carboxylic acid (200 mg), (R)-methyl 2-methylpyrrolidine-2-carboxylate hydrochloride (130 mg) and DMF (3.0 mL) were added HATU (380 mg) and DIPEA (0.57 mL), and the mixture was stirred overnight at room temperature. The mixture was diluted with water, and extracted with ethyl acetate. The organic layer was washed with saturated brine, and dried over anhydrous magnesium sulfate, and the solvent was evaporated under reduced pressure. The residue was purified by silica gel column chromatography (NH, ethyl acetate/hexane) to give the title compound (250 mg).
MS (API+): [M+H]$^+$ 430.1.

B) (R)-2-methyl-1-(1-(4-(5-methyl-1,3,4-thiadiazol-2-yl)pyridin-3-yl)piperidine-4-carbonyl)pyrrolidine-2-carboxylic acid To a mixture of (R)-methyl 2-methyl-1-(1-(4-(5-methyl-1,3,4-thiadiazol-2-yl)pyridin-3-yl)piperidine-4-carbonyl)pyrrolidine-2-carboxylate (250 mg), THF (1.5 mL) and methanol (0.50 mL) was added 2M aqueous sodium hydroxide solution (1.1 mL), and the mixture was heated with reflux for 2 hr. The mixture was acidified (pH=4 to 5) with 1M hydrochloric acid, diluted with saturated brine, and extracted with ethyl acetate/THF. The organic layer was washed with saturated brine, and dried over anhydrous magnesium sulfate, and the solvent was evaporated under reduced pressure to give the title compound (230 mg).
MS (API+): [M+H]$^+$ 416.2.

C) 2-methyl-1-((1-(4-(5-methyl-1,3,4-thiadiazol-2-yl)pyridin-3-yl)piperidin-4-yl)carbonyl)-D-prolinamide To a mixture of (R)-2-methyl-1-(1-(4-(5-methyl-1,3,4-thiadiazol-2-yl)pyridin-3-yl)piperidine-4-carbonyl)pyrrolidine-2-carboxylic acid (220 mg), DIPEA (0.14 mL) and DMF (2.0 mL) was added HATU (300 mg), and the mixture was stirred at room temperature for 1 hr under nitrogen atmosphere. To the mixture was added 0.4 M ammonia/THF solution (2.0 mL), and the mixture was stirred overnight at room temperature. The mixture was diluted with saturated brine, and extracted with ethyl acetate/THF. The organic layer was washed with saturated brine, and dried over anhydrous magnesium sulfate, and the solvent was evaporated under reduced pressure. The residue was purified by silica gel column chromatography (NH, methanol/ethyl acetate) to give the title compound (160 mg).

$^1$H NMR (300 MHz, CDCl$_3$) δ 1.71 (3H, s), 1.73-2.23 (7H, m), 2.49-2.68 (2H, m), 2.84 (3H, s), 2.89-3.01 (2H, m), 3.11-3.22 (2H, m), 3.60-3.81 (2H, m), 5.29 (1H, brs), 6.83 (1H, brs), 8.20 (1H, d, J=5.3 Hz), 8.52 (1H, d, J=5.3 Hz), 8.65 (1H, s).

Example 127

(2R)-2-methyl-1-((1-(4-(4-methyl-1H-pyrazol-1-yl) pyridin-3-yl)piperidin-4-yl)carbonyl)pyrrolidine-2-carbonitrile To a mixture of 2-methyl-1-((1-(4-(4-methyl-1H-pyrazol-1-yl)pyridin-3-yl)piperidin-4-yl)carbonyl)-D-prolinamide (100 mg) and pyridine (2.0 mL) was added trifluoroacetic anhydride (0.039 mL) under ice-cooling, and the mixture was stirred at room temperature for 30 min. To the mixture was added again trifluoroacetic anhydride (0.039 mL) under ice-cooling, and the mixture was stirred at room temperature for 30 min. To the mixture was added trifluoroacetic anhydride (0.078 mL), and the mixture was stirred at room temperature for 30 min. To the mixture was added water, and the mixture was extracted with ethyl acetate. The organic layer was washed with saturated brine, and dried over anhydrous magnesium sulfate, and the solvent was evaporated under reduced pressure. The residue was purified by silica gel column chromatography (NH, ethyl acetate/hexane) to give the title compound (76 mg).

$^1$H NMR (300 MHz, CDCl$_3$) δ 1.76 (3H, s), 1.80-2.14 (7H, m), 2.18 (3H, s), 2.36-2.60 (2H, m), 2.71 (2H, t, J=11.7 Hz), 3.07-3.24 (2H, m), 3.53-3.76 (2H, m), 7.54 (1H, s), 7.61 (1H, d, J=5.3 Hz), 8.31-8.36 (2H, m), 8.40 (1H, s).

Example 128

(2R)-2-methyl-1-((1-(4-(5-methyl-1,3,4-thiadiazol-2-yl)pyridin-3-yl)piperidin-4-yl)carbonyl)pyrrolidine-2-carbonitrile To a mixture of 2-methyl-1-((1-(4-(5-methyl-1,3,4-thiadiazol-2-yl)pyridin-3-yl)piperidin-4-yl)carbonyl)-D-prolinamide (160 mg) and pyridine (2.0 mL) was added trifluoroacetic anhydride (0.12 mL) under ice-cooling, and the mixture was stirred under nitrogen atmosphere, under ice-cooling for 15 min. To the mixture was added saturated aqueous sodium bicarbonate solution under ice-cooling, and the mixture was diluted with saturated brine, and extracted with ethyl acetate. The organic layer was washed with saturated brine, and dried over anhydrous magnesium sulfate, and the solvent was evaporated under reduced pressure. The residue was purified by silica gel column chromatography (NH, ethyl acetate/hexane), and the obtained solid was recrystallized from ethyl acetate/hexane to give the title compound (87 mg).

$^1$H NMR (300 MHz, CDCl$_3$) δ 1.78 (3H, s), 1.82-1.97 (2H, m), 2.03-2.28 (5H, m), 2.44-2.61 (2H, m), 2.86 (3H, s), 2.93 (2H, tt, J=11.9, 2.5 Hz), 3.11-3.22 (2H, m, J=5.9, 3.6 Hz), 3.59-3.79 (2H, m), 8.20 (1H, d, J=4.5 Hz), 8.53 (1H, d, J=4.9 Hz), 8.64 (1H, s).

Example 129

(2R)-1-((1-(4-(5-methyl-1,3-thiazol-2-yl)pyridin-3-yl)piperidin-4-yl)carbonyl)pyrrolidine-2-carbonitrile A) 3-fluoro-N-(2-hydroxypropyl)isonicotinamide A mixture of 3-fluoroisonicotine acid (4.5 g) and thionyl chloride (20 mL) was heated with reflux under nitrogen atmosphere for 4 hr. The mixture was concentrated under reduced pressure, and to the residue was added anhydrous THF (20 mL). To the mixture was added dropwise a mixture of 1-aminopropan-2-ol (2.9 g), DIPEA (12 mL) and THF (20 mL) at 0° C., and the mixture was stirred overnight at room temperature. The mixture was concentrated under reduced pressure, and to the residue was added THF. The insoluble substance was removed by filtration, and the filtrate was concentrated under reduced pressure. The residue was purified by silica gel column chromatography (methanol/ethyl acetate) to give the title compound (4.9 g).

MS (API+): [M+H]$^+$ 199.1.

B) 3-fluoro-N-(2-oxopropyl)isonicotinamide

To a mixture of 3-fluoro-N-(2-hydroxypropyl)isonicotinamide (4.4 g), triethylamine (6.2 mL) and DMSO (70 mL) was added sulfur trioxide complex (7.0 g) at room temperature, and the mixture was stirred overnight. The mixture was concentrated under reduced pressure, and to the residue were added water and ethyl acetate. The mixture was basified with 1M aqueous sodium hydroxide solution, and extracted with ethyl acetate and THF. The organic layer was washed with saturated brine, and dried over anhydrous magnesium sulfate, and the solvent was evaporated under reduced pressure. The residue was purified by silica gel column chromatography (ethyl acetate/hexane) to give the title compound (1.9 g).

MS (API+): [M+H]$^+$ 197.2.

C) 2-(3-fluoropyridin-4-yl)-5-methylthiazole

To a mixture of 3-fluoro-N-(2-oxopropyl)isonicotinamide (1.9 g) and toluene (30 mL) was added 2,4-bis(4-methoxyphenyl)-1,3-dithia-2,4-diphosphetane 2,4-disulfide (4.7 g), and the mixture was stirred at 110° C. for 1 hr. The mixture was concentrated under reduced pressure, and the residue was purified by silica gel column chromatography (NH, ethyl acetate/hexane) to give the title compound (1.0 g).

MS (API+): [M+H]$^+$ 195.1.

D) ethyl 1-(4-(5-methylthiazol-2-yl)pyridin-3-yl) piperidine-4-carboxylate

A mixture of 2-(3-fluoropyridin-4-yl)-5-methylthiazole (500 mg), ethyl piperidine-4-carboxylate (610 mg), potassium carbonate (530 mg) and NMP (2.0 mL) was stirred overnight at 150° C. The mixture was allowed to be cooled to room temperature, and ethyl piperidine-4-carboxylate (2.0 mL) was added thereto. The mixture was stirred at 180° C. for 2 hr, and then overnight at room temperature. The mixture was allowed to be cooled to room temperature, water was added thereto, and the mixture was extracted with ethyl acetate. The organic layer was washed with saturated brine, and dried over anhydrous magnesium sulfate, and the solvent was evaporated under reduced pressure. The residue was purified by silica gel column chromatography (ethyl acetate/hexane) to give the title compound (780 mg).

MS (API+): [M+H]$^+$ 332.2.

E) 1-(4-(5-methylthiazol-2-yl)pyridin-3-yl)piperidine-4-carboxylic acid

Ethyl 1-(4-(5-methylthiazol-2-yl)pyridin-3-yl)piperidine-4-carboxylate (770 mg) was dissolved in THF (5.0 mL) and methanol (2.0 mL), to the solution was added 2M aqueous sodium hydroxide solution (2.3 mL), and the mixture was stirred at room temperature for 2 hr. The mixture was neutralized with 1M hydrochloric acid (4.7 mL), and the precipitated solid was collected by filtration to give the title compound (480 mg).

MS (API+): [M+H]+ 304.1.

F) (2R)-1-((1-(4-(5-methyl-1,3-thiazol-2-yl)pyridin-3-yl)piperidin-4-yl)carbonyl)pyrrolidine-2-carbonitrile To a mixture of 1-(4-(5-methylthiazol-2-yl)pyridin-3-yl)piperidine-4-carboxylic acid and DMF (1.0 mL) were added HATU (86 mg), triethylamine (0.053 mL) and (R)-pyrrolidine-2-carbonitrile hydrochloride (28 mg) at room temperature, and the mixture was stirred for 2 hr. To the mixture was added water, and the mixture was extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane), and the obtained solid was crystallized from ethyl acetate/hexane to give the title compound (39 mg).

$^1$H NMR (300 MHz, DMSO-$d_6$) δ 1.75-2.30 (8H, m), 2.53 (3H, d, J=0.8 Hz), 2.61-2.75 (1H, m), 2.91-3.11 (4H, m), 3.52-3.63 (1H, m), 3.68-3.78 (1H, m), 4.75 (1H, dd, J=7.2, 3.8 Hz), 7.72 (1H, d, J=1.1 Hz), 8.03 (1H, d, J=5.3 Hz), 8.44 (1H, d, J=5.3 Hz), 8.68 (1H, s).

Example 130

(2R)-4,4-difluoro-1-((1-(4-(4-methyl-1H-pyrazol-1-yl)pyridin-3-yl)piperidin-4-yl)carbonyl)pyrrolidine-2-carbonitrile A) (2R,4R)-1-(tert-butoxycarbonyl)-4-hydroxypyrrolidine-2-carboxylic acid A mixture of (2R,4R)-4-hydroxypyrrolidine-2-carboxylic acid (5.3 g), di-tert-butyl dicarbonate (19 mL), triethylamine (10 mL) and methanol (90 mL) was heated with reflux for 2 hr. The mixture was allowed to be cooled to room temperature, and the solvent was evaporated under reduced pressure. The residue was adjusted to pH2 with sodium dihydrogenphosphate (400 mg) and dilute hydrochloric acid under ice-cooling. The mixture was stirred under ice-cooling for 30 min, and extracted with ethyl acetate/2-propanol (5:1). The organic layer was separated, washed with saturated brine, and dried over magnesium sulfate, and the solvent was evaporated under reduced pressure to give the title compound (9.3 g).

$^1$H NMR (300 MHz, DMSO-$d_6$) δ 1.31-1.41 (9H, m), 1.75-1.86 (1H, m), 2.23-2.39 (1H, m), 3.03-3.15 (1H, m), 3.43-3.54 (1H, m), 4.03-4.13 (1H, m), 4.15-4.25 (1H, m).

B) (2R,4R)-tert-butyl 2-carbamoyl-4-hydroxypyrrolidine-1-carboxylate

To a mixture of (2R,4R)-1-(tert-butoxycarbonyl)-4-hydroxypyrrolidine-2-carboxylic acid (500 mg) and acetonitrile (6.0 mL) were added WSC hydrochloride (500 mg) and HOBt monohydrate (400 mg) under ice-cooling. The mixture was stirred at room temperature for 1.5 hr, and cooled to 0° C., and 28% aqueous ammonia (0.60 mL) was added thereto. The mixture was stirred at the same temperature for 15 min, and then at room temperature for 30 min. To the mixture was added sodium sulfate, the insoluble substance was removed through silica gel (NH, ethyl acetate), and the filtrate was concentrated under reduced pressure. The residue was purified by silica gel column chromatography (methanol/ethyl acetate) to give the title compound (320 mg).

$^1$H NMR (400 MHz, DMSO-$d_6$) δ 1.30-1.43 (9H, m), 1.65-1.75 (1H, m), 2.21-2.35 (1H, m), 3.13-3.22 (1H, m), 3.41-3.50 (1H, m), 3.97-4.17 (2H, m), 5.25 (1H, d, J=6.8 Hz), 7.04-7.16 (1H, m), 7.39-7.49 (1H, m).

C) (R)-tert-butyl 2-carbamoyl-4-oxopyrrolidine-1-carboxylate

To a mixture of (2R,4R)-tert-butyl 2-carbamoyl-4-hydroxypyrrolidine-1-carboxylate (4.0 g) and ethyl acetate (40 mL)/water (40 mL) were added ruthenium(IV) oxide monohydrate (0.13 g) and sodium periodate (11 g) under ice-cooling. The mixture was stirred at room temperature for 4 hr, and extracted with ethyl acetate/2-propanol (5:1). The organic layer was washed with water and saturated brine, and dried over magnesium sulfate, and the solvent was evaporated under reduced pressure. The residue was purified by silica gel column chromatography (ethyl acetate/hexane) to give the title compound (2.4 g).

$^1$H NMR (300 MHz, DMSO-$d_6$) δ 1.36-1.44 (9H, m), 2.24-2.37 (1H, m), 2.93-3.12 (1H, m), 3.63-3.85 (2H, m), 4.44-4.58 (1H, m), 7.04-7.21 (1H, m), 7.58 (1H, brs).

D) (R)-tert-butyl 2-carbamoyl-4,4-difluoropyrrolidine-1-carboxylate

To a mixture of (R)-tert-butyl 2-carbamoyl-4-oxopyrrolidine-1-carboxylate (2.4 g) and dichloromethane (50 mL) was added bis(2-methoxyethyl)aminosulfur trifluoride (5.8 mL) at −5° C. The mixture was stirred at the same temperature for 15 min, and then at room temperature for 3.5 hr. The mixture was poured into sodium bicarbonate and ice, stirred for 40 min, and extracted with ethyl acetate. The organic layer was washed with water and saturated brine, and dried over sodium sulfate, and the solvent was evaporated under reduced pressure. The residue was purified by silica gel column chromatography (ethyl acetate/hexane) to give the title compound (1.4 g).

$^1$H NMR (300 MHz, DMSO-$d_6$) δ 1.30-1.46 (9H, m), 2.20-2.42 (1H, m), 2.65-2.88 (1H, m), 3.61-3.83 (2H, m), 4.19-4.32 (1H, m), 7.05-7.19 (1H, m), 7.40-7.53 (1H, m).

E) (R)-tert-butyl 2-cyano-4,4-difluoropyrrolidine-1-carboxylate

To a mixture of (R)-tert-butyl 2-carbamoyl-4,4-difluoropyrrolidine-1-carboxylate (1.1 g) and pyridine (10 mL) was added trifluoroacetic anhydride (0.79 mL) at −5° C. The mixture was stirred at the same temperature for 15 min, and then at room temperature for 1 hr. The mixture was diluted with ethyl acetate/water, and extracted with ethyl acetate. The organic layer was washed with water and saturated brine, and dried over magnesium sulfate, and the solvent was evaporated under reduced pressure. The residue was purified by silica gel column chromatography (ethyl acetate/hexane) to give the title compound (0.82 g).

$^1$H NMR (300 MHz, DMSO-$d_6$) δ 1.45 (9H, s), 2.67-3.01 (2H, m), 3.63-3.87 (2H, m), 4.96 (1H, dd, J=9.1, 2.7 Hz).

F) (R)-4,4-difluoropyrrolidine-2-carbonitrile 4-methylbenzenesulfonate

A mixture of (R)-tert-butyl 2-cyano-4,4-difluoropyrrolidine-1-carboxylate (0.82 g), p-toluenesulfonic acid monohydrate (1.3 g) and acetonitrile (15 mL) was stirred at room temperature for 18 hr. The solvent was evaporated under reduced pressure, the residue was dissolved in ethyl acetate, and the solution was concentrated again under reduced pressure. To the resulting solid were added successively diethyl ether and ethyl acetate, and the precipitate was collected by filtration, and washed with cooled ethyl acetate to give the title compound (0.67 g).
$^1$H NMR (300 MHz, CD$_3$OD) δ 2.37 (3H, s), 2.81-3.13 (2H, m), 3.71-3.95 (2H, m), 5.02-5.11 (1H, m), 7.23 (2H, d, J=8.0 Hz), 7.68-7.74 (2H, m).

G) (2R)-4,4-difluoro-1-((1-(4-(4-methyl-1H-pyrazol-1-yl)pyridin-3-yl)piperidin-4-yl)carbonyl)pyrrolidine-2-carbonitrile A mixture of 1-(4-(4-methyl-1H-pyrazol-1-yl)pyridin-3-yl)piperidine-4-carboxylic acid (60 mg), (R)-4,4-difluoropyrrolidine-2-carbonitrile 4-methylbenzenesulfonate (96 mg), HATU (110 mg), DIPEA (0.11 mL) and DMF (2.0 mL) was stirred at room temperature for 18 hr. The mixture was diluted with ethyl acetate/water, and extracted with ethyl acetate. The organic layer was washed with water and saturated brine, and dried over sodium sulfate, and the solvent was evaporated under reduced pressure. The residue was purified by silica gel column chromatography (NH, ethyl acetate/hexane) to give the title compound (70 mg).
$^1$H NMR (300 MHz, DMSO-d$_6$) δ 1.60-1.84 (4H, m), 2.12 (3H, s), 2.54-3.04 (7H, m), 4.04-4.30 (2H, m), 5.04 (1H, dd, J=9.3, 3.2 Hz), 7.53 (1H, d, J=5.3 Hz), 7.63 (1H, s), 8.31 (1H, d, J=4.9 Hz), 8.39-8.44 (2H, m).

Example 131

(2R)-1-((4-fluoro-1-(4-(5-methyl-1,3,4-thiadiazol-2-yl)pyridin-3-yl)piperidin-4-yl)carbonyl)pyrrolidine-2-carbonitrile A) ethyl 4-fluoro-1-(4-(5-methyl-1,3,4-thiadiazol-2-yl)pyridin-3-yl)piperidine-4-carboxylate A mixture of 2-(3-fluoropyridin-4-yl)-5-methyl-1,3,4-thiadiazole (300 mg), ethyl 4-fluoropiperidine-4-carboxylate (650 mg), potassium carbonate (320 mg) and NMP (1.0 mL) was stirred with microwave irradiation at 180° C. for 1 hr. The mixture was diluted with water, and extracted with ethyl acetate. The organic layer was washed with saturated brine, and dried over anhydrous magnesium sulfate, and the solvent was evaporated under reduced pressure. The residue was purified by silica gel column chromatography (NH, ethyl acetate/hexane) to give the title compound (130 mg).
MS (API+): [M+H]$^+$ 351.1.

B) (2R)-1-((4-fluoro-1-(4-(5-methyl-1,3,4-thiadiazol-2-yl)pyridin-3-yl)piperidin-4-yl)carbonyl)pyrrolidine-2-carbonitrile To a mixture of ethyl 4-fluoro-1-(4-(5-methyl-1,3,4-thiadiazol-2-yl)pyridin-3-yl)piperidine-4-carboxylate (120 mg), THF (1.0 mL) and methanol (0.30 mL) was added 2M aqueous sodium hydroxide solution (0.35 mL) at room temperature, and the mixture was stirred at room temperature for 4 hr. The mixture was acidified (pH=4) with 1M hydrochloric acid, and extracted with ethyl acetate/THF/2-propanol, and the solvent was evaporated under reduced pressure. The residue was suspended in toluene, and the solvent was evaporated under reduced pressure. The obtained solid was washed with ethyl acetate. To a mixture of the obtained solid, (R)-pyrrolidine-2-carbonitrile hydrochloride (56 mg) and DMF (1.0 mL) were added HATU (160 mg) and DIPEA (0.19 mL), and the mixture was stirred overnight at room temperature. The mixture was diluted with saturated brine, and extracted with ethyl acetate. The organic layer was dried over anhydrous magnesium sulfate, and the solvent was evaporated under reduced pressure. The residue was purified by silica gel column chromatography (NH, ethyl acetate/hexane), and the obtained solid was recrystallized from ethyl acetate/hexane to give the title compound (20 mg).
$^1$H NMR (300 MHz, CDCl$_3$) δ 1.96-2.76 (8H, m), 2.80-2.91 (3H, m), 2.96-3.11 (2H, m), 3.17-3.39 (2H, m), 3.47-4.03 (2H, m), 4.70-5.21 (1H, m), 8.21 (1H, d, J=5.3 Hz), 8.55 (1H, d, J=5.3 Hz), 8.70 (1H, s).

Example 132

(2R)-4,4-difluoro-1-((1-(4-(5-methyl-1,3,4-thiadiazol-2-yl)pyridin-3-yl)piperidin-4-yl)carbonyl)pyrrolidine-2-carbonitrile To a mixture of 1-(4-(5-methyl-1,3,4-thiadiazol-2-yl)pyridin-3-yl)piperidine-4-carboxylic acid (60 mg), (R)-4,4-difluoropyrrolidine-2-carbonitrile 4-methylbenzenesulfonate (54 mg) and DMF (1 mL) were added HATU (100 mg) and DIPEA (0.12 mL), and the mixture was stirred overnight at room temperature. The mixture was diluted with saturated brine, and extracted with ethyl acetate/THF. The organic layer was dried over anhydrous magnesium sulfate, and the solvent was evaporated under reduced pressure. The residue was purified by silica gel column chromatography (NH, ethyl acetate/hexane), and the obtained solid was recrystallized from ethyl acetate/hexane to give the title compound (41 mg).
$^1$H NMR (300 MHz, CDCl$_3$) δ 1.80-1.99 (2H, m), 2.08-2.28 (2H, m), 2.37-2.56 (1H, m), 2.72-2.84 (2H, m), 2.86 (3H, s), 2.95 (2H, td, J=11.9, 2.7 Hz), 3.12-3.25 (2H, m), 3.92-4.11 (2H, m), 5.00 (1H, t, J=6.6 Hz), 8.21 (1H, d, J=4.9 Hz), 8.54 (1H, d, J=5.3 Hz), 8.64 (1H, s).

Example 133

((2R)-2-(methoxymethyl)pyrrolidin-1-yl)(1-(4-(5-methyl-1,3,4-thiadiazol-2-yl)pyridin-3-yl)piperidin-4-yl)methanone To a mixture of 1-(4-(5-methyl-1,3,4-thiadiazol-2-yl)pyridin-3-yl)piperidine-4-carboxylic acid (80 mg), (R)-2-(methoxymethyl)pyrrolidine (36 mg) and DMF (1.0 mL) were added HATU (150 mg) and DIPEA (0.14 mL), and the mixture was stirred at room temperature for 3 hr. The mixture was diluted with water, and extracted with ethyl acetate. The organic layer was washed with saturated brine, and dried over anhydrous magnesium sulfate, and the solvent was evaporated under reduced pressure. The residue was purified by silica gel column chromatography (NH, ethyl acetate/hexane), and the obtained solid was recrystallized from ethyl acetate/hexane to give the title compound (76 mg).
$^1$H NMR (300 MHz, CDCl$_3$) δ 1.73-2.38 (8H, m), 2.46-2.81 (1H, m), 2.84 (3H, s), 2.94 (2H, t, J=12.1 Hz), 3.08-3.22 (2H, m), 3.27-3.67 (7H, m), 4.08-4.36 (1H, m), 8.20 (1H, d, J=5.3 Hz), 8.52 (1H, d, J=5.3 Hz), 8.64 (1H, s).

Example 142

(2R)-1-((1-(2,4'-bipyridine-3'-yl)piperidin-4-yl)carbonyl)pyrrolidine-2-carbonitrile

A) 1,3-dimethyl-2,3-dihydro-2-oxopyridinium sulfate

To a mixture of 1,3-dimethylurea (40 g), 1,1,3,3-tetramethoxypropane (55 mL) and methanol (400 mL) was added dropwise slowly conc. sulfuric acid (27 mL) at room temperature, and the mixture was stirred at 50° C. for 30 min. The mixture was cooled to 5° C., and the precipitate was collected by filtration, and washed with methanol to give the title compound (31 g).
$^1$H NMR (300 MHz, DMSO-$d_6$) δ 3.71 (6H, s), 7.05 (1H, t, J=6.1 Hz), 9.09 (2H, d, J=6.1 Hz).

B) 3'-bromo-2,4'-bipyridine

To a mixture of 1-(3-bromopyridin-4-yl)ethanone (1.0 g), 1,3-dimethyl-2,3-dihydro-2-oxopyridinium sulfate (0.91 g) and acetonitrile (4.0 mL) was added triethylamine (1.1 mL) under ice-cooling, and the mixture was warmed to 45° C. The mixture was stirred at the same temperature for 1.5 hr, and concentrated under reduced pressure. To the residue were added acetic acid (4.0 mL) and ammonium acetate (2.1 g), and the mixture was stirred at 120° C. for 4 hr. The mixture was allowed to be cooled to room temperature, poured into 8M aqueous sodium hydroxide solution (35 mL, cooled to 0° C.), and the mixture was extracted with ethyl acetate. The organic layer was separated, washed with water and saturated brine, and dried over sodium sulfate, and the solvent was evaporated under reduced pressure. The residue was purified by silica gel column chromatography (NH, ethyl acetate/hexane) to give the title compound (0.55 g).
$^1$H NMR (300 MHz, CDCl$_3$) δ 7.38 (1H, ddd, J=7.6, 4.9, 1.1 Hz), 7.52 (1H, dd, J=4.9, 0.8 Hz), 7.66-7.73 (1H, m), 7.78-7.87 (1H, m), 8.61 (1H, d, J=4.9 Hz), 8.73-8.79 (1H, m), 8.85 (1H, s).

C) ethyl 1-([2,4'-bipyridine]-3'-yl)piperidine-4-carboxylate

A mixture of 3'-bromo-2,4'-bipyridine (1.1 g), 1,4-diazabicyclo[2.2.2]octane (0.25 g), ethyl isonipecotate (7.0 mL) and DIPEA (5.0 mL) was stirred with microwave irradiation at 200° C. for 18 hr. The mixture was diluted with ethyl acetate/water, and extracted with ethyl acetate. The organic layer was separated, washed with water and saturated brine, and dried over sodium sulfate, and the solvent was evaporated under reduced pressure. The residue was purified by silica gel column chromatography (NH, ethyl acetate/hexane) to give the title compound (0.44 g).
$^1$H NMR (300 MHz, CDCl$_3$) δ 1.25 (3H, t, J=7.2 Hz), 1.58-1.75 (1H, m), 1.82-1.93 (2H, m), 2.28-2.40 (1H, m), 2.67-2.78 (2H, m), 3.12-3.22 (2H, m), 4.14 (2H, q, J=7.2 Hz), 7.25-7.31 (2H, m), 7.50 (1H, d, J=4.5 Hz), 7.72-7.80 (1H, m), 8.08 (1H, d, J=8.3 Hz), 8.36-8.40 (2H, m), 8.71-8.76 (1H, m).

D) 1-([2,4'-bipyridine]-3'-yl)piperidine-4-carboxylic acid

To a mixture of ethyl 1-([2,4'-bipyridine]-3'-yl)piperidine-4-carboxylate (0.44 g) and THF (4.0 mL)/ethanol (1.0 mL) was added 2M aqueous sodium hydroxide solution (1.8 mL), and the mixture was stirred at 60° C. for 1.5 hr. The mixture was neutralized with 2M hydrochloric acid (1.8 mL) under ice-cooling. The precipitate was collected by filtration, and washed with water to give the title compound (0.40 g).
$^1$H NMR (300 MHz, DMSO-$d_6$) δ 1.43-1.60 (2H, m), 1.71-1.82 (2H, m), 2.21-2.35 (1H, m), 2.64-2.76 (2H, m), 2.99-3.10 (2H, m), 7.38-7.44 (1H, m), 7.47 (1H, d, J=4.9 Hz), 7.87-7.95 (1H, m), 8.08-8.14 (1H, m), 8.31 (1H, d, J=4.9 Hz), 8.38 (1H, s), 8.70-8.74 (1H, m), 12.21 (1H, s).

E) (2R)-1-((1-(2,4'-bipyridine-3'-yl)piperidin-4-yl)carbonyl)pyrrolidine-2-carbonitrile A mixture of 1-([2,4'-bipyridine]-3'-yl)piperidine-4-carboxylic acid (57 mg), (R)-pyrrolidine-2-carbonitrile hydrochloride (32 mg), HATU (92 mg), DIPEA (0.11 mL) and DMF (2.0 mL) was stirred at room temperature for 16 hr. The mixture was diluted with ethyl acetate/water, and extracted with ethyl acetate. The organic layer was washed with water and saturated brine, and dried over sodium sulfate, and the solvent was evaporated under reduced pressure. The residue was purified by silica gel column chromatography (NH, ethyl acetate/hexane and methanol/ethyl acetate) to give the title compound (52 mg).
$^1$H NMR (300 MHz, CDCl$_3$) δ 1.67-1.92 (4H, m), 2.09-2.45 (5H, m), 2.66-2.79 (2H, m), 3.18-3.31 (2H, m), 3.45-3.56 (1H, m), 3.63-3.73 (1H, m), 4.61-4.78 (1H, m), 7.27-7.31 (1H, m), 7.52 (1H, d, J=4.9 Hz), 7.75-7.83 (1H, m), 8.10 (1H, d, J=8.0 Hz), 8.37-8.41 (2H, m), 8.71-8.75 (1H, m).

Example 144

(2R,4S)-4-methoxy-1-((1-(4-(4-methyl-1H-pyrazol-1-yl)pyridin-3-yl)piperidin-4-yl)carbonyl)pyrrolidine-2-carbonitrile

A) (2R,4S)-1-(tert-butoxycarbonyl)-4-hydroxypyrrolidine-2-carboxylic acid

A mixture of (2R,4S)-4-hydroxypyrrolidine-2-carboxylic acid (7.1 g), di-tert-butyl dicarbonate (25 mL), triethylamine (14 mL) and methanol (130 mL) was heated with reflux for 2 hr. The mixture was allowed to be cooled to room temperature, and the solvent was evaporated under reduced pressure. To the residue was added sodium dihydrogenphosphate (590 mg) at 0° C., and the mixture was acidified (pH=2) with dilute hydrochloric acid. The mixture was stirred at 0° C. for 30 min, and extracted with ethyl acetate/2-propanol (5:1). The organic layer was washed with saturated brine, and dried over anhydrous magnesium sulfate, and the solvent was evaporated under reduced pressure to give the title compound (11 g).
$^1$H NMR (300 MHz, CDCl$_3$) δ 1.40-1.52 (9H, m), 2.07-2.43 (2H, m), 3.43-3.68 (2H, m), 4.34-4.57 (2H, m), 5.00 (2H, brs).

B) (2R,4S)-tert-butyl 2-carbamoyl-4-hydroxypyrrolidine-1-carboxylate

To a mixture of (2R,4S)-1-(tert-butoxycarbonyl)-4-hydroxypyrrolidine-2-carboxylic acid (11 g) and acetonitrile (130 mL) were added WSC hydrochloride (11 g) and HOBt monohydrate (8.7 g) at 0° C., and the mixture was stirred at room temperature for 2.5 hr. The mixture was cooled to 0° C., 28% aqueous ammonia (25 mL) was added thereto, and the mixture was stirred at 0° C. for 15 min, and then overnight at room temperature. The insoluble substance was removed by, filtration, and the filtrate was concentrated under reduced pressure. The residue was dissolved in ethyl acetate-methanol (4:1), the insoluble substance was removed by filtration, and the filtrate was concentrated under reduced pressure. The residue was purified by silica gel column chromatography (methanol/ethyl acetate) to give the title compound (7.0 g).

$^1$H NMR (300 MHz, DMSO-$d_6$) δ 1.31-1.41 (9H, m), 1.73-1.87 (1H, m), 1.93-2.09 (1H, m), 3.20-3.28 (1H, m), 3.33-3.44 (1H, m), 4.02-4.13 (1H, m), 4.21 (1H, d, J=1.9 Hz), 4.96 (1H, d, J=3.4 Hz), 6.79-6.93 (1H, m), 7.26-7.39 (1H, m).

C) (2R,4S)-tert-butyl 2-cyano-4-hydroxypyrrolidine-1-carboxylate

To a mixture of (2R,4S)-tert-butyl 2-carbamoyl-4-hydroxypyrrolidine-1-carboxylate (3.0 g) and pyridine (30 mL) was added trifluoroacetic anhydride (4.6 mL) at 0° C., and the mixture was stirred at room temperature for 3 hr. To the mixture were added ethyl acetate and saturated aqueous sodium bicarbonate solution, and the mixture was extracted with ethyl acetate. The organic layer was washed with water and saturated brine, and dried over anhydrous sodium sulfate, and the solvent was evaporated under reduced pressure. The residue was purified by silica gel column chromatography (ethyl acetate/hexane) to give the title compound (2.7 g).

$^1$H NMR (300 MHz, CD$_3$OD) δ 1.46-1.54 (9H, m), 2.29-2.40 (2H, m), 3.37-3.56 (2H, m), 4.37-4.45 (1H, m), 4.61 (1H, t, J=8.0 Hz).

D) (2R,4S)-tert-butyl 2-cyano-4-methoxypyrrolidine-1-carboxylate

A mixture of (2R,4S)-tert-butyl 2-cyano-4-hydroxypyrrolidine-1-carboxylate (550 mg), methyl iodide (3.2 mL), silver oxide (1.0 g) and acetonitrile (6.0 mL) was heated with reflux for 5 hr under nitrogen atmosphere, and stirred at room temperature for 9 hr. The mixture was filtered through NH-silica gel and Celite pad, and the filtrate was concentrated under reduced pressure. The residue was purified by silica gel column chromatography (ethyl acetate/hexane) to give the title compound (470 mg).

$^1$H NMR (300 MHz, DMSO-$d_6$) δ 1.43 (9H, s) 2.20-2.35 (1H, m), 2.37-2.47 (1H, m), 3.31 (3H, s), 3.39-3.45 (2H, m), 3.98 (1H, brs), 4.55 (1H, t, J=7.8 Hz).

E) (2R,4S)-4-methoxypyrrolidine-2-carbonitrile

To a mixture of (2R,4S)-tert-butyl 2-cyano-4-methoxypyrrolidine-1-carboxylate (85 mg) and acetonitrile (1.0 mL) was added p-toluenesulfonic acid monohydrate (140 mg) at room temperature, and the mixture was stirred for 2 hr, and heated at 50° C. for 2 hr. The mixture was concentrated under reduced pressure, and the residue was purified by MP-Carbonate (macroporous polystyrene anion exchange resin) to give the title compound (45 mg).

$^1$H NMR (300 MHz, CDCl$_3$) δ 2.09-2.36 (2H, m), 2.99-3.09 (1H, m), 3.12-3.21 (1H, m), 3.29 (3H, s), 3.97-4.04 (1H, m), 4.10-4.21 (1H, m), 5.25 (1H, brs).

F) (2R,4S)-4-methoxy-1-((1-(4-(4-methyl-1H-pyrazol-1-yl)pyridin-3-yl)piperidin-4-yl)carbonyl)pyrrolidine-2-carbonitrile To a mixture of 1-(4-(4-methyl-1H-pyrazol-1-yl)pyridin-3-yl)piperidine-4-carboxylic acid (52 mg) and DMF (1.0 mL) were added HATU (90 mg), triethylamine (0.051 mL) and (2R,4S)-4-methoxypyrrolidine-2-carbonitrile (45 mg) at room temperature, and the mixture was stirred for 1.5 hr. To the mixture was added water, and the mixture was extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane) to give the title compound (32 mg).

$^1$H NMR (300 MHz, DMSO-$d_6$) δ 1.62-1.84 (4H, m), 2.13 (3H, s), 2.22-2.32 (1H, m), 2.37-2.47 (1H, m), 2.67-2.83 (1H, m), 2.90-3.05 (2H, m), 3.25 (3H, s), 3.34-3.40 (1H, m), 3.66-3.76 (2H, m), 4.05-4.11 (1H, m), 4.63 (1H, t, J=8.0 Hz), 7.53 (1H, d, J=5.3 Hz), 7.63 (1H, s), 8.31 (1H, d, J=5.3 Hz), 8.41 (1H, s), 8.43 (1H, s).

Example 160 tert-butyl (1S,4S)-5-(4-phenylpyridin-3-yl)-2,5-diazabicyclo[2.2.1]heptane-2-carboxylate A) (1S,4S)-tert-butyl 5-(4-chloropyridin-3-yl)-2,5-diazabicyclo[2.2.1]heptane-2-carboxylate A mixture of 3-bromo-4-chloropyridine (580 mg), (1S,4S)-tert-butyl 2,5-diazabicyclo[2.2.1]heptane-2-carboxylate (500 mg), Pd$_2$(dba)$_3$ (69 mg), Xantphos (130 mg), sodium tert-butoxide (364 mg) and toluene (10 mL) was stirred under argon atmosphere at 110° C. for 3 hr. The mixture was filtered through Celite, and the filtrate was concentrated under reduced pressure. The residue was purified by silica gel column chromatography (ethyl acetate/hexane), and then silica gel column chromatography (NH, ethyl acetate/hexane) to give the title compound (590 mg).

$^1$H NMR (300 MHz, CDCl$_3$) δ 1.34-1.55 (9H, m), 1.86-2.03 (2H, m), 3.24-3.51 (2H, m), 3.55-3.75 (1H, m), 3.92 (1H, dd, J=9.4, 2.3 Hz), 4.44-4.66 (2H, m), 7.20 (1H, d, J=4.5 Hz), 7.95 (1H, d, J=5.3 Hz), 8.08 (1H, s).

B) tert-butyl (1S,4S)-5-(4-phenylpyridin-3-yl)-2,5-diazabicyclo[2.2.1]heptane-2-carboxylate A mixture of (1S,4S)-tert-butyl 5-(4-chloropyridin-3-yl)-2,5-diazabicyclo[2.2.1]heptane-2-carboxylate (590 mg), phenylboronic acid (260 mg), tetrakis(triphenylphosphine) palladium(0) (110 mg) and potassium carbonate (790 mg) in DME/water (10/2.0 mL) was stirred with microwave irradiation at 140° C. for 1 hr. The mixture was diluted with water, and the mixture was extracted with ethyl acetate. The organic layer was washed with saturated brine, dried over anhydrous sodium sulfate, and filtered through NH silica gel (ethyl acetate), and the solvent was evaporated under reduced pressure. The obtained solid was recrystallized from ethyl acetate/hexane to give the title compound (440 mg).

$^1$H NMR (300 MHz, CDCl$_3$) δ 1.39 (9H, s), 1.72-1.89 (2H, m), 2.55 (1H, d, J=9.4 Hz), 2.87-3.04 (1H, m), 3.25-3.35 (1H, m), 3.51-3.61 (1H, m), 4.17-4.40 (2H, m), 6.98-7.10 (1H, m), 7.29-7.46 (5H, m), 8.03-8.20 (2H, m).

Example 161

2-cyclopropyl-1-((1S,4S)-5-(4-phenylpyridin-3-yl)-2,5-diazabicyclo[2.2.1]hept-2-yl) ethanone A) (1S,4S)-2-(4-phenylpyridin-3-yl)-2,5-diazabicyclo[2.2.1]heptane dihydrochloride To a mixture of tert-butyl (1S,4S)-5-(4-phenylpyridin-3-yl)-2,5-diazabicyclo[2.2.1]heptane-2-carboxylate (440 mg)

and methanol (5.0 mL) was added 4M hydrogen chloride/ethyl acetate solution (10 mL), and the mixture was stirred at room temperature for 2 hr. The mixture was concentrated under reduced pressure, to the residue were added methanol and toluene, and the solvent was evaporated under reduced pressure to give the title compound (410 mg).
$^1$H NMR (300 MHz, DMSO-d$_6$) δ 1.85-2.10 (2H, m), 2.81-3.00 (2H, m), 3.08-3.42 (2H, m), 4.22 (1H, brs), 4.63 (1H, s), 7.41-7.61 (5H, m), 7.72 (1H, d, J=5.7 Hz), 8.34 (1H, d, J=5.7 Hz), 8.54 (1H, s), 9.14 (1H, brs), 9.82 (1H, brs).

B) 2-cyclopropyl-1-((1S,4S)-5-(4-phenylpyridin-3-yl)-2,5-diazabicyclo[2.2.1]hept-2-yl)ethanone A mixture of (1S,4S)-2-(4-phenylpyridin-3-yl)-2,5-diazabicyclo[2.2.1]heptane dihydrochloride (140 mg), cyclopropylacetic acid (0.047 mL), HATU (190 mg), triethylamine (0.29 mL) and DMF (3.0 mL) was stirred at room temperature for 3 hr. To the mixture was added water, and the mixture was extracted with ethyl acetate. The organic layer was washed with saturated brine, and dried over anhydrous sodium sulfate, and the solvent was evaporated under reduced pressure. The residue was purified by silica gel column chromatography (NH, ethyl acetate/hexane), and the obtained solid was recrystallized from ethyl acetate/hexane to give the title compound (65 mg).
$^1$H NMR (300 MHz, CDCl$_3$) δ 0.02-0.15 (2H, m), 0.41-0.56 (2H, m), 0.89-1.05 (1H, m), 1.74-2.26 (4H, m), 2.47-2.59 (1H, m), 2.97 (0.6H, dd, J=9.8, 2.3 Hz), 3.05 (0.4H, dd, J=9.4, 1.9 Hz), 3.37-3.47 (1H, m), 3.66 (0.6H, d, J=9.4 Hz), 3.74 (0.4H, dd, J=11.5, 1.3 Hz), 4.22 (0.4H, s), 4.36 (1H, brs), 4.75 (0.6H, s), 7.00-7.09 (1H, m), 7.30-7.46 (5H, m), 8.06-8.21 (2H, m).

Example 165 cyclopropyl(4-(5-fluoro-4-phenylpyridin-3-yl)piperazin-1-yl)methanone

A) 3-bromo-5-fluoro-4-phenylpyridine

To a mixture of 3-bromo-5-fluoropyridine (2.5 g), copper iodide (0.28 g), lithium chloride (0.12 g) and THF (23 mL) was added dropwise phenyl chloroformate (2.0 mL) at −20° C., and the mixture was stirred at the same temperature for 30 min. To the mixture was added dropwise 2M phenylmagnesium bromide THF solution (7.9 mL), and the mixture was stirred at the same temperature for 1.5 hr. The mixture was stirred again at room temperature for 30 min, saturated aqueous ammonium chloride solution was added thereto, and the mixture was extracted with ethyl acetate. The organic layer was separated, washed with water and saturated brine, and dried over sodium sulfate, and the solvent was evaporated under reduced pressure. A mixture of the obtained residue, 2,3,5,6-tetrachlorocyclohexa-2,5-diene-1,4-dione (3.6 g) and toluene (15 mL) was heated with reflux for 6 hr. The mixture was allowed to be cooled to room temperature, diluted with 2M aqueous sodium hydroxide solution (15 mL), stirred at room temperature for 10 min, and filtered through Celite (ethyl acetate). The organic layer of the filtrate was separated, washed with 2M aqueous sodium hydroxide solution and water, dried over sodium sulfate, and filtered through silica gel (NH, ethyl acetate), and the filtrate was concentrated under reduced pressure. The residue was purified by silica gel column chromatography (NH, ethyl acetate/hexane) to give the title compound (1.6 g).

$^1$H NMR (300 MHz, CDCl$_3$) δ 7.33-7.41 (2H, m), 7.46-7.56 (3H, m), 8.48 (1H, s), 8.67 (1H, s).

B) tert-butyl 4-(5-fluoro-4-phenylpyridin-3-yl)piperazine-1-carboxylate

A mixture of 3-bromo-5-fluoro-4-phenylpyridine (600 mg), tert-butyl 1-piperazine carboxylate (490 mg), Pd$_2$(dba)$_3$ (65 mg), Xantphos (83 mg), sodium tert-butoxide (270 mg) and toluene (10 mL) was stirred with microwave irradiation at 110° C. for 2 hr. The mixture was filtered through silica gel (NH, ethyl acetate), and the filtrate was concentrated under reduced pressure. The residue was purified by silica gel column chromatography (NH, ethyl acetate/hexane) to give the title compound (480 mg).
$^1$H NMR (300 MHz, CDCl$_3$) δ 1.43 (9H, s), 2.77-2.89 (4H, m), 3.22-3.33 (4H, m), 7.37-7.57 (5H, m), 8.14 (1H, s), 8.27 (1H, s).

C) 1-(5-fluoro-4-phenylpyridin-3-yl)piperazine dihydrochloride

A mixture of tert-butyl 4-(5-fluoro-4-phenylpyridin-3-yl)piperazine-1-carboxylate (480 mg) and 2M hydrogen chloride/methanol solution (16 mL) was stirred at room temperature for 5 hr, and the solvent was evaporated under reduced pressure to give the title compound (440 mg).
$^1$H NMR (300 MHz, DMSO-d$_6$) δ 2.84-2.97 (4H, m), 3.02-3.13 (4H, m), 7.45-7.64 (5H, m), 8.33 (1H, s), 8.47 (1H, d, J=0.8 Hz), 9.33 (2H, brs).

D) cyclopropyl(4-(5-fluoro-4-phenylpyridin-3-yl)piperazin-1-yl)methanone

To a mixture of 1-(5-fluoro-4-phenylpyridin-3-yl)piperazine dihydrochloride (100 mg) and THF (2.0 mL) were added successively DIPEA (0.21 mL) and cyclopropanecarbonyl chloride (0.036 mL) under ice-cooling, and the mixture was stirred at room temperature for 2 hr. The mixture was diluted with ethyl acetate/saturated aqueous sodium bicarbonate solution, and extracted with ethyl acetate. The organic layer was separated, washed with water and saturated brine, dried over sodium sulfate, and filtered through silica gel (NH, ethyl acetate), and the filtrate was concentrated under reduced pressure. The residue was purified by silica gel column chromatography (ethyl acetate/hexane and methanol/ethyl acetate) to give the title compound (92 mg).
$^1$H NMR (300 MHz, CDCl$_3$) δ 0.69-0.79 (2H, m), 0.90-1.01 (2H, m), 1.58-1.71 (1H, m), 2.80-2.97 (4H, m), 3.44-3.59 (4H, m), 7.37-7.58 (5H, m), 8.15 (1H, s), 8.28 (1H, s).

Example 169 benzyl 4-(4-phenylpyrimidin-5-yl)piperazine-1-carboxylate

A) benzyl 4-(2-oxo-2-phenylethyl)piperazine-1-carboxylate

To a mixture of benzyl piperazine-1-carboxylate (3.1 g), potassium carbonate (2.7 g) and acetonitrile (30 mL) was added dropwise a mixture of 2-chloro-1-phenylethanone (2.0 g) and acetonitrile (20 mL) at room temperature, and the mixture was stirred overnight at room temperature. The solvent was evaporated under reduced pressure, the residue was diluted with water, and the mixture was extracted with ethyl acetate. The organic layer was washed with saturated brine, and dried over anhydrous magnesium sulfate, and the solvent was evaporated under reduced pressure. The residue was purified by silica gel column chromatography (NH, ethyl acetate/hexane) to give the title compound (4.2 g).

MS (API+): [M+H]+ 339.1.

B) benzyl 4-(4-phenylpyrimidin-5-yl)piperazine-1-carboxylate

A mixture of benzyl 4-(2-oxo-2-phenylethyl)piperazine-1-carboxylate (4.2 g) and N,N-dimethylformamide dimethyl acetal (40 mL) was stirred overnight at 100° C. The solvent was evaporated under reduced pressure. To a mixture of the residue, n-butanol (50 mL) and DIPEA (50 mL) was added formamidine acetate (7.7 g), and the mixture was stirred overnight at 110° C. The solvent was evaporated under reduced pressure, the residue was diluted with water, and the mixture was extracted with ethyl acetate. The organic layer was washed with water and saturated brine, and dried over anhydrous magnesium sulfate, and the solvent was evaporated under reduced pressure. The residue was purified by purified by silica gel column chromatography (ethyl acetate/hexane), and then silica gel column chromatography (NH, ethyl acetate/hexane) to give the title compound (3.1 g).

$^1$H NMR (300 MHz, CDCl$_3$) δ 2.92 (4H, brs), 3.46-3.59 (4H, m), 5.12 (2H, s), 7.29-7.39 (5H, m), 7.42-7.52 (3H, m), 7.99-8.07 (2H, m), 8.39 (1H, s), 8.95 (1H, s).

Example 175

N-benzyl-4-(4-phenylpyrimidin-5-yl)piperazine-1-carboxamide

A) 4-phenyl-5-(piperazin-1-yl)pyrimidine

A mixture of benzyl 4-(4-phenylpyrimidin-5-yl)piperazine-1-carboxylate (3.1 g), 10% palladium carbon (about 50% water wet product, 0.30 g) and ethanol (30 mL) was stirred at 50° C. for 3 hr under hydrogen atmosphere. The catalyst was removed by filtration, and the solvent was evaporated under reduced pressure to give the title compound (1.9 g).

MS (API+): [M+H]+ 241.1.

B) N-benzyl-4-(4-phenylpyrimidin-5-yl)piperazine-1-carboxamide

To a mixture of 4-phenyl-5-(piperazin-1-yl)pyrimidine (100 mg) and THF (2.0 mL) was added benzyl isocyanate (0.054 mL) at room temperature, and the mixture was stirred at room temperature for 4 hr. The solvent was evaporated under reduced pressure. The residue was purified by silica gel column chromatography (NH, ethyl acetate/hexane), and the obtained solid was recrystallized from ethyl acetate/hexane to give the title compound (120 mg).

$^1$H NMR (300 MHz, CDCl$_3$) δ 2.85-3.00 (4H, m), 3.28-3.47 (4H, m), 4.42 (2H, d, J=5.3 Hz), 4.69 (1H, t, J=5.1 Hz), 7.27-7.37 (5H, m), 7.41-7.51 (3H, m), 7.99-8.07 (2H, m), 8.40 (1H, s), 8.95 (1H, s).

Example 186 methyl 4-methyl-1-(4-phenylpyrimidin-5-yl)piperidine-4-carboxylate

A degassed mixture of 5-bromo-4-phenylpyrimidine (600 mg), methyl 4-methylpiperidine-4-carboxylate hydrochloride (520 mg), Pd$_2$(dba)$_3$ (120 mg), Xantphos (150 mg), sodium tert-butoxide (620 mg) and 1,4-dioxane (20 mL) was stirred with microwave irradiation at 110° C. for 9 hr. The mixture was filtered through silica gel (NH, ethyl acetate), and the filtrate was concentrated under reduced pressure. The residue was purified by silica gel column chromatography (NH, ethyl acetate/hexane) to give the title compound (130 mg).

$^1$H NMR (300 MHz, CDCl$_3$) δ 1.22 (3H, s), 1.41-1.54 (2H, m), 2.06-2.15 (2H, m), 2.68-2.79 (2H, m), 2.98-3.08 (2H, m), 3.69 (3H, s), 7.39-7.51 (3H, m), 8.01-8.07 (2H, m), 8.39 (1H, s), 8.89 (1H, s).

Example 198

(2R)-1-((4-(4-(4-fluorophenyl)pyrimidin-5-yl)piperazin-1-yl)carbonyl)pyrrolidine-2-carbonitrile A) tert-butyl 4-(2-(4-fluorophenyl)-2-oxoethyl)piperazine-1-carboxylate To a mixture of tert-butyl piperazine-1-carboxylate (5.9 g), potassium carbonate (6.0 g) and acetonitrile (60 mL) was added dropwise a mixture of 2-chloro-1-(4-fluorophenyl)ethanone (5.0 g) and acetonitrile (40 mL) at room temperature, and the mixture was stirred overnight at room temperature. The solvent was evaporated under reduced pressure, the residue was diluted with water, and the mixture was extracted with ethyl acetate. The organic layer was washed with saturated brine, and dried over anhydrous magnesium sulfate, and the solvent was evaporated under reduced pressure to give the title compound (10 g).

MS (API+): [M+H]+ 323.2.

B) tert-butyl 4-(4-(4-fluorophenyl)pyrimidin-5-yl)piperazine-1-carboxylate

A mixture of tert-butyl 4-(2-(4-fluorophenyl)-2-oxoethyl)piperazine-1-carboxylate (8.2 g) and N,N-dimethylformamide dimethyl acetal (50 mL) was heated with reflux for 5 hr. The solvent was evaporated under reduced pressure. To a mixture of the residue, n-butanol (40 mL) and DIPEA (40 mL) was added formamidine acetate (9.3 g), and the mixture was stirred overnight at 100° C. The solvent was evaporated under reduced pressure, the residue was diluted with water, and the mixture was extracted with ethyl acetate. The organic layer was washed with water and saturated brine, and dried over anhydrous magnesium sulfate, and the solvent was evaporated under reduced pressure. The residue was purified by silica gel column chromatography (ethyl acetate/hexane) to give the title compound (5.81 g).

MS (API+): [M+H]+ 359.2.

C) 4-(4-fluorophenyl)-5-(piperazin-1-yl)pyrimidine dihydrochloride

To a mixture of tert-butyl 4-(4-(4-fluorophenyl)pyrimidin-5-yl)piperazine-1-carboxylate (5.8 g) and ethyl acetate (50 mL) was added 4M hydrogen chloride/ethyl acetate solution (50 mL) at room temperature, and the mixture was stirred overnight at room temperature. The mixture was diluted with ethyl acetate, and the precipitate was collected by filtration to give the title compound (5.6 g).

MS (API+): [M+H]+ 259.1.

D) (2R)-1-((4-(4-(4-fluorophenyl)pyrimidin-5-yl)piperazin-1-yl)carbonyl)pyrrolidine-2-carbonitrile To a mixture of 4-(4-fluorophenyl)-5-(piperazin-1-yl)pyrimidine dihydrochloride (200 mg), DIPEA (0.74 mL) and acetonitrile (2.0 mL) was added bis(trichloromethyl) carbonate (72 mg) at room temperature. The mixture was stirred at room temperature for 10 min, to the mixture was added (R)-pyrrolidine-2-carbonitrile hydrochloride (160 mg), and the mixture was stirred overnight at room temperature. The mixture was diluted with water, and extracted with ethyl acetate. The organic layer was washed with saturated brine, and dried over anhydrous magnesium sulfate, and the solvent was evaporated under reduced pressure. The residue was purified by silica gel column chromatography (NH, ethyl acetate/hexane and methanol/ethyl acetate) to give the title compound (58 mg).

$^1$H NMR (300 MHz, CDCl$_3$) δ 1.83-2.01 (1H, m), 2.01-2.39 (3H, m), 2.87-3.05 (4H, m), 3.27-3.52 (6H, m), 4.73-4.85 (1H, m), 7.12-7.22 (2H, m), 8.07-8.16 (2H, m), 8.42 (1H, s), 8.95 (1H, s).

Example 219

N-(4-fluorobenzyl)-4-(4-(4-methyl-1H-pyrazol-1-yl) pyridin-3-yl)piperazine-1-carboxamide A) text-butyl 4-(4-(4-methyl-1H-pyrazol-1-yl)pyridin-3-yl)piperazine-1-carboxylate To a mixture of tert-butyl piperazine-1-carboxylate (0.41 g) and THF (5.0 mL) was added n-butyllithium hexane solution (1.6 M, 1.4 mL) at −78° C., and the mixture was stirred under nitrogen atmosphere for 30 min. To the mixture was added a solution of 3-fluoro-4-(4-methyl-1H-pyrazol-1-yl)pyridine (0.30 g) in THF (1.0 mL), and the mixture was stirred under nitrogen atmosphere at −78° C. for 15 min. The mixture was allowed to be warmed to room temperature, and stirred for 1 hr. To the mixture was added saturated aqueous ammonium chloride solution, and the mixture was extracted with ethyl acetate. The organic layer was washed with saturated brine, and dried over anhydrous magnesium sulfate, and the solvent was evaporated under reduced pressure. The residue was purified by silica gel column chromatography (ethyl acetate/hexane) to give the title compound (0.26 g).

$^1$H NMR (300 MHz, CDCl$_3$) δ 1.46-1.49 (9H, m), 2.17 (3H, s), 2.81-2.88 (4H, m), 3.45-3.56 (4H, m), 7.55 (1H, s), 7.58 (1H, d, J=5.3 Hz), 8.29 (1H, s), 8.38 (2H, t, J=2.7 Hz).

B) 1-(4-(4-methyl-1H-pyrazol-1-yl)pyridin-3-yl)piperazine

To a mixture of tert-butyl 4-(4-(4-methyl-1H-pyrazol-1-yl)pyridin-3-yl)piperazine-1-carboxylate (1.2 g), ethyl acetate (10 mL) and methanol (5.0 mL) was added 4M hydrogen chloride/ethyl acetate solution (10 mL), and the mixture was stirred overnight at room temperature. The solvent was evaporated under reduced pressure. To the residue was added water, and the mixture was extracted with ethyl acetate. The aqueous solution was basified with 1M aqueous sodium hydroxide solution, saturated brine was added thereto, and the mixture was extracted with a mixed solvent of ethyl acetate and THF. The organic layer was washed with saturated brine, and dried over anhydrous magnesium sulfate, and the solvent was evaporated under reduced pressure to give the title compound (0.86 g).

$^1$H NMR (300 MHz, CDCl$_3$) δ2.17 (3H, s), 2.81-2.90 (4H, m), 2.91-3.00 (4H, m), 7.54 (1H, s), 7.59 (1H, d, J=4.9 Hz), 8.32-8.43 (3H, m).

C) N-(4-fluorobenzyl)-4-(4-(4-methyl-1H-pyrazol-1-yl)pyridin-3-yl)piperazine-1-carboxamide To a mixture of bis(trichloromethyl) carbonate (31 mg), DIPEA (0.11 mL) and THF (2.0 mL) was added a solution of (4-fluorophenyl)methanamine (0.035 mL) in THF (0.5 mL) under ice-cooling, and the mixture was stirred for 10 min. To the mixture was added a solution of 1-(4-(4-methyl-1H-pyrazol-1-yl)pyridin-3-yl)piperazine (50 mL) in THF (0.5 mL), and the mixture was stirred at room temperature for 30 min. To the mixture was added water, and the mixture was extracted with ethyl acetate. The organic layer was washed with saturated brine, and dried over anhydrous magnesium sulfate, and the solvent was evaporated under reduced pressure. The residue was purified by silica gel column chromatography (NH, ethyl acetate/hexane), and the obtained solid was crystallized from ethyl acetate/hexane to give the title compound (51 mg).

$^1$H NMR (300 MHz, CDCl$_3$) δ 2.16 (3H, s), 2.84-2.92 (4H, m), 3.41-3.51 (4H, m), 4.40 (2H, d, J=5.7 Hz), 4.74 (1H, t, J=5.3 Hz), 6.97-7.06 (2H, m), 7.27-7.33 (2H, m), 7.53-7.59 (2H, m), 8.24 (1H, d, J=0.8 Hz), 8.34-8.42 (2H, m).

Example 265

(5-(methoxymethyl)-2,2-dimethylpyrrolidin-1-yl)(1-(4-(5-methyl-1,3,4-thiadiazol-2-yl)pyridin-3-yl)piperidin-4-yl)methanone (optical isomer)

Racemic (5-(methoxymethyl)-2,2-dimethylpyrrolidin-1-yl)(1-(4-(5-methyl-1,3,4-thiadiazol-2-yl)pyridin-3-yl)piperidin-4-yl)methanone (120 mg) was resolved by HPLC (column: CHIRALPAK AD, 50 mmID×500 mmL, mobile phase: hexane/ethanol/diethylamine=860/140/1) to give the title compound (56 mg) having a shorter retention time.

Example 266

(5-(methoxymethyl)-2,2-dimethylpyrrolidin-1-yl)(1-(4-(5-methyl-1,3,4-thiadiazol-2-yl)pyridin-3-yl)piperidin-4-yl)methanone (optical isomer)

Racemic (5-(methoxymethyl)-2,2-dimethylpyrrolidin-1-yl)(1-(4-(5-methyl-1,3,4-thiadiazol-2-yl)pyridin-3-yl)piperidin-4-yl)methanone (120 mg) was resolved by HPLC (column: CHIRALPAK AD, 50 mmID×500 mmL, mobile phase: hexane/ethanol/diethylamine=860/140/1) to give the title compound (56 mg) having a longer retention time.

Example 267

5,5-dimethyl-1-((1-(4-(5-methyl-1,3,4-thiadiazol-2-yl)pyridin-3-yl)piperidin-4-yl)carbonyl)prolinamide (optical isomer)

Racemic 5,5-dimethyl-1-((1-(4-(5-methyl-1,3,4-thiadiazol-2-yl)pyridin-3-yl)piperidin-4-yl)carbonyl)prolinamide (63 mg) was resolved by HPLC (column: CHIRALPAK AS, 50 mmID×500 mmL, mobile phase: hexane/ethanol/diethylamine=700/300/1) to give the title compound (30 mg) having a shorter retention time.

Example 268

5,5-dimethyl-1-((1-(4-(5-methyl-1,3,4-thiadiazol-2-yl)pyridin-3-yl)piperidin-4-yl)carbonyl)prolinamide (optical isomer)

Racemic 5,5-dimethyl-1-((1-(4-(5-methyl-1,3,4-thiadiazol-2-yl)pyridin-3-yl)piperidin-4-yl)carbonyl)prolinamide (63 mg) was resolved by HPLC (column: CHIRALPAK AS, 50 mmID×500 mmL, mobile phase: hexane/ethanol/diethylamine=700/300/1) to give the title compound (22 mg) having a longer retention time.

Example 277

N-cyclopropyl-1-(4-(4-fluorophenyl)pyrimidin-5-yl)-N-methylpiperidine-4-carboxamide A) ethyl 1-(2-(4-fluorophenyl)-2-oxoethyl)piperidine-4-carboxylate To a mixture of ethyl piperidine-4-carboxylate (5.0 g), potassium carbonate (6.0 g) and acetonitrile (60 mL) was added dropwise a mixture of 2-chloro-1-(4-fluorophenyl)ethanone (5.0 g) and acetonitrile (40 mL) at room temperature, and the mixture was stirred overnight at room temperature. The solvent was evaporated under reduced pressure, the residue was diluted with water, and the mixture was extracted with ethyl acetate. The organic layer was washed with saturated brine, and dried over anhydrous magnesium sulfate, and the solvent was evaporated under reduced pressure to give the title compound (8.7 g).
$^1$H NMR (300 MHz, CDCl$_3$) δ 1.19-1.30 (3H, m), 1.75-1.98 (4H, m), 2.15-2.37 (3H, m), 2.92 (2H, dt, J=11.6, 3.5 Hz), 3.72 (2H, s), 4.13 (2H, q, J=7.2 Hz), 7.05-7.17 (2H, m), 8.01-8.13 (2H, m).

B) ethyl 1-(4-(4-fluorophenyl)pyrimidin-5-yl)piperidine-4-carboxylate

A mixture of ethyl 1-(2-(4-fluorophenyl)-2-oxoethyl)piperidine-4-carboxylate (8.0 g) and N,N-dimethylformamide dimethyl acetal (50 mL) was heated with reflux for 5 hr, and the solvent was evaporated under reduced pressure. To a mixture of the obtained residue, n-butanol (40 mL) and DIPEA (40 mL) was added formamidine acetate (9.9 g), and the mixture was stirred overnight at 100° C. To the mixture was added 1M hydrochloric acid, and the solvent was evaporated under reduced pressure. The residue was diluted with water, and the mixture was extracted with ethyl acetate. The organic layer was washed with water and saturated brine, and dried over anhydrous magnesium sulfate, and the solvent was evaporated under reduced pressure. The residue was purified by silica gel column chromatography (ethyl acetate/hexane), and the obtained solid was crystallized from ethyl acetate/hexane to give the title compound (4.7 g).
$^1$H NMR (300 MHz, CDCl$_3$) δ 1.27 (3H, t, J=7.2 Hz), 1.67-1.84 (2H, m), 1.87-2.00 (2H, m), 2.38 (1H, tt, J=11.2, 4.0 Hz), 2.68 (2H, td, J=11.5, 2.7 Hz), 3.21 (2H, dt, J=12.2, 3.2 Hz), 4.16 (2H, q, J=7.2 Hz), 7.12-7.21 (2H, m), 8.07-8.18 (2H, m), 8.41 (1H, s), 8.90 (1H, s).

C) 1-(4-(4-fluorophenyl)pyrimidin-5-yl)piperidine-4-carboxylic acid

Ethyl 1-(4-(4-fluorophenyl)pyrimidin-5-yl)piperidine-4-carboxylate (2.2 g) was dissolved in THF (20 mL) and methanol (5.0 mL), to the mixture was added 2M aqueous sodium hydroxide solution (6.6 mL), and the mixture was stirred at room temperature for 3.5 hr. The mixture was concentrated, the residue was neutralized with 2M hydrochloric acid, and the precipitated solid was collected by filtration to give the title compound (2.0 g).
$^1$H NMR (300 MHz, DMSO-d$_6$) δ 1.51-1.68 (2H, m), 1.76-1.88 (2H, m), 2.24-2.38 (1H, m), 2.62-2.75 (2H, m), 3.06-3.18 (2H, m), 7.30-7.41 (2H, m), 8.09-8.20 (2H, m), 8.54 (1H, s), 8.85 (1H, s), 12.25 (1H, brs).

D) N-cyclopropyl-1-(4-(4-fluorophenyl)pyrimidin-5-yl)-N-methylpiperidine-4-carboxamide A mixture of 1-(4-(4-fluorophenyl)pyrimidin-5-yl)piperidine-4-carboxylic acid (0.10 g), N-methylcyclopropanamine (28 mg), HATU (0.15 g), DIPEA (0.15 mL) and DMF (2.0 mL) was stirred at room temperature for 4 hr. To the mixture was added water, and the mixture was extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane), and the obtained solid was crystallized from ethyl acetate/heptane to give the title compound (94 mg).
$^1$H NMR (300 MHz, CDCl$_3$) δ 0.70-0.81 (2H, m), 0.85-0.96 (2H, m), 1.65-1.77 (2H, m), 1.82-1.99 (2H, m), 2.62-2.75 (3H, m), 2.93 (3H, s), 3.02-3.17 (1H, m), 3.24-3.37 (2H, m), 7.13-7.22 (2H, m), 8.11-8.20 (2H, m), 8.42 (1H, s), 8.90 (1H, s).

Example 278

(3-fluoroazetidin-1-yl)(1-(4-(4-fluorophenyl)pyrimidin-5-yl)piperidin-4-yl)methanone A mixture of 1-(4-(4-fluorophenyl)pyrimidin-5-yl)piperidine-4-carboxylic acid (0.10 g), 3-fluoroazetidine hydrochloride (0.056 g), HATU (0.16 g), DIPEA (0.23 mL) and DMF (2.0 mL) was stirred at room temperature for 18 hr. The mixture was diluted with ethyl acetate and water, and extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane), and triturated with diethyl ether to give the title compound (0.11 g).
$^1$H NMR (300 MHz, CDCl$_3$) δ1.62-1.94 (4H, m), 2.18-2.31 (1H, m), 2.59-2.73 (2H, m), 3.21-3.34 (2H, m), 4.03-4.49 (4H, m), 5.18-5.46 (1H, m), 7.12-7.21 (2H, m), 8.09-8.17 (2H, m), 8.41 (1H, s), 8.90 (1H, s).

Example 280

(3-fluoroazetidin-1-yl)(1-(4-(4-methyl-1H-pyrazol-1-yl)pyridin-3-yl)piperidin-4-yl)methanone A mixture of 1-(4-(4-methyl-1H-pyrazol-1-yl)pyridin-3-yl)piperidine-4-carboxylic acid (60 mg), 3-fluoroazetidine hydrochloride (28 mg), HATU (96 mg), DIPEA (0.091 mL) and DMF (2.0 mL) was stirred at room temperature for 4 hr. To the mixture was added water, and the mixture was extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane), and the obtained solid was crystallized from ethyl acetate/heptane to give the title compound (68 mg).

$^1$H NMR (300 MHz, CDCl$_3$) δ 1.67-1.99 (4H, m), 2.17 (3H, s), 2.20-2.33 (1H, m), 2.64-2.78 (2H, m), 3.07-3.19 (2H, m), 4.04-4.52 (4H, m), 5.19-5.48 (1H, m), 7.54 (1H, s), 7.60 (1H, d, J=5.3 Hz), 8.32-8.36 (2H, m), 8.39 (1H, s).

Example 281

(1-(4-(4-chloro-1H-pyrazol-1-yl)pyridin-3-yl)piperidin-4-yl) (3-fluoroazetidin-1-yl)methanone A mixture of 1-(4-(4-chloro-1H-pyrazol-1-yl)pyridin-3-yl)piperidine-4-carboxylic acid (0.060 g), 3-fluoroazetidine hydrochloride (0.026 g), HATU (0.089 g), DIPEA (0.085 mL) and DMF (2.0 mL) was stirred at room temperature for 4 hr. The mixture was diluted with ethyl acetate and water, and extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane), and crystallized from ethyl acetate/heptane to give the title compound (0.062 g).

$^1$H NMR (300 MHz, CDCl$_3$) δ 1.69-2.01 (4H, m), 2.21-2.36 (1H, m), 2.68-2.81 (2H, m), 3.05-3.18 (2H, m), 4.03-4.53 (4H, m), 5.19-5.48 (1H, m), 7.59 (1H, d, J=5.3 Hz), 7.66 (1H, s), 8.39 (1H, d, J=5.3 Hz), 8.44 (1H, s), 8.56 (1H, s).

Example 282

((3S)-3-fluoropyrrolidin-1-yl)(1-(4-(4-methyl-1H-pyrazol-1-yl)pyridin-3-yl)piperidin-4-yl)methanone A mixture of 1-(4-(4-methyl-1H-pyrazol-1-yl)pyridin-3-yl)piperidine-4-carboxylic acid (60 mg), (S)-3-fluoropyrrolidine hydrochloride (32 mg), HATU (96 mg), DIPEA (0.091 mL) and DMF (2.0 mL) was stirred at room temperature for 4 hr. To the mixture was added water, and the mixture was extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane), and the obtained solid was crystallized from ethyl acetate/heptane to give the title compound (68 mg).

$^1$H NMR (300 MHz, CDCl$_3$) δ1.68-2.10 (5H, m), 2.17 (3H, s), 2.20-2.56 (2H, m), 2.66-2.79 (2H, m), 3.09-3.20 (2H, m), 3.45-3.99 (4H, m), 5.14-5.44 (1H, m), 7.54 (1H, s), 7.61 (1H, d, J=5.3 Hz), 8.32-8.37 (2H, m), 8.40 (1H, s).

Example 283

((3R)-3-fluoropyrrolidin-1-yl)(1-(4-(4-methyl-1H-pyrazol-1-yl)pyridin-3-yl)piperidin-4-yl)methanone A mixture of 1-(4-(4-methyl-1H-pyrazol-1-yl)pyridin-3-yl)piperidine-4-carboxylic acid (60 mg), (R)-3-fluoropyrrolidine hydrochloride (32 mg), HATU (96 mg), DIPEA (0.091 mL) and DMF (2.0 mL) was stirred at room temperature for 4 hr. To the mixture was added water, and the mixture was extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane), and the obtained solid was crystallized from ethyl acetate/heptane to give the title compound (64 mg).

$^1$H NMR (300 MHz, CDCl$_3$) δ1.70-2.15 (5H, m), 2.17 (3H, s), 2.21-2.56 (2H, m), 2.65-2.80 (2H, m), 3.08-3.20 (2H, m), 3.45-4.00 (4H, m), 5.15-5.43 (1H, m), 7.54 (1H, s), 7.61 (1H, d, J=5.3 Hz), 8.33-8.37 (2H, m), 8.40 (1H, s).

Example 284

(1-(4-(4-chloro-1H-pyrazol-1-yl)pyridin-3-yl)piperidin-4-yl)((3S)-3-fluoropyrrolidin-1-yl)methanone A mixture of 1-(4-(4-chloro-1H-pyrazol-1-yl)pyridin-3-yl)piperidine-4-carboxylic acid (0.060 g), (S)-3-fluoropyrrolidine hydrochloride (0.030 g), HATU (0.089 g), DIPEA (0.085 mL) and DMF (2.0 mL) was stirred at room temperature for 4 hr. The mixture was diluted with ethyl acetate and water, and extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane), and crystallized from ethyl acetate/heptane to give the title compound (0.064 g).

$^1$H NMR (300 MHz, CDCl$_3$) δ 1.72-2.58 (7H, m), 2.69-2.84 (2H, m), 3.08-3.20 (2H, m), 3.46-4.01 (4H, m), 5.13-5.44 (1H, m), 7.60 (1H, d, J=5.3 Hz), 7.66 (1H, s), 8.39 (1H, d, J=5.3 Hz), 8.45 (1H, s), 8.59 (1H, s).

Example 285

(1-(4-(4-chloro-1H-pyrazol-1-yl)pyridin-3-yl)piperidin-4-yl)((3R)-3-fluoropyrrolidin-1-yl)methanone A mixture of 1-(4-(4-chloro-1H-pyrazol-1-yl)pyridin-3-yl)piperidine-4-carboxylic acid (60 mg), (R)-3-fluoropyrrolidine hydrochloride (30 mg), HATU (89 mg), DIPEA (0.085 mL) and DMF (2.0 mL) was stirred at room temperature for 2 hr. To the mixture was added water, and the mixture was extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane), and the obtained solid was crystallized from ethyl acetate/heptane to give the title compound (63 mg).

$^1$H NMR (300 MHz, CDCl$_3$) δ 1.74-2.59 (7H, m), 2.69-2.84 (2H, m), 3.07-3.20 (2H, m), 3.45-3.99 (4H, m), 5.15-5.44 (1H, m), 7.60 (1H, d, J=5.3 Hz), 7.66 (1H, s), 8.39 (1H, d, J=5.3 Hz), 8.46 (1H, s), 8.59 (1H, s).

Example 286

(1-(4-(4-fluorophenyl)pyrimidin-5-yl)piperidin-4-yl)((3S)-3-fluoropyrrolidin-1-yl)methanone A mixture of 1-(4-(4-fluorophenyl)pyrimidin-5-yl)piperidine-4-carboxylic acid (0.060 g), (S)-3-fluoropyrrolidine hydrochloride (0.030 g), HATU (0.091 g), DIPEA (0.087 mL) and DMF (2.0 mL) was stirred at room temperature for 4 hr. The mixture was diluted with ethyl acetate and water, and extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane), and crystallized from ethyl acetate/heptane to give the title compound (0.059 g).

$^1$H NMR (300 MHz, CDCl$_3$) δ1.66-2.54 (7H, m), 2.61-2.74 (2H, m), 3.25-3.36 (2H, m), 3.45-3.98 (4H, m), 5.14-5.41 (1H, m), 7.12-7.22 (2H, m), 8.11-8.18 (2H, m), 8.42 (1H, s), 8.90 (1H, s).

Example 287

(1-(4-(4-fluorophenyl)pyrimidin-5-yl)piperidin-4-yl)((3R)-3-fluoropyrrolidin-1-yl)methanone A mixture of 1-(4-(4-fluorophenyl)pyrimidin-5-yl)piperidine-4-carboxylic acid (60 mg), (R)-3-fluoropyrrolidine hydrochloride (30 mg), HATU (91 mg), DIPEA (0.087 mL) and DMF (2.0 mL) was stirred at room temperature for 4 hr. To the mixture was added water, and the mixture was extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane), and the obtained solid was crystallized from ethyl acetate/heptane to give the title compound (60 mg).

$^1$H NMR (300 MHz, CDCl$_3$) δ 1.64-2.53 (7H, m), 2.61-2.75 (2H, m), 3.24-3.37 (2H, m), 3.46-3.98 (4H, m), 5.13-5.43 (1H, m), 7.12-7.21 (2H, m), 8.10-8.18 (2H, m), 8.42 (1H, s), 8.90 (1H, s).

Example 288

1-(4-(4-fluorophenyl)pyrimidin-5-yl)-N-methyl-N-(tetrahydro-2H-pyran-4-yl)piperidine-4-carboxamide A mixture of 1-(4-(4-fluorophenyl)pyrimidin-5-yl)piperidine-4-carboxylic acid (60 mg), N-methyl-N-(tetrahydro-2H-pyran-4-yl)amine (28 mg), HATU (91 mg), DIPEA (0.087 mL) and DMF (2.0 mL) was stirred at room temperature for 4 hr. To the mixture was added water, and the mixture was extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane), and the obtained solid was crystallized from ethyl acetate/heptane to give the title compound (68 mg).

$^1$H NMR (300 MHz, CDCl$_3$) δ 1.46-2.06 (8H, m), 2.48-2.77 (3H, m), 2.81-2.95 (3H, m), 3.21-3.57 (4H, m), 3.96-4.13 (2H, m), 4.62-4.84 (1H, m), 7.12-7.21 (2H, m), 8.10-8.19 (2H, m), 8.42 (1H, s), 8.90 (1H, s).

Example 290

1-(4-(4-fluorophenyl)pyrimidin-5-yl)-N-((3S)-tetrahydrofuran-3-yl)piperidine-4-carboxamide A mixture of 1-(4-(4-fluorophenyl)pyrimidin-5-yl)piperidine-4-carboxylic acid (0.30 g), (S)-tetrahydrofuran-3-amine hydrochloride (0.15 g), HATU (0.45 g), DIPEA (0.43 mL) and DMF (5.0 mL) was stirred at room temperature for 4 hr. To the mixture was added water, and the mixture was extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane), and the obtained solid was crystallized from ethyl acetate/heptane to give the title compound (0.32 g).

$^1$H NMR (300 MHz, CDCl$_3$) δ 1.70-1.87 (5H, m), 2.06-2.19 (1H, m), 2.22-2.36 (1H, m), 2.59-2.71 (2H, m), 3.21-3.34 (2H, m), 3.66 (1H, dd, J=9.4, 2.3 Hz), 3.74-3.85 (2H, m), 3.89-3.99 (1H, m), 4.47-4.60 (1H, m), 5.63 (1H, d, J=6.4 Hz), 7.12-7.21 (2H, m), 8.08-8.16 (2H, m), 8.41 (1H, s), 8.90 (1H, s).

Example 291

1-(4-(4-fluorophenyl)pyrimidin-5-yl)-N-((3R)-tetrahydrofuran-3-yl)piperidine-4-carboxamide A mixture of 1-(4-(4-fluorophenyl)pyrimidin-5-yl)piperidine-4-carboxylic acid (0.30 g), (R)-tetrahydrofuran-3-amine hydrochloride (0.15 g), HATU (0.45 g), DIPEA (0.43 mL) and DMF (5.0 mL) was stirred at room temperature for 4 hr. To the mixture was added water, and the mixture was extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane), and the obtained solid was crystallized from ethyl acetate/heptane to give the title compound (0.34 g).

$^1$H NMR (300 MHz, CDCl$_3$) δ1.71-1.86 (5H, m), 2.04-2.18 (1H, m), 2.22-2.36 (1H, m), 2.59-2.71 (2H, m), 3.22-3.32 (2H, m), 3.62-3.69 (1H, m), 3.74-3.85 (2H, m), 3.89-3.99 (1H, m), 4.47-4.60 (1H, m), 5.63 (1H, d, J=7.5 Hz), 7.12-7.22 (2H, m), 8.06-8.17 (2H, m), 8.41 (1H, s), 8.90 (1H, s).

Example 292

1-(4-(4-methyl-1H-pyrazol-1-yl)pyridin-3-yl)-N-((3S)-tetrahydrofuran-3-yl)piperidine-4-carboxamide A mixture of 1-(4-(4-methyl-1H-pyrazol-1-yl)pyridin-3-yl)piperidine-4-carboxylic acid (1.0 g), (S)-tetrahydrofuran-3-amine hydrochloride (0.43 g), HATU (1.7 g), triethylamine (1.9 mL) and DMF (12 mL) was stirred at room temperature for 3 hr. To the mixture was added water, and the mixture was extracted with ethyl acetate. The organic layer was washed with water and saturated brine, and dried over anhydrous magnesium sulfate, and the solvent was evaporated under reduced pressure. The residue was purified by silica gel column chromatography (NH, ethyl acetate/hexane), and the obtained solid was crystallized from ethyl acetate/hexane to give the title compound (0.82 g).

$^1$H NMR (300 MHz, CDCl$_3$) δ 1.72-1.92 (5H, m), 2.07-2.21 (4H, m), 2.22-2.38 (1H, m), 2.69 (2H, dt, J=11.7, 7.2 Hz), 3.12 (2H, d, J=12.1 Hz), 3.66 (1H, dd, J=9.5, 2.7 Hz), 3.74-3.87 (2H, m), 3.88-4.01 (1H, m), 4.47-4.61 (1H, m), 5.73 (1H, d, J=7.2 Hz), 7.54 (1H, s), 7.60 (1H, d, J=5.3 Hz), 8.31 (1H, d, J=0.8 Hz), 8.35 (1H, d, J=5.3 Hz), 8.39 (1H, s).

Example 293

1-(4-(4-chloro-1H-pyrazol-1-yl)pyridin-3-yl)-N-((3S)-tetrahydrofuran-3-yl)piperidine-4-carboxamide A mixture of 1-(4-(4-chloro-1H-pyrazol-1-yl)pyridin-3-yl)piperidine-4-carboxylic acid (0.50 g), (S)-tetrahydrofuran-3-amine hydrochloride (0.20 g), HATU (0.81 g), triethylamine (0.91 mL) and DMF (5.4 mL) was stirred at room temperature for 3 hr. To the mixture was added water, and the mixture was extracted with ethyl acetate. The organic layer was washed with water and saturated brine, and dried over anhydrous magnesium sulfate, and the solvent was evaporated under reduced pressure. The residue was purified by silica gel column chromatography (NH, ethyl acetate/hexane), and the obtained solid was crystallized from ethyl acetate/hexane to give the title compound (0.51 g).

$^1$H NMR (300 MHz, CDCl$_3$) δ1.72-1.96 (5H, m), 2.10-2.37 (2H, m), 2.73 (2H, td, J=10.8, 4.2 Hz), 3.04-3.18 (2H, m), 3.67 (1H, dd, J=9.5, 2.3 Hz), 3.74-3.87 (2H, m), 3.89-4.00 (1H, m), 4.49-4.62 (1H, m), 5.71 (1H, d, J=7.2 Hz), 7.59 (1H, d, J=5.3 Hz), 7.66 (1H, d, J=0.8 Hz), 8.39 (1H, d, J=5.3 Hz), 8.44 (1H, s), 8.54 (1H, d, J=0.8 Hz).

Example 294

1-(4-(4-methyl-1H-pyrazol-1-yl)pyridin-3-yl)-N-((3R)-tetrahydrofuran-3-yl)piperidine-4-carboxamide A mixture of 1-(4-(4-methyl-1H-pyrazol-1-yl)pyridin-3-yl)piperidine-4-carboxylic acid (1.0 g), (R)-tetrahydrofuran-3-amine hydrochloride (0.43 g), HATU (1.7 g), triethylamine (1.9 mL) and DMF (12 mL) was stirred at room temperature for 3 hr. To the mixture was added water, and the mixture was extracted with ethyl acetate. The organic layer was washed with water and saturated brine, and dried over anhydrous magnesium sulfate, and the solvent was evaporated under reduced pressure. The residue was purified by silica gel column chromatography (NH, ethyl acetate/hexane), and the obtained solid was crystallized from ethyl acetate/hexane to give the title compound (0.83 g).

$^1$H NMR (300 MHz, CDCl$_3$) δ1.67-1.93 (5H, m), 2.05-2.37 (5H, m), 2.69 (2H, dt, J=12.0, 7.2 Hz), 3.12 (2H, d, J=11.7 Hz), 3.67 (1H, dd, J=9.5, 2.3 Hz), 3.73-3.87 (2H, m), 3.88-4.00 (1H, m), 4.55 (1H, dtd, J=7.6, 4.8, 2.8 Hz), 5.75 (1H, d, J=7.2 Hz), 7.54 (1H, s), 7.60 (1H, d, J=4.9 Hz), 8.31 (1H, s), 8.34 (1H, d, J=5.3 Hz), 8.39 (1H, s).

Example 295

1-(4-(4-chloro-1H-pyrazol-1-yl)pyridin-3-yl)-N-((3R)-tetrahydrofuran-3-yl)piperidine-4-carboxamide A mixture of 1-(4-(4-chloro-1H-pyrazol-1-yl)pyridin-3-yl)piperidine-4-carboxylic acid (0.50 g), (R)-tetrahydrofuran-3-amine hydrochloride (0.20 g), HATU (0.81 g), triethylamine (0.91 mL) and DMF (5.4 mL) was stirred at room temperature for 3 hr. To the mixture was added water, and the mixture was extracted with ethyl acetate. The organic layer was washed with water and saturated brine, and dried over anhydrous magnesium sulfate, and the solvent was evaporated under reduced pressure. The residue was purified by silica gel column chromatography (NH, ethyl acetate/hexane), and the obtained solid was crystallized from ethyl acetate/hexane to give the title compound (0.50 g).

$^1$H NMR (300 MHz, CDCl$_3$) δ1.69-1.97 (5H, m), 2.10-2.37 (2H, m), 2.73 (2H, td, J=10.8, 4.2 Hz), 3.05-3.17 (2H, m), 3.67 (1H, dd, J=9.5, 2.3 Hz), 3.73-3.87 (2H, m), 3.89-4.01 (1H, m), 4.55 (1H, ddt, J=7.6, 5.1, 2.4 Hz), 5.69 (1H, d, J=7.2 Hz), 7.59 (1H, d, J=5.3 Hz), 7.66 (1H, s), 8.39 (1H, d, J=5.3 Hz), 8.44 (1H, s), 8.54 (1H, d, J=0.8 Hz).

Example 296

N-methyl-1-(4-(4-methyl-1H-pyrazol-1-yl)pyridin-3-yl)-N-(tetrahydro-2H-pyran-4-yl)piperidine-4-carboxamide A mixture of 1-(4-(4-methyl-1H-pyrazol-1-yl)pyridin-3-yl)piperidine-4-carboxylic acid (80 mg), N-methyl-N-(tetrahydro-2H-pyran-4-yl)amine (39 mg), HATU (0.13 g), DIPEA (0.12 mL) and DMF (2.0 mL) was stirred at room temperature for 4 hr. To the mixture was added water, and the mixture was extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane), and the obtained solid was crystallized from ethyl acetate/heptane to give the title compound (73 mg).

$^1$H NMR (300 MHz, CDCl$_3$) δ 1.49-2.07 (8H, m), 2.17 (3H, s), 2.52-2.81 (3H, m), 2.84-2.96 (3H, m), 3.08-3.21 (2H, m), 3.38-3.57 (2H, m), 3.97-4.13 (2H, m), 4.67-4.83 (1H, m), 7.54 (1H, s), 7.61 (1H, d, J=5.3 Hz), 8.33-8.39 (2H, m), 8.40 (1H, s).

Example 297

N-(4-fluorobenzyl)-N-methyl-4-(4-(4-methyl-1H-pyrazol-1-yl)pyridin-3-yl)piperazine-1-carboxamide To a mixture of N-(4-fluorobenzyl)-4-(4-(4-methyl-1H-pyrazol-1-yl)pyridin-3-yl)piperazine-1-carboxamide (0.20 g) and DMF (3.0 mL) was added sodium hydride (60%, 30 mg) under ice-cooling, and the mixture was stirred at the same temperature for 30 min. To the mixture was added methyl iodide (0.047 mL) under ice-cooling, and the mixture was stirred at the same temperature for 30 min. To the mixture were added saturated aqueous ammonium chloride solution, ethyl acetate and pyridine, and the mixture was extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane) to give the title compound (0.18 g).

$^1$H NMR (300 MHz, CDCl$_3$) δ2.17 (3H, s), 2.78 (3H, s), 2.88-2.95 (4H, m), 3.30-3.38 (4H, m), 4.38 (2H, s), 6.97-7.07 (2H, m), 7.19-7.26 (2H, m), 7.55 (1H, s), 7.58 (1H, d, J=5.3 Hz), 8.30 (1H, s), 8.35-8.41 (2H, m).

Example 298

N-benzyl-N-methyl-4-(4-phenylpyrimidin-5-yl)piperazine-1-carboxamide

To a mixture of N-benzyl-4-(4-phenylpyrimidin-5-yl)piperazine-1-carboxamide (0.15 g) and DMF (3.0 mL) was added sodium hydride (60%, 24 mg) under ice-cooling, and the mixture was stirred at the same temperature for 30 min. To the mixture was added methyl iodide (0.038 mL), and the mixture was stirred for 1.5 hr under ice-cooling. To the mixture were added saturated aqueous ammonium chloride solution, ethyl acetate and pyridine, and the mixture was extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane), and crystallized from ethyl acetate/heptane to give the title compound (0.11 g).

$^1$H NMR (300 MHz, CDCl$_3$) δ2.75 (3H, s), 2.93-3.02 (4H, m), 3.25-3.33 (4H, m), 4.40 (2H, s), 7.19-7.37 (5H, m), 7.42-7.52 (3H, m), 8.03-8.11 (2H, m), 8.41 (1H, s), 8.94 (1H, s).

Example 299

(1-(4-(4-chloro-1H-pyrazol-1-yl)pyridin-3-yl)piperidin-4-yl)((3S)-3-methoxypyrrolidin-1-yl)methanone A mixture of 1-(4-(4-chloro-1H-pyrazol-1-yl)pyridin-3-yl)piperidine-4-carboxylic acid (0.10 g), (S)-3-methoxypyrrolidine hydrochloride (49 mg), HATU (0.16 g), triethylamine (0.18 mL) and DMF (1.1 mL) was stirred at room temperature for 3 hr. To the mixture was added water, and the mixture was extracted with ethyl acetate. The organic layer was washed with water and saturated brine, and dried over anhydrous magnesium sulfate, and the solvent was evaporated under reduced pressure. The residue was purified by silica gel column chromatography (NH, ethyl acetate/hexane), and the obtained solid was crystallized from ethyl acetate/hexane to give the title compound (0.066 g).

$^1$H NMR (300 MHz, CDCl$_3$) δ 1.73-2.22 (6H, m), 2.37-2.55 (1H, m), 2.69-2.82 (2H, m), 3.06-3.20 (2H, m), 3.34 (3H, d, J=5.3 Hz), 3.41-3.76 (4H, m), 3.92-4.07 (1H, m), 7.60 (1H, d, J=5.3 Hz), 7.66 (1H, s), 8.38 (1H, d, J=5.3 Hz), 8.45 (1H, s), 8.60 (1H, s).

Example 300

(1-(4-(4-chloro-1H-pyrazol-1-yl)pyridin-3-yl)piperidin-4-yl)((3R)-3-methoxypyrrolidin-1-yl)methanone A mixture of 1-(4-(4-chloro-1H-pyrazol-1-yl)pyridin-3-yl)piperidine-4-carboxylic acid (0.10 g), (R)-3-methoxypyrrolidine hydrochloride (49 mg), HATU (0.16 g), triethylamine (0.18 mL) and DMF (1.1 mL) was stirred at room temperature for 3 hr. To the mixture was added water, and the mixture was extracted with ethyl acetate. The organic layer was washed with water and saturated brine, and dried over anhydrous magnesium sulfate, and the solvent was evaporated under reduced pressure. The residue was purified by silica gel column chromatography (NH, ethyl acetate/hexane), and the obtained solid was crystallized from ethyl acetate/hexane to give the title compound (0.076 g).

$^1$H NMR (300 MHz, CDCl$_3$) δ 1.73-2.20 (6H, m), 2.36-2.55 (1H, m), 2.68-2.83 (2H, m), 3.13 (2H, dd, J=11.4, 3.0 Hz), 3.34 (3H, d, J=5.3 Hz), 3.41-3.76 (4H, m), 3.92-4.07 (1H, m), 7.60 (1H, d, J=5.3 Hz), 7.66 (1H, s), 8.39 (1H, d, J=5.3 Hz), 8.45 (1H, s), 8.60 (1H, s).

Example 301

((3S)-3-methoxypyrrolidin-1-yl)(1-(4-(4-methyl-1H-pyrazol-1-yl)pyridin-3-yl)piperidin-4-yl)methanone A mixture of 1-(4-(4-methyl-1H-pyrazol-1-yl)pyridin-3-yl)piperidine-4-carboxylic acid (0.10 g), (S)-3-methoxypyrrolidine hydrochloride (53 mg), HATU (0.17 g), triethylamine (0.20 mL) and DMF (1.2 mL) was stirred at room temperature for 3 hr. To the mixture was added water, and the mixture was extracted with ethyl acetate. The organic layer was washed with water and saturated brine, and dried over anhydrous magnesium sulfate, and the solvent was evaporated under reduced pressure. The residue was purified by silica gel column chromatography (NH, ethyl acetate/hexane) to give the title compound (0.050 g).

$^1$H NMR (300 MHz, CDCl$_3$) δ 1.71-2.20 (9H, m), 2.44 (1H, d, J=17.0 Hz), 2.72 (2H, td, J=11.9, 2.7 Hz), 3.14 (2H, d, J=12.1 Hz), 3.34 (3H, d, J=5.3 Hz), 3.42-3.77 (4H, m), 3.92-4.06 (1H, m), 7.53 (1H, s), 7.61 (1H, d, J=5.3 Hz), 8.31-8.42 (3H, m).

Example 302

((3R)-3-methoxypyrrolidin-1-yl)(1-(4-(4-methyl-1H-pyrazol-1-yl)pyridin-3-yl)piperidin-4-yl)methanone A mixture of 1-(4-(4-methyl-1H-pyrazol-1-yl)pyridin-3-yl)piperidine-4-carboxylic acid (100 mg), (R)-3-methoxypyrrolidine hydrochloride (53 mg), HATU (0.17 g), triethylamine (0.20 mL) and DMF (1.2 mL) was stirred at room temperature for 3 hr. To the mixture was added water, and the mixture was extracted with ethyl acetate. The organic layer was washed with water and saturated brine, and dried over anhydrous magnesium sulfate, and the solvent was evaporated under reduced pressure. The residue was purified by silica gel column chromatography (NH, ethyl acetate/hexane) to give the title compound (0.039 g).

$^1$H NMR (300 MHz, CDCl$_3$) δ 1.72-2.21 (9H, m), 2.33-2.55 (1H, m), 2.72 (2H, td, J=12.0, 2.5 Hz), 3.14 (2H, d, J=12.1 Hz), 3.34 (3H, d, J=5.3 Hz), 3.43-3.76 (4H, m), 3.90-4.11 (1H, m), 7.53 (1H, s), 7.61 (1H, d, J=4.9 Hz), 8.29-8.43 (3H, m).

Example 303

(1-(4-(4-fluorophenyl)pyrimidin-5-yl)piperidin-4-yl)((3S)-3-methoxypyrrolidin-1-yl)methanone A mixture of 1-(4-(4-fluorophenyl)pyrimidin-5-yl)piperidine-4-carboxylic acid (0.10 g), (S)-3-methoxypyrrolidine hydrochloride (50 mg), HATU (0.16 g), triethylamine (0.19 mL) and DMF (1.1 mL) was stirred at room temperature for 3 hr. To the mixture was added water, and the mixture was extracted with ethyl acetate. The organic layer was washed with water and saturated brine, and dried over anhydrous magnesium sulfate, and the solvent was evaporated under reduced pressure. The residue was purified by silica gel column chromatography (NH, ethyl acetate/hexane) to give the title compound (0.073 g).

$^1$H NMR (300 MHz, CDCl$_3$) δ 1.65-2.20 (6H, m), 2.34-2.51 (1H, m), 2.67 (2H, td, J=11.8, 2.5 Hz), 3.21-3.37 (5H, m), 3.41-3.74 (4H, m), 3.89-4.05 (1H, m), 7.09-7.23 (2H, m), 8.07-8.19 (2H, m), 8.41 (1H, s), 8.90 (1H, s).

Example 304

(1-(4-(4-fluorophenyl)pyrimidin-5-yl)piperidin-4-yl)((3R)-3-methoxypyrrolidin-1-yl)methanone A mixture of 1-(4-(4-fluorophenyl)pyrimidin-5-yl)piperidine-4-carboxylic acid (0.10 g), (R)-3-methoxypyrrolidine hydrochloride (50 mg), HATU (0.16 g), triethylamine (0.19 mL) and DMF (1.1 mL) was stirred at room temperature for 3 hr. To the mixture was added water, and the mixture was extracted with ethyl acetate. The organic layer was washed with water and saturated brine, and dried over anhydrous magnesium sulfate, and the solvent was evaporated under reduced pressure. The residue was purified by silica gel column chromatography (NH, ethyl acetate/hexane) to give the title compound (0.074 g).

$^1$H NMR (300 MHz, CDCl$_3$) δ 1.66-2.22 (6H, m), 2.31-2.51 (1H, m), 2.58-2.76 (2H, m), 3.21-3.38 (5H, m), 3.39-3.77 (4H, m), 3.90-4.07 (1H, m), 7.16 (2H, t, J=8.7 Hz), 8.15 (2H, dd, J=8.7, 5.7 Hz), 8.41 (1H, s), 8.90 (1H, s).

Example 305

N-methyl-1-(4-(4-methyl-1H-pyrazol-1-yl)pyridin-3-yl)-N-((3S)-tetrahydrofuran-3-yl)piperidine-4-carboxamide To a mixture of 1-(4-(4-methyl-1H-pyrazol-1-yl)pyridin-3-yl)-N-((3S)-tetrahydrofuran-3-yl)piperidine-4-carboxamide (0.12 g) and DMF (2.0 mL) was added sodium hydride (60%, 20 mg) under ice-cooling, and the mixture was stirred for 30 min. To the mixture was added methyl iodide (0.032 mL), and the mixture was stirred for 1 hr under ice-cooling. To the mixture were added saturated aqueous ammonium chloride solution, ethyl acetate and pyridine, and the mixture was extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane), and crystallized from ethyl acetate/heptane to give the title compound (0.084 g).

$^1$H NMR (300 MHz, CDCl$_3$) δ1.69-2.05 (5H, m), 2.17 (3H, s), 2.20-2.35 (1H, m), 2.51-3.03 (6H, m), 3.08-3.20 (2H, m), 3.60-3.85 (3H, m), 4.00-4.13 (1H, m), 5.30-5.43 (1H, m), 7.54 (1H, s), 7.61 (1H, d, J=5.3 Hz), 8.33-8.37 (2H, m), 8.40 (1H, s).

Example 306

N-methyl-1-(4-(4-methyl-1H-pyrazol-1-yl)pyridin-3-yl)-N-((3R)-tetrahydrofuran-3-yl)piperidine-4-carboxamide To a mixture of 1-(4-(4-methyl-1H-pyrazol-1-yl)pyridin-3-yl)-N-((3R)-tetrahydrofuran-3-yl)piperidine-4-carboxamide (0.12 g) and DMF (2.0 mL) was added sodium hydride (60%, 20 mg) under ice-cooling, and the mixture was stirred for 30 min. To the mixture was added methyl iodide (0.032 mL), and the mixture was stirred for 1 hr under ice-cooling. To the mixture were added saturated aqueous ammonium chloride solution, ethyl acetate and pyridine, and the mixture was extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane), and crystallized from ethyl acetate/heptane to give the title compound (0.066 g).

$^1$H NMR (300 MHz, CDCl$_3$) δ1.70-2.03 (5H, m), 2.17 (3H, s), 2.20-2.35 (1H, m), 2.51-3.03 (6H, m), 3.09-3.19 (2H, m), 3.61-3.85 (3H, m), 4.01-4.14 (1H, m), 5.30-5.43 (1H, m), 7.54 (1H, s), 7.61 (1H, d, J=5.3 Hz), 8.33-8.37 (2H, m), 8.40 (1H, s).

Example 307

1-(4-(4-chloro-1H-pyrazol-1-yl)pyridin-3-yl)-N-methyl-N-((3S)-tetrahydrofuran-3-yl)piperidine-4-carboxamide To a mixture of 1-(4-(4-chloro-1H-pyrazol-1-yl)pyridin-3-yl)-N-((3S)-tetrahydrofuran-3-yl)piperidine-4-carboxamide (0.12 g) and DMF (2.0 mL) was added sodium hydride (60%, 19 mg) under ice-cooling, and the mixture was stirred for 30 min. To the mixture was added methyl iodide (0.030 mL), and the mixture was stirred for 1 hr under ice-cooling. To the mixture were added saturated aqueous ammonium chloride solution, ethyl acetate and pyridine, and the mixture was extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane) to give the title compound (0.094 g).

$^1$H NMR (300 MHz, CDCl$_3$) δ1.71-2.03 (5H, m), 2.19-2.35 (1H, m), 2.53-3.02 (6H, m), 3.07-3.19 (2H, m), 3.60-3.85 (3H, m), 4.01-4.12 (1H, m), 5.30-5.44 (1H, m), 7.60 (1H, d, J=5.3 Hz), 7.66 (1H, s), 8.39 (1H, d, J=4.9 Hz), 8.45 (1H, s), 8.58 (1H, s).

Example 308

1-(4-(4-chloro-1H-pyrazol-1-yl)pyridin-3-yl)-N-methyl-N-((3R)-tetrahydrofuran-3-yl)piperidine-4-carboxamide To a mixture of 1-(4-(4-chloro-1H-pyrazol-1-yl)pyridin-3-yl)-N-((3R)-tetrahydrofuran-3-yl)piperidine-4-carboxamide (0.12 g) and DMF (2.0 mL) was added sodium hydride (60%, 19 mg) under ice-cooling, and the mixture was stirred for 30 min. To the mixture was added methyl iodide (0.030 mL), and the mixture was stirred for 1 hr under ice-cooling. To the mixture were added saturated aqueous ammonium chloride solution, ethyl acetate and pyridine, and the mixture was extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane) to give the title compound (0.092 g).

$^1$H NMR (300 MHz, CDCl$_3$) δ1.70-2.03 (5H, m), 2.18-2.35 (1H, m), 2.53-3.04 (6H, m), 3.08-3.20 (2H, m), 3.60-3.85 (3H, m), 4.01-4.12 (1H, m), 5.31-5.43 (1H, m), 7.60 (1H, d, J=5.3 Hz), 7.66 (1H, s), 8.39 (1H, d, J=5.3 Hz), 8.45 (1H, s), 8.58 (1H, s).

Example 309

1-(4-(4-fluorophenyl)pyrimidin-5-yl)-N-methyl-N-((3S)-tetrahydrofuran-3-yl)piperidine-4-carboxamide To a mixture of 1-(4-(4-fluorophenyl)pyrimidin-5-yl)-N-((3S)-tetrahydrofuran-3-yl)piperidine-4-carboxamide (0.12 g) and DMF (2.0 mL) was added sodium hydride (60%, 19 mg) under ice-cooling, and the mixture was stirred for 30 min. To the mixture was added methyl iodide (0.034 mL), and the mixture was stirred for 2.5 hr under ice-cooling. To the mixture were added saturated aqueous ammonium chloride solution, ethyl acetate and pyridine, and the mixture was extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane), and crystallized from ethyl acetate/heptane to give the title compound (0.091 g).

$^1$H NMR (300 MHz, CDCl$_3$) δ1.66-2.03 (5H, m), 2.17-2.35 (1H, m), 2.46-2.75 (3H, m), 2.83-3.01 (3H, m), 3.23-

3.35 (2H, m), 3.60-3.82 (3H, m), 4.00-4.12 (1H, m), 5.27-5.42 (1H, m), 7.12-7.22 (2H, m), 8.09-8.19 (2H, m), 8.42 (1H, s), 8.90 (1H, s).

Example 310

1-(4-(4-fluorophenyl)pyrimidin-5-yl)-N-methyl-N-((3R)-tetrahydrofuran-3-yl)piperidine-4-carboxamide To a mixture of 1-(4-(4-fluorophenyl)pyrimidin-5-yl)-N-((3R)-tetrahydrofuran-3-yl)piperidine-4-carboxamide (0.12 g) and DMF (2.0 mL) was added sodium hydride (60%, 19 mg) under ice-cooling, and the mixture was stirred for 30 min. To the mixture was added methyl iodide (0.034 mL), and the mixture was stirred for 2.5 hr under ice-cooling. To the mixture were added saturated aqueous ammonium chloride solution, ethyl acetate and pyridine, and the mixture was extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane), and crystallized from ethyl acetate/heptane to give the title compound (0.087 g).
$^1$H NMR (300 MHz, CDCl$_3$) δ1.65-2.02 (5H, m), 2.16-2.36 (1H, m), 2.48-2.77 (3H, m), 2.84-3.02 (3H, m), 3.24-3.35 (2H, m), 3.60-3.81 (3H, m), 4.00-4.11 (1H, m), 5.29-5.41 (1H, m), 7.12-7.21 (2H, m), 8.10-8.19 (2H, m), 8.42 (1H, s), 8.90 (1H, s).

Example 311

N-(2-fluoroethyl)-1-(4-(4-methyl-1H-pyrazol-1-yl)pyridin-3-yl)-N-(tetrahydro-2H-pyran-4-yl)piperidine-4-carboxamide To a mixture of 1-(4-(4-methyl-1H-pyrazol-1-yl)pyridin-3-yl)-N-(tetrahydro-2H-pyran-4-yl)piperidine-4-carboxamide (0.12 g) and DMF (2.0 mL) was added sodium hydride (60%, 19 mg), and the mixture was stirred for 30 min. To the mixture was added a solution of 2-fluoroethyl 4-methylbenzenesulfonate (0.11 g) in DMF (1.0 mL), and the mixture was stirred at room temperature for 16 hr. To the mixture was added saturated aqueous ammonium chloride solution, and the mixture was extracted with ethyl acetate. The organic layer was washed with water and saturated brine, and dried over anhydrous sodium sulfate, and the solvent was evaporated under reduced pressure. The residue was purified by silica gel column chromatography (ethyl acetate/hexane) to give the title compound (3.4 mg).
$^1$H NMR (300 MHz, CDCl$_3$) δ 1.61-2.04 (8H, m), 2.17 (3H, s), 2.56-2.85 (3H, m), 3.06-3.22 (2H, m), 3.38-3.89 (5H, m), 3.97-4.15 (2H, m), 4.35-4.74 (2H, m), 7.54 (1H, s), 7.61 (1H, d, J=5.3 Hz), 8.31-8.45 (3H, m).

Example 312

N-(2-fluoroethyl)-1-(4-(4-methyl-1H-pyrazol-1-yl)pyridin-3-yl)-N-((3S)-tetrahydrofuran-3-yl)piperidine-4-carboxamide To a mixture of 1-(4-(4-methyl-1H-pyrazol-1-yl)pyridin-3-yl)-N-((3S)-tetrahydrofuran-3-yl)piperidine-4-carboxamide (0.12 g) and DMF (2.0 mL) was added sodium hydride (60%, 20 mg), and the mixture was stirred for 30 min. To the mixture was added a solution of 2-fluoroethyl 4-methylbenzenesulfonate (0.11 g) in DMF (1.0 mL), and the mixture was stirred at room temperature for 16 hr. To the mixture was added saturated aqueous ammonium chloride solution, and the mixture was extracted with ethyl acetate. The organic layer was washed with water and saturated brine, and dried over anhydrous sodium sulfate, and the solvent was evaporated under reduced pressure. The residue was purified by silica gel column chromatography (ethyl acetate/hexane) to give the title compound (12 mg).
$^1$H NMR (300 MHz, CDCl$_3$) δ 1.70-2.06 (5H, m), 2.18 (3H, s), 2.23-2.41 (1H, m), 2.62-2.84 (3H, m), 3.06-3.22 (2H, m), 3.51-3.90 (5H, m), 4.03-4.14 (1H, m), 4.42-5.00 (3H, m), 7.54 (1H, s), 7.61 (1H, d, J=5.3 Hz), 8.31-8.43 (3H, m).

Example 313

N-(2-fluoroethyl)-1-(4-(4-methyl-1H-pyrazol-1-yl)pyridin-3-yl)-N-((3R)-tetrahydrofuran-3-yl)piperidine-4-carboxamide To a mixture of 1-(4-(4-methyl-1H-pyrazol-1-yl)pyridin-3-yl)-N-((3R)-tetrahydrofuran-3-yl)piperidine-4-carboxamide (0.12 g) and DMF (2.0 mL) was added sodium hydride (60%, 20 mg), and the mixture was stirred for 30 min. To the mixture was added a solution of 2-fluoroethyl 4-methylbenzenesulfonate (0.11 g) in DMF (1.0 mL), and the mixture was stirred at room temperature for 16 hr. To the mixture was added saturated aqueous ammonium chloride solution, and the mixture was extracted with ethyl acetate. The organic layer was washed with water and saturated brine, and dried over anhydrous sodium sulfate, and the solvent was evaporated under reduced pressure. The residue was purified by silica gel column chromatography (ethyl acetate/hexane) to give the title compound (12 mg).
$^1$H NMR (300 MHz, CDCl$_3$) δ 1.70-2.04 (5H, m), 2.17 (3H, s), 2.22-2.39 (1H, m), 2.62-2.84 (3H, m), 3.07-3.22 (2H, m), 3.50-3.92 (5H, m), 4.03-4.14 (1H, m), 4.43-5.01 (3H, m), 7.54 (1H, s), 7.61 (1H, d, J=5.3 Hz), 8.31-8.44 (3H, m).

Example 314

N-benzyl-N-(2-fluoroethyl)-4-(4-phenylpyrimidin-5-yl)piperazine-1-carboxamide

To a mixture of N-benzyl-4-(4-phenylpyrimidin-5-yl)piperazine-1-carboxamide (0.11 g), 15-crown 5-ether (0.078 mL) and THF (2.0 mL) was added sodium hydride (16 mg) under ice-cooling, and the mixture was stirred at room temperature for 30 min. To the mixture was added a solution (1.0 mL) of 2-fluoroethyl 4-methylbenzenesulfonate (0.12 g) in THF, and the mixture was stirred at room temperature for 4 days. The reaction was quenched with aqueous ammonium chloride solution, and the mixture was extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane and methanol/ethyl acetate) to give the title compound (43 mg).
$^1$H NMR (300 MHz, CDCl$_3$) δ 2.91-3.01 (4H, m), 3.28-3.50 (6H, m), 4.42-4.65 (4H, m), 7.17-7.38 (5H, m), 7.43-7.52 (3H, m), 8.03-8.10 (2H, m), 8.40 (1H, s), 8.94 (1H, s).

Example 315

N-(4-fluorobenzyl)-N-(2-fluoroethyl)-4-(4-(4-methyl-1H-pyrazol-1-yl)pyridin-3-yl)piperazine-1-carboxamide To a mixture of N-(4-fluorobenzyl)-4-(4-(4-methyl-1H-pyrazol-1-yl)pyridin-3-yl)piperazine-1-carboxamide (0.12 g), 15-crown 5-ether (0.079 mL) and THF (2.0 mL) was added sodium hydride (0.016 g) at 0° C., and the mixture was stirred at room temperature for 30 min. To the mixture was added a solution (1.0 mL) of 2-fluoroethyl 4-methylbenzenesulfonate (0.12 g) in THF, and the mixture was stirred at room temperature for 4 days. To the mixture was added aqueous ammonium chloride solution, and the mixture was extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane and methanol/ethyl acetate) to give the title compound (0.072 g).
$^1$H NMR (300 MHz, CDCl$_3$) δ 2.17 (3H, s), 2.87-2.96 (4H, m), 3.32-3.50 (6H, m), 4.44-4.67 (4H, m), 6.99-7.09 (2H, m), 7.17-7.25 (2H, m), 7.55 (1H, s), 7.58 (1H, d, J=4.9 Hz), 8.28 (1H, s), 8.36-8.40 (2H, m).

Example 316

((3S)-3-fluoropyrrolidin-1-yl)(1-(4-(5-methyl-1,3-thiazol-2-yl)pyridin-3-yl)piperidin-4-yl)methanone A mixture of 1-(4-(5-methyl-1,3-thiazol-2-yl)pyridin-3-yl)piperidine-4-carboxylic acid (0.080 g), (S)-3-fluoropyrrolidine hydrochloride (0.040 g), HATU (0.12 g), DIPEA (0.12 mL) and DMF (2.0 mL) was stirred at room temperature for 18 hr. The mixture was diluted with ethyl acetate and water, and extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane), and crystallized from ethyl acetate/heptane to give the title compound (0.075 g).
$^1$H NMR (300 MHz, CDCl$_3$) δ 1.78-2.65 (10H, m), 2.87-3.02 (2H, m), 3.17-3.28 (2H, m), 3.49-4.03 (4H, m), 5.16-5.47 (1H, m), 7.60 (1H, d, J=0.9 Hz), 8.09 (1H, d, J=5.1 Hz), 8.45 (1H, d, J=5.1 Hz), 8.59 (1H, s).

Example 317

(3-fluoroazetidin-1-yl) (1-(4-(5-methyl-1,3-thiazol-2-yl)pyridin-3-yl)piperidin-4-yl)methanone A mixture of 1-(4-(5-methyl-1,3-thiazol-2-yl)pyridin-3-yl)piperidine-4-carboxylic acid (0.080 g), 3-fluoroazetidine hydrochloride (0.035 g), HATU (0.12 g), DIPEA (0.12 mL) and DMF (2.0 mL) was stirred at room temperature for 18 hr. The mixture was diluted with ethyl acetate and water, and extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane), and crystallized from ethyl acetate/heptane to give the title compound (0.071 g).
$^1$H NMR (300 MHz, CDCl$_3$) δ 1.74-1.92 (2H, m), 2.12-2.28 (2H, m), 2.29-2.41 (1H, m), 2.53 (3H, d, J=0.9 Hz), 2.86-2.99 (2H, m), 3.15-3.27 (2H, m), 4.07-4.57 (4H, m), 5.22-5.50 (1H, m), 7.60 (1H, d, J=0.9 Hz), 8.09 (1H, d, J=5.1 Hz), 8.45 (1H, d, J=5.1 Hz), 8.58 (1H, s).

Example 318

(1-(4-(4-bromo-1H-pyrazol-1-yl)pyridin-3-yl)piperidin-4-yl)((3S)-3-fluoropyrrolidin-1-yl)methanone

A) ethyl 1-(4-(4-bromo-1H-pyrazol-1-yl)pyridin-3-yl)piperidine-4-carboxylate A mixture of 4-(4-bromo-1H-pyrazol-1-yl)-3-fluoropyridine (3.0 g), ethyl piperidine-4-carboxylate (4.2 mL) and NMP (12 mL) was stirred at 180° C. for 4 hr. The mixture was purified by silica gel column chromatography (ethyl acetate/hexane), and washed with ethyl acetate/hexane to give the title compound (2.3 g).
$^1$H NMR (300 MHz, CDCl$_3$) δ 1.28 (3H, t, J=7.1 Hz), 1.73-1.91 (2H, m), 1.95-2.07 (2H, m), 2.35-2.50 (1H, m), 2.68-2.82 (2H, m), 2.99-3.13 (2H, m), 4.18 (2H, q, J=7.2 Hz), 7.58 (1H, d, J=5.1 Hz), 7.70 (1H, s), 8.39 (1H, d, J=5.1 Hz), 8.44 (1H, s), 8.58 (1H, s).

B) 1-(4-(4-bromo-1H-pyrazol-1-yl)pyridin-3-yl)piperidine-4-carboxylic acid

A mixture of ethyl 1-(4-(4-bromo-1H-pyrazol-1-yl)pyridin-3-yl)piperidine-4-carboxylate (1.2 g), 2M aqueous sodium hydroxide solution (2.4 mL), THF (4.0 mL) and ethanol (4.0 mL) was stirred at room temperature for 3 hr. The mixture was concentrated, and the residue was neutralized with 2M hydrochloric acid (2.4 mL). The precipitate was collected by filtration, washed with water, and dried under reduced pressure to give the title compound (1.1 g).
$^1$H NMR (300 MHz, DMSO-d$_6$) δ 1.54-1.72 (2H, m), 1.77-1.90 (2H, m), 2.26-2.41 (1H, m), 2.64-2.77 (2H, m), 2.83-2.95 (2H, m), 7.52 (1H, d, J=5.1 Hz), 7.96 (1H, s), 8.36 (1H, d, J=5.1 Hz), 8.48 (1H, s), 8.77 (1H, s), 12.26 (1H, s).

C) (1-(4-(4-bromo-1H-pyrazol-1-yl)pyridin-3-yl)piperidin-4-yl)((3S)-3-fluoropyrrolidin-1-yl)methanone A mixture of 1-(4-(4-bromo-1H-pyrazol-1-yl)pyridin-3-yl)piperidine-4-carboxylic acid (0.30 g), (S)-3-fluoropyrrolidine hydrochloride (0.13 g), HATU (0.39 g), DIPEA (0.37 mL) and DMF (3.0 mL) was stirred at room temperature for 18 hr. The mixture was diluted with ethyl acetate and water, and extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane), and crystallized from ethyl acetate/heptane to give the title compound (0.31 g).
$^1$H NMR (300 MHz, CDCl$_3$) δ 1.73-2.59 (7H, m), 2.68-2.85 (2H, m), 3.06-3.21 (2H, m), 3.47-4.01 (4H, m), 5.14-5.44 (1H, m), 7.59 (1H, d, J=5.3 Hz), 7.69 (1H, s), 8.39 (1H, d, J=5.3 Hz), 8.46 (1H, s), 8.61 (1H, s).

Example 319

(1-(4-(4-bromo-1H-pyrazol-1-yl)pyridin-3-yl)piperidin-4-yl) (3-fluoroazetidin-1-yl)methanone A mixture of 1-(4-(4-bromo-1H-pyrazol-1-yl)pyridin-3-yl)piperidine-4-carboxylic acid (0.078 g), 3-fluoroazetidine hydrochloride (0.025 g), HATU (0.11 g), triethylamine (0.12 mL) and DMF (1.0 mL) was stirred at room temperature for 3 hr. To the mixture was added water, and the mixture was extracted with ethyl acetate. The organic layer was washed with water and saturated brine, and dried over anhydrous magnesium sulfate, and the solvent was evaporated under reduced pressure. The residue was purified by silica gel column chromatography (NH, ethyl acetate/hexane), and crystallized from ethyl acetate/hexane to give the title compound (0.052 g).

$^1$H NMR (300 MHz, CDCl$_3$) δ 1.68-2.03 (4H, m), 2.17-2.37 (1H, m), 2.64-2.84 (2H, m), 3.03-3.19 (2H, m), 4.02-4.53 (4H, m), 5.15-5.49 (1H, m), 7.59 (1H, d, J=5.3 Hz), 7.69 (1H, s), 8.39 (1H, d, J=5.3 Hz), 8.44 (1H, s), 8.59 (1H, s).

Example 322

(1-(4-(4-cyclopropyl-1H-pyrazol-1-yl)pyridin-3-yl)piperidin-4-yl)((3S)-3-fluoropyrrolidin-1-yl)methanone A mixture of (S)-(1-(4-(4-bromo-1H-pyrazol-1-yl)pyridin-3-yl)piperidin-4-yl)(3-fluoropyrrolidin-1-yl)methanone (0.10 g), potassium carbonate (0.13 g), bis(di-tert-butyl(4-dimethylaminophenyl)phosphine)dichloropalladium(II) (0.017 g), cyclopropyl trifluoroborate potassium salt (0.11 g), toluene (2.0 mL) and water (0.40 mL) was stirred with microwave irradiation at 110° C. for 12 hr. The mixture was purified by silica gel column chromatography (NH, ethyl acetate/hexane) and HPLC (C18, mobile phase: water/acetonitrile (containing 0.1% TFA)). The obtained fractions were concentrated, the residue was neutralized with aqueous sodium hydrogen carbonate solution, and the mixture was extracted with ethyl acetate. The organic layer was washed with water and saturated brine, dried over anhydrous sodium sulfate, and the solvent was evaporated under reduced pressure to give the title compound (0.046 g).

$^1$H NMR (300 MHz, CDCl$_3$) δ 0.55-0.66 (2H, m), 0.87-0.99 (2H, m), 1.70-2.57 (8H, m), 2.65-2.83 (2H, m), 3.07-3.21 (2H, m), 3.46-4.01 (4H, m), 5.13-5.45 (1H, m), 7.48-7.71 (2H, m), 8.32-8.64 (3H, m).

Example 323

(1-(4-(4-cyclopropyl-1H-pyrazol-1-yl)pyridin-3-yl)piperidin-4-yl)(3-fluoroazetidin-1-yl)methanone A mixture of (1-(4-(4-bromo-1H-pyrazol-1-yl)pyridin-3-yl)piperidin-4-yl) (3-fluoroazetidin-1-yl)methanone (0.10 g), potassium carbonate (0.14 g), bis(di-tert-butyl(4-dimethylaminophenyl)phosphine)dichloropalladium(II) (0.017 g), cyclopropyl trifluoroborate potassium salt (0.11 g), toluene (2.0 mL) and water (0.40 mL) was stirred with microwave irradiation at 110° C. for 12 hr. The mixture was purified by silica gel column chromatography (NH, ethyl acetate/hexane) and HPLC (C18, mobile phase: water/acetonitrile (containing 0.1% TFA)). The obtained fractions were concentrated, the residue was neutralized with aqueous sodium hydrogen carbonate solution, and the mixture was extracted with ethyl acetate. The organic layer was washed with water and saturated brine, dried over anhydrous sodium sulfate, and the solvent was evaporated under reduced pressure to give the title compound (0.045 g).

$^1$H NMR (300 MHz, CDCl$_3$) δ 0.56-0.63 (2H, m), 0.88-0.97 (2H, m), 1.67-2.00 (5H, m), 2.21-2.33 (1H, m), 2.63-2.80 (2H, m), 3.05-3.18 (2H, m), 4.04-4.52 (4H, m), 5.18-5.50 (1H, m), 7.46-7.73 (2H, m), 8.30-8.61 (3H, m).

The compounds of Examples produced according to the above-mentioned methods or a method analogous thereto are shown in the following tables. MS in the tables means actual measured value.

TABLE 1-1

| EXAMPLE | IUPACNAME | Structure | MS |
|---|---|---|---|
| 1 | 1-(4-(4-chloro-1H-pyrazol-1-yl)pyridin-3-yl)-N,N-dimethylpiperidine-4-carboxamide | 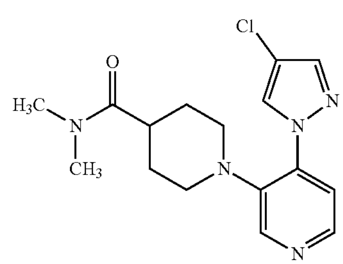 [SMILES: CN(C)C(=O)C1CCN(c2cnccc2-n2cc(Cl)cn2)CC1] | 334.2 |
| 2 | N,N-dimethyl-1-(4-(5-methyl-1,3-oxazol-2-yl)pyridin-3-yl)piperidine-4-carboxamide | 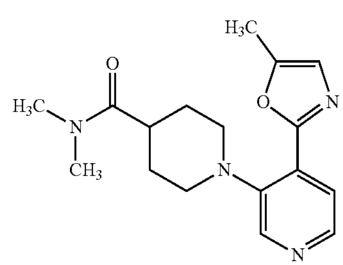 [SMILES: Cc1cnc(-c2ccncc2N2CCC(C(=O)N(C)C)CC2)o1] | 315.2 |

TABLE 1-1-continued

| EXAMPLE | IUPACNAME | Structure | MS |
|---|---|---|---|
| 3 | N-cyclopropyl-4-fluoro-1-(4-(4-methyl-1H-pyrazol-1-yl)pyrimidin-5-yl)piperidine-4-carboxamide | 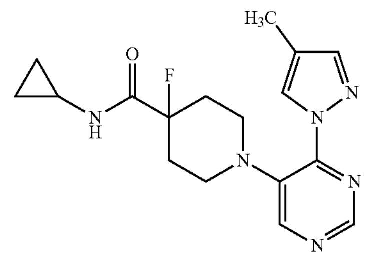 [SMILES: Cc1cnn(-c2ncncc2N2CCC(F)(C(=O)NC3CC3)CC2)c1] | 345.2 |
| 4 | N-(cyclopropylmethyl)-4-fluoro-1-(4-(4-methyl-1H-pyrazol-1-yl)pyrimidin-5-yl)piperidine-4-carboxamide | 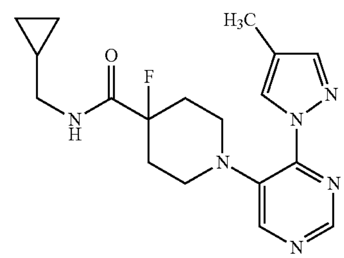 [SMILES: Cc1cnn(-c2ncncc2N2CCC(F)(C(=O)NCC3CC3)CC2)c1] | 359.2 |
| 5 | 4-fluoro-N-(4-fluorobenzyl)-1-(4-(4-methyl-1H-pyrazol-1-yl)pyrimidin-5-yl)piperidine-4-carboxamide | 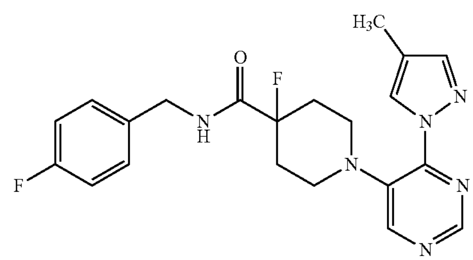 [SMILES: Cc1cnn(-c2ncncc2N2CCC(F)(C(=O)NCc3ccc(F)cc3)CC2)c1] | 413.2 |
| 6 | N,N-dimethyl-1-(4-(2-methyl-1,3-oxazol-4-yl)pyridin-3-yl)piperidine-4-carboxamide | 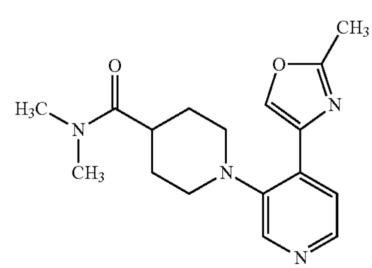 | 315.2 |
| 7 | 3-oxa-6-azabicyclo[3.1.1]hept-6-yl(1-(4-(4-(trifluoromethyl)-1H-pyrazol-1-yl)pyridin-3-yl)piperidin-4-yl)methanone | 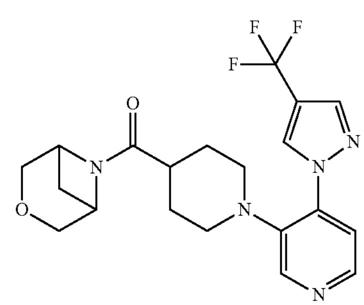 [SMILES: O=C(C1CCN(c2cnccc2-n2cc(C(F)(F)F)cn2)CC1)N1C2COCC1C2] | 422.1 |

TABLE 1-1-continued

| EXAMPLE | IUPACNAME | Structure | MS |
|---|---|---|---|
| 8 | N-cyclopropyl-1-(4-(4-(trifluoromethyl)-1H-pyrazol-1-yl)pyridin-3-yl)piperidine-4-carboxamide | 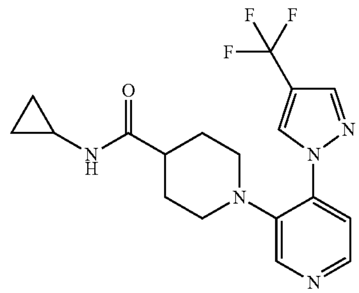 [SMILES: O=C(NC1CC1)C1CCN(c2cnccc2-n2cc(C(F)(F)F)cn2)CC1] | 380.2 |
| 9 | N-(cyclopropylmethyl)-1-(4-(4-(trifluoromethyl)-1H-pyrazol-1-yl)pyridin-3-yl)piperidine-4-carboxamide | 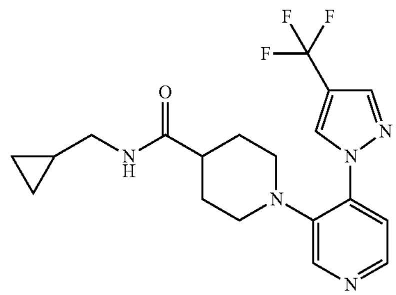 [SMILES: O=C(NCC1CC1)C1CCN(c2cnccc2-n2cc(C(F)(F)F)cn2)CC1] | 394.2 |
| 10 | N,N-dimethyl-1-(4-(4-methyl-1,3-thiazol-2-yl)pyridin-3-yl)piperidine-4-carboxamide | 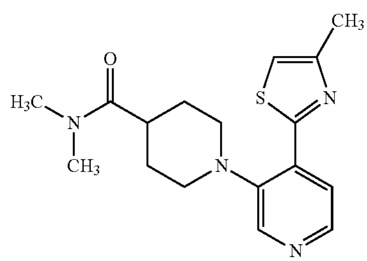 | 331.2 |

TABLE 1-2

| EXAMPLE | IUPACNAME | Structure | MS |
|---|---|---|---|
| 11 | N,N-dimethyl-1-(4-(4-methyl-1,3-oxazol-2-yl)pyridin-3-yl)piperidine-4-carboxamide | 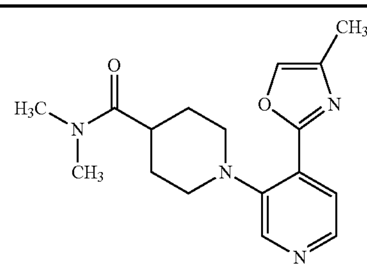 | 315.2 |
| 12 | N-methyl-1-(4-(4-(trifluoromethyl)-1H-pyrazol-1-yl)pyridin-3-yl)piperidine-4-carboxamide | 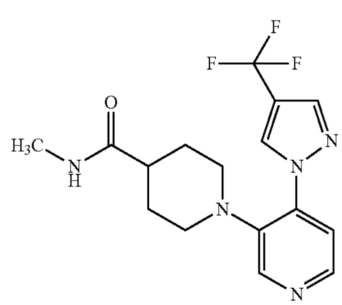 [SMILES: CNC(=O)C1CCN(c2cnccc2-n2cc(C(F)(F)F)cn2)CC1] | 354.1 |

TABLE 1-2-continued

| EXAMPLE | IUPACNAME | Structure | MS |
|---------|-----------|-----------|-----|
| 13 | (3-exo)-N,N-dimethyl-8-(4-(4-methyl-1H-pyrazol-1-yl)pyridin-3-yl)-8-azabicyclo[3.2.1]octane-3-carboxamide | 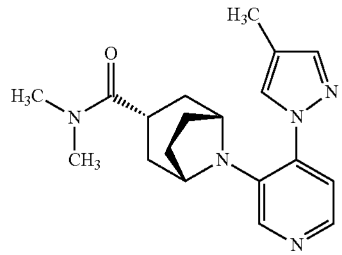 | 340.2 |
| 14 | N-(cyclopropylmethyl)-3,3-difluoro-1-(4-(4-methyl-1H-pyrazol-1-yl)pyridin-3-yl)piperidine-4-carboxamide | 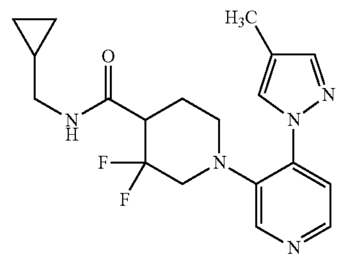 [SMILES: Cc1cnn(-c2ccncc2N2CCC(C(=O)NCC3CC3)C(F)(F)C2)c1] | 376.1 |
| 15 | 3,3-difluoro-N-methyl-1-(4-(4-methyl-1H-pyrazol-1-yl)pyridin-3-yl)piperidine-4-carboxamide | 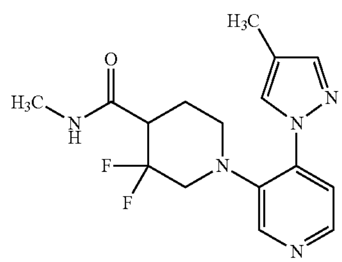 [SMILES: CNC(=O)C1CCN(c2cnccc2-n2cc(C)cn2)CC1(F)F] | 336.1 |
| 16 | (3,3-difluoroazetidin-1-yl)(3,3-difluoro-1-(4-(4-methyl-1H-pyrazol-1-yl)pyridin-3-yl)piperidin-4-yl)methanone | 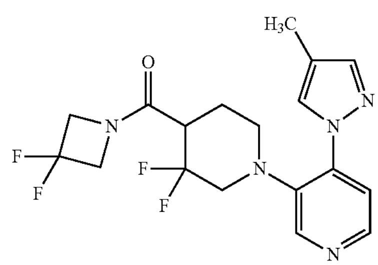 [SMILES: Cc1cnn(-c2ccncc2N2CCC(C(=O)N3CC(F)(F)C3)C(F)(F)C2)c1] | 398.1 |
| 17 | (3,3-difluoro-1-(4-(4-methyl-1H-pyrazol-1-yl)pyridin-3-yl)piperidin-4-yl)(3-oxa-6-azabicyclo[3.1.1]hept-6-yl)methanone | 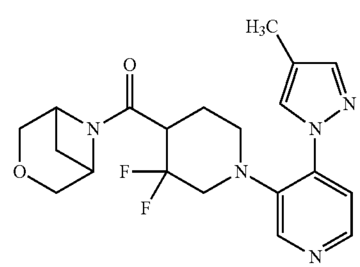 [SMILES: Cc1cnn(-c2ccncc2N2CCC(C(=O)N3C4COCC3C4)C(F)(F)C2)c1] | 404.2 |
| 18 | 1-(4-(2H-indazol-2-yl)pyridin-3-yl)-N,N-dimethylpiperidine-4-carboxamide | 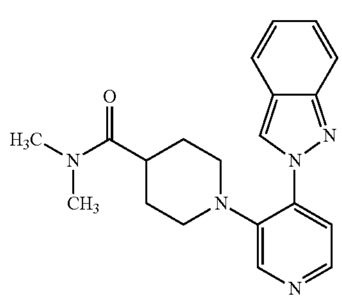 [SMILES: CN(C)C(=O)C1CCN(c2cnccc2-n2cc3ccccc3n2)CC1] | 350.2 |

TABLE 1-2-continued

| EXAMPLE | IUPACNAME | Structure | MS |
|---|---|---|---|
| 19 | N-cyclopropyl-1-(5-fluoro-4-(3-methyl-1H-pyrazol-1-yl)pyridin-3-yl)piperidine-4-carboxamide | 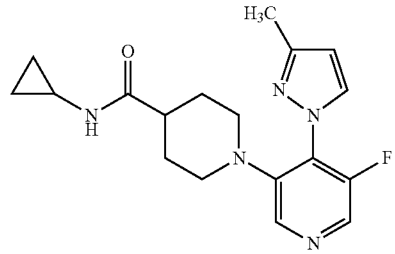 | 344.2 |
| 20 | 1-(5-fluoro-4-(3-methyl-1H-pyrazol-1-yl)pyridin-3-yl)-N,N-dimethylpiperidine-4-carboxamide | 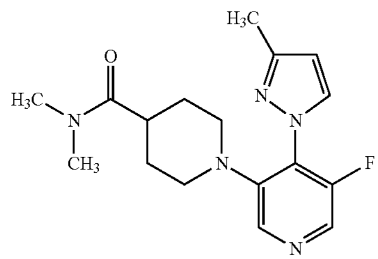 [SMILES: Cc1ccn(-c2c(F)cncc2N2CCC(C(=O)N(C)C)CC2)n1] | 332.3 |

25

TABLE 1-3

| EXAMPLE | IUPACNAME | Structure | MS |
|---|---|---|---|
| 21 | 1-(4-(1,3-benzothiazol-2-yl)pyridin-3-yl)-N,N-dimethylpiperidine-4-carboxamide | 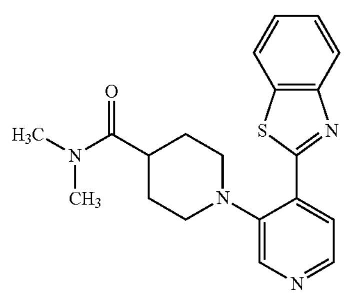 [SMILES: CN(C)C(=O)C1CCN(c2cnccc2-c2nc3ccccc3s2)CC1] | 367.1 |
| 22 | N,N-dimethyl-1-(4-(5-methyl-1,3,4-thiadiazol-2-yl)pyridin-3-yl)piperidine-4-carboxamide | 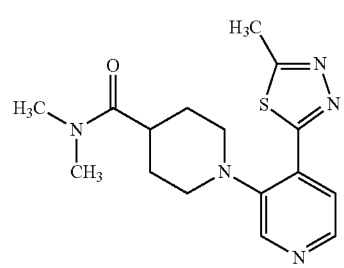 | 332.2 |
| 23 | 1-(4-(4-chloro-1H-pyrazol-1-yl)pyridin-3-yl)-N-cyclopropylpiperidine-4-carboxamide | 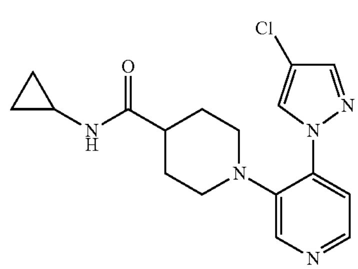 [SMILES: O=C(NC1CC1)C1CCN(c2cnccc2-n2cc(Cl)cn2)CC1] | 346.2 |

TABLE 1-3-continued

| EXAMPLE | IUPACNAME | Structure | MS |
|---------|-----------|-----------|-----|
| 24 | 1-(4-(4-chloro-1H-pyrazol-1-yl)pyridin-3-yl)-N-(tetrahydro-2H-pyran-4-yl)piperidine-4-carboxamide | 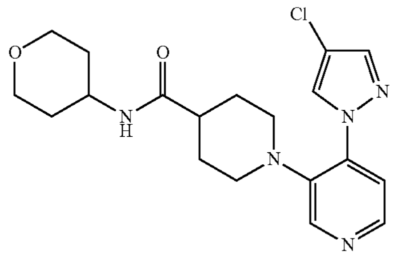 [SMILES: O=C(NC1CCOCC1)C1CCN(c2cnccc2-n2cc(Cl)cn2)CC1] | 390.1 |
| 25 | (1-(4-(4-chloro-1H-pyrazol-1-yl)pyridin-3-yl)piperidin-4-yl)(2-methylpyrrolidin-1-yl)methanone | 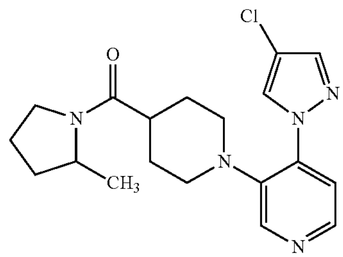 [SMILES: CC1CCCN1C(=O)C1CCN(c2cnccc2-n2cc(Cl)cn2)CC1] | 374.1 |
| 26 | (1-(4-(4-chloro-1H-pyrazol-1-yl)pyridin-3-yl)piperidin-4-yl)(2,2-dimethylpyrrolidin-1-yl)methanone | 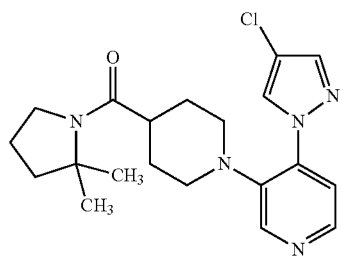 [SMILES: CC1(C)CCCN1C(=O)C1CCN(c2cnccc2-n2cc(Cl)cn2)CC1] | 388.1 |
| 27 | 1-(4-(4-chloro-1H-pyrazol-1-yl)pyridin-3-yl)-N-(cyclopropylmethyl)piperidine-4-carboxamide | 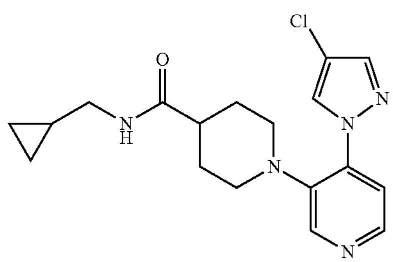 [SMILES: O=C(NCC1CC1)C1CCN(c2cnccc2-n2cc(Cl)cn2)CC1] | 360.1 |
| 28 | 1-(4-(4-chloro-1H-pyrazol-1-yl)pyridin-3-yl)-N-(oxetan-3-yl)piperidine-4-carboxamide | 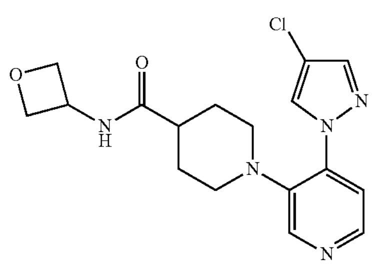 [SMILES: O=C(NC1COC1)C1CCN(c2cnccc2-n2cc(Cl)cn2)CC1] | 362.1 |
| 29 | (1-(4-(4-chloro-1H-pyrazol-1-yl)pyridin-3-yl)piperidin-4-yl)(2-isopropylpyrrolidin-1-yl)methanone | 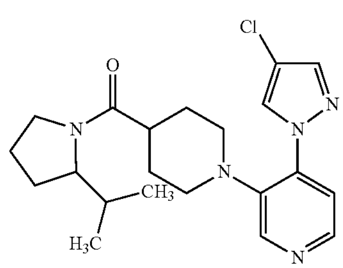 [SMILES: CC(C)C1CCCN1C(=O)C1CCN(c2cnccc2-n2cc(Cl)cn2)CC1] | 402.1 |

TABLE 1-3-continued

| EXAMPLE | IUPACNAME | Structure | MS |
|---|---|---|---|
| 30 | (1-(4-(4-chloro-1H-pyrazol-1-yl)pyridin-3-yl)piperidin-4-yl)(1,1-dioxidothiomorpholin-4-yl)methanone | 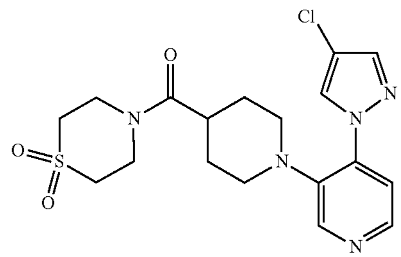 [SMILES: O=C(C1CCN(c2cnccc2-n2cc(Cl)cn2)CC1)N1CCS(=O)(=O)CC1] | 424.0 |

TABLE 1-4

| EXAMPLE | IUPACNAME | Structure | MS |
|---|---|---|---|
| 31 | 1-(4-(4-chloro-1H-pyrazol-1-yl)pyridin-3-yl)-N-((3-methyloxetan-3-yl)methyl)piperidine-4-carboxamide | 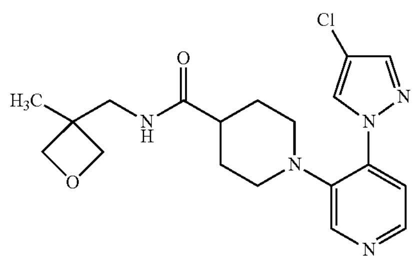 [SMILES: CC1(CNC(=O)C2CCN(c3cnccc3-n3cc(Cl)cn3)CC2)COC1] | 390.2 |
| 32 | (1-(4-(4-chloro-1H-pyrazol-1-yl)pyridin-3-yl)piperidin-4-yl)(2-methylazetidin-1-yl)methanone | 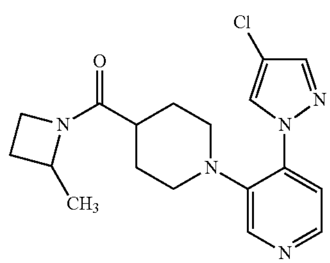 [SMILES: CC1CCN1C(=O)C1CCN(c2cnccc2-n2cc(Cl)cn2)CC1] | 360.1 |
| 33 | (2R)-1-((1-(4-(4-chloro-1H-pyrazol-1-yl)pyridin-3-yl)piperidin-4-yl)carbonyl)pyrrolidine-2-carbonitrile | 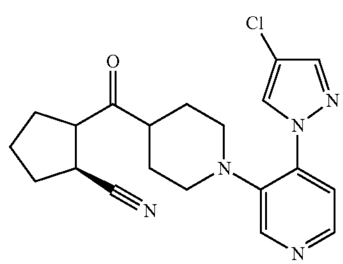 [SMILES: N#C[C@H]1CCCC1C(=O)C1CCN(c2cnccc2-n2cc(Cl)cn2)CC1] | 385.1 |
| 34 | 1-(4-(4-chloro-1H-pyrazol-1-yl)pyridin-3-yl)-N-(tetrahydrofuran-3-yl)piperidine-4-carboxamide | 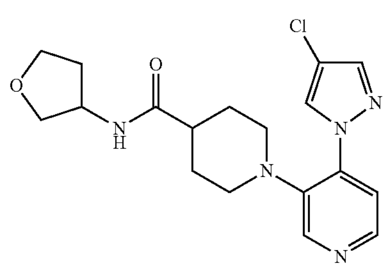 [SMILES: O=C(NC1CCOC1)C1CCN(c2cnccc2-n2cc(Cl)cn2)CC1] | 376.1 |

TABLE 1-4-continued

| EXAMPLE | IUPACNAME | Structure | MS |
|---|---|---|---|
| 35 | (1-(4-(4-chloro-1H-pyrazol-1-yl)pyridin-3-yl)piperidin-4-yl)(3-oxa-6-azabicyclo[3.1.1]hept-6-yl)methanone | 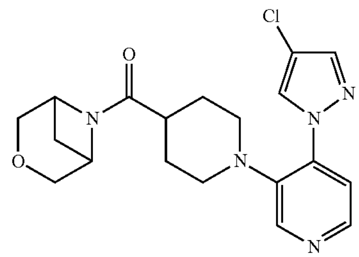 [SMILES: O=C(C1CCN(c2cnccc2-n2cc(Cl)cn2)CC1)N1C2COCC1C2] | 388.1 |
| 36 | 1-(4-(4-chloro-1H-pyrazol-1-yl)pyridin-3-yl)-N-cyclopropyl-3,3-difluoropiperidine-4-carboxamide | 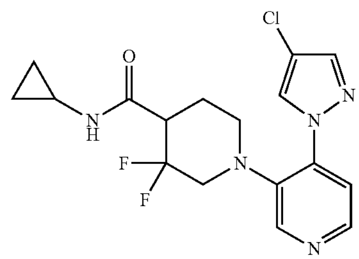 [SMILES: O=C(NC1CC1)C1CCN(c2cnccc2-n2cc(Cl)cn2)CC1(F)F] | 382.1 |
| 37 | 1-(4-(4-chloro-1H-chloro-1-yl)pyridin-3-yl)-N-cyclobutyl-3,3-difluoropiperidine-4-carboxamide | 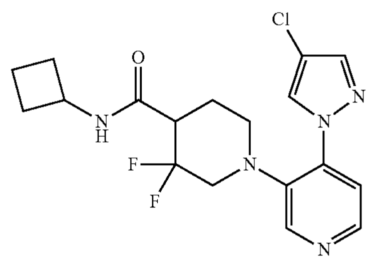 [SMILES: O=C(NC1CCC1)C1CCN(c2cnccc2-n2cc(Cl)cn2)CC1(F)F] | 396.2 |
| 38 | 1-(4-(4-chloro-1H-pyrazol-1-yl)pyridin-3-yl)-N-cyclopentyl-3,3-difluoropiperidine-4-carboxamide | 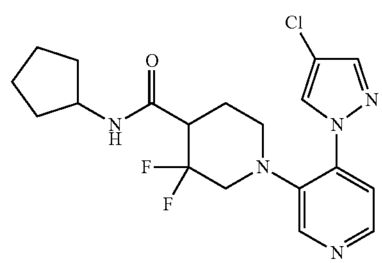 [SMILES: O=C(NC1CCCC1)C1CCN(c2cnccc2-n2cc(Cl)cn2)CC1(F)F] | 410.1 |
| 39 | 1-(4-(4-chloro-1H-pyrazol-1-yl)pyridin-3-yl)-3,3-difluoro-N,N-dimethylpiperidine-4-carboxamide | 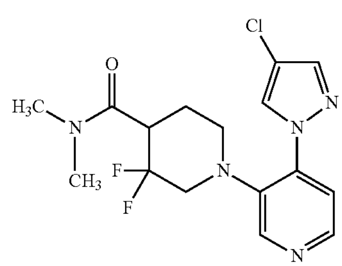 [SMILES: CN(C)C(=O)C1CCN(c2cnccc2-n2cc(Cl)cn2)CC1(F)F] | 370.0 |
| 40 | (1-(4-(4-chloro-1H-pyrazol-1-yl)pyridin-3-yl)piperidin-4-yl)(2-ethylpyrrolidin-1-yl)methanone | 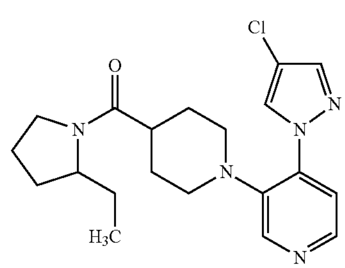 [SMILES: CCC1CCCN1C(=O)C1CCN(c2cnccc2-n2cc(Cl)cn2)CC1] | 388.2 |

TABLE 1-5

| EXAMPLE | IUPACNAME | Structure | MS |
|---|---|---|---|
| 41 | 1-(4-(4-chloro-1H-pyrazol-1-yl)pyridin-3-yl)-N-(2,2-difluorocyclopropyl)piperidine-4-carboxamide | 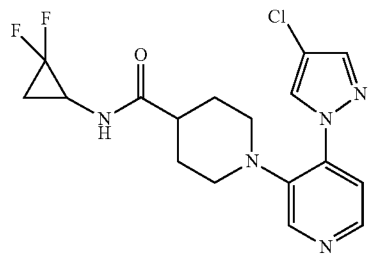 [SMILES: O=C(NC1CC1(F)F)C1CCN(c2cnccc2-n2cc(Cl)cn2)CC1] | 382.1 |
| 42 | N-cyclopropyl-3,3-difluoro-1-(4-(5-methyl-1,3-thiazol-2-yl)pyridin-3-yl)piperidine-4-carboxamide | 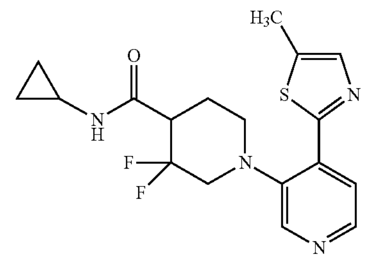 [SMILES: Cc1cnc(-c2ccncc2N2CCC(C(=O)NC3CC3)C(F)(F)C2)s1] | 379.2 |
| 43 | 1-(4-(4-bromo-1H-pyrazol-1-yl)pyridin-3-yl)-N,N-dimethylpiperidine-4-carboxamide | 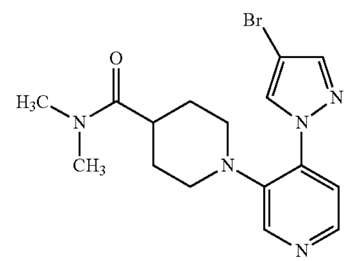 [SMILES: CN(C)C(=O)C1CCN(c2cnccc2-n2cc(Br)cn2)CC1] | 378.1 |
| 44 | (1-(4-(4-chloro-1H-pyrazol-1-yl)pyridin-3-yl)piperidin-4-yl)(3-methoxypyrrolidin-1-yl)methanone | 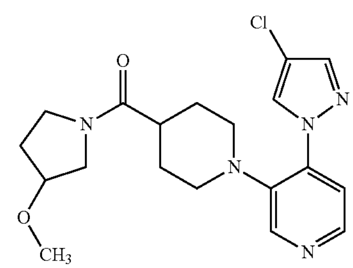 [SMILES: COC1CCN(C(=O)C2CCN(c3cnccc3-n3cc(Cl)cn3)CC2)C1] | 390.2 |
| 45 | 1-(4-(4-chloro-1H-pyrazol-1-yl)pyridin-3-yl)-N-cyclobutylpiporidine-4-carboxamide | 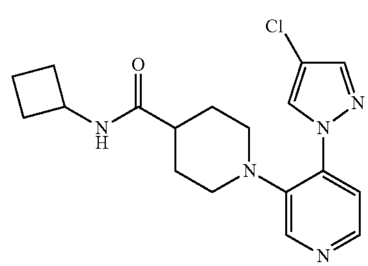 [SMILES: O=C(NC1CCC1)C1CCN(c2cnccc2-n2cc(Cl)cn2)CC1] | 360.1 |
| 46 | (1-(4-(4-chloro-1H-pyrazol-1-yl)pyridin-3-yl)piperidin-4-yl)(3-methylmorpholin-4-yl)methanone | 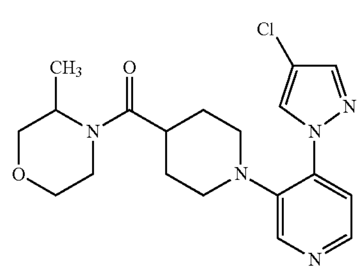 [SMILES: CC1COCCN1C(=O)C1CCN(c2cnccc2-n2cc(Cl)cn2)CC1] | 390.2 |

TABLE 1-5-continued

| EXAMPLE | IUPACNAME | Structure | MS |
|---|---|---|---|
| 47 | (1-(4-(4-chloro-1H-pyrazol-1-yl)pyridin-3-yl)piperidin-4-yl)(8-oxa-3-azabicyclo[3.2.1]oct-3-yl)methanone | 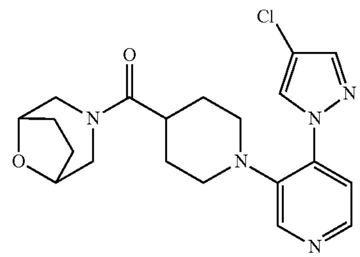 [SMILES: O=C(C1CCN(c2cnccc2-n2cc(Cl)cn2)CC1)N1CC2CCC(C1)O2] | 402.1 |
| 48 | (1-(4-(4-chloro-1H-pyrazol-1-yl)pyridin-3-yl)piperidin-4-yl)(3,3-difluoroazetidin-1-yl)methanone | 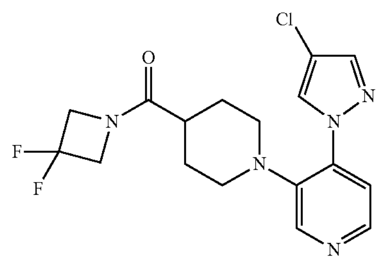 [SMILES: O=C(C1CCN(c2cnccc2-n2cc(Cl)cn2)CC1)N1CC(F)(F)C1] | 382.1 |
| 49 | (1-(4-(4-chloro-1H-pyrazol-1-yl)pyridin-3-yl)piperidin-4-yl)((1S,4S)-2-oxa-5-azabicyclo[2.2.1]hept-5-yl)methanone | 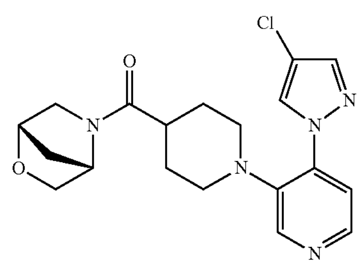 [SMILES: O=C(C1CCN(c2cnccc2-n2cc(Cl)cn2)CC1)N1C[C@@H]2C[C@H]1CO2] | 388.1 |
| 50 | (1-(4-(4-chloro-1H-pyrazol-1-yl)pyridin-3-yl)piperidin-4-yl)((2R,6S)-2,6-dimethylmorpholin-4-yl)methanone | 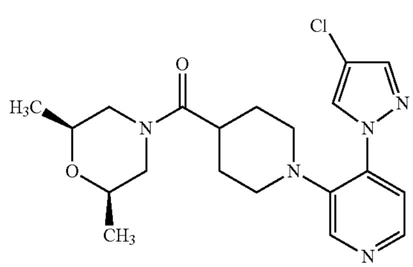 [SMILES: C[C@@H]1CN(C(=O)C2CCN(c3cnccc3-n3cc(Cl)cn3)CC2)C[C@H](C)O1] | 404.2 |

TABLE 1-6

| EXAMPLE | IUPACNAME | Structure | MS |
|---|---|---|---|
| 51 | 1-(4-(4-chloro-1H-pyrazol-1-yl)pyridin-3-yl)-N-cyclopropyl-N-ethylpiperidine-4-carboxamide | 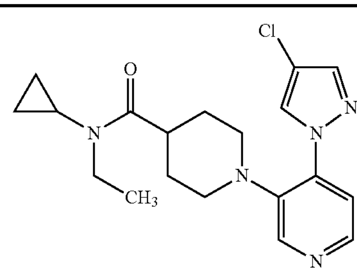 | 374.1 |

TABLE 1-6-continued

| EXAMPLE | IUPACNAME | Structure | MS |
|---|---|---|---|
| 52 | (1-(4-(4-chloro-1H-pyrazol-1-yl)pyridin-3-yl)piperidin-4-yl)(4,4-difluoropiperidin-1-yl)methanone | 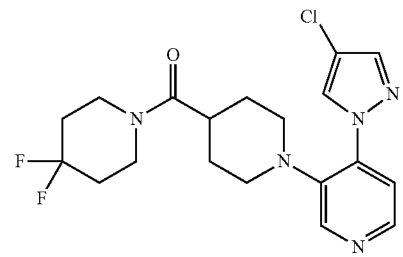 [SMILES: O=C(C1CCN(c2cnccc2-n2cc(Cl)cn2)CC1)N1CCC(F)(F)CC1] | 410.3 |
| 53 | (1-(4-(4-chloro-1H-pyrazol-1-yl)pyridin-3-yl)piperidin-4-yl)(3-oxa-8-azabicyclo[3.2.1]oct-8-yl)methanone | 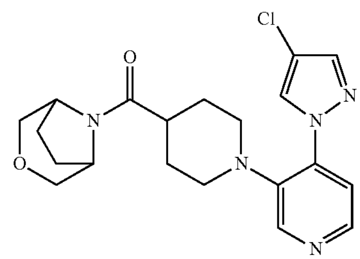 [SMILES: O=C(C1CCN(c2cnccc2-n2cc(Cl)cn2)CC1)N1C2CCC1COC2] | 402.1 |
| 54 | 1-(4-(4-chloro-1H-pyrazol-1-yl)pyridin-3-yl)-N-methyl-N-(tetrahydro-2H-pyran-4-yl)piperidine-4-carboxamide | 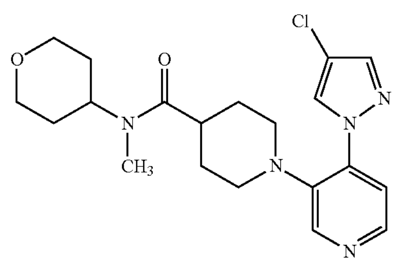 [SMILES: CN(C(=O)C1CCN(c2cnccc2-n2cc(Cl)cn2)CC1)C1CCOCC1] | 404.2 |
| 55 | (1-(4-(4-chloro-1H-pyrazol-1-yl)pyridin-3-yl)piperidin-4-yl)(3,5-dimethylmorpholin-4-yl)methanone | 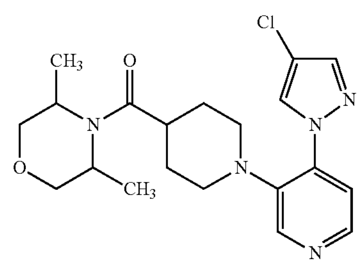 [SMILES: CC1COCC(C)N1C(=O)C1CCN(c2cnccc2-n2cc(Cl)cn2)CC1] | 404.2 |
| 56 | 1-(4-(4-chloro-1H-pyrazol-1-yl)pyridin-3-yl)-N-cyclopentylpiperidine-4-carboxamide | 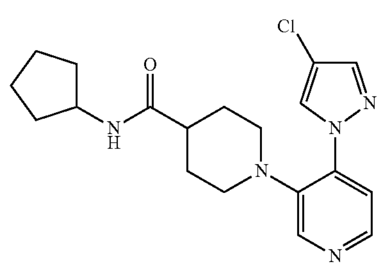 [SMILES: O=C(NC1CCCC1)C1CCN(c2cnccc2-n2cc(Cl)cn2)CC1] | 374.1 |
| 57 | (1-(4-(4-chloro-1H-pyrazol-1-yl)pyridin-3-yl)piperidin-4-yl)(3,3-difluoropyrrolidin-1-yl)methanone | 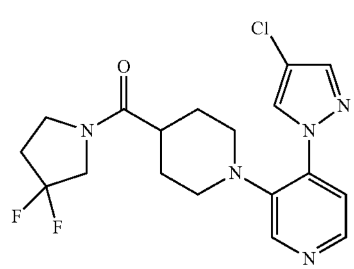 [SMILES: O=C(C1CCN(c2cnccc2-n2cc(Cl)cn2)CC1)N1CCC(F)(F)C1] | 396.2 |

TABLE 1-6-continued

| EXAMPLE | IUPACNAME | Structure | MS |
|---|---|---|---|
| 58 | 1-(4-(4-chloro-1H-pyrazol-1-yl)pyridin-3-yl)-N-cyclopropyl-N-methylpiperidine-4-carboxamide | 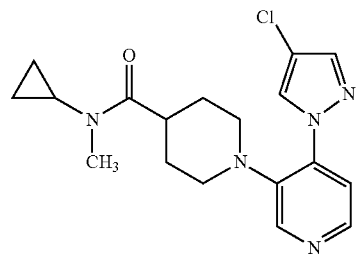 [SMILES: CN(C(=O)C1CCN(c2cnccc2-n2cc(Cl)cn2)CC1)C1CC1] | 360.1 |
| 59 | 1-(4-(4-cyclopropyl-1H-pyrazol-1-yl)pyridin-3-yl)-N,N-dimethylpiperidine-4-carboxamide | 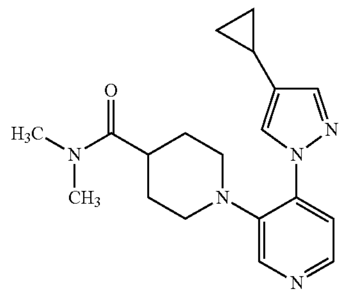 [SMILES: CN(C)C(=O)C1CCN(c2cnccc2-n2cc(C3CC3)cn2)CC1] | 340.3 |
| 60 | (1-(4-(4-chloro-1H-pyrazol-1-yl)pyridin-3-yl)piperidin-4-yl)(6-oxa-3-azabicyclo[3.1.1]hept-3-yl)methanone | 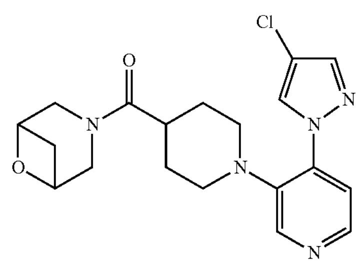 [SMILES: O=C(C1CCN(c2cnccc2-n2cc(Cl)cn2)CC1)N1CC2CC(C1)O2] | 388.1 |

TABLE 1-7

| EXAMPLE | IUPACNAME | Structure | MS |
|---|---|---|---|
| 61 | (1-(4-(4-chloro-1H-pyrazol-1-yl)pyridin-3-yl)piperidin-4-yl)(2-methylmorpholin-4-yl)methanone | 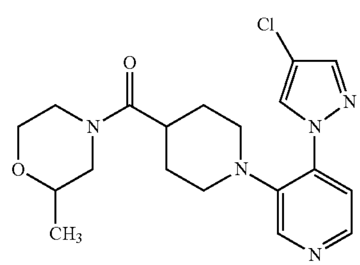 [SMILES: CC1CN(C(=O)C2CCN(c3cnccc3-n3cc(Cl)cn3)CC2)CCO1] | 390.2 |
| 62 | 1-(4-(4-chloro-1H-pyrazol-1-yl)pyridin-3-yl)-N-methylpiperidine-4-carboxamide | 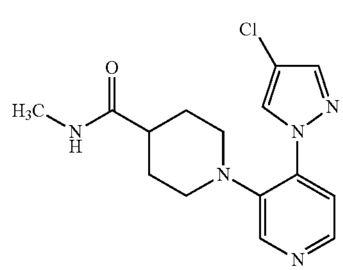 [SMILES: CNC(=O)C1CCN(c2cnccc2-n2cc(Cl)cn2)CC1] | 320.1 |

TABLE 1-7-continued

| EXAMPLE | IUPACNAME | Structure | MS |
|---|---|---|---|
| 63 | (1-(4-(4-chloro-1H-pyrazol-1-yl)pyridin-3-yl)piperidin-4-yl)(3-hydroxy-3-methylpyrrolidin-1-yl)methanone | 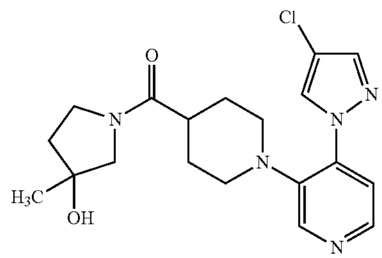 [SMILES: CC1(O)CCN(C(=O)C2CCN(c3cnccc3-n3cc(Cl)cn3)CC2)C1] | 390.2 |
| 64 | 1-(4-(4-chloro-1H-pyrazol-1-yl)pyridin-3-yl)-N-methyl-N-(1-methylpyrrolidin-3-yl)piperidine-4-carboxamide | 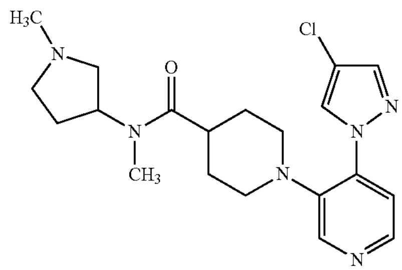 [SMILES: CN1CCC(N(C)C(=O)C2CCN(c3cnccc3-n3cc(Cl)cn3)CC2)C1] | 403.2 |
| 65 | 3,3-difluoro-N,N-dimethyl-1-(4-(5-methyl-1,3-thiazol-2-yl)pyridin-3-yl)piperidine-4-carboxamide | 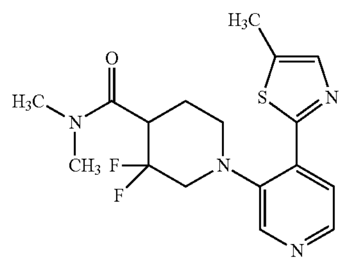 [SMILES: Cc1cnc(-c2ccncc2N2CCC(C(=O)N(C)C)C(F)(F)C2)s1] | 367.1 |
| 66 | (1-(4-(4-chloro-1H-pyrazol-1-yl)pyridin-3-yl)piperidin-4-yl)((1R,4R)-2-oxa-5-azabicyclo[2.2.1]hept-5-yl)methanone | 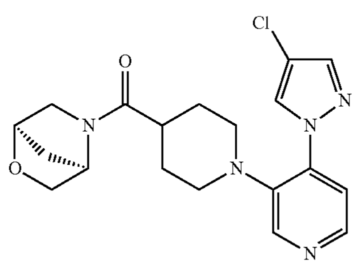 [SMILES: O=C(C1CCN(c2cnccc2-n2cc(Cl)cn2)CC1)N1C[C@H]2C[C@@H]1CO2] | 388.2 |
| 67 | azetidin-1-yl(1-(4-(4-chloro-1H-pyrazol-1-yl)pyridin-3-yl)piperidin-4-yl)methanone | 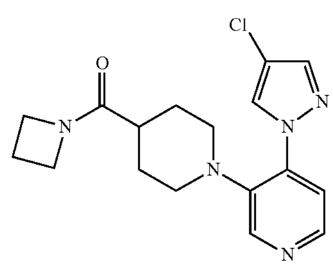 [SMILES: O=C(C1CCN(c2cnccc2-n2cc(Cl)cn2)CC1)N1CCC1] | 346.2 |
| 68 | 1-(4-(4-methyl-1H-pyrazol-1-yl)pyridin-3-yl)-N-(tetrahydro-2H-pyran-4-yl)piperidine-4-carboxamide | 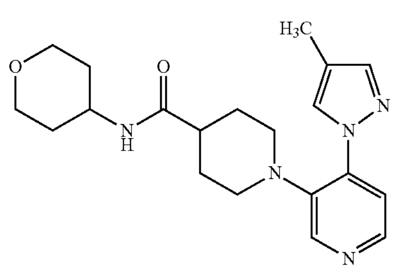 [SMILES: Cc1cnn(-c2ccncc2N2CCC(C(=O)NC3CCOCC3)CC2)c1] | 370.2 |

TABLE 1-7-continued

| EXAMPLE | IUPACNAME | Structure | MS |
|---|---|---|---|
| 69 | (1,1-dioxidothiomorpholin-4-yl)(1-(4-(4-methyl-1H-pyrazol-1-yl)pyridin-3-yl)piperidin-4-yl)methanone | 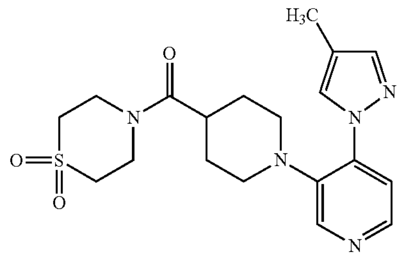 [SMILES: Cc1cnn(-c2ccncc2N2CCC(C(=O)N3CCS(=O)(=O)CC3)CC2)c1] | 404.2 |
| 70 | (2R)-1-((1-(4-(4-methyl-1H-pyrazol-1-yl)pyridin-3-yl)piperidin-4-yl)carbonyl)pyrrolidine-2-carbonitrile | 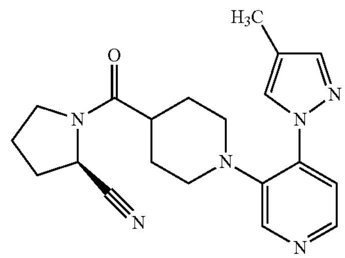 [SMILES: Cc1cnn(-c2ccncc2N2CCC(C(=O)N3CCC[C@@H]3C#N)CC2)c1] | 365.2 |

25

TABLE 1-8

| EXAMPLE | IUPACNAME | Structure | MS |
|---|---|---|---|
| 71 | (1-(4-(4-methyl-1H-pyrazol-1-yl)pyridin-3-yl)piperidin-4-yl)(3-oxa-8-azabicyclo[3.2.1]oct-8-yl)methanone | 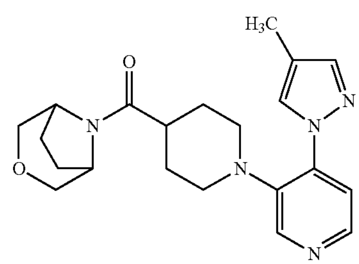 [SMILES: Cc1cnn(-c2ccncc2N2CCC(C(=O)N3C4CCC3COC4)CC2)c1] | 382.2 |
| 72 | 1-((1-(4-(4-methyl-1H-pyrazol-1-yl)pyridin-3-yl)piperidin-4-yl)carbonyl)pyrrolidine-3-carbonitrile | 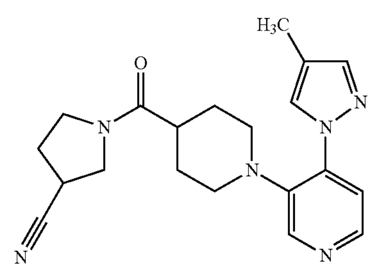 [SMILES: Cc1cnn(-c2ccncc2N2CCC(C(=O)N3CCC(C#N)C3)CC2)c1] | 365.2 |
| 73 | 1-(4-(4-methyl-1H-pyrazol-1-yl)pyridin-3-yl)-N-phenylpiperidine-4-carboxamide | 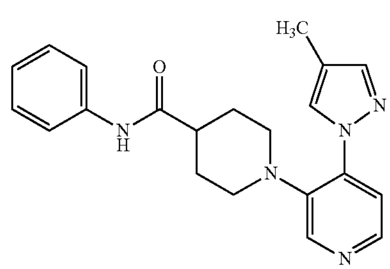 [SMILES: Cc1cnn(-c2ccncc2N2CCC(C(=O)Nc3ccccc3)CC2)c1] | 360.0 |

TABLE 1-8-continued

| EXAMPLE | IUPACNAME | Structure | MS |
|---|---|---|---|
| 74 | (2R)-1-(((4R)-1-(4-(4-chloro-1H-pyrazol-1-yl)pyridin-3-yl)-3,3-difluoropiperidin-4-yl)carbonyl)pyrrolidine-2-carbonitrile | 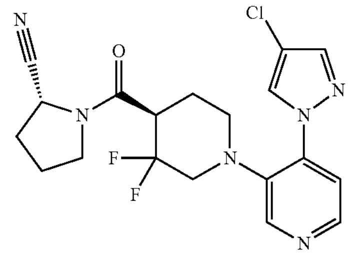 [SMILES: N#C[C@H]1CCCN1C(=O)[C@H]1CCN(c2cnccc2-n2cc(Cl)cn2)CC1(F)F] | 421.1 |
| 75 | (2R)-1-(((4S)-1-(4-(4-chloro-1H-pyrazol-1-yl)pyridin-3-yl)-3,3-difluoropiperidin-4-yl)carbonyl)pyrrolidine-2-carbonitrile | 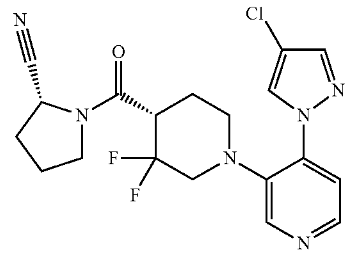 [SMILES: N#C[C@H]1CCCN1C(=O)[C@@H]1CCN(c2cnccc2-n2cc(Cl)cn2)CC1(F)F] | 421.1 |
| 76 | (1-(4-(4-chloro-1H-pyrazol-1-yl)pyridin-3-yl)-3,3-difluoropiperidin-4-yl)((1S,4S)-2-oxa-5-azabicyclo[2.2.1]hept-5-yl)methanone | 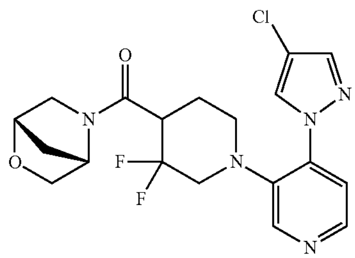 [SMILES: O=C(C1CCN(c2cnccc2-n2cc(Cl)cn2)CC1(F)F)N1C[C@@H]2C[C@H]1CO2] | 424.1 |
| 77 | (1-(4-(4-chloro-1H-pyrazol-1-yl)pyridin-3-yl)-3,3-difluoropiperidin-4-yl)(morpholin-4-yl)methanone | 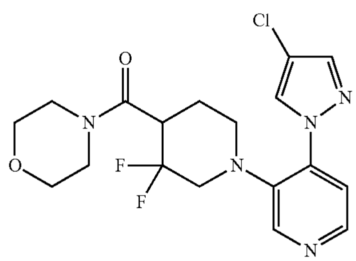 [SMILES: O=C(C1CCN(c2cnccc2-n2cc(Cl)cn2)CC1(F)F)N1CCOCC1] | 412.2 |
| 78 | (1-(4-(4-chloro-1H-pyrazol-1-yl)pyridin-3-yl)-3,3-difluoropiperidin-4-yl)(1,1-dioxidothiomorpholin-4-yl)methanone | 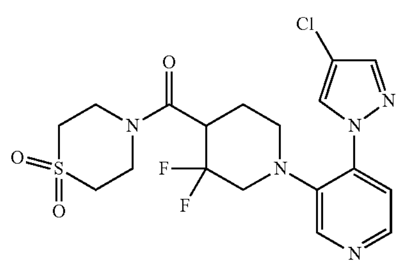 [SMILES: O=C(C1CCN(c2cnccc2-n2cc(Cl)cn2)CC1(F)F)N1CCS(=O)(=O)CC1] | 460.1 |
| 79 | 1-(4-(4-chloro-1H-pyrazol-1-yl)pyridin-3-yl)-3,3-difluoro-N-(tetrahydro-2H-pyran-4-yl)piperidine-4-carboxamide | 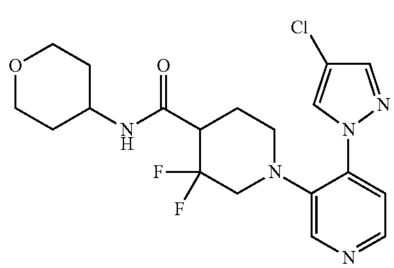 [SMILES: O=C(NC1CCOCC1)C1CCN(c2cnccc2-n2cc(Cl)cn2)CC1(F)F] | 426.1 |

TABLE 1-8-continued

| EXAMPLE | IUPACNAME | Structure | MS |
|---|---|---|---|
| 80 | (1-(4-(4-chloro-1H-pyrazol-1-yl)pyridin-3-yl)piperidin-4-yl)(morpholin-4-yl)methanone | 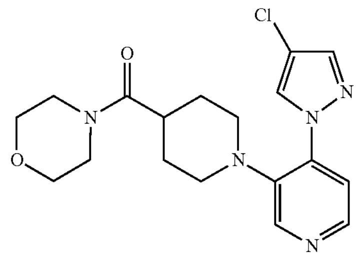 [SMILES: O=C(C1CCN(c2cnccc2-n2cc(Cl)cn2)CC1)N1CCOCC1] | 376.1 |

TABLE 1-9

| EXAMPLE | IUPACNAME | Structure | MS |
|---|---|---|---|
| 81 | (1-(4-(4-chloro-1H-pyrazol-1-yl)pyridin-3-yl)piperidin-4-yl)(pyrrolidin-1-yl)methanone | 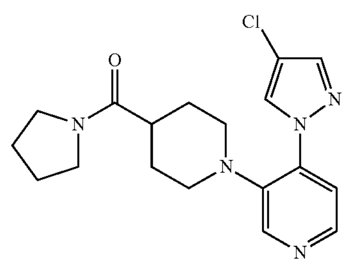 [SMILES: O=C(C1CCN(c2cnccc2-n2cc(Cl)cn2)CC1)N1CCCC1] | 360.1 |
| 82 | 2-methyl-8-(4-(4-methyl-1H-pyrazol-1-yl)pyridin-3-yl)-2,8-diazaspiro[4.5]decan-1-one | 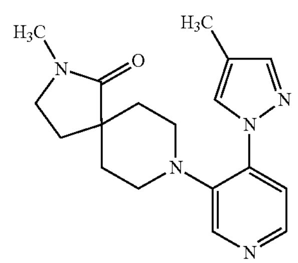 [SMILES: Cc1cnn(-c2ccncc2N2CCC3(CCN(C)C3=O)CC2)c1] | 326.3 |
| 83 | 1-(4-(4-cyano-1H-pyrazol-1-yl)pyridin-3-yl)-N,N-dimethylpiperidine-4-carboxamide | 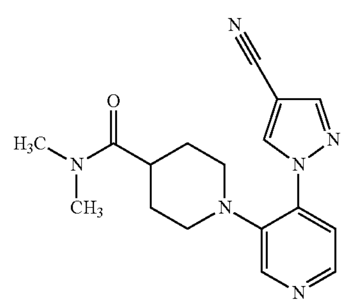 [SMILES: CN(C)C(=O)C1CCN(c2cnccc2-n2cc(C#N)cn2)CC1] | 325.2 |
| 84 | (3,3-difluoropyrrolidin-1-yl)(1-(4-(4-methyl-1H-pyrazol-1-yl)pyridin-3-yl)piperidin-4-yl)methanone | 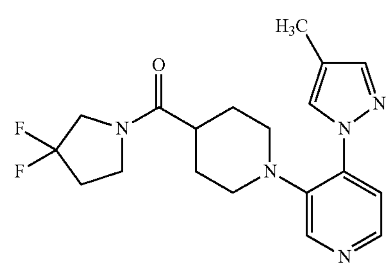 [SMILES: Cc1cnn(-c2ccncc2N2CCC(C(=O)N3CCC(F)(F)C3)CC2)c1] | 376.1 |

TABLE 1-9-continued

| EXAMPLE | IUPACNAME | Structure | MS |
|---|---|---|---|
| 85 | (3,3-difluoroazetidin-1-yl)(1-(4-(4-methyl-1H-pyrazol-1-yl)pyridin-3-yl)piperidin-4-yl)methanone | 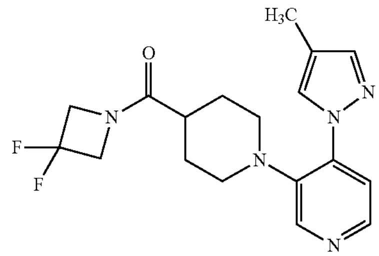 [SMILES: Cc1cnn(-c2ccncc2N2CCC(C(=O)N3CC(F)(F)C3)CC2)c1] | 362.1 |
| 86 | N-cyclopropyl-N-methyl-1-(4-(4-methyl-1H-pyrazol-1-yl)pyridin-3-yl)piperidine-4-carboxamide | 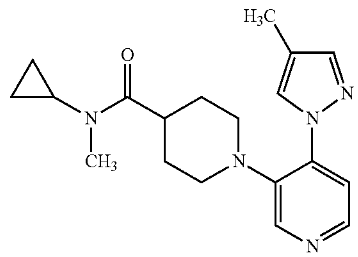 [SMILES: Cc1cnn(-c2ccncc2N2CCC(C(=O)N(C)C3CC3)CC2)c1] | 340.2 |
| 87 | (2R)-1-((1-(4-(5-methyl-1,3,4-thiadiazol-2-yl)pyridin-3-yl)piperidin-4-yl)carbonyl)pyrrolidine-2-carbonitrile | 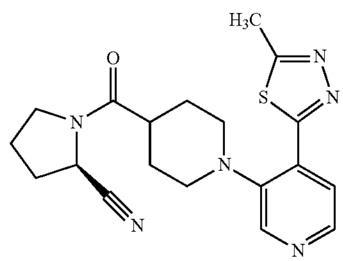 | 383.1 |
| 88 | (2-methylpyrrolidin-1-yl)-(1-(4-(5-methyl-1,3,4-thiadiazol-2-yl)pyridin-3-yl)piperidin-4-yl)methanone | 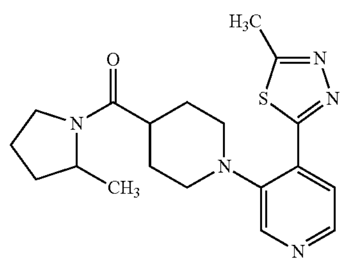 [SMILES: Cc1nnc(-c2ccncc2N2CCC(C(=O)N3CCCC3C)CC2)s1] | 372.2 |
| 89 | (2,2-dimethylpyrrolidin-1-yl)(1-(4-(5-methyl-1,3,4-thiadiazol-2-yl)pyridin-3-yl)piperidin-4-yl)methanone | 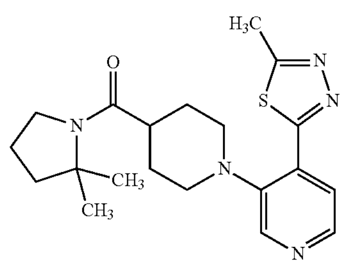 [SMILES: Cc1nnc(-c2ccncc2N2CCC(C(=O)N3CCCC3(C)C)CC2)s1] | 386.2 |
| 90 | N-cyclopropyl-N-methyl-1-(4-(5-methyl-1,3,4-thiadiazol-2-yl)pyridin-3-yl)piperidine-4-carboxamide | 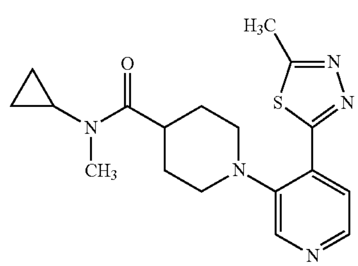 [SMILES: Cc1nnc(-c2ccncc2N2CCC(C(=O)N(C)C3CC3)CC2)s1] | 358.1 |

TABLE 1-10

| EXAMPLE | IUPACNAME | Structure | MS |
|---|---|---|---|
| 91 | (3,3-difluoropyrrolidin-1-yl)(1-(4-(5-methyl-1,3,4-thiadiazol-2-yl)pyridin-3-yl)piperidin-4-yl)methanone | 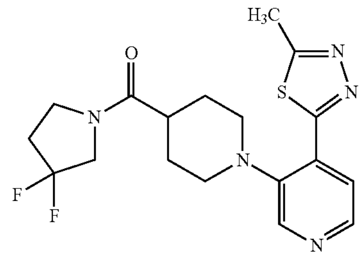 [SMILES: Cc1nnc(-c2ccncc2N2CCC(C(=O)N3CCC(F)(F)C3)CC2)s1] | 394.2 |
| 92 | (1-(4-(4-chloro-1H-pyrazol-1-yl)pyridin-3-yl)-3,3-difluoropiperidin-4-yl)(8-oxa-3-azabicyclo[3.2.1]oct-3-yl)methanone | 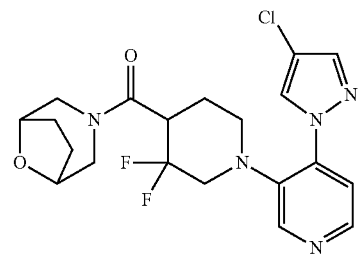 [SMILES: O=C(C1CCN(c2cnccc2-n2cc(Cl)cn2)CC1(F)F)N1CC2CCC(C1)O2] | 438.1 |
| 93 | (1-(4-(4-chloro-1H-pyrazol-1-yl)pyridin-3-yl)-3,3-difluoropiperidin-4-yl)(6-oxa-3-azabicyclo[3.1.1]hept-3-yl)methanone | 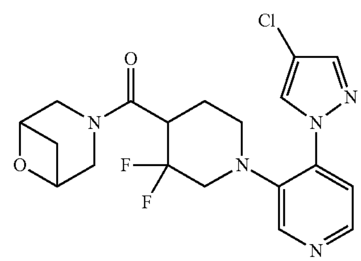 [SMILES: O=C(C1CCN(c2cnccc2-n2cc(Cl)cn2)CC1(F)F)N1CC2CC(C1)O2] | 424.2 |
| 94 | (4S)-1-(4-(4-chloro-1H-pyrazol-1-yl)pyridin-3-yl)-N-cyclopropyl-3,3-difluoropiperidine-4-carboxamide | 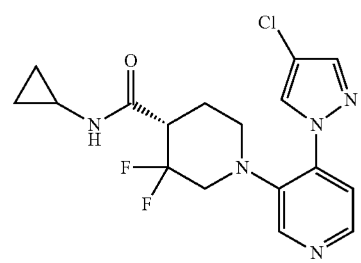 [SMILES: O=C(NC1CC1)[C@@H]1CCN(c2cnccc2-n2cc(Cl)cn2)CC1(F)F] | 382.1 |
| 95 | (4R)-1-(4-(4-chloro-1H-pyrazol-1-yl)pyridin-3-yl)-N-cyclopropyl-3,3-difluoropiperidine-4-carboxamide | 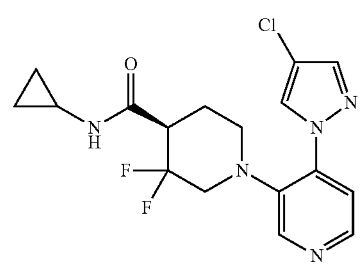 [SMILES: O=C(NC1CC1)[C@H]1CCN(c2cnccc2-n2cc(Cl)cn2)CC1(F)F] | 382.1 |
| 96 | 1-(4-(4-chloro-1H-pyrazol-1-yl)pyridin-3-yl)-3,3-difluoro-N,N-dimethylpiperidine-4-carboxamide | 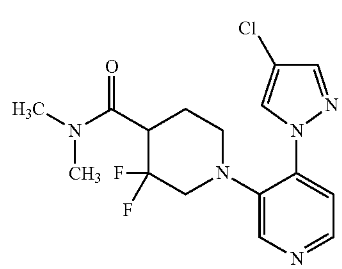 [SMILES: CN(C)C(=O)C1CCN(c2cnccc2-n2cc(Cl)cn2)CC1(F)F] | 370.0 |

TABLE 1-10-continued

| EXAMPLE | IUPACNAME | Structure | MS |
|---|---|---|---|
| 97 | 1-(4-(4-chloro-1H-pyrazol-1-yl)pyridin-3-yl)-3,3-difluoro-N,N-dimethylpiperidine-4-carboxamide | 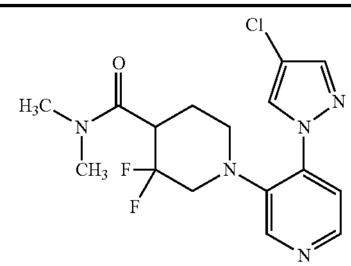 | 370.1 |
| 98 | N-cyclopropyl-4-fluoro-1-(4-(4-methyl-1H-pyrazol-1-yl)pyridin-3-yl)piperidine-4-carboxamide | 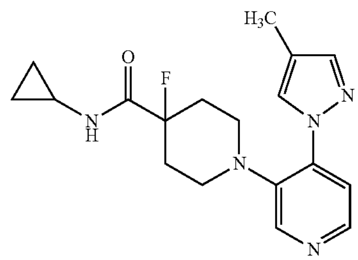 [SMILES: Cc1cnn(-c2ccncc2N2CCC(F)(C(=O)NC3CC3)CC2)c1] | 344.2 |
| 99 | 4-fluoro-N-methyl-1-(4-(4-methyl-1H-pyrazol-1-yl)pyridin-3-yl)piperidine-4-carboxamide | 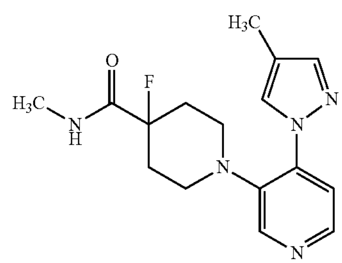 [SMILES: CNC(=O)C1(F)CCN(c2cnccc2-n2cc(C)cn2)CC1] | 318.2 |
| 100 | (1-(4-(4-chloro-1H-pyrazol-1-yl)pyridin-3-yl)-3,3-difluoropiperidin-4-yl)(3-oxa-8-azabicyclo[3.2.1]oct-8-yl)methanone | 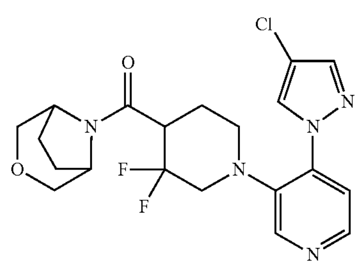 [SMILES: O=C(C1CCN(c2cnccc2-n2cc(Cl)cn2)CC1(F)F)N1C2CCC1COC2] | 438.1 |

TABLE 1-11

| EXAMPLE | IUPACNAME | Structure | MS |
|---|---|---|---|
| 101 | 1-(4-(4-chloro-1H-pyrazol-1-yl)pyridin-3-yl)-3,3-difluoro-N-methyl-N-(tetrahydro-2H-pyran-4-yl)piperidine-4-carboxamide | 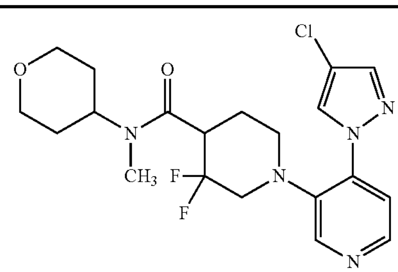 | 440.1 |

TABLE 1-11-continued

| EXAMPLE | IUPACNAME | Structure | MS |
|---|---|---|---|
| 102 | 4-((1-(4-(4-chloro-1H-pyrazol-1-yl)pyridin-3-yl)piperidin-4-yl)carbonyl)piperazin-2-one | 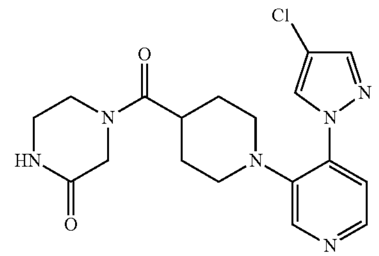 [SMILES: O=C1CN(C(=O)C2CCN(c3cnccc3-n3cc(Cl)cn3)CC2)CCN1] | 389.1 |
| 103 | (1-(4-(4-chloro-1H-pyrazol-1-yl)pyridin-3-yl)piperidin-4-yl)(4-methylpiperazin-1-yl)methanone | 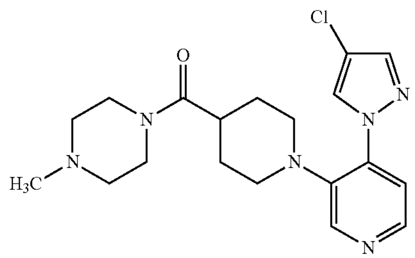 [SMILES: CN1CCN(C(=O)C2CCN(c3cnccc3-n3cc(Cl)cn3)CC2)CC1] | 389.2 |
| 104 | (3-methoxypyrrolidin-1-yl)(1-(4-(4-methyl-1H-pyrazol-1-yl)pyridin-3-yl)piperidin-4-yl)methanone | 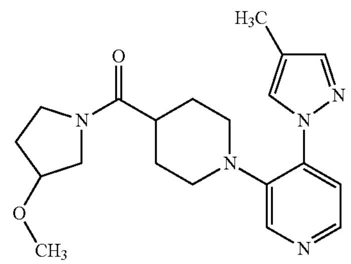 [SMILES: COC1CCN(C(=O)C2CCN(c3cnccc3-n3cc(C)cn3)CC2)C1] | 370.2 |
| 105 | (1-(4-(4-methyl-1H-pyrazol-1-yl)pyridin-3-yl)piperidin-4-yl)(2-methylpyrrolidin-1-yl)methanone | 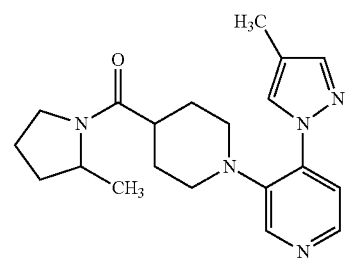 [SMILES: Cc1cnn(-c2ccncc2N2CCC(C(=O)N3CCCC3C)CC2)c1] | 354.2 |
| 106 | (1-(4-(4-methyl-1H-pyrazol-1-yl)pyridin-3-yl)piperidin-4-yl)(3,3,4,4-tetrafluoropyrrolidin-1-yl)methanone | 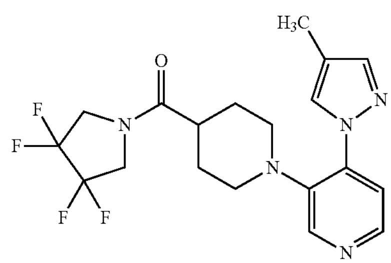 [SMILES: Cc1cnn(-c2ccncc2N2CCC(C(=O)N3CC(F)(F)C(F)(F)C3)CC2)c1] | 412.2 |
| 107 | 4-((1-(4-(4-chloro-1H-pyrazol-1-yl)pyridin-3-yl)piperidin-4-yl)carbonyl)-1-methylpiperazin-2-one | 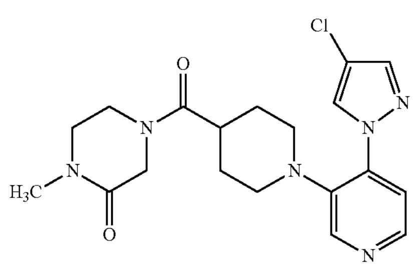 [SMILES: CN1CCN(C(=O)C2CCN(c3cnccc3-n3cc(Cl)cn3)CC2)CC1=O] | 403.1 |

TABLE 1-11-continued

| EXAMPLE | IUPACNAME | Structure | MS |
|---|---|---|---|
| 108 | methyl 1-((1-(4-(4-chloro-1H-pyrazol-1-yl)pyridin-3-yl)piperidin-4-yl)carbonyl)-L-prolinate | 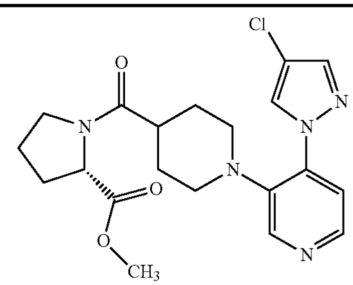 | 418.2 |
| 109 | methyl 1-((1-(4-(4-chloro-1H-pyrazol-1-yl)pyridin-3-yl)piperidin-4-yl)carbonyl)-D-prolinate | 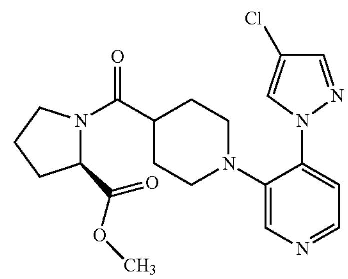 [SMILES: COC(=O)[C@H]1CCCN1C(=O)C1CCN(c2cnccc2-n2cc(Cl)cn2)CC1] | 418.2 |
| 110 | (1-(4-(4-chloro-1H-pyrazol-1-yl)pyridin-3-yl)-3,3-difluoropiperidin-4-yl)(3,3-difluoropyrrolidin-1-yl)methanone | 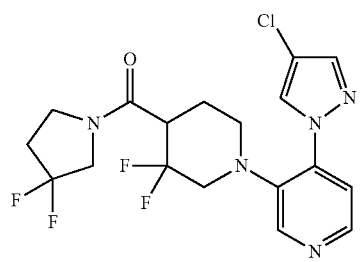 [SMILES: O=C(C1CCN(c2cnccc2-n2cc(Cl)cn2)CC1(F)F)N1CCC(F)(F)C1] | 432.1 |

TABLE 1-12

| EXAMPLE | IUPACNAME | Structure | MS |
|---|---|---|---|
| 111 | (1-(4-(4-chloro-1H-pyrazol-1-yl)pyridin-3-yl)piperidin-4-yl)((2S)-2-(2-hydroxypropan-2-yl)pyrrolidin-1-yl)methanone | 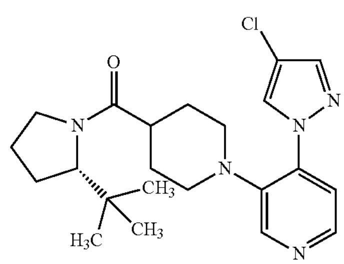 [SMILES: CC(C)(C)[C@@H]1CCCN1C(=O)C1CCN(c2cnccc2-n2cc(Cl)cn2)CC1] | 418.2 |
| 112 | (1-(4-(4-chloro-1H-pyrazol-1-yl)pyridin-3-yl)piperidin-4-yl)((2R)-2-(2-hydroxypropan-2-yl)pyrrolidin-1-yl)methanone | 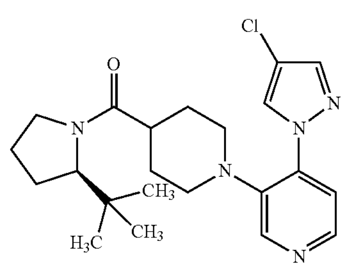 [SMILES: CC(C)(C)[C@H]1CCCN1C(=O)C1CCN(c2cnccc2-n2cc(Cl)cn2)CC1] | 418.2 |

TABLE 1-12-continued

| EXAMPLE | IUPACNAME | Structure | MS |
|---|---|---|---|
| 113 | methyl 2-methyl-1-((1-(4-(4-methyl-1H-pyrazol-1-yl)pyridin-3-yl)piperidin-4-yl)carbonyl)-D-prolinate | 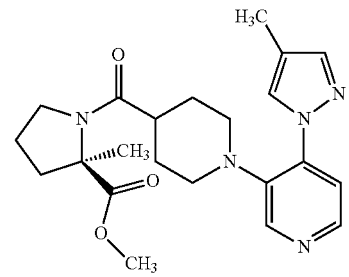 [SMILES: COC(=O)[C@@]1(C)CCCN1C(=O)C1CCN(c2cnccc2-n2cc(C)cn2)CC1] | 412.3 |
| 114 | 1-((1-(4-(4-methyl-1H-pyrazol-1-yl)pyridin-3-yl)piperidin-4-yl)carbonyl)-L-prolinamide | 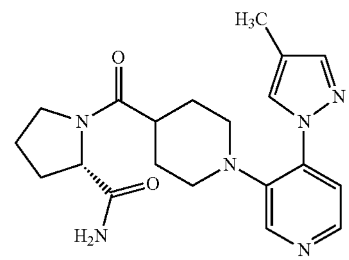 [SMILES: Cc1cnn(-c2ccncc2N2CCC(C(=O)N3CCC[C@H]3C(N)=O)CC2)c1] | 383.2 |
| 115 | (1-(4-(4-chloro-1H-pyrazol-1-yl)pyridin-3-yl)piperidin-4-yl)((2s)-2-(methoxymethyl)pyrrolidin-1-yl)methanone | 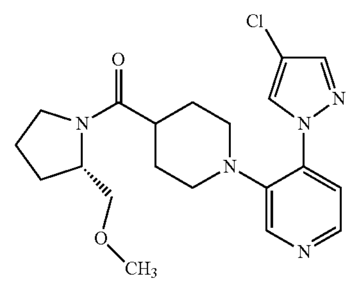 [SMILES: COC[C@@H]1CCCN1C(=O)C1CCN(c2cnccc2-n2cc(Cl)cn2)CC1] | 404.2 |
| 116 | (1-(4-(4-chloro-1H-pyrazol-1-yl)pyridin-3-yl)piperidin-4-yl)((2R)-2-(methoxymethyl)pyrrolidin-1-yl)methanone | 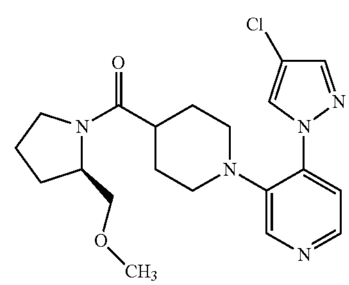 [SMILES: COC[C@H]1CCCN1C(=O)C1CCN(c2cnccc2-n2cc(Cl)cn2)CC1] | 404.2 |
| 117 | 1-((1-(4-(4-chloro-1H-pyrazol-1-yl)pyridin-3-yl)piperidin-4-yl)carbonyl)-4,4-difluoro-L-prolinamide | 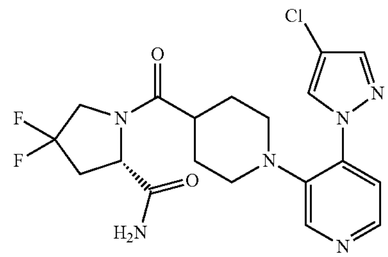 | 439.2 |

TABLE 1-12-continued

| EXAMPLE | IUPACNAME | Structure | MS |
|---|---|---|---|
| 118 | 4,4-difluoro-1-((1-(4-(4-methyl-1H-pyrazol-1-yl)pyridin-3-yl)piperidin-4-yl)carbonyl)-L-prolinamide | 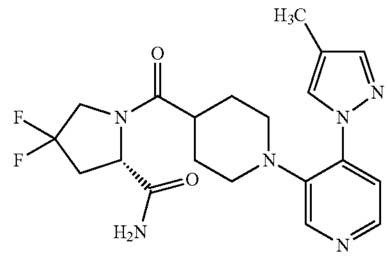 [SMILES: Cc1cnn(-c2ccncc2N2CCC(C(=O)N3CC(F)(F)C[C@H]3C(N)=O)CC2)c1] | 419.2 |
| 119 | (2S)-1-((1-(4-(4-chloro-1H-pyrazol-1-yl)pyridin-3-yl)piperidin-4-yl)carbonyl)-4,4-difluoropyrrolidine-2-carbonitrile | 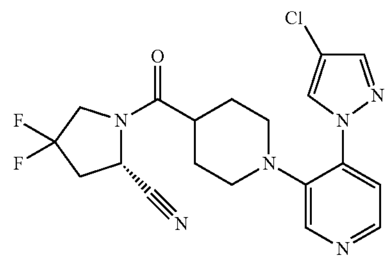 [SMILES: N#C[C@@H]1CC(F)(F)CN1C(=O)C1CCN(c2cnccc2-n2cc(Cl)cn2)CC1] | 421.1 |
| 120 | (2S)-1-((1-(4-(4-methyl-1H-pyrazol-1-yl)pyridin-3-yl)piperidin-4-yl)carbonyl)pyrrolidine-2-carbonitrile | 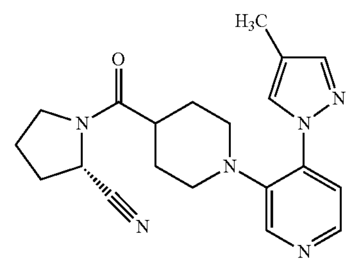 [SMILES: Cc1cnn(-c2ccncc2N2CCC(C(=O)N3CCC[C@H]3C#N)CC2)c1] | 365.2 |

TABLE 1-13

| EXAMPLE | IUPACNAME | Structure | MS |
|---|---|---|---|
| 121 | (2S)-4,4-difluoro-1-((1-(4-(4-methyl-1H-pyrazol-1-yl)pyridin-3-yl)piperidin-4-yl)carbonyl)pyrrolidine-2-carbonitrile | 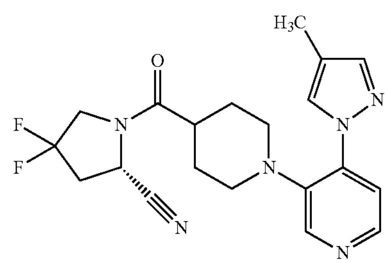 [SMILES: Cc1cnn(-c2ccncc2N2CCC(C(=O)N3CC(F)(F)C[C@H]3C#N)CC2)c1] | 401.2 |
| 122 | (1-(4-(5-methyl-1,3,4-thiadiazol-2-yl)pyridin-3-yl)piperidin-4-yl)(3-oxa-8-azabicyclo[3.2.1]oct-8-yl)methanone | 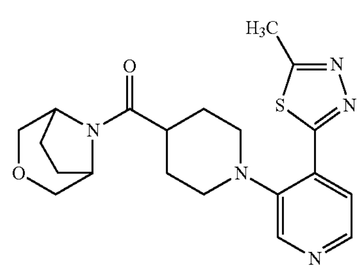 [SMILES: Cc1nnc(-c2ccncc2N2CCC(C(=O)N3C4CCC3COC4)CC2)s1] | 400.1 |

TABLE 1-13-continued

| EXAMPLE | IUPACNAME | Structure | MS |
|---|---|---|---|
| 123 | (1-(4-(5-methyl-1,3,4-thiadiazol-2-yl)pyridin-3-yl)piperidin-4-yl)(3,3,4,4-tetrafluoropyrrolidin-1-yl)methanone | 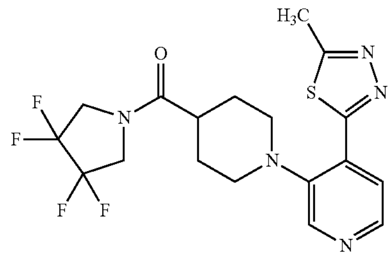 [SMILES: Cc1nnc(-c2ccncc2N2CCC(C(=O)N3CC(F)(F)C(F)(F)C3)CC2)s1] | 430.1 |
| 124 | 1-((1-(4-(4-methyl-1H-pyrazol-1-yl)pyridin-3-yl)piperidin-4-yl)carbonyl)-D-prolinamide | 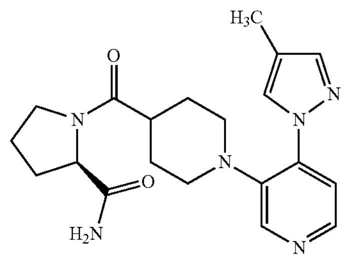 [SMILES: Cc1cnn(-c2ccncc2N2CCC(C(=O)N3CCC[C@@H]3C(N)=O)CC2)c1] | 383.2 |
| 125 | 2-methyl-1-((1-(4-(4-methyl-1H-pyrazol-1-yl)pyridin-3-yl)piperidin-4-yl)carbonyl)-D-prolinamide | 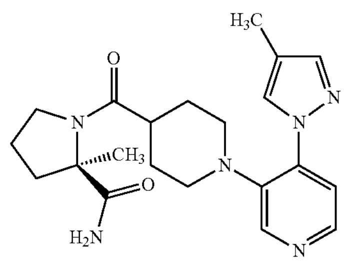 [SMILES: Cc1cnn(-c2ccncc2N2CCC(C(=O)N3CCC[C@]3(C)C(N)=O)CC2)c1] | 397.2 |
| 126 | 2-methyl-1-((1-(4-(5-methyl-1,3,4-thiadiazol-2-yl)pyridin-3-yl)piperidin-4-yl)carbonyl)-D-prolinamide | 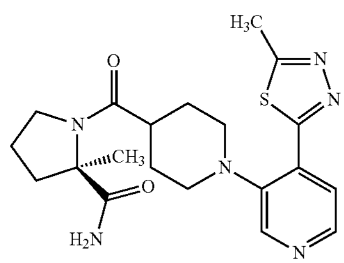 [SMILES: Cc1nnc(-c2ccncc2N2CCC(C(=O)N3CCC[C@]3(C)C(N)=O)CC2)s1] | 415.2 |
| 127 | (2R)-2-methyl-1-((1-(4-(4-methyl-1H-pyrazol-1-yl)pyridin-3-yl)piperidin-4-yl)carbonyl)pyrrolidine-2-carbonitrile | 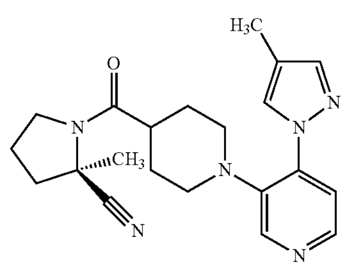 [SMILES: Cc1cnn(-c2ccncc2N2CCC(C(=O)N3CCC[C@]3(C)C#N)CC2)c1] | 379.3 |
| 128 | (2R)-2-methyl-1-((1-(4-(5-methyl-1,3,4-thiadiazol-2-yl)pyridin-3-yl)piperidin-4-yl)carbonyl)pyrrolidine-2-carbonitrile | 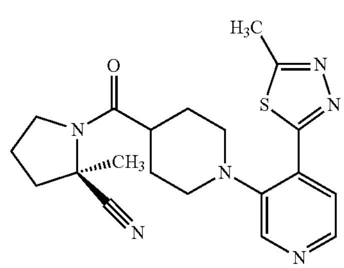 [SMILES: Cc1nnc(-c2ccncc2N2CCC(C(=O)N3CCC[C@]3(C)C#N)CC2)s1] | 397.2 |

TABLE 1-13-continued

| EXAMPLE | IUPACNAME | Structure | MS |
|---|---|---|---|
| 129 | (2R)-1-((1-(4-(5-methyl-1,3-thiazol-2-yl)pyridin-3-yl)piperidin-4-yl)carbonyl)pyrrolidine-2-carbonitrile | 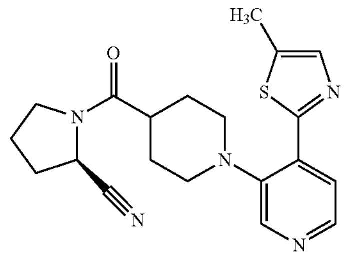 [SMILES: Cc1cnc(-c2ccncc2N2CCC(C(=O)N3CCC[C@@H]3C#N)CC2)s1] | 382.1 |
| 130 | (2R)-4,4-difluoro-1-((1-(4-(4-methyl-1H-pyrazol-1-yl)pyridin-3-yl)piperidin-4-yl)carbonyl)pyrrolidine-2-carbonitrile | 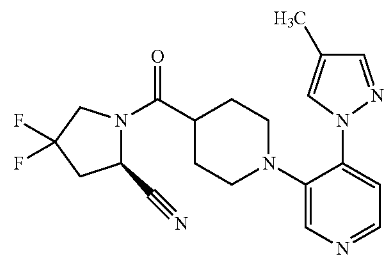 [SMILES: Cc1cnn(-c2ccncc2N2CCC(C(=O)N3CC(F)(F)C[C@@H]3C#N)CC2)c1] | 401.2 |

TABLE 1-14

| EXAMPLE | IUPACNAME | Structure | MS |
|---|---|---|---|
| 131 | (2R)-1-((4-fluoro-1-(4-(5-methyl-1,3,4-thiadiazol-2-yl)pyridin-3-yl)piperidin-4-yl)carbonyl)pyrrolidine-2-carbonitrile | 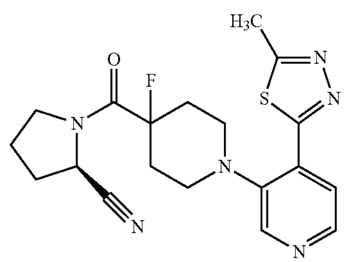 [SMILES: Cc1nnc(-c2ccncc2N2CCC(F)(C(=O)N3CCC[C@@H]3C#N)CC2)s1] | 401.1 |
| 132 | (2R)-4,4-difluoro-1-((1-(4-(5-methyl-1,3,4-thiadiazol-2-yl)pyridin-3-yl)piperidin-4-yl)carbonyl)pyrrolidine-2-carbonitrile | 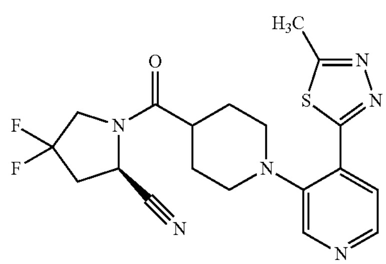 [SMILES: Cc1nnc(-c2ccncc2N2CCC(C(=O)N3CC(F)(F)C[C@@H]3C#N)CC2)s1] | 419.1 |
| 133 | ((2R)-2-(methoxymethyl)pyrrolidin-1-yl)(1-(4-(5-methyl-1,3,4-thiadiazol-2-yl)pyridin-3-yl)piperidin-4-yl)methanone | 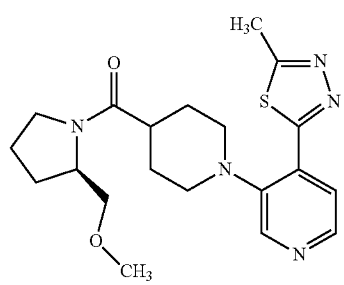 [SMILES: COC[C@H]1CCCN1C(=O)C1CCN(c2cnccc2-c2nnc(C)s2)CC1] | 402.1 |

TABLE 1-14-continued

| EXAMPLE | IUPACNAME | Structure | MS |
|---|---|---|---|
| 134 | (2R,4S)-4-hydroxy-1-((1-(4-(4-methyl-1H-pyrazol-1-yl)pyridin-3-yl)piperidin-4-yl)carbonyl)pyrrolidine-2-carbonitrile | 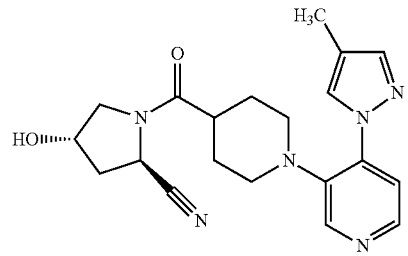 [SMILES: Cc1cnn(-c2ccncc2N2CCC(C(=O)N3C[C@@H](O)C[C@@H]3C#N)CC2)c1] | 381.2 |
| 135 | (2R,4S)-1-((1-(4-(4-chloro-1H-pyrazol-1-yl)pyridin-3-yl)piperidin-4-yl)carbonyl)-4-hydroxypyrrolidine-2-carbonitrile | 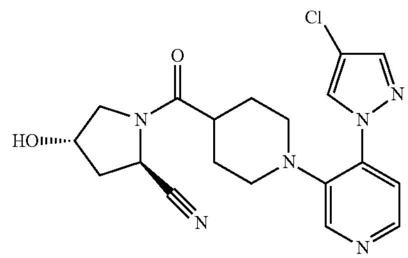 [SMILES: N#C[C@H]1C[C@H](O)CN1C(=O)C1CCN(c2cnccc2-n2cc(Cl)cn2)CC1] | 401.1 |
| 136 | (2R,4R)-4-hydroxy-1-((1-(4-(4-methyl-1H-pyrazol-1-yl)pyridin-3-yl)piperidin-4-yl)carbonyl)pyrrolidine-2-carbonitrile | 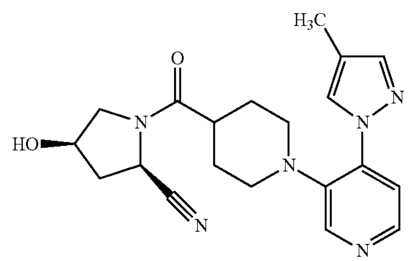 [SMILES: Cc1cnn(-c2ccncc2N2CCC(C(=O)N3C[C@H](O)C[C@@H]3C#N)CC2)c1] | 381.1 |
| 137 | (2R,4R)-1-((1-(4-(4-chloro-1H-pyrazol-1-yl)pyridin-3-yl)piperidin-4-yl)carbonyl)-4-hydroxypyrrolidine-2-carbonitrile | 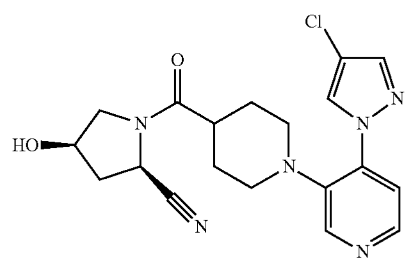 [SMILES: N#C[C@H]1C[C@@H](O)CN1C(=O)C1CCN(c2cnccc2-n2cc(Cl)cn2)CC1] | 401.1 |
| 138 | (2R,4R)-4-methoxy-1-((1-(4-(4-methyl-1H-pyrazol-1-yl)pyridin-3-yl)piperidin-4-yl)carbonyl)pyrrolidine-2-carbonitrile | 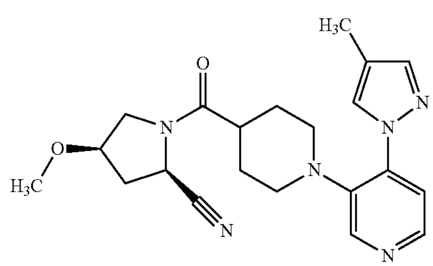 [SMILES: CO[C@@H]1C[C@H](C#N)N(C(=O)C2CCN(c3cnccc3-n3cc(C)cn3)CC2)C1] | 395.3 |
| 139 | (2R,4R)-1-((1-(4-(4-chloro-1H-pyrazol-1-yl)pyridin-3-yl)piperidin-4-yl)carbonyl)-4-methoxypyrrolidine-2-carbonitrile | 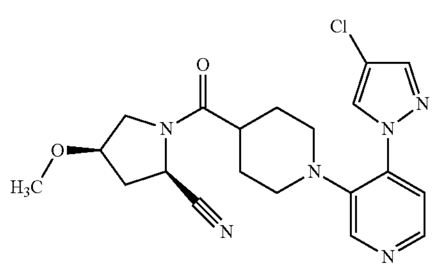 [SMILES: CO[C@@H]1C[C@H](C#N)N(C(=O)C2CCN(c3cnccc3-n3cc(Cl)cn3)CC2)C1] | 415.2 |

TABLE 1-14-continued

| EXAMPLE | IUPACNAME | Structure | MS |
|---|---|---|---|
| 140 | (2R,4R)-4-methoxy-1-((1-(4-(5-methyl-1,3,4-thiadiazol-2-yl)pyridin-3-yl)piperidin-4-yl)carbonyl)pyrrolidine-2-carbonitrile | 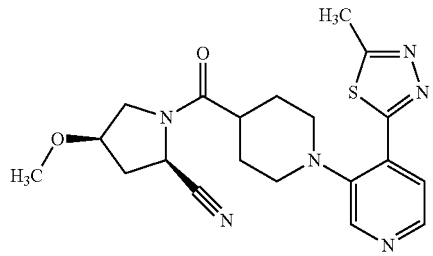 [SMILES: CO[C@@H]1C[C@H](C#N)N(C(=O)C2CCN(c3cnccc3-c3nnc(C)s3)CC2)C1] | 413.2 |

TABLE 1-15

| EXAMPLE | IUPACNAME | Structure | MS |
|---|---|---|---|
| 141 | (2R)-1-((1-(4-(2H-indazol-2-yl)pyridin-3-yl)piperidin-4-yl)carbonyl)pyrrolidine-2-carbonitrile | 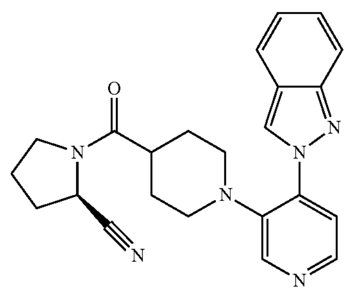 [SMILES: N#C[C@H]1CCCN1C(=O)C1CCN(c2cnccc2-n2cc3ccccc3n2)CC1] | 401.2 |
| 142 | (2R)-1-((1-(2,4'-bipyridin-3'-yl)piperidin-4-yl)carbonyl)pyrrolidine-2-carbonitrile | 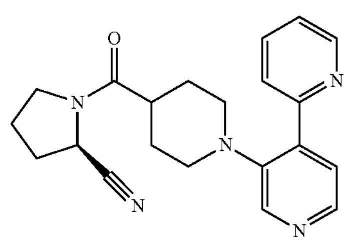 [SMILES: N#C[C@H]1CCCN1C(=O)C1CCN(c2cnccc2-c2ccccn2)CC1] | 362.2 |
| 143 | (2R)-1-((1-(2,4'-bipyridin-3'-yl)piperidin-4-yl)carbonyl)-4,4-difluoropyrrolidine-2-carbonitrile | 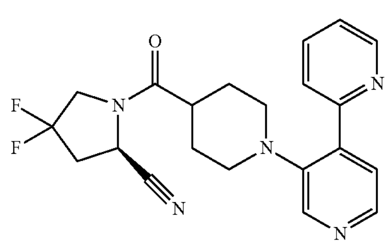 [SMILES: N#C[C@H]1CC(F)(F)CN1C(=O)C1CCN(c2cnccc2-c2ccccn2)CC1] | 398.1 |
| 144 | (2R,4S)-4-methoxy-1-((1-(4-(4-methyl-1H-pyrazol-1-yl)pyridin-3-yl)piperidin-4-yl)carbonyl)pyrrolidine-2-carbonitrile | 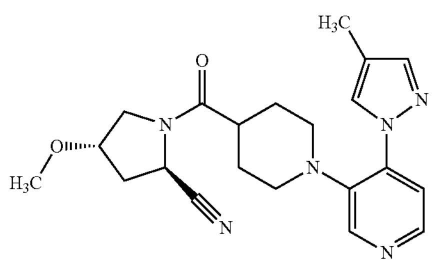 [SMILES: CO[C@H]1C[C@H](C#N)N(C(=O)C2CCN(c3cnccc3-n3cc(C)cn3)CC2)C1] | 395.3 |

TABLE 1-15-continued

| EXAMPLE | IUPACNAME | Structure | MS |
|---|---|---|---|
| 145 | 2-(4-methoxyphenyl)-1-(4-(4-phenylpyridin-3-yl)piperazin-1-yl)ethanone | 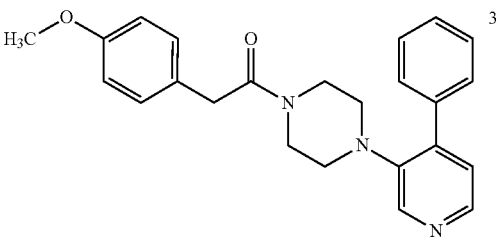 | 388.2 |
| 146 | 3-phenyl-1-(4-(4-phenylpyridin-3-yl)piperazin-1-yl)propan-1-one | 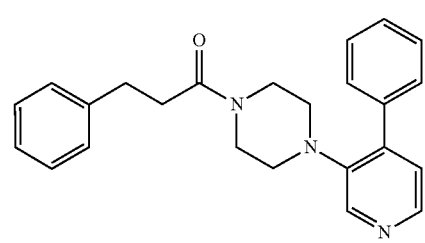 [SMILES: O=C(CCc1ccccc1)N1CCN(c2cnccc2-c2ccccc2)CC1] | 372.2 |
| 147 | 2-cyclopropyl-1-(4-(4-phenylpyridin-3-yl)piperazin-1-yl)ethanone | 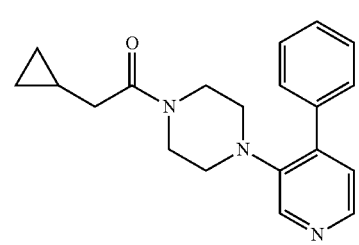 [SMILES: O=C(CC1CC1)N1CCN(c2cnccc2-c2ccccc2)CC1] | 322.2 |
| 148 | 2-cyclopropyl-1-(4-(4-(4-methylphenyl)pyridin-3-yl)piperazin-1-yl)ethanone | 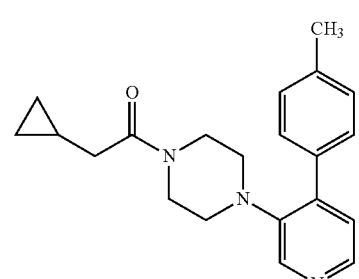 | 336.2 |
| 149 | 2-cyclopropyl-1-(4-(4-(4-fluorophenyl)pyridin-3-yl)piperazin-1-yl)ethanone | 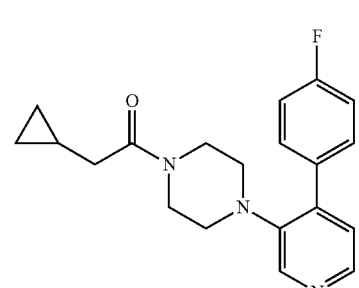 | 340.2 |
| 150 | 2-cyclopropyl-1-(4-(4-(1-methyl-1H-pyrazol-4-yl)pyridin-3-yl)piperazin-1-yl)ethanone | 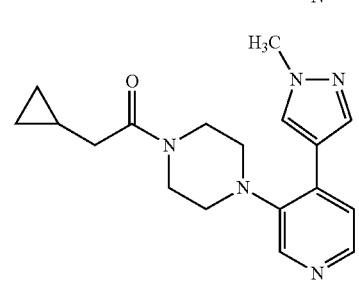 | 326.3 |

TABLE 1-16

| EXAMPLE | IUPACNAME | Structure | MS |
|---------|-----------|-----------|-----|
| 151 | 2-cyclopropyl-1-(4-(4-phenylpyrimidin-5-yl)piperazin-1-yl)ethanone | 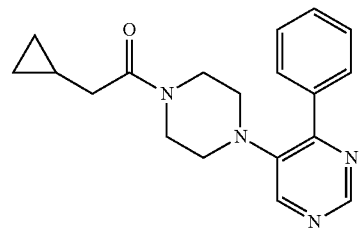 [SMILES: O=C(CC1CC1)N1CCN(c2cncnc2-c2ccccc2)CC1] | 323.2 |
| 152 | cyclopropyl(4-(4-phenylpyridin-3-yl)piperazin-1-yl)methanone | 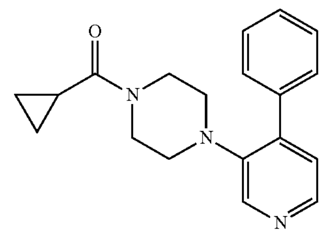 [SMILES: O=C(C1CC1)N1CCN(c2cnccc2-c2ccccc2)CC1] | 308.2 |
| 153 | N-cyclopropyl-4-(4-phenylpyridin-3-yl)piperazine-1-carboxamide | 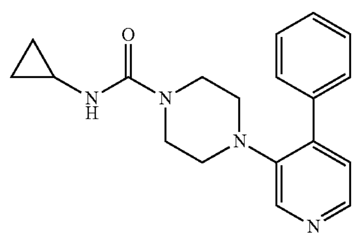 [SMILES: O=C(NC1CC1)N1CCN(c2cnccc2-c2ccccc2)CC1] | 323.2 |
| 154 | 2-cyclopropyl-1-(4-(4-(4-methyl-1H-pyrazol-1-yl)pyridin-3-yl)piperazin-1-yl)ethanone | 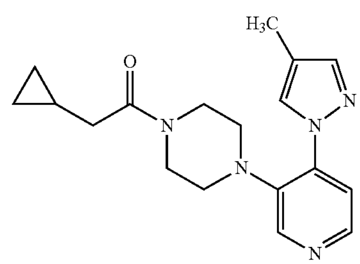 [SMILES: Cc1cnn(-c2ccncc2N2CCN(C(=O)CC3CC3)CC2)c1] | 326.2 |
| 155 | (3,3-difluoroazetidin-1-yl)(4-(4-phenylpyridin-3-yl)piperazin-1-yl)methanone | 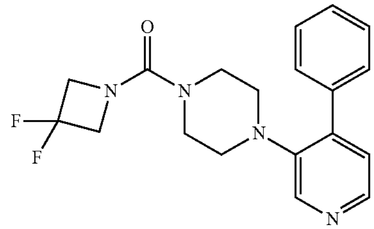 [SMILES: O=C(N1CCN(c2cnccc2-c2ccccc2)CC1)N1CC(F)(F)C1] | 359.1 |
| 156 | (4-(4-phenylpyridin-3-yl)piperazin-1-yl)(tetrahydro-2H-pyran-4-yl)methanone | 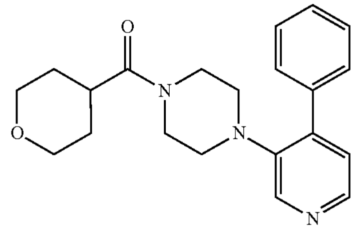 [SMILES: O=C(C1CCOCC1)N1CCN(c2cnccc2-c2ccccc2)CC1] | 352.2 |

TABLE 1-16-continued

| EXAMPLE | IUPACNAME | Structure | MS |
|---|---|---|---|
| 157 | morpholin-4-yl(4-(4-phenylpyridin-3-yl)piperazin-1-yl)methanone | 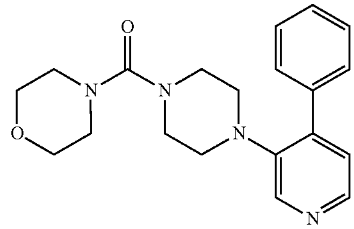 [SMILES: O=C(N1CCOCC1)N1CCN(c2cnccc2-c2ccccc2)CC1] | 353.2 |
| 158 | benzyl (2R)-2-methyl-4-(4-phenylpyrimidin-5-yl)piperazine-1-carboxylate | 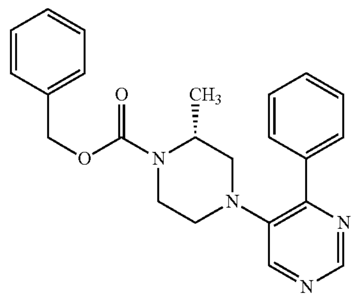 [SMILES: C[C@@H]1CN(c2cncnc2-c2ccccc2)CCN1C(=O)OCc1ccccc1] | 389.2 |
| 159 | 2-cyclopropyl-1-((2R)-2-methyl-4-(4-phenylpyrimidin-5-yl)piperazin-1-yl)ethanone | 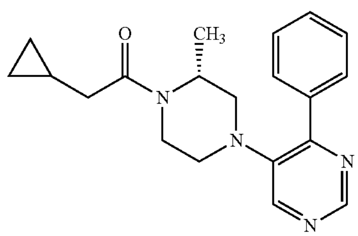 [SMILES: C[C@@H]1CN(c2cncnc2-c2ccccc2)CCN1C(=O)CC1CC1] | 337.2 |
| 160 | tert-butyl (1S,4S)-5-(4-phenylpyridin-3-yl)-2,5-diazabicyclo[2.2.1]heptane-2-carboxylate | 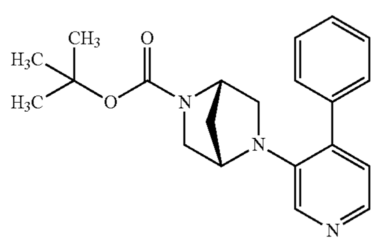 [SMILES: CC(C)(C)OC(=O)N1C[C@@H]2C[C@H]1CN2c1cnccc1-c1ccccc1] | 352.2 |

TABLE 1-17

| EXAMPLE | IUPACNAME | Structure | MS |
|---|---|---|---|
| 161 | 2-cyclopropyl-1-((1S,4S)-5-(4-phenylpyridin-3-yl)-2,5-diazabicyclo[2.2.1]hept-2-yl)ethanone | 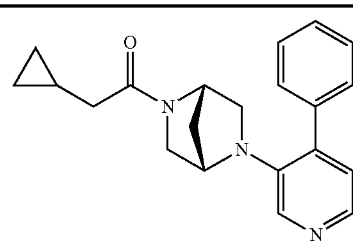 | 334.2 |

TABLE 1-17-continued

| EXAMPLE | IUPACNAME | Structure | MS |
|---|---|---|---|
| 162 | benzyl (2S)-2-methyl-4-(4-phenylpyrimidin-5-yl)piperazine-1-carboxylate | 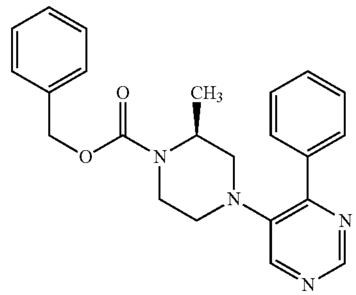 [SMILES: C[C@H]1CN(c2cncnc2-c2ccccc2)CCN1C(=O)OCc1ccccc1] | 389.2 |
| 163 | 1-(4-(2,4'-hipyridin-3'-yl)piperazin-1-yl)-2-cyclopropylethanone | 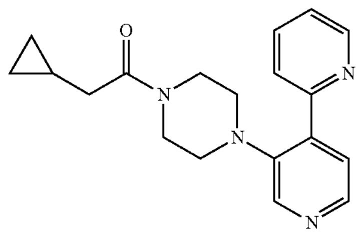 [SMILES: O=C(CC1CC1)N1CCN(c2cnccc2-c2ccccn2)CC1] | 323.2 |
| 164 | 2-cyclopropyl-1-(4-(4-(3-fluorophenyl)pyridin-3-yl)piperazin-1-yl)ethanone | 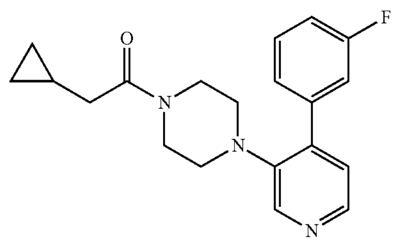 [SMILES: O=C(CC1CC1)N1CCN(c2cnccc2-c2cccc(F)c2)CC1] | 340.2 |
| 165 | cyclopropyl(4-(5-fluoro-4-phenylpyridin-3-yl)piperazin-1-yl)methanone | 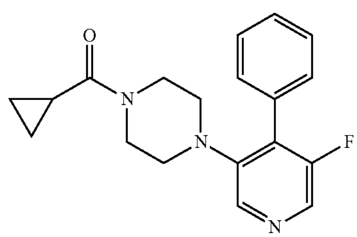 [SMILES: O=C(C1CC1)N1CCN(c2cncc(F)c2-c2ccccc2)CC1] | 326.2 |
| 166 | 2-cyclopropyl-1-(4-(5-fluoro-4-phenylpyridin-3-yl)piperazin-1-yl)ethanone | 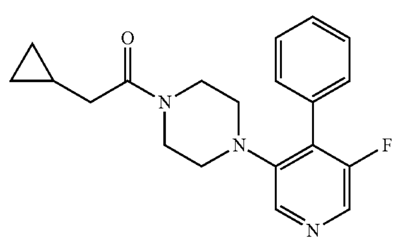 [SMILES: O=C(CC1CC1)N1CCN(c2cncc(F)c2-c2ccccc2)CC1] | 340.2 |
| 167 | 2-cyclopropyl-1-(4-(4-(2-fluorophenyl)pyridin-3-yl)piperazin-1-yl)ethanone | 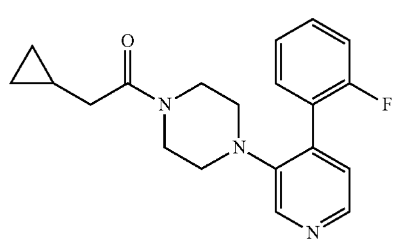 [SMILES: O=C(CC1CC1)N1CCN(c2cnccc2-c2ccccc2F)CC1] | 340.2 |

TABLE 1-17-continued

| EXAMPLE | IUPACNAME | Structure | MS |
|---|---|---|---|
| 168 | 1-(4-(4-(2-chlorophenyl)pyridin-3-yl)piperazin-1-yl)-2-cyclopropylethanone | 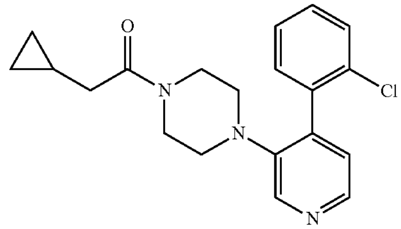 [SMILES: O=C(CC1CC1)N1CCN(c2cnccc2-c2ccccc2Cl)CC1] | 356.2 |
| 169 | benzyl 4-(4-phenylpyrimidin-5-yl)piperazine-1-carboxylate | 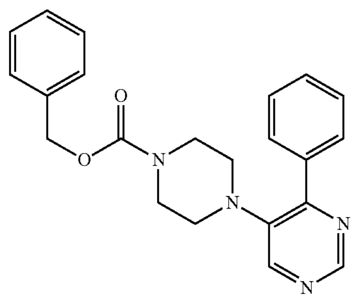 [SMILES: O=C(OCc1ccccc1)N1CCN(c2cncnc2-c2ccccc2)CC1] | 375.2 |
| 170 | 2-cyclopropyl-1-((2S)-2-methyl-4-(4-phenylpyrimidin-5-yl)piperazin-1-yl)ethanone | 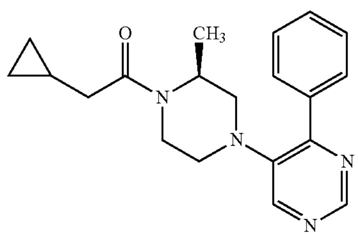 [SMILES: C[C@H]1CN(c2cncnc2-c2ccccc2)CCN1C(=O)CC1CC1] | 337.2 |

TABLE 1-18

| EXAMPLE | IUPACNAME | Structure | MS |
|---|---|---|---|
| 171 | 2-cyclopropyl-1-(4-(4-(1H-pyrazol-1-yl)pyridin-3-yl)piperazin-1-yl)ethanone | 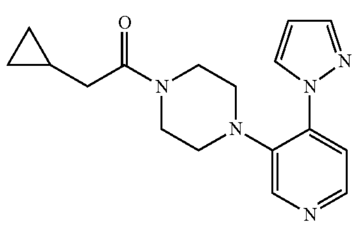 [SMILES: O=C(CC1CC1)N1CCN(c2cnccc2-n2cccn2)CC1] | 312.2 |
| 172 | N-cyclopropyl-1-(4-phenylpyridin-3-yl)piperidine-4-carboxamide | 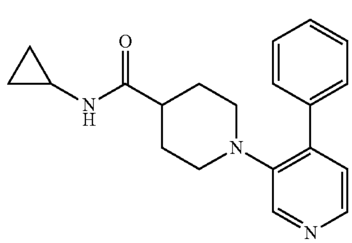 [SMILES: O=C(NC1CC1)C1CCN(c2cnccc2-c2ccccc2)CC1] | 322.2 |

TABLE 1-18-continued

| EXAMPLE | IUPACNAME | Structure | MS |
|---------|-----------|-----------|-----|
| 173 | tert-butyl 4-(4-phenylpyridin-3-yl)piperazine-1-carboxylate | 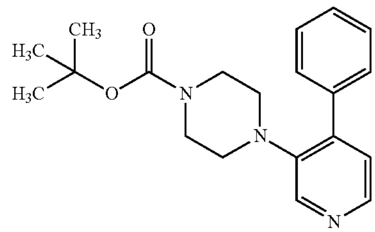 [SMILES: CC(C)(C)OC(=O)N1CCN(c2cnccc2-c2ccccc2)CC1] | 340.2 |
| 174 | 2-phenoxy-1-(4-(4-phenylpyrimidin-5-yl)piperazin-1-yl)ethanone | 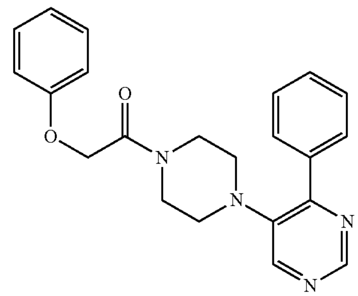 [SMILES: O=C(COc1ccccc1)N1CCN(c2cncnc2-c2ccccc2)CC1] | 375.2 |
| 175 | N-benzyl-4-(4-phenylpyrimidin-5-yl)piperazine-1-carboxamide | 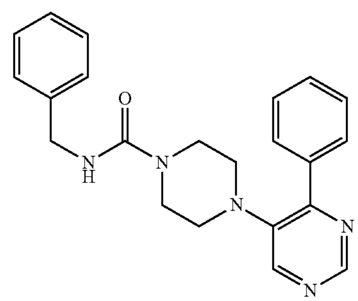 [SMILES: O=C(NCc1ccccc1)N1CCN(c2cncnc2-c2ccccc2)CC1] | 374.2 |
| 176 | N-ethyl-4-(4-phenylpyrimidin-5-yl)piperazine-1-carboxamide | 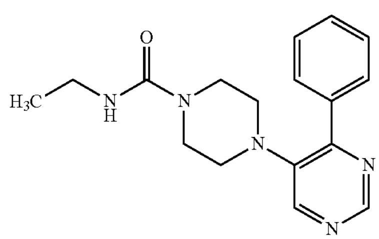 [SMILES: CCNC(=O)N1CCN(c2cncnc2-c2ccccc2)CC1] | 312.2 |
| 177 | N-methyl-4-(4-phenylpyrimidin-5-yl)piperazine-1-carboxamide | 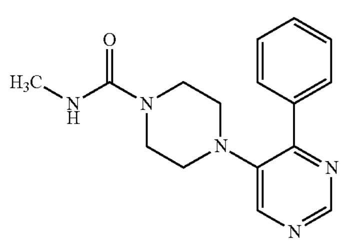 [SMILES: CNC(=O)N1CCN(c2cncnc2-c2ccccc2)CC1] | 298.2 |
| 178 | cyclopropyl(4-(4-phenylpyrimidin-5-yl)piperazin-1-yl)methanone | 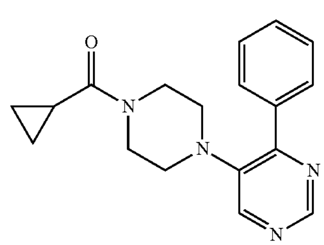 [SMILES: O=C(C1CC1)N1CCN(c2cncnc2-c2ccccc2)CC1] | 309.2 |

TABLE 1-18-continued

| EXAMPLE | IUPACNAME | Structure | MS |
|---|---|---|---|
| 179 | ((1S,2S)-2-phenylcyclopropyl)(4-(4-phenylpyrimidin-5-yl)piperazin-1-yl)methanone | 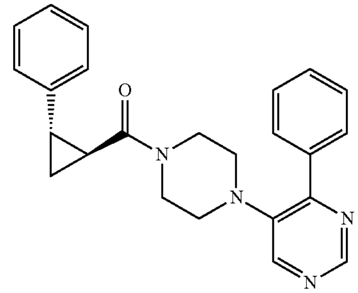 [SMILES: O=C([C@H]1C[C@@H]1c1ccccc1)N1CCN(c2cncnc2-c2ccccc2)CC1] | 385.1 |
| 180 | N-cyclopropyl-1-(4-phenylpyrimidin-5-yl)piperidine-4-carboxamide | 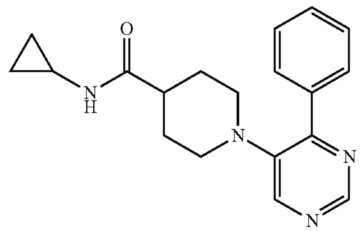 [SMILES: O=C(NC1CC1)C1CCN(c2cncnc2-c2ccccc2)CC1] | 323.2 |

TABLE 1-19

| EXAMPLE | IUPACNAME | Structure | MS |
|---|---|---|---|
| 181 | 1-(2-oxo-2-(4-(4-phenylpyridin-3-yl)piperazin-1-yl)ethyl)Pyridin-2(1H)-one | 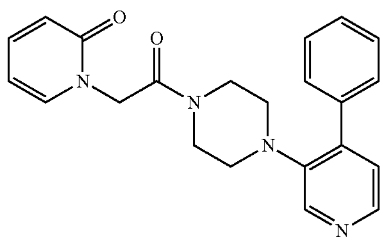 [SMILES: O=C(Cn1ccccc1=O)N1CCN(c2cnccc2-c2ccccc2)CC1] | 375.1 |
| 182 | 1-(4-(4-phenylpyridin-3-yl)piperazin-1-yl)-2-(1H-pyrazol-1-yl)ethanone | 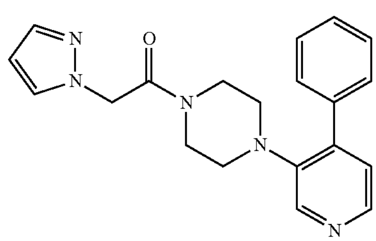 [SMILES: O=C(Cn1cccn1)N1CCN(c2cnccc2-c2ccccc2)CC1] | 348.2 |
| 183 | 3-(1H-indazol-1-yl)-1-(4-(4-phenylpyridin-3-yl)piperazin-1-yl)propan-1-one | 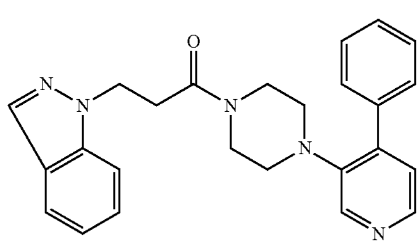 [SMILES: O=C(CCn1ncc2ccccc21)N1CCN(c2cnccc2-c2ccccc2)CC1] | 412.6 |

TABLE 1-19-continued

| EXAMPLE | IUPACNAME | Structure | MS |
|---|---|---|---|
| 184 | 4-oxo-4-(4-(4-phenylpyridin-3-yl)piperazin-1-yl)butanenitrile | 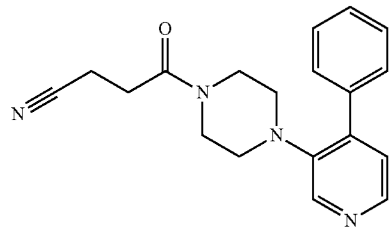 [SMILES: N#CCCC(=O)N1CCN(c2cnccc2-c2ccccc2)CC1] | 321.1 |
| 185 | phenyl (4-(4-phenylpyridin-3-yl)piperazin-1-yl)methanone | 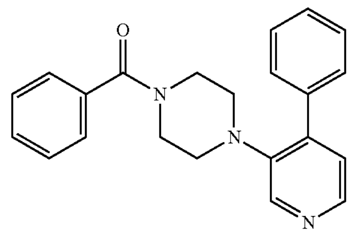 [SMILES: O=C(c1ccccc1)N1CCN(c2cnccc2-c2ccccc2)CC1] | 344.1 |
| 186 | methyl 4-methyl-1-(4-phenylpyrimidin-5-yl)piperidine-4-carboxylate | 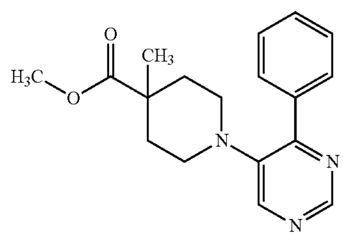 [SMILES: COC(=O)C1(C)CCN(c2cncnc2-c2ccccc2)CC1] | 312.2 |
| 187 | N,N-dimethyl-1-(4-phenylpyrimidin-5-yl)piperidine-4-carboxamide | 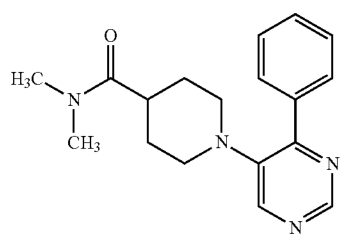 [SMILES: CN(C)C(=O)C1CCN(c2cncnc2-c2ccccc2)CC1] | 311.2 |
| 188 | 4-(4-phenylpyrimidin-5-yl)-N-(pyridin-2-ylmethyl)piperazine-1-carboxamide | 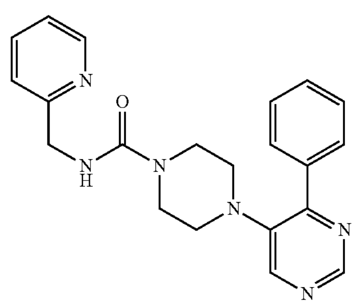 [SMILES: O=C(NCc1ccccn1)N1CCN(c2cncnc2-c2ccccc2)CC1] | 375.2 |
| 189 | N-cyclopropyl-1-(4-(4-methyl-1H-pyrazol-1-yl)pyridin-3-yl)piperidine-4-carboxamide | 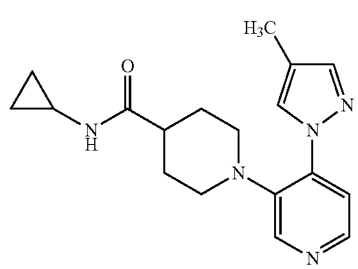 [SMILES: Cc1cnn(-c2ccncc2N2CCC(C(=O)NC3CC3)CC2)c1] | 326.2 |

TABLE 1-19-continued

| EXAMPLE | IUPACNAME | Structure | MS |
|---|---|---|---|
| 190 | (2-(4-fluorophenyl)azetidin-1-yl) (4-(4-phenylpyridin-3-yl)piperazin-1-yl)methanone | 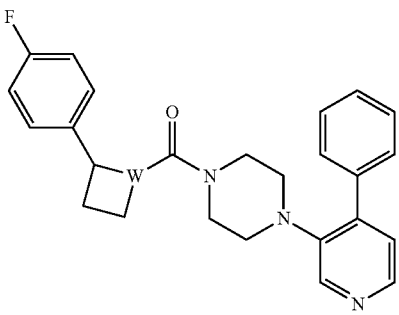 | 417.1 |

TABLE 1-20

| EXAMPLE | IUPACNAME | Structure | MS |
|---|---|---|---|
| 191 | 4-(4-phenylpyridin-3-yl)-N-(2,2,2-trifluoroethyl)piperazine-1-carboxamide | 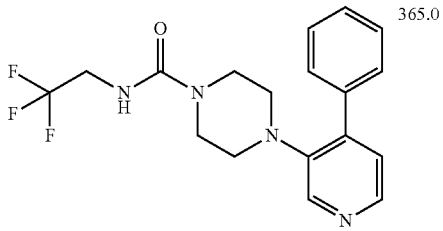 | 365.0 |
| 192 | 8-oxa-3-azabicyclo[3.2.1]oct-3-yl(4-(4-phenylpyridin-3-yl)piperazin-1-yl)methanone | 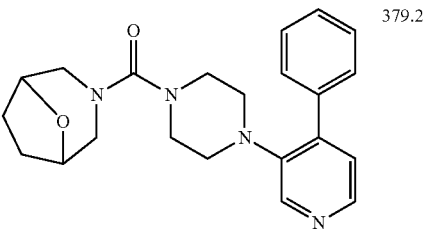 | 379.2 |
| 193 | N-cyclopropyl-1-(4-(4-fluorophenyl)pyrimidin-5-yl)piperidine-4-carboxamide | 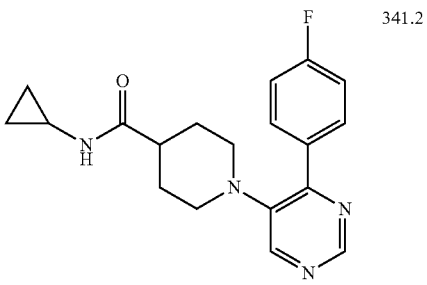 | 341.2 |
| 194 | N,N-dimethyl-1-(4-(4-methyl-1H-pyrazol-1-yl)pyridin-3-yl)piperidine-4-carboxamide | 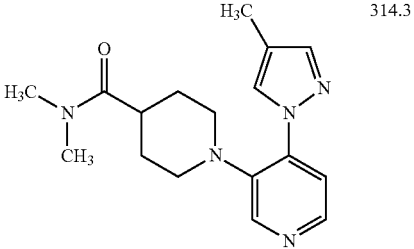 | 314.3 |

TABLE 1-20-continued

| EXAMPLE | IUPACNAME | Structure | MS |
|---|---|---|---|
| 195 | azetidin-1-yl(1-(4-(4-methyl-1H-pyrazol-1-yl)pyridin-3-yl)piperidin-4-yl)methanone | 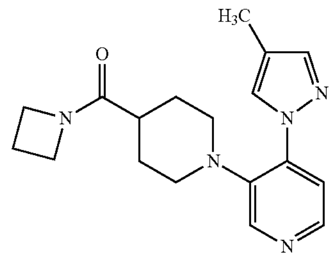 [SMILES: Cc1cnn(-c2ccncc2N2CCC(C(=O)N3CCC3)CC2)c1] | 326.2 |
| 196 | 1-(4-(4-fluorophenyl)pyrimidin-5-yl)-N,N-dimethylpiperidine-4-carboxamide | 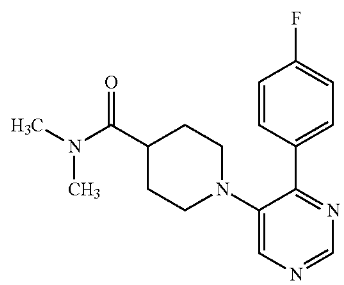 [SMILES: CN(C)C(=O)C1CCN(c2cncnc2-c2ccc(F)cc2)CC1] | 329.2 |
| 197 | N-cyclopropyl-1-(4-(1H-pyrazol-1-yl)pyridin-3-yl)piperidine-4-carboxamide | 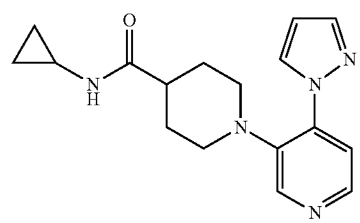 [SMILES: O=C(NC1CC1)C1CCN(c2cnccc2-n2cccn2)CC1] | 312.2 |
| 198 | (2R)-1-((4-(4-(4-fluorophenyl)pyrimidin-5-yl)piperazin-1-yl)carbonyl)pyrrolidine-2-carbonitrile | 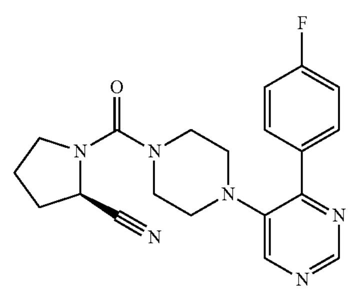 [SMILES: N#C[C@H]1CCCN1C(=O)N1CCN(c2cncnc2-c2ccc(F)cc2)CC1] | 381.1 |
| 199 | (4-(4-(4-fluorophenyl)pyrimidin-5-yl)piperazin-1-yl) (pyrrolidin-1-yl)methanone | 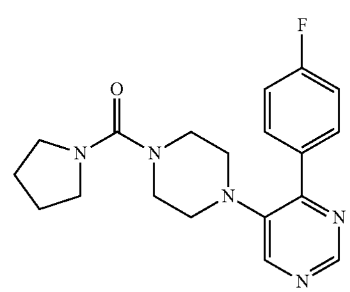 [SMILES: O=C(N1CCCC1)N1CCN(c2cncnc2-c2ccc(F)cc2)CC1] | 356.2 |

TABLE 1-20-continued

| EXAMPLE | IUPACNAME | Structure | MS |
|---|---|---|---|
| 200 | N-cyclopropyl-1-(4-(3,4-dimethyl-1H-pyrazol-1-yl)pyridin-3-yl)piperidine-4-carboxamide | 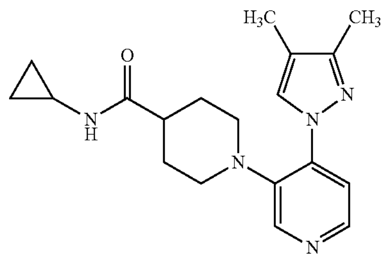 [SMILES: Cc1cn(-c2ccncc2N2CCC(C(=O)NC3CC3)CC2)nc1C] | 340.3 |

TABLE 1-21

| EXAMPLE | IUPACNAME | Structure | MS |
|---|---|---|---|
| 201 | N-methyl-1-(4-(4-methyl-1H-pyrazol-1-yl)pyridin-3-yl)piperidine-4-carboxamide | 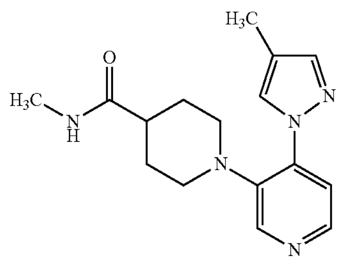 [SMILES: CNC(=O)C1CCN(c2cnccc2-n2cc(C)cn2)CC1] | 300.2 |
| 202 | (1-(4-(4-methyl-1H-pyrazol-1-yl)pyridin-3-yl)piperidin-4-yl) (3-oxa-6-azabicyclo[3.1.1]hept-6-yl)methanone | 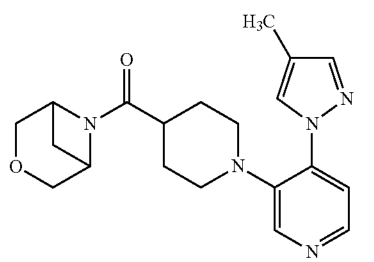 [SMILES: Cc1cnn(-c2ccncc2N2CCC(C(=O)N3C4COCC3C4)CC2)c1] | 368.2 |
| 203 | 1-(2,4'-bipyridin-3'-yl)-N-cyclopropylpiperidine-4-carboxamide | 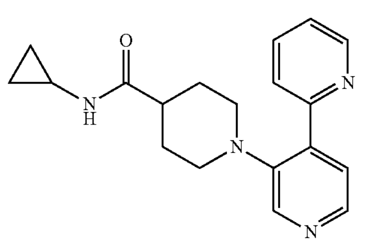 [SMILES: O=C(NC1CC1)C1CCN(c2cnccc2-c2ccccn2)CC1] | 323.2 |
| 204 | 1-(2,4'-bipyridin-3'-yl)-N-methylpiperidine-4-carboxamide | 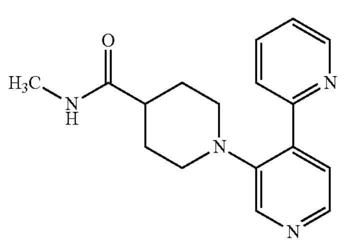 [SMILES: CNC(=O)C1CCN(c2cnccc2-c2ccccn2)CC1] | 297.2 |

TABLE 1-21-continued

| EXAMPLE | IUPACNAME | Structure | MS |
|---|---|---|---|
| 205 | 1-(2,4'-bipyridin-3'-yl)-N,N-dimethylpiperidine-4-carboxamide | 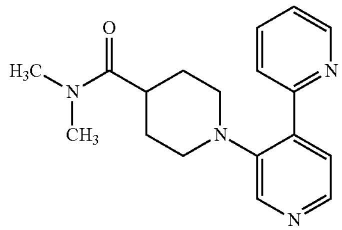 [SMILES: CN(C)C(=O)C1CCN(c2cnccc2-c2ccccn2)CC1] | 311.2 |
| 206 | 4-fluoro-1-(4-(4-fluorophenyl)pyrimidin-5-yl)piperidine-4-carboxamide | 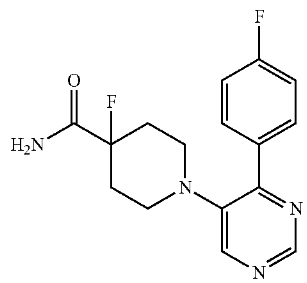 [SMILES: NC(=O)C1(F)CCN(c2cncnc2-c2ccc(F)cc2)CC1] | 319.2 |
| 207 | N-(4-fluorobenzyl)-4-(4-(4-fluorophenyl)pyrimidin-5-yl)piperazine-1-carboxamide | 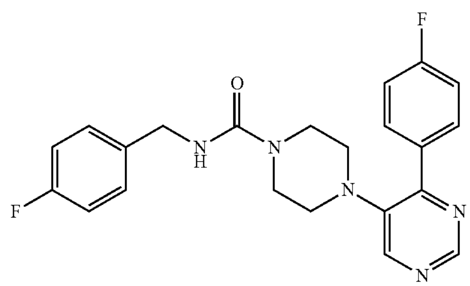 [SMILES: O=C(NCc1ccc(F)cc1)N1CCN(c2cncnc2-c2ccc(F)cc2)CC1] | 410.2 |
| 208 | (3S)-N-ethyl-4-(4-(4-fluorophenyl)pyrimidin-5-yl)-3-methylpiperazine-1-carboxamide | 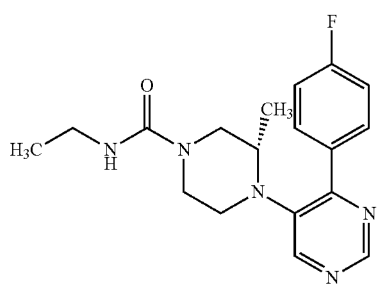 [SMILES: CCNC(=O)N1CCN(c2cncnc2-c2ccc(F)cc2)[C@@H](C)C1] | 344.2 |
| 209 | (3S)-4-(4-(4-fluorophenyl)pyrimidin-5-yl)-N,N,3-trimethylpiperazine-1-carboxamide | 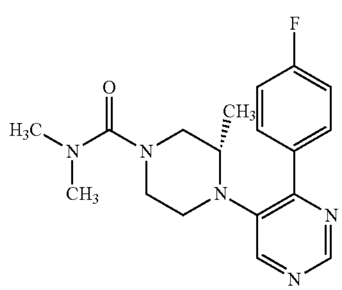 [SMILES: C[C@H]1CN(C(=O)N(C)C)CCN1c1cncnc1-c1ccc(F)cc1] | 344.2 |

TABLE 1-21-continued

| EXAMPLE | IUPACNAME | Structure | MS |
|---|---|---|---|
| 210 | N-cyclopropyl-1-(4-(4-methyl-1H-pyrazol-1-yl)pyridin-3-yl)-2-oxopiperidine-4-carboxamide | 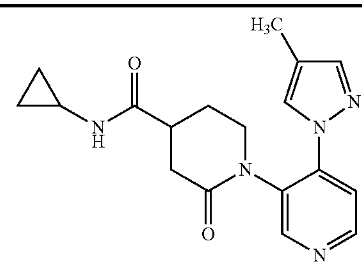 | 340.2 |

15

TABLE 1-22

| EXAMPLE | IUPACNAME | Structure | MS |
|---|---|---|---|
| 211 | 4-((3,3-difluoroazetidin-1-yl)carbonyl)-1-(4-(4-methyl-1H-pyrazol-1-yl)pyridin-3-yl)piperidin-2-one | 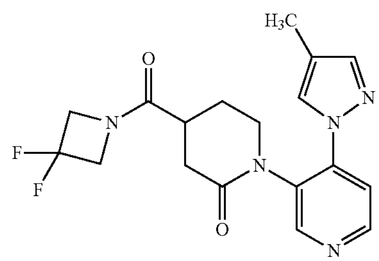 [SMILES: Cc1cnn(-c2ccncc2N2CCC(C(=O)N3CC(F)(F)C3)CC2=O)c1] | 376.1 |
| 212 | N-(cyclobutylmethyl)-4-(4-fluorophenyl)pyrimidin-5-yl)piperazine-1-carboxamide | 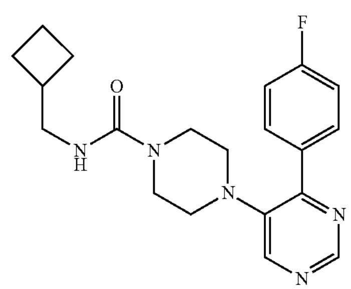 [SMILES: O=C(NCC1CCC1)N1CCN(c2cncnc2-c2ccc(F)cc2)CC1] | 370.2 |
| 213 | (1-(2,4'-bipyridin-3'-yl)piperidin-4-yl) (3,3-difluoroazetidin-1-yl)methanone | 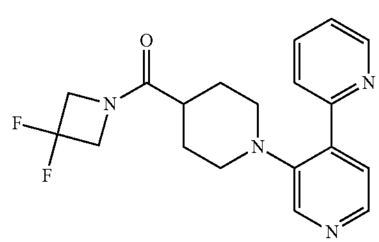 [SMILES: O=C(C1CCN(c2cnccc2-c2ccccn2)CC1)N1CC(F)(F)C1] | 359.1 |
| 214 | (1-(2,4'-bipyridin-3'-yl)piperidin-4-yl) (3,3-difluoropyrrolidin-1-yl)methanone | 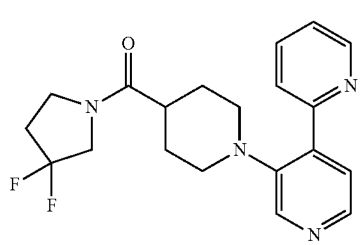 [SMILES: O=C(C1CCN(c2cnccc2-c2ccccn2)CC1)N1CCC(F)(F)C1] | 373.2 |

TABLE 1-22-continued

| EXAMPLE | IUPACNAME | Structure | MS |
|---|---|---|---|
| 215 | (1-(2,4'-bipyridin-3'-yl)piperidin-4-yl) (3-oxa-6-azabicyclo[3.1.1]hept-6-yl)methanone | 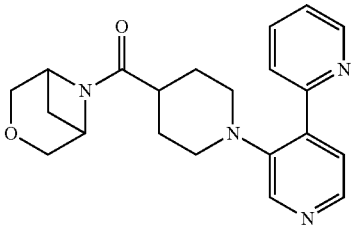 [SMILES: O=C(C1CCN(c2cnccc2-c2ccccn2)CC1)N1C2COCC1C2] | 365.2 |
| 216 | 1-(2,4'-bipyridin-3'-yl)-N-cyclopropyl-N-ethylpiperidine-4-carboxamide | 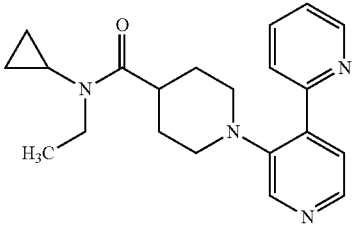 [SMILES: CCN(C(=O)C1CCN(c2cnccc2-c2ccccn2)CC1)C1CC1] | 351.2 |
| 217 | N-(cyclopropylmethyl)-4-(4-(4-methyl-1H-pyrazol-1-yl)pyridin-3-yl)piperazine-1-carboxamide | 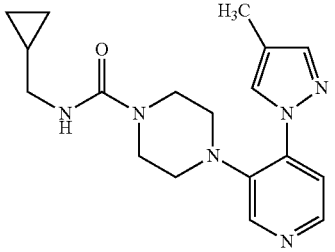 [SMILES: Cc1cnn(-c2ccncc2N2CCN(C(=O)NCC3CC3)CC2)c1] | 341.2 |
| 218 | N-ethyl-4-(4-(4-methyl-1H-pyrazol-1-yl)pyridin-3-yl)piperazine-1-carboxamide | 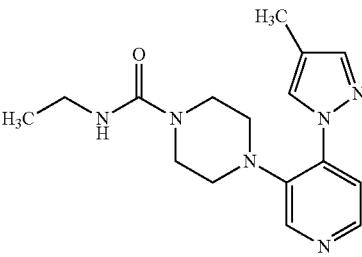 | 315.3 |
| 219 | N-(4-fluorobenzyl)-4-(4-(4-methyl-1H-pyrazol-1-yl)pyridin-3-yl)piperazine-1-carboxamide | 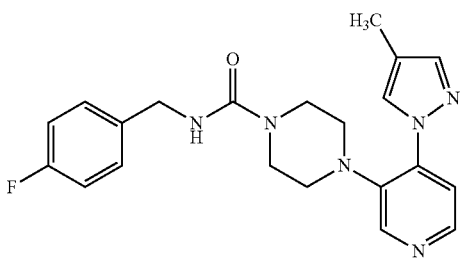 [SMILES: Cc1cnn(-c2ccncc2N2CCN(C(=O)NCc3ccc(F)cc3)CC2)c1] | 395.3 |
| 220 | 8-(4-(4-fluorophenyl)pyrimidin-5-yl)-2,8-diazaspiro[4.5]decan-1-one | 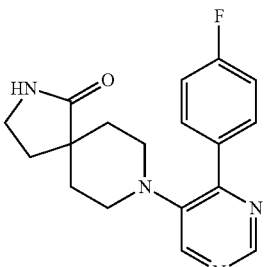 | 327.2 |

TABLE 1-23

| EXAMPLE | IUPACNAME | Structure | MS |
|---|---|---|---|
| 221 | N-cyclopropyl-1-(4-(4-methyl-1H-pyrazol-1-yl)pyrimidin-5-yl)piperidine-4-carboxamide | 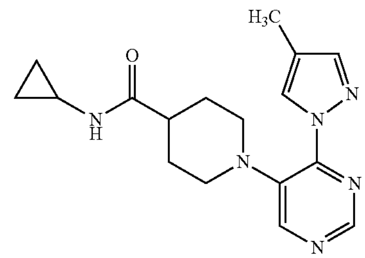 [SMILES: Cc1cnn(-c2ncncc2N2CCC(C(=O)NC3CC3)CC2)c1] | 327.2 |
| 222 | 8-(4-(4-fluorophenyl)pyrimidin-5-yl)-2-methyl-2,8-diazaspiro[4.5]decan-1-one | 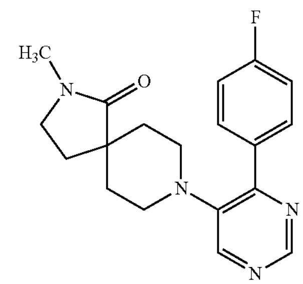 [SMILES: CN1CCC2(CCN(c3cncnc3-c3ccc(F)cc3)CC2)C1=O] | 341.1 |
| 223 | N,N-dimethyl-1-(4-(4-methyl-1H-pyrazol-1-yl)pyrimidin-5-yl)piperidine-4-carboxamide | 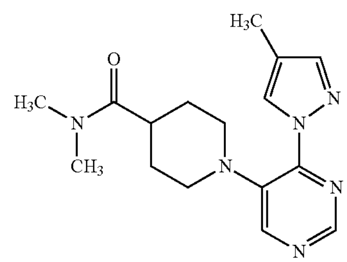 [SMILES: Cc1cnn(-c2ncncc2N2CCC(C(=O)N(C)C)CC2)c1] | 315.3 |
| 224 | (3,3-difluoroacetidin-1-yl) (1-(4-(4-methyl-1H-pyrazol-1-yl)pyrimidin-5-yl)piperidin-4-yl)methanone | 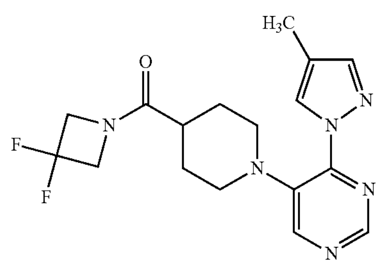 [SMILES: Cc1cnn(-c2ncncc2N2CCC(C(=O)N3CC(F)(F)C3)CC2)c1] | 363.2 |
| 225 | N-cyclopropyl-1-(4-(4-(trifluoromethyl)phenyl)pyrimidin-5-yl)piperidine-4-carboxamide | 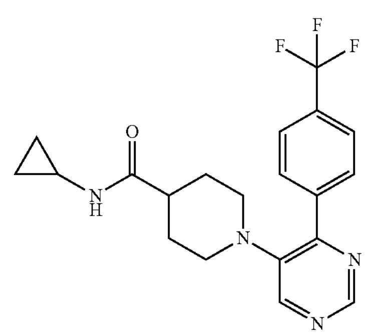 [SMILES: O=C(NC1CC1)C1CCN(c2cncnc2-c2ccc(C(F)(F)F)cc2)CC1] | 391.2 |

TABLE 1-23-continued

| EXAMPLE | IUPACNAME | Structure | MS |
|---|---|---|---|
| 226 | N,N-dimethyl-1-(4-(4-(trifluoromethyl)phenyl)pyrimidin-5-yl)piperidine-4-carboxamide | 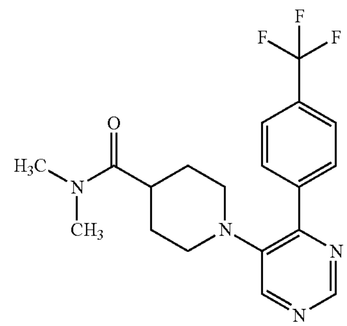 [SMILES: CN(C)C(=O)C1CCN(c2cncnc2-c2ccc(C(F)(F)F)cc2)CC1] | 379.2 |
| 227 | (1R,5S,6r)-N-cyclopropyl-3-(4-(4-fluorophenyl)pyrimidin-5-yl)-3-azabicyclo[3.1.0]hexane-6-carboxamide | 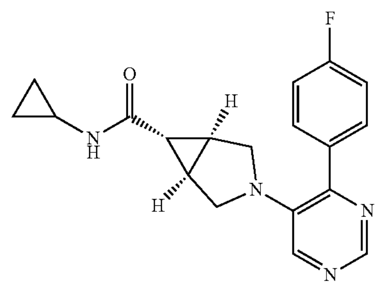 [SMILES: O=C(NC1CC1)[C@H]1[C@@H]2CN(c3cncnc3-c3ccc(F)cc3)C[C@@H]21] | 339.2 |
| 228 | (3,3-difluoroazetidin-1-yl) ((1R,5S,6r)-3-(4-(4-fluorophenyl)pyrimidin-5-yl)-3-azabicyclo[3.1.0]hex-6-yl)methanone | 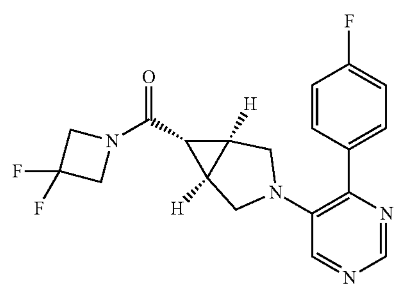 [SMILES: O=C([C@H]1[C@@H]2CN(c3cncnc3-c3ccc(F)cc3)C[C@@H]21)N1CC(F)(F)C1] | 375.1 |
| 229 | N,N-dimethyl-1-(4-(4-(trifluoromethyl)-1H-pyrazol-1-yl)pyridin-3-yl)piperidine-4-carboxamide | 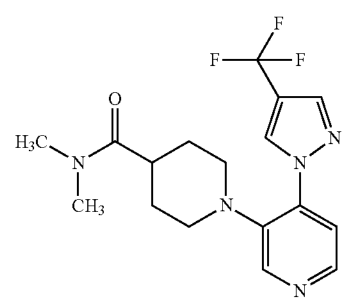 [SMILES: CN(C)C(=O)C1CCN(c2cnccc2-n2cc(C(F)(F)F)cn2)CC1] | 368.1 |
| 230 | N-(4-fluorobenzyl)-4-(4-(4-methyl-1H-pyrazol-1-yl)pyrimidin-5-yl)piperazine-1-carboxamide | 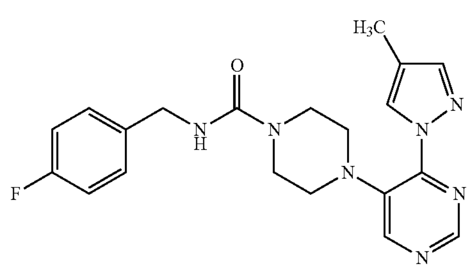 [SMILES: Cc1cnn(-c2ncncc2N2CCN(C(=O)NCc3ccc(F)cc3)CC2)c1] | 396.2 |

TABLE 1-24

| EXAMPLE | IUPACNAME | Structure | MS |
|---|---|---|---|
| 231 | N-(cyclopropylmethyl)-4-(4-(4-methyl-1H-pyrazol-1-yl)pyrimidin-5-yl)piperazine-1-carboxamide | 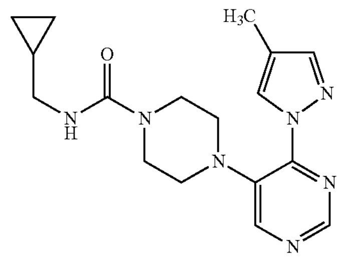 [SMILES: Cc1cnn(-c2ncncc2N2CCN(C(=O)NCC3CC3)CC2)c1] | 342.2 |
| 232 | N-ethyl-4-(4-(4-methyl-1H-pyrazol-1-yl)pyrimidin-5-yl)piperazine-1-carboxamide | 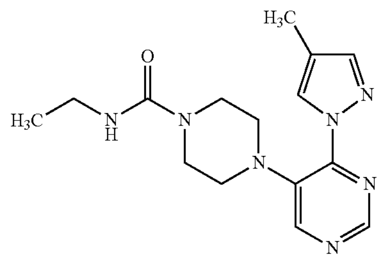 [SMILES: CCNC(=O)N1CCN(c2cncnc2-n2cc(C)cn2)CC1] | 316.2 |
| 233 | (3,3-difluoroazetidin-1-yl) (1-(4-(2-methyl-1,3-thiazol-4-yl)pyridin-3-yl)piperidin-4-yl)methanone | 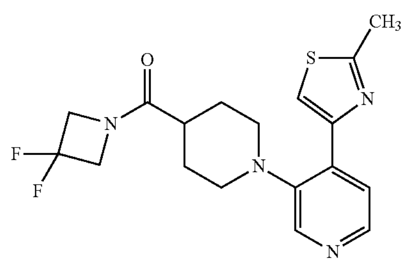 [SMILES: Cc1nc(-c2ccncc2N2CCC(C(=O)N3CC(F)(F)C3)CC2)cs1] | 379.2 |
| 234 | N-cyclopropyl-1-(5-fluoro-4-(4-methyl-1H-pyrazol-1-yl)pyridin-3-yl)piperidine-4-carboxamide | 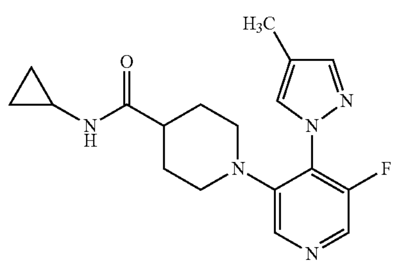 [SMILES: Cc1cnn(-c2c(F)cncc2N2CCC(C(=O)NC3CC3)CC2)c1] | 344.2 |
| 235 | 1-(5-fluoro-4-(4-methyl-1H-pyrazol-1-yl)pyridin-3-yl)-N,N-dimethylpiperidine-4-carboxamide | 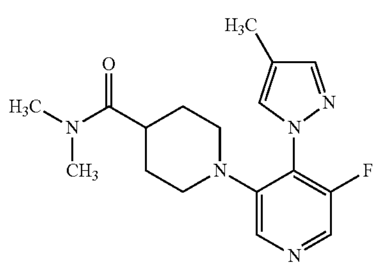 [SMILES: Cc1cnn(-c2c(F)cncc2N2CCC(C(=O)N(C)C)CC2)c1] | 332.2 |
| 236 | (3,3-difluoroazetidin-1-yl) (1-(5-fluoro-4-(4-methyl-1H-pyrazol-1-yl)pyridin-3-yl)piperidin-4-yl)methanone | 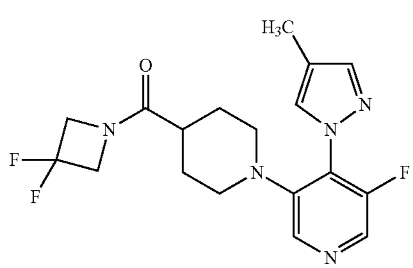 [SMILES: Cc1cnn(-c2c(F)cncc2N2CCC(C(=O)N3CC(F)(F)C3)CC2)c1] | 380.2 |

TABLE 1-24-continued

| EXAMPLE | IUPACNAME | Structure | MS |
|---|---|---|---|
| 237 | N-cyclopropyl-3,3-difluoro-1-(4-(4-methyl-1H-pyrazol-1-yl)pyridin-3-yl)piperidine-4-carboxamide | 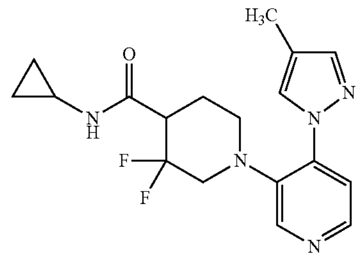 [SMILES: Cc1cnn(-c2ccncc2N2CCC(C(=O)NC3CC3)C(F)(F)C2)c1] | 362.1 |
| 238 | 3,3-difluoro-N,N-dimethyl-1-(4-(4-methyl-1H-pyrazol-1-yl)pyridin-3-yl)piperidine-4-carboxamide | 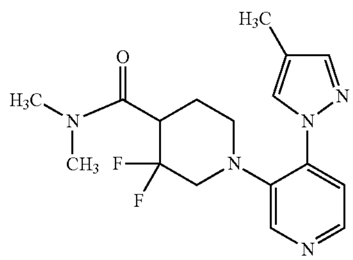 [SMILES: Cc1cnn(-c2ccncc2N2CCC(C(=O)N(C)C)C(F)(F)C2)c1] | 350.1 |
| 239 | (3,3-difluoroazetidin-1-yl) (1-(4-(3-methyl-1H-pyrazol-1-yl)pyrimidin-5-yl)piperidin-4-yl)methanone | 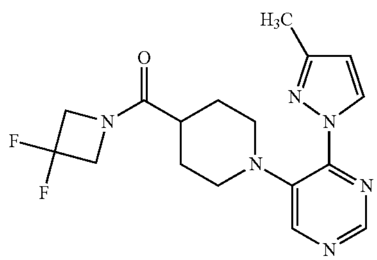 [SMILES: Cc1ccn(-c2ncncc2N2CCC(C(=O)N3CC(F)(F)C3)CC2)n1] | 363.2 |
| 240 | N,N-dimethyl-1-(4-(3-methyl-1H-pyrazol-1-yl)pyrimidin-5-yl)piperidine-4-carboxamide | 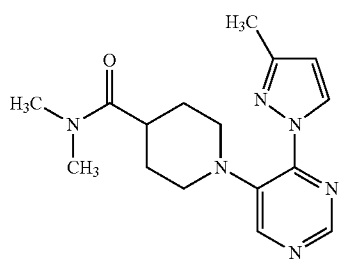 [SMILES: Cc1ccn(-c2ncncc2N2CCC(C(=O)N(C)C)CC2)n1] | 315.3 |

TABLE 1-25

| EXAMPLE | IUPACNAME | Structure | MS |
|---|---|---|---|
| 241 | (3R)-N-ethyl-4-(4-(4-fluorophenyl)pyrimidin-5-yl)-3-methylpiperazine-1-carboxamide | 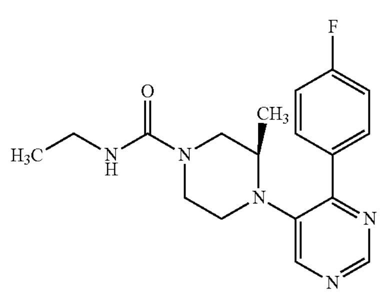 [SMILES: CCNC(=O)N1CCN(c2cncnc2-c2ccc(F)cc2)[C@H](C)C1] | 344.3 |

TABLE 1-25-continued

| EXAMPLE | IUPACNAME | Structure | MS |
|---|---|---|---|
| 242 | (3R)-N-(cyclopropylmethyl)-4-(4-(4-fluorophenyl)pyrimidin-5-yl)-3-methylpiperazine-1-carboxamide | 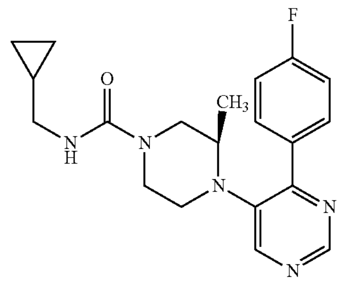 [SMILES: C[C@@H]1CN(C(=O)NCC2CC2)CCN1c1cncnc1-c1ccc(F)cc1] | 370.2 |
| 243 | N,N-dimethyl-1-(4-(3-methyl-1H-pyrazol-1-yl)pyridin-3-yl)piperidine-4-carboxamide | 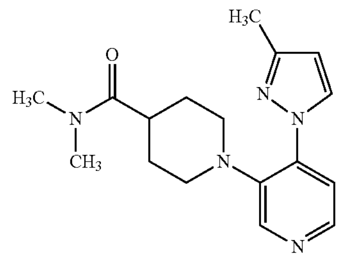 [SMILES: Cc1ccn(-c2ccncc2N2CCC(C(=O)N(C)C)CC2)n1] | 314.3 |
| 244 | 1-(4-(4-ethyl-1H-pyrazol-1-yl)pyridin-3-yl)-N,N-dimethylpiperidine-4-carboxamide | 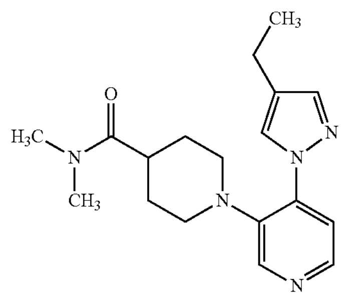 [SMILES: CCc1cnn(-c2ccncc2N2CCC(C(=O)N(C)C)CC2)c1] | 328.2 |
| 245 | (3,3-difluoroazetidin-1-yl) (1-(4-(2-methyl-1,3-oxazol-4-yl)pyridin-3-yl)piperidin-4-yl)methanone | 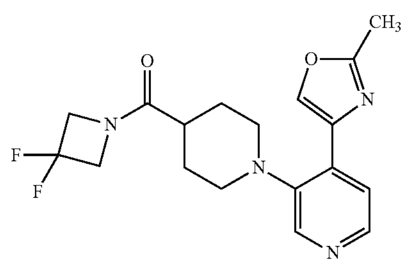 [SMILES: Cc1nc(-c2ccncc2N2CCC(C(=O)N3CC(F)(F)C3)CC2)co1] | 363.2 |
| 246 | N,N-dimethyl-1-(4-(5-methyl-1,3-thiazol-2-yl)pyridin-3-yl)piperidine-4-carboxamide | 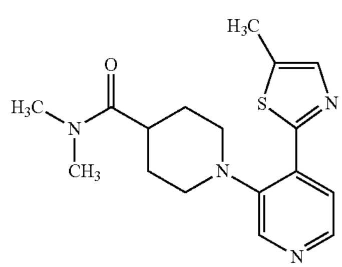 [SMILES: Cc1cnc(-c2ccncc2N2CCC(C(=O)N(C)C)CC2)s1] | 331.2 |

TABLE 1-25-continued

| EXAMPLE | IUPACNAME | Structure | MS |
| --- | --- | --- | --- |
| 247 | 1-(4-(4-chloro-1H-pyrazol-1-yl)pyridin-3-yl)-N-(cyanomethyl)-N-methylpiperidine-4-carboxamide | 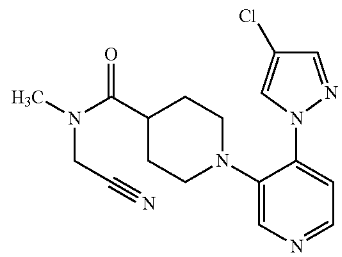 | 359.1 |
| 248 | N-(cyanomethyl)-N-methyl-1-(4-(4-methyl-1H-pyrazol-1-yl)pyridin-3-yl)piperidine-4-carboxamide | 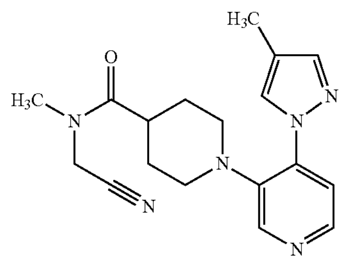 [SMILES: Cc1cnn(-c2ccncc2N2CCC(C(=O)N(C)CC#N)CC2)c1] | 339.2 |
| 249 | N-cyclopropyl-1-(4-(5-methyl-1,3,4-thiadiazol-2-yl)pyridin-3-yl)piperidine-4-carboxamide | 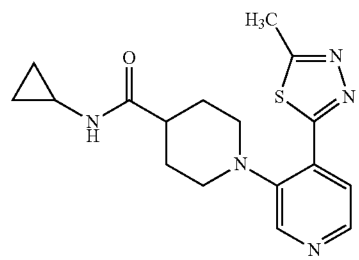 [SMILES: Cc1nnc(-c2ccncc2N2CCC(C(=O)NC3CC3)CC2)s1] | 344.1 |
| 250 | (2R)-1-((1-(4-(5-cyclopropyl-1,3,4-thiadiazol-2-yl)pyridin-3-yl)piperidin-4-yl)carbonyl)pyrrolidine-2-carbonitrile | 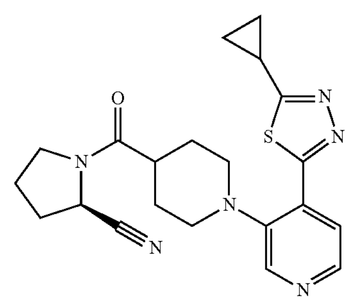 [SMILES: N#C[C@H]1CCCN1C(=O)C1CCN(c2cnccc2-c2nnc(C3CC3)s2)CC1] | 409.2 |

TABLE 1-26

| EXAMPLE | IUPACNAME | Structure | MS |
| --- | --- | --- | --- |
| 251 | (2R,4S)-4-ethoxy-1-((1-(4-(5-methyl-1,3,4-thiadiazol-2-yl)pyridin-3-yl)piperidin-4-yl)carbonyl)pyrrolidine-2-carbonitrile | 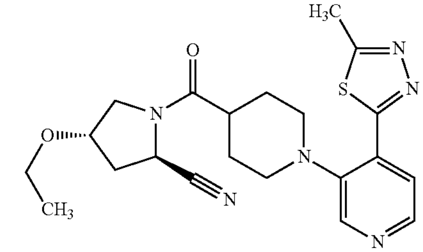 [SMILES: CCO[C@H]1C[C@H](C#N)N(C(=O)C2CCN(c3cnccc3-c3nnc(C)s3)CC2)C1] | 427.2 |

TABLE 1-26-continued

| EXAMPLE | IUPACNAME | Structure | MS |
|---|---|---|---|
| 252 | (2R,4S)-4-isopropoxy-1-((1-(4-(5-methyl-1,3,4-thiadiazol-2-yl)pyridin-3-yl)piperidin-4-yl)carbonyl)pyrrolidine-2-carbonitrile | 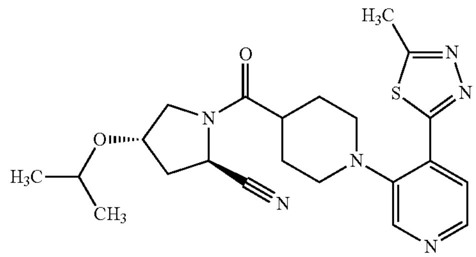 [SMILES: Cc1nnc(-c2ccncc2N2CCC(C(=O)N3C[C@@H](OC(C)C)C[C@@H]3C#N)CC2)s1] | 441.1 |
| 253 | (2R,4S)-4-methoxy-1-((1-(4-(5-methyl-1,3,4-thiadiazol-2-yl)pyridin-3-yl)piperidin-4-yl)carbonyl)pyrrolidine-2-carbonitrile | 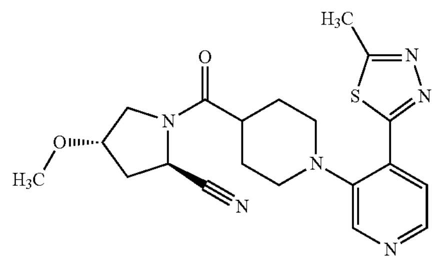 [SMILES: CO[C@H]1C[C@H](C#N)N(C(=O)C2CCN(c3cnccc3-c3nnc(C)s3)CC2)C1] | 413.2 |
| 254 | ((2R)-2-(methoxymethyl)pyrrolidin-1-yl) (1-(4-(4-methyl-1H-pyrazol-1-yl)pyridin-3-yl)piperidin-4-yl)methanone | 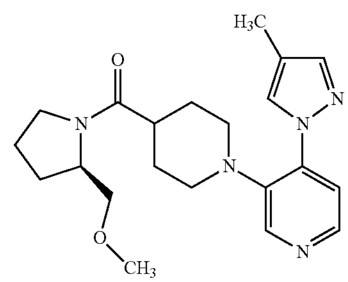 [SMILES: COC[C@H]1CCCN1C(=O)C1CCN(c2cnccc2-n2cc(C)cn2)CC1] | 384.2 |
| 255 | (2R)-1-((1-(4-(5-ethyl-1,3,4-thiadiazol-2-yl)pyridin-3-yl)piperidin-4-yl)carbonyl)pyrrolidine-2-carbonitrile | 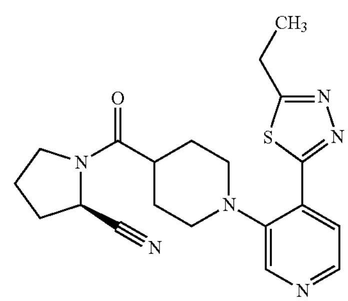 [SMILES: CCc1nnc(-c2ccncc2N2CCC(C(=O)N3CCC[C@@H]3C#N)CC2)s1] | 397.2 |

TABLE 1-27

| EXAMPLE | IUPACNAME | Structure | MS |
|---|---|---|---|
| 256 | 3,7-dioxa-9-azabicyclo[3.3.1]non-9-yl(1-(4-(4-methyl-1H-pyrazol-1-yl)pyridin-3-yl)piperidin-4-yl)methanone | 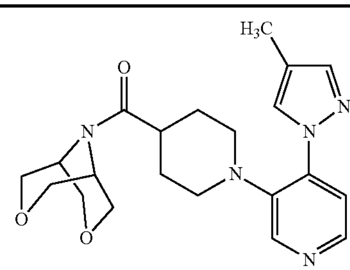 | 398.2 |

TABLE 1-27-continued

| EXAMPLE | IUPACNAME | Structure | MS |
|---|---|---|---|
| 257 | (2R,4S)-4-ethoxy-1-((1-(4-(4-methyl-1H-pyrazol-1-yl)pyridin-3-yl)piperidin-4-yl)carbonyl)pyrrolidine-2-carbonitrile | 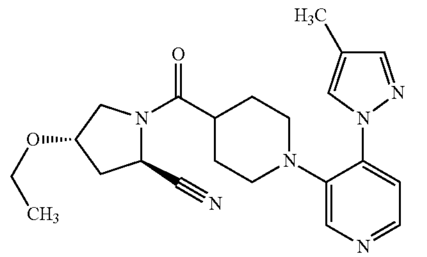 [SMILES: CCO[C@H]1C[C@H](C#N)N(C(=O)C2CCN(c3cnccc3-n3cc(C)cn3)CC2)C1] | 409.2 |
| 258 | (2R,4S)-4-isopropoxy-1-((1-(4-(4-methyl-1H-pyrazol-1-yl)pyridin-3-yl)piperidin-4-yl)carbonyl)pyrrolidine-2-carbonitrile | 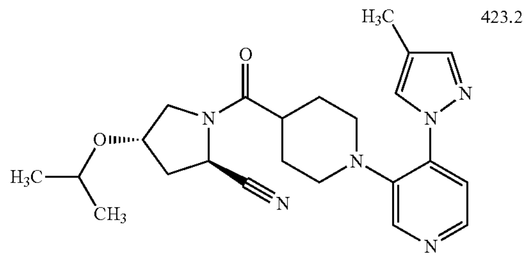 | 423.2 |
| 259 | (2R,4S)-4-(difluoromethoxy)-1-((1-(4-(4-methyl-1H-pyrazol-1-yl)pyridin-3-yl)piperidin-4-yl)carbonyl)pyrrolidine-2-carbonitrile | 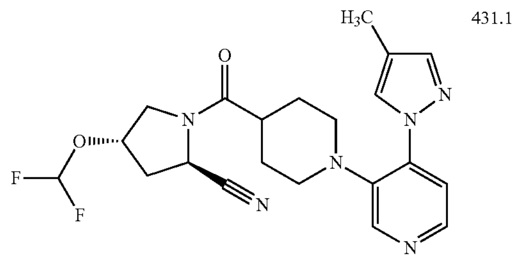 | 431.1 |
| 260 | (2R,4S)-4-(difluoromethoxy)-1-((1-(4-(5-methyl-1,3,4-thiadiazol-2-yl)pyridin-3-yl)piperidin-4-yl)carbonyl)pyrrolidine-2-carbonitrile | 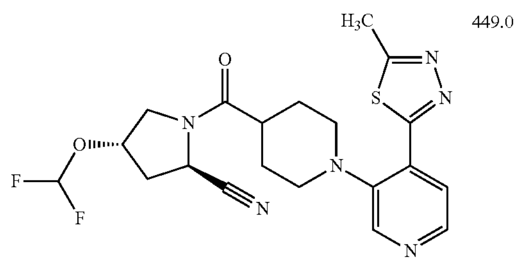 | 449.0 |
| 261 | methyl 5,5-dimethyl-1-((1-(4-(5-methyl-1,3,4-thiadiazol-2-yl)pyridin-3-yl)piperidin-4-yl)carbonyl)prolinate | 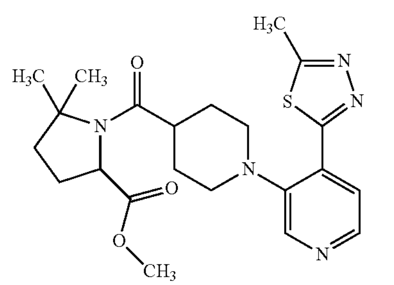 [SMILES: COC(=O)C1CCC(C)(C)N1C(=O)C1CCN(c2cnccc2-c2nnc(C)s2)CC1] | 444.2 |
| 262 | N,N-dimethyl-1-((1-(4-(4-methyl-1H-pyrazol-1-yl)pyridin-3-yl)piperidin-4-yl)carbonyl)-D-prolinamide | 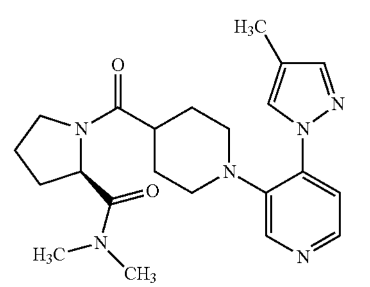 [SMILES: Cc1cnn(-c2ccncc2N2CCC(C(=O)N3CCC[C@@H]3C(=O)N(C)C)CC2)c1] | 411.3 |

TABLE 1-27-continued

| EXAMPLE | IUPACNAME | Structure | MS |
|---|---|---|---|
| 263 | N,N-dimethyl-1-((1-(4-(5-methyl-1,3,4-thiadiazol-2-yl)pyridin-3-yl)piperidin-4-yl)carbonyl)-D-prolinamide | 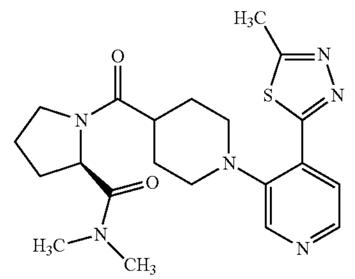 [SMILES: Cc1nnc(-c2ccncc2N2CCC(C(=O)N3CCC[C@@H]3C(=O)N(C)C)CC2)s1] | 429.2 |
| 265 | (5-(methoxymethyl)-2,2-dimethylpyrrolidin-1-yl) (1-(4-(5-methyl-1,3,4-thiadiazol-2-yl)pyridin-3-yl)piperidin-4-yl)methanone (optical isomer) | 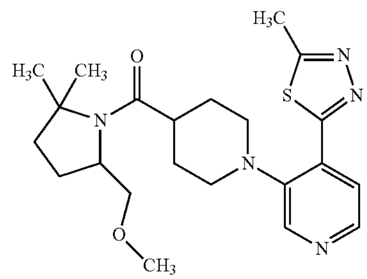 [SMILES: COCC1CCC(C)(C)N1C(=O)C1CCN(c2cnccc2-c2nnc(C)s2)CC1] | 430.2 |

TABLE 1-28

| EXAMPLE | IUPACNAME | Structure | MS |
|---|---|---|---|
| 266 | (5-(methoxymethyl)-2,2-dimethylpyrrolidin-1-yl) (1-(4-(5-methyl-1,3,4-thiadiazol-2-yl)pyridin-3-yl)piperidin-4-yl)methanone (optical isomer) | 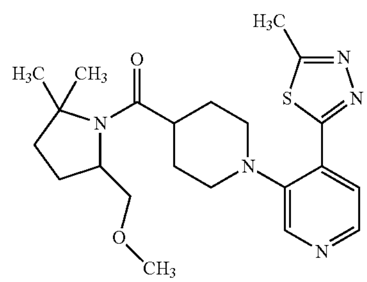 [SMILES: COCC1CCC(C)(C)N1C(=O)C1CCN(c2cnccc2-c2nnc(C)s2)CC1] | 430.2 |
| 267 | 5,5-dimethyl-1-((1-(4-(5-methyl-1,3,4-thiadiazol-2-yl)pyridin-3-yl)piperidin-4-yl)carbonyl)prolinamide (optical isomer) | 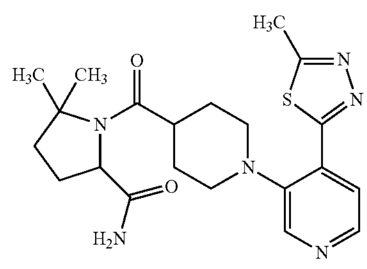 [SMILES: Cc1nnc(-c2ccncc2N2CCC(C(=O)N3C(C(N)=O)CCC3(C)C)CC2)s1] | 429.2 |
| 268 | 5,5-dimethyl-1-((1-(4-(5-methyl-1,3,4-thiadiazol-2-yl)pyridin-3-yl)piperidin-4-yl)carbonyl)prolinamide (optical isomer) | 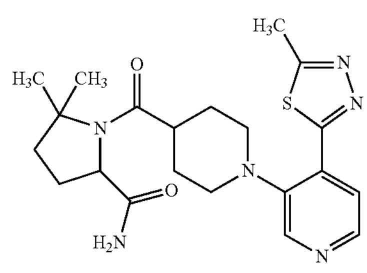 [SMILES: Cc1nnc(-c2ccncc2N2CCC(C(=O)N3C(C(N)=O)CCC3(C)C)CC2)s1] | 429.2 |

TABLE 1-28-continued

| EXAMPLE | IUPACNAME | Structure | MS |
|---|---|---|---|
| 269 | N,N-dimethyl-1-(4-(1H-pyrazol-1-yl)pyridin-3-yl)piperidine-4-carboxamida | 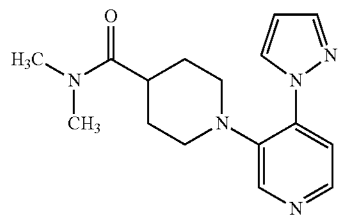 [SMILES: CN(C)C(=O)C1CCN(c2cnccc2-n2cccn2)CC1] | 300.2 |
| 270 | N-phenyl-1-(4-phenylpyrimidin-5-yl)piperidine-4-carboxamide | 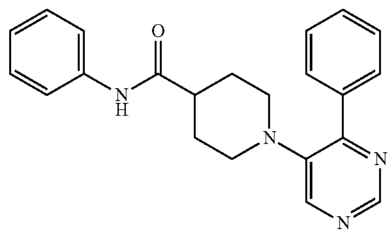 [SMILES: O=C(Nc1ccccc1)C1CCN(c2cncnc2-c2ccccc2)CC1] | 359.2 |
| 271 | 1-(4-phenylpyrimidin-5-yl)-N-(pyridin-2-ylmethyl)piperidine-4-carboxamide | 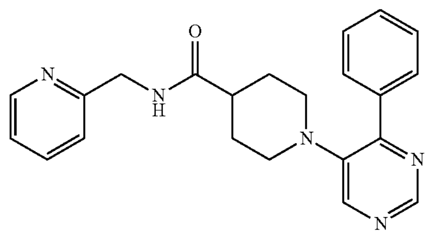 [SMILES: O=C(NCc1ccccn1)C1CCN(c2cncnc2-c2ccccc2)CC1] | 374.2 |
| 272 | (1-(4-phenylpyrimidin-5-yl)piperidin-4-yl) (piperidin-1-yl)methanone | 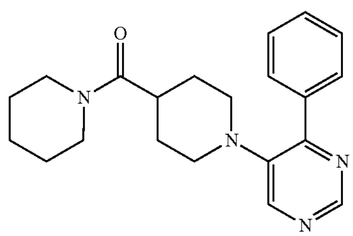 [SMILES: O=C(C1CCN(c2cncnc2-c2ccccc2)CC1)N1CCCCC1] | 351.2 |
| 273 | (1-(4-(4-methyl-1H-pyrazol-1-yl)pyridin-3-yl)piperidin-4-yl) (piperidin-1-yl)methanone | 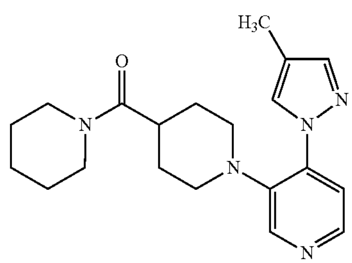 [SMILES: Cc1cnn(-c2ccncc2N2CCC(C(=O)N3CCCCC3)CC2)c1] | 354.2 |
| 274 | (1-(4-(4-methyl-1H-pyrazol-1-yl)pyridin-3-yl)piperidin-4-yl) (pyrrolidin-1-yl)methanone | 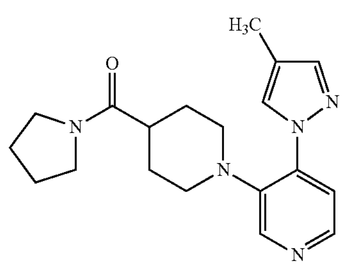 | 340.0 |

TABLE 1-28-continued

| EXAMPLE | IUPACNAME | Structure | MS |
|---------|-----------|-----------|-----|
| 275 | (1-(4-(4-methyl-1H-pyrazol-1-yl)pyridin-3-yl)piperidin-4-yl) (morpholin-4-yl)methanone | 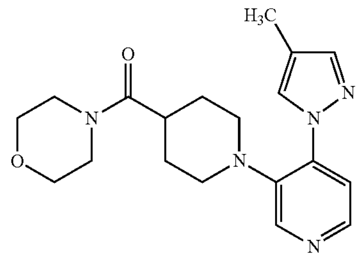 [SMILES: Cc1cnn(-c2ccncc2N2CCC(C(=O)N3CCOCC3)CC2)c1] | 356.2 |

TABLE 1-29

| EXAMPLE | IUPACNAME | Structure | MS |
|---------|-----------|-----------|-----|
| 276 | (3-methoxyazetidin-1-yl) (1-(4-(4-methyl-1H-pyrazol-1-yl)pyridin-3-yl)piperidin-4-yl)methanone | 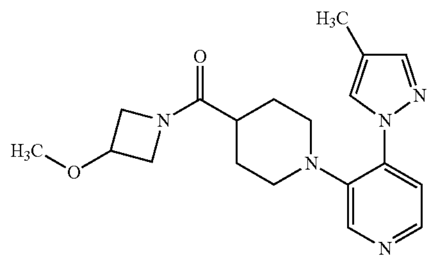 [SMILES: COC1CN(C(=O)C2CCN(c3cnccc3-n3cc(C)cn3)CC2)C1] | 356.2 |
| 277 | N-cyclopropyl-1-(4-(4-fluorophenyl)pyrimidin-5-yl)-N-methylpiperidine-4-carboxamide | 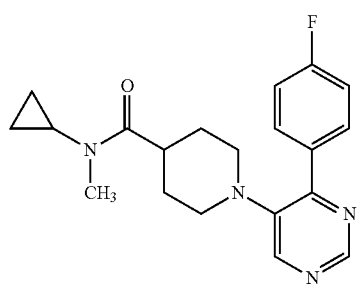 [SMILES: CN(C(=O)C1CCN(c2cncnc2-c2ccc(F)cc2)CC1)C1CC1] | 355.2 |
| 278 | (3-fluoroazetidin-1-yl) (1-(4-(4-fluorophenyl)pyrimidin-5-yl)piperidin-4-yl)methanone | 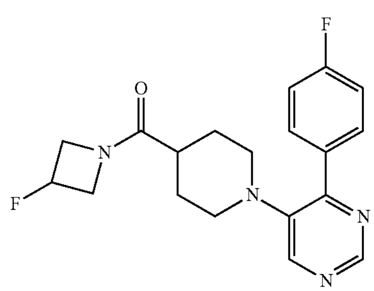 [SMILES: O=C(C1CCN(c2cncnc2-c2ccc(F)cc2)CC1)N1CC(F)C1] | 359.2 |
| 279 | N-(4-methoxybenzyl)-4-(4-phenylpyrimidin-5-yl)piperazine-1-carboxamide | 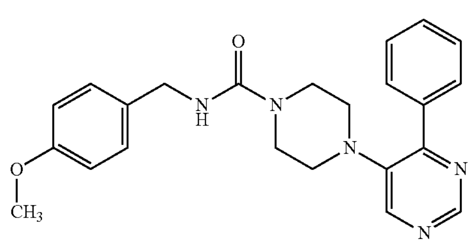 [SMILES: COc1ccc(CNC(=O)N2CCN(c3cncnc3-c3ccccc3)CC2)cc1] | 404.2 |

TABLE 1-29-continued

| EXAMPLE | IUPACNAME | Structure | MS |
|---|---|---|---|
| 280 | (3-fluoroazetidin-1-yl) (1-(4-(4-methyl-1H-pyrazol-1-yl)pyridin-3-yl)piperidin-4-yl)methanone | 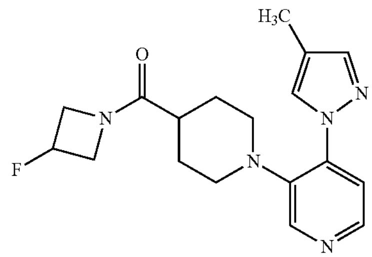 [SMILES: Cc1cnn(-c2ccncc2N2CCC(C(=O)N3CC(F)C3)CC2)c1] | 344.1 |
| 281 | (1-(4-(4-chloro-1H-pyrazol-1-yl)pyridin-3-yl)piperidin-4-yl) (3-fluoreazetidin-1-yl)methanone | 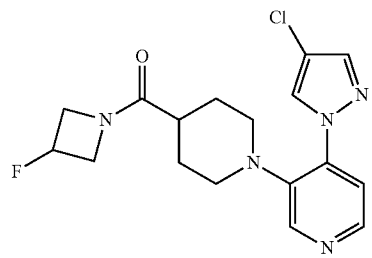 [SMILES: O=C(C1CCN(c2cnccc2-n2cc(Cl)cn2)CC1)N1CC(F)C1] | 364.2 |
| 282 | ((3S)-3-fluoropyrrolidin-1-yl) (1-(4-(4-methyl-1H-pyrazol-1-yl)pyridin-3-yl)piperidin-4-yl)methanone | 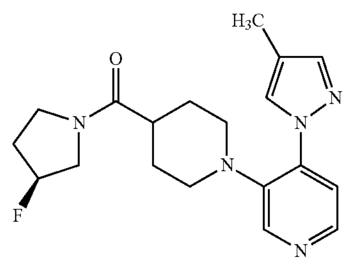 [SMILES: Cc1cnn(-c2ccncc2N2CCC(C(=O)N3CC[C@H](F)C3)CC2)c1] | 358.1 |
| 283 | ((3R)-3-fluoropyrrolidin-1-yl) (1-(4-(4-methyl-1H-pyrazol-1-yl)pyridin-3-yl)piperidin-4-yl)methanone | 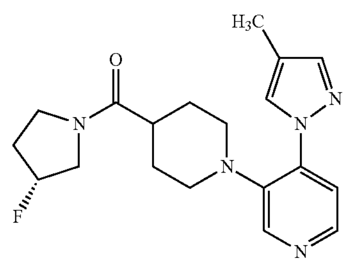 [SMILES: Cc1cnn(-c2ccncc2N2CCC(C(=O)N3CC[C@@H](F)C3)CC2)c1] | 358.1 |
| 284 | (1-(4-(4-chloro-1H-pyrazol-1-yl)pyridin-3-yl)piperidin-4-yl) ((3S)-3-fluoropyrrolidin-1-yl)methanone | 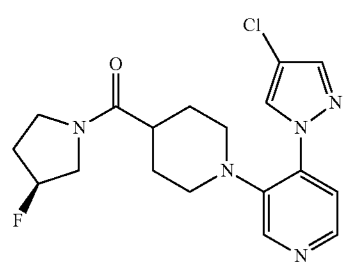 [SMILES: O=C(C1CCN(c2cnccc2-n2cc(Cl)cn2)CC1)N1CC[C@H](F)C1] | 378.1 |
| 285 | (1-(4-(4-chloro-1H-pyrazol-1-yl)pyridin-3-yl)piperidin-4-yl) ((3R)-3-fluoropyrrolidin-1-yl)methanone | 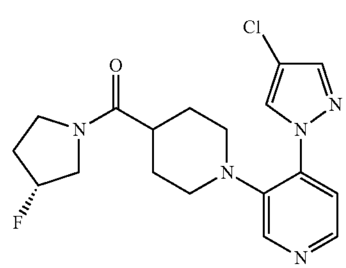 | 378.1 |

TABLE 1-30

| EXAMPLE | IUPACNAME | Structure | MS |
|---|---|---|---|
| 286 | (1-(4-(4-fluorophenyl)pyrimidin-5-yl)piperidin-4-yl) ((3S)-3-fluoropyrrolidin-1-yl)methanone | 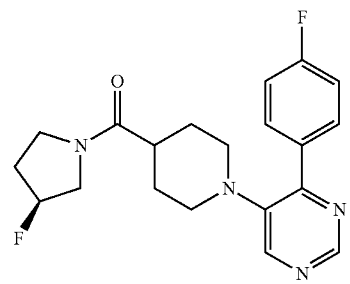 [SMILES: O=C(C1CCN(c2cncnc2-c2ccc(F)cc2)CC1)N1CC[C@H](F)C1] | 373.1 |
| 287 | (1-(4-(4-fluorophenyl)pyrimidin-5-yl)piperidin-4-yl) ((3R)-3-fluoropyrrolidin-1-yl)methanone | 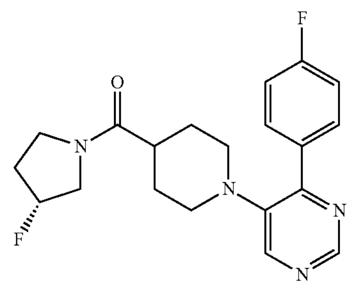 | 373.2 |
| 288 | 1-(4-(4-fluorophenyl)pyrimidin-5-yl)-N-methyl-N-(tetrahydro-2H-pyran-4-yl)piperidine-4-carboxamide | 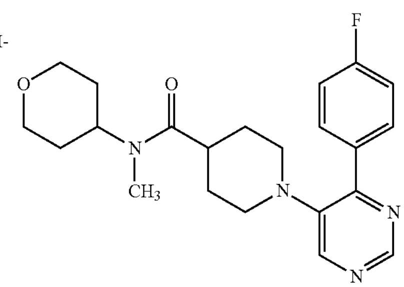 | 399.1 |
| 289 | 1-(4-(4-fluorophenyl)pyrimidin-5-yl)-N-(tetrahydro-2H-pyran-4-yl)piperidine-4-carboxamide | 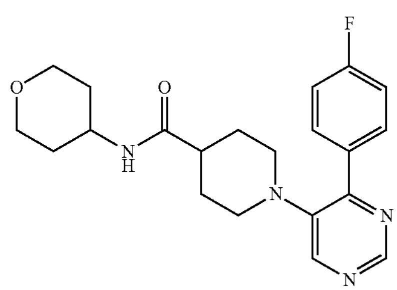 [SMILES: O=C(NC1CCOCC1)C1CCN(c2cncnc2-c2ccc(F)cc2)CC1] | 383.1 |
| 290 | 1-(4-(4-fluorophenyl)pyrimidin-5-yl)-N-((3S)-tetrahydrofuran-3-yl)piperidine-4-carboxamide | 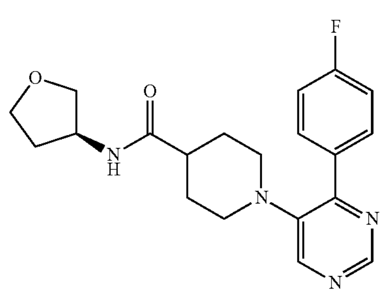 [SMILES: O=C(N[C@H]1CCOC1)C1CCN(c2cncnc2-c2ccc(F)cc2)CC1] | 368.9 |

TABLE 1-30-continued

| EXAMPLE | IUPACNAME | Structure | MS |
|---|---|---|---|
| 291 | 1-(4-(4-fluorophenyl)pyrimidin-5-yl)-N-((3R)-tetrahydrofuran-3-yl)piperidine-4-carboxamide | 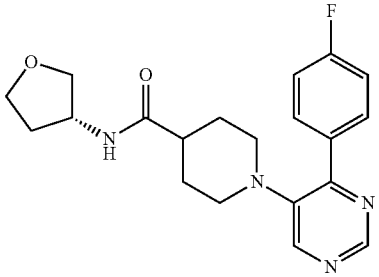 [SMILES: O=C(N[C@@H]1CCOC1)C1CCN(c2cncnc2-c2ccc(F)cc2)CC1] | 368.9 |
| 292 | 1-(4-(4-methyl-1H-pyrazol-1-yl)pyridin-3-yl)-N-((3S)-tetrahydrofuran-3-yl)piperidine-4-carboxamide | 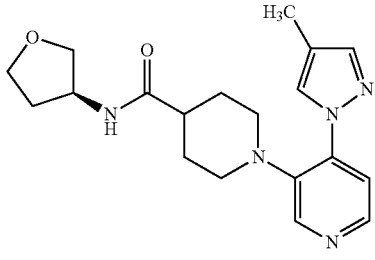 [SMILES: Cc1cnn(-c2ccncc2N2CCC(C(=O)N[C@H]3CCOC3)CC2)c1] | 356.2 |
| 293 | 1-(4-(4-chloro-1H-pyrazol-1-yl)pyridin-3-yl)-N-((3S)-tetrahydrofuran-3-yl)piperidine-4-carboxamide | 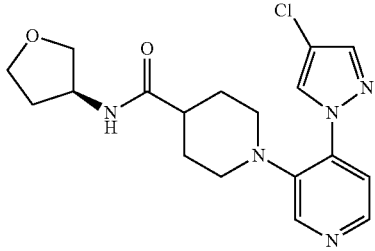 | 376.1 |
| 294 | 1-(4-(4-methyl-1H-pyrazol-1-yl)pyridin-3-yl)-N-((3R)-tetrahydrofuran-3-yl)piperidine-4-carboxamide | 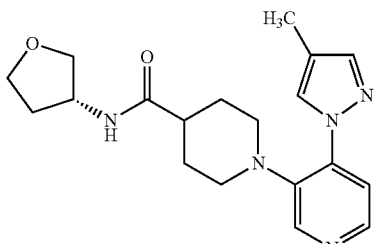 | 356.2 |
| 295 | 1-(4-(4-chloro-1H-pyrazol-1-yl)pyridin-3-yl)-N-((3R)-tetrahydrofuran-3-yl)piperidine-4-carboxamide | 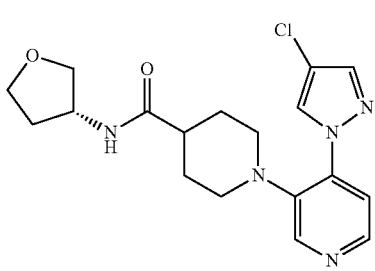 [SMILES: O=C(N[C@@H]1CCOC1)C1CCN(c2cnccc2-n2cc(Cl)cn2)CC1] | 376.1 |

TABLE 1-31

| EXAMPLE | IUPACNAME | Structure | MS |
|---|---|---|---|
| 296 | N-methyl-1-(4-(4-methyl-1H-pyrazol-1-yl)pyridin-3-yl)-N-(tetrahydro-2H-pyran-4-yl)piperidine-4-carboxamide | 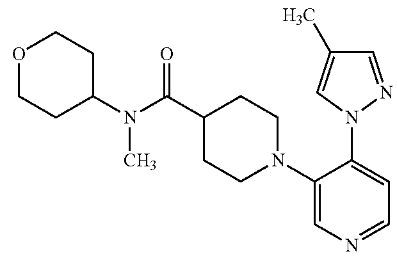 [SMILES: Cc1cnn(-c2ccncc2N2CCC(C(=O)N(C)C3CCOCC3)CC2)c1] | 384.2 |
| 297 | N-(4-fluorobenzyl)-N-methyl-4-(4-(4-methyl-1H-pyrazol-1-yl)pyridin-3-yl)piperazine-1-carboxamide | 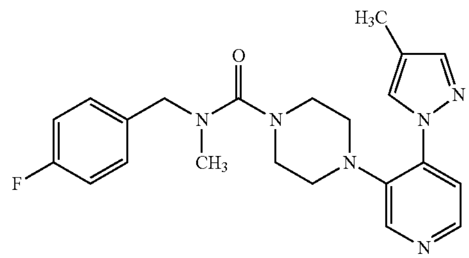 [SMILES: Cc1cnn(-c2ccncc2N2CCN(C(=O)N(C)Cc3ccc(F)cc3)CC2)c1] | 409.2 |
| 298 | N-benzyl-N-methyl-4-(4-phenylpyrimidin-5-yl)piperazine-1-carboxamide | 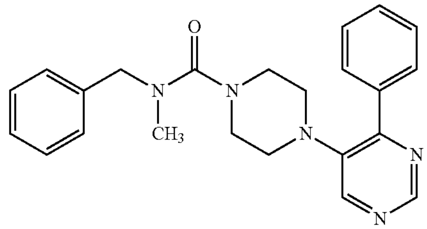 [SMILES: CN(Cc1ccccc1)C(=O)N1CCN(c2cncnc2-c2ccccc2)CC1] | 388.1 |
| 299 | (1-(4-(4-chloro-1H-pyrazol-1-yl)pyridin-3-yl)piperidin-4-yl) ((3S)-3-methoxypyrrolidin-1-yl)methanone | 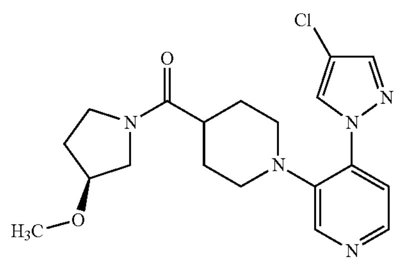 | 390.1 |
| 300 | (1-(4-(4-chloro-1H-pyrazol-1-yl)pyridin-3-yl)piperidin-4-yl) ((3R)-3-methoxypyrrolidin-1-yl)methanone | 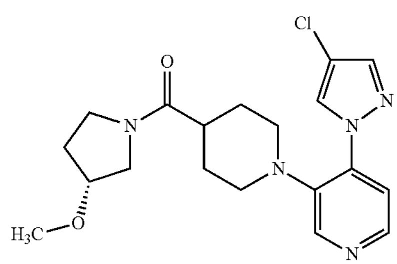 [SMILES: CO[C@@H]1CCN(C(=O)C2CCN(c3cnccc3-n3cc(Cl)cn3)CC2)C1] | 390.1 |
| 301 | ((3S)-3-methoxypyrrolidin-1-yl) (1-(4-(4-methyl-1H-pyrazol-1-yl)pyridin-3-yl)piperidin-4-yl)methanone | 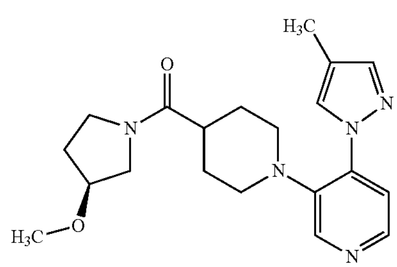 [SMILES: CO[C@H]1CCN(C(=O)C2CCN(c3cnccc3-n3cc(C)cn3)CC2)C1] | 370.1 |

TABLE 1-31-continued

| EXAMPLE | IUPACNAME | Structure | MS |
|---------|-----------|-----------|-----|
| 302 | ((3R)-3-methoxypyrrolidin-1-yl) (1-(4-(4-methyl-1H-pyrazol-1-yl)pyridin-3-yl)piperidin-4-yl)methanone | 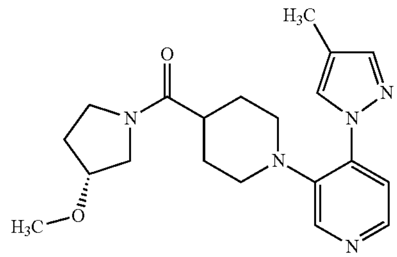 [SMILES: CO[C@@H]1CCN(C(=O)C2CCN(c3cnccc3-n3cc(C)cn3)CC2)C1] | 370.1 |
| 303 | (1-(4-(4-fluorophenyl)pyrimidin-5-yl)piperidin-4-yl) ((3S)-3-methoxypyrrolidin-1-yl)methanone | 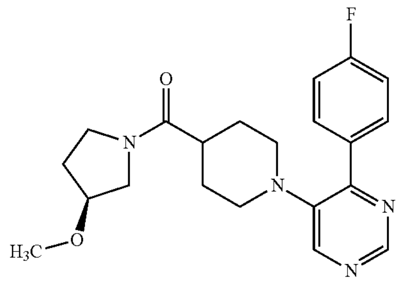 [SMILES: CO[C@H]1CCN(C(=O)C2CCN(c3cncnc3-c3ccc(F)cc3)CC2)C1] | 385.1 |
| 304 | (1-(4-(4-fluorophenyl)pyrimidin-5-yl)piperidin-4-yl) ((3R)-3-methoxypyrrolidin-1-yl)methanone | 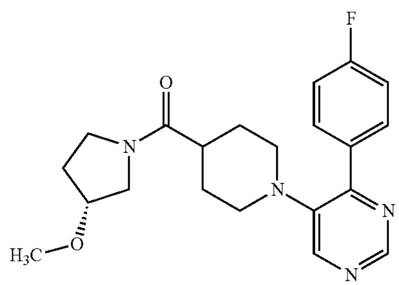 [SMILES: CO[C@@H]1CCN(C(=O)C2CCN(c3cncnc3-c3ccc(F)cc3)CC2)C1] | 385.1 |
| 305 | N-methyl-1-(4-(4-methyl-1H-pyrazol-1-yl)pyridin-3-yl)-N-((3S)-tetrahydrofuran-3-yl)piperidine-4-carboxamide | 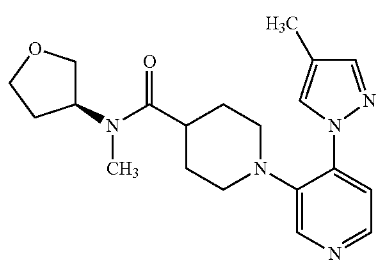 [SMILES: Cc1cnn(-c2ccncc2N2CCC(C(=O)N(C)[C@H]3CCOC3)CC2)c1] | 370.1 |

TABLE 1-32

| EXAMPLE | IUPACNAME | Structure | MS |
|---------|-----------|-----------|-----|
| 306 | N-methyl-1-(4-(4-methyl-1H-pyrazol-1-yl)pyridin-3-yl)-N-((3R)-tetrahydrofuran-3-yl)piperidine-4-carboxamide | 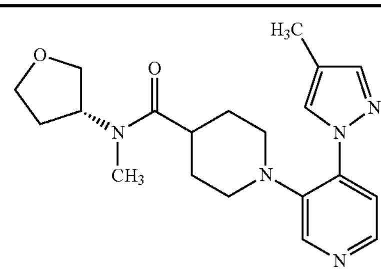 | 370.1 |

TABLE 1-32-continued

| EXAMPLE | IUPACNAME | Structure | MS |
|---|---|---|---|
| 307 | 1-(4-(4-chloro-1H-pyrazol-1-yl)pyridin-3-yl)-N-methyl-N-((3S)-tetrahydrofuran-3-yl)piperidine-4-carboxamide | 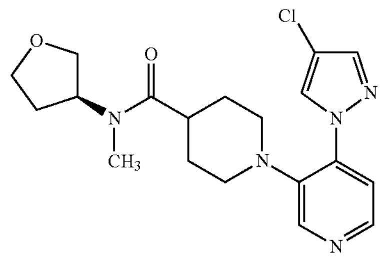 | 390.1 |
| 308 | 1-(4-(4-chloro-1H-pyrazol-1-yl)pyridin-3-yl)-N-methyl-N-((3R)-tetrahydrofuran-3-yl)piperidine-4-carboxamide | 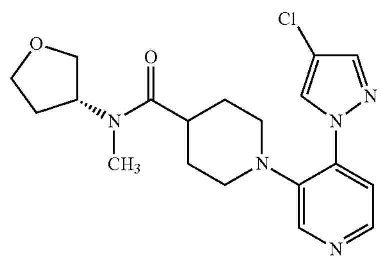 [SMILES: Cc1cnn(-c2ccncc2N2CCC(C(=O)N(C)[C@@H]3CCOC3)CC2)c1] | 390.1 |
| 309 | 1-(4-(4-fluorophenyl)pyrimidin-5-yl)-N-methyl-N-((3S)-tetrahydrofuran-3-yl)piperidine-4-carboxamide | 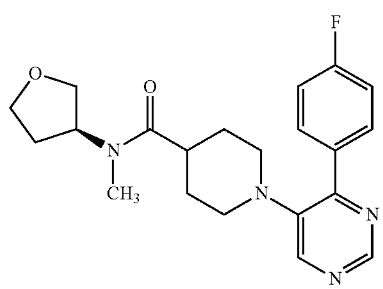 [SMILES: CN(C(=O)C1CCN(c2cncnc2-c2ccc(F)cc2)CC1)[C@H]1CCOC1] | 385.1 |
| 310 | 1-(4-(4-fluorophenyl)pyrimidin-5-yl)-N-methyl-N-((3R)-tetrahydrofuran-3-yl)piperidine-4-carboxamide | 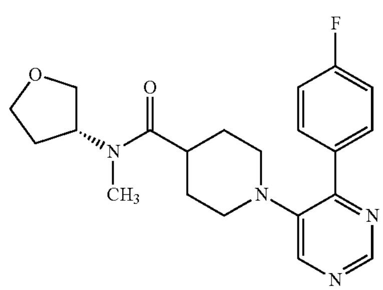 [SMILES: CN(C(=O)C1CCN(c2cncnc2-c2ccc(F)cc2)CC1)[C@@H]1CCOC1] | 385.1 |
| 311 | N-(2-fluoroethyl)-1-(4-(4-methyl-1H-pyrazol-1-yl)pyridin-3-yl)-N-(tetrahydro-2H-pyran-4-yl)piperidine-4-carboxamide | 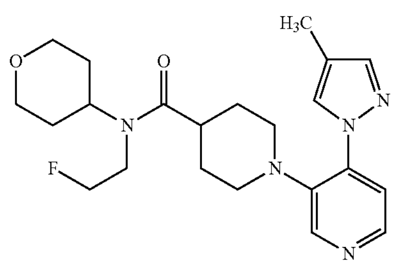 [SMILES: Cc1cnn(-c2ccncc2N2CCC(C(=O)N(CCF)C3CCOCC3)CC2)c1] | 416.2 |
| 312 | N-(2-fluoroethyl)-1-(4-(4-methyl-1H-pyrazol-1-yl)pyridin-3-yl)-N-((3S)-tetrahydrofuran-3-yl)piperidine-4-carboxamide | 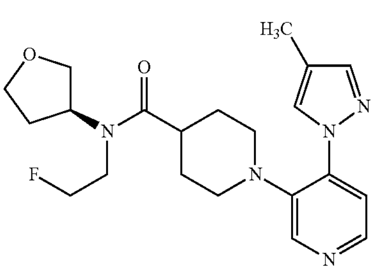 [SMILES: Cc1cnn(-c2ccncc2N2CCC(C(=O)N(CCF)[C@H]3CCOC3)CC2)c1] | 402.1 |

TABLE 1-32-continued

| EXAMPLE | IUPACNAME | Structure | MS |
|---|---|---|---|
| 313 | N-(2-fluoroethyl)-1-(4-(4-methyl-1H-pyrazol-1-yl)pyridin-3-yl)-N-((3R)-tetrahydrofuran-3-yl)piperidine-4-carboxamide | 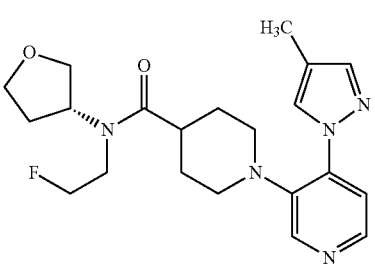 [SMILES: Cc1cnn(-c2ccncc2N2CCC(C(=O)N(CCF)[C@@H]3CCOC3)CC2)c1] | 402.1 |

TABLE 1-33

| EXAMPLE | IUPACNAME | Structure | MS |
|---|---|---|---|
| 314 | N-benzyl-N-(2-fluoroethyl)-4-(4-phenylpyrimidin-5-yl)piperazine-1-carboxamide | 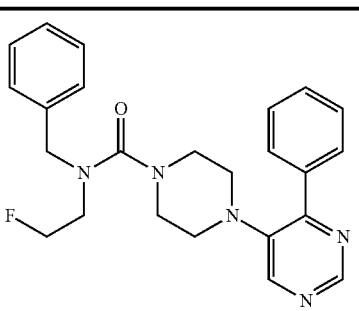 | 420.0 |
| 315 | N-(4-fluorobenzyl)-N-(2-fluoroethyl)-4-(4-(4-methyl-1H-pyrazol-1-yl)pyridin-3-yl)piperazine-1-carboxamide | 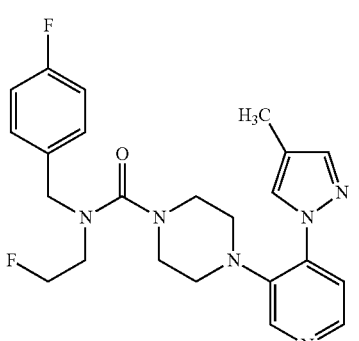 | 441.1 |
| 316 | ((3S)-3-fluoropyrrolidin-1-yl) (1-(4-(5-methyl-1,3-thiazol-2-yl)pyridin-3-yl)piperidin-4-yl)methanone | 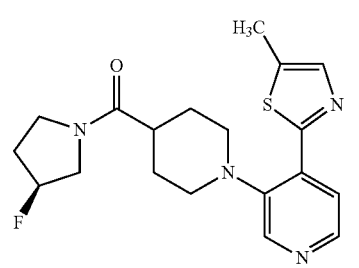 [SMILES: Cc1cnc(-c2ccncc2N2CCC(C(=O)N3CC[C@H](F)C3)CC2)s1] | 375.0 |
| 317 | (3-fluoroazetidin-1-yl) (1-(4-(5-methyl-1,3-thiazol-2-yl)pyridin-3-yl)piperidin-4-yl)methanone | 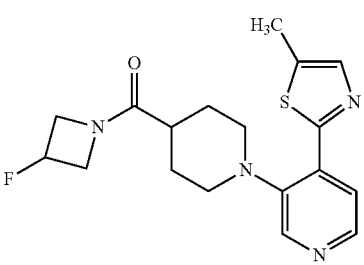 [SMILES: Cc1cnc(-c2ccncc2N2CCC(C(=O)N3CC(F)C3)CC2)s1] | 361.1 |

TABLE 1-33-continued

| EXAMPLE | IUPACNAME | Structure | MS |
|---|---|---|---|
| 318 | (1-(4-(4-bromo-1H-pyrazol-1-yl)pyridin-3-yl)piperidin-4-yl) ((3S)-3-fluoropyrrolidin-1-yl)methanone | 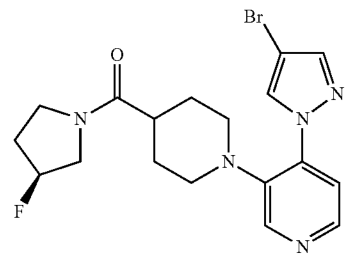 [SMILES: O=C(C1CCN(c2cnccc2-n2cc(Br)cn2)CC1)N1CC[C@H](F)C1] | 421.9 |
| 319 | (1-(4-(4-bromo-1H-pyrazol-1-yl)pyridin-3-yl)piperidin-4-yl) (3-fluoroazetidin-1-yl)methanone | 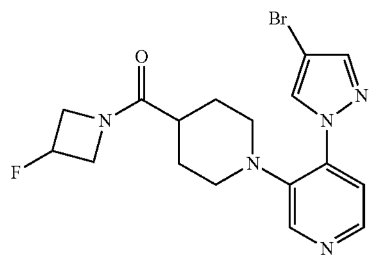 [SMILES: O=C(C1CCN(c2cnccc2-n2cc(Br)cn2)CC1)N1CC(F)C1] | 408.0 |
| 320 | N,N-diethyl-1-(4-(4-methyl-1H-pyrazol-1-yl)pyridin-3-yl)piperidine-4-carboxamide | 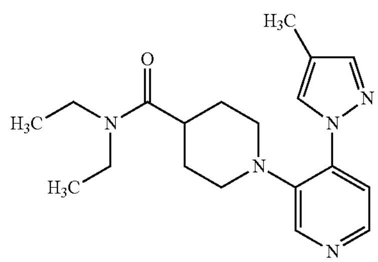 [SMILES: CCN(CC)C(=O)C1CCN(c2cnccc2-n2cc(C)cn2)CC1] | 342.1 |
| 321 | N-ethyl-N-methyl-1-(4-(4-methyl-1H-pyrazol-1-yl)pyridin-3-yl)piperidine-4-carboxamide | 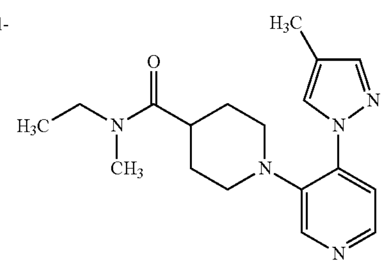 | 328.2 |
| 322 | (1-(4-(4-cyclopropyl-1H-pyrazol-1-yl)pyridin-3-yl)piperidin-4-yl) ((3S)-3-fluoropyrrolidin-1-yl)methanone | 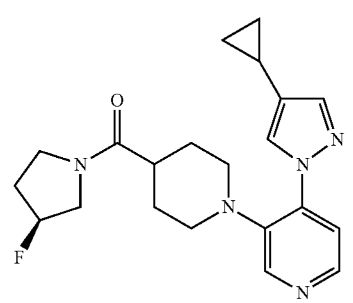 [SMILES: O=C(C1CCN(c2cnccc2-n2cc(C3CC3)cn2)CC1)N1CC[C@H](F)C1] | 384.0 |

TABLE 1-33-continued

| EXAMPLE | IUPACNAME | Structure | MS |
|---|---|---|---|
| 323 | (1-(4-(4-cyclopropyl-1H-pyrazol-1-yl)pyridin-3-yl)piperidin-4-yl) (3-fluoroazetidin-1-yl)methanone | 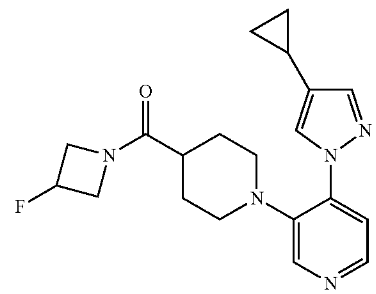 [SMILES: O=C(C1CCN(c2cnccc2-n2cc(C3CC3)cn2)CC1)N1CC(F)C1] | 370.0 |

Formulation Example 1

Production of Capsule

| | | |
|---|---|---|
| 1) compound of Example 1 | 30 mg | |
| 2) fine powder cellulose | 10 mg | |
| 3) lactose | 19 mg | |
| 4) magnesium stearate | 1 mg | |
| Total | 60 mg | |

1), 2), 3) and 4) are mixed and filled in a gelatin capsule.

Formulation Example 2

Production of Tablet

| | | |
|---|---|---|
| 1) compound of Example 1 | 30 g | |
| 2) lactose | 50 g | |
| 3) cornstarch | 15 g | |
| 4) calcium carboxymethylcellulose | 44 g | |
| 5) magnesium stearate | 1 g | |
| 1000 tablets total | 140 g | |

The total amount of 1), 2) and 3) and 4) (30 g) is kneaded with water, vacuum dried, and sieved. The sieved powder is mixed with 4) (14 g) and 5) (1 g), and the mixture is punched by a tableting machine, whereby 1000 tablets containing 30 mg of the compound of Example 1 per tablet are obtained.

Experimental Example 1

Construction of Human CH24H (CYP46) Expression Vector

A plasmid DNA for expressing human CH24H in a FreeStyle 293 cell was produced as follows. Using Full-Length Mammalian Gene Collection No. 4819975 (Invitrogen) as a template, and the following two kinds of synthesized DNAs:

```
5'-GCCCCGGAGCCATGAGCCCCGGGCTG-3'   (SEQ ID NO: 1)
and

5'-GTCCTGCCTGGAGGCCCCCTCAGCAG-3',  (SEQ ID NO: 2)
```

PCR was performed to amplify 91-1625 bp region of human CH24H (BC022539). The obtained fragment was cloned using TOPO TA Cloning Kit (Invitrogen). The obtained fragment was subcloned to pcDNA3.1(+) digested with BamHI and XhoI to give a plasmid DNA for human CH24H expression (pcDNA3.1(+)/hCH24H).

Experimental Example 2

Expression of Human CH24H and Preparation of Human CH24H Lysate

The expression of human CH24H was performed using FreeStyle 293 Expression System (Invitrogen). According to the manual attached to FreeStyle 293 Expression System and using the plasmid DNA for human CH24H expression (pcDNA3.1(+)/hCH24H) constructed in Experimental Example 1, a transient expression using FreeStyle 293-F cell was performed. After transfection, the cells were cultured at 37° C., 8% $CO_2$ with shaking at 125 rpm for 2 days. The cells were collected by centrifugation, and suspended in a suspension buffer (100 mM potassium phosphate (pH 7.4), 0.1 mM EDTA, 1 mM DTT, 20% Glycerol). The suspended product was disrupted by a polytron homogenizer (manufactured by Kinematica), and centrifuged at 9000×g for 10 min, and the supernatant was collected. The collected supernatant was cryopreserved (−80° C.) as a human CH24H lysate standard product.

Experimental Example 3

Measurement of CH24H Inhibitory Activity

For the measurement of CH24H inhibitory activity, using the human CH24H lysate prepared in Experimental Example 2, the amount of 24-HC produced from cholesterol by catalytic activity of CH24H was measured in the presence of a test compound, and compared with that measured in the absence of the test compound. That is, a test compound solution at various concentrations was mixed with a reaction buffer (50 mM potassium phosphate containing 0.1% BSA and Complete, EDTA-free, pH 7.4) and human CH24H lysate. Then, [$^{14}$C] cholesterol (53 mCi/mmol specific activity, 15 μM) was added, and CH24H reaction was performed at 37° C. for 5 hr. After completion of the reaction, a quenching solution consisting of chloroform/methanol/distilled water (2:2:1 v/v) was added, and the resulting 24-HC was extracted by shaking. The extract was applied to silica gel thin layer chromatography (ethyl acetate:toluene=4:6), and the obtained $^{14}$C-24HC fraction was measured with BAS2500 (Fujifilm Corporation).

The inhibitory rate (%) was calculated from the ratio of radioactivity in the presence of a test compound relative to the radioactivity in the absence of the test compound. The results are shown in the following Table 2.

TABLE 2

| Test Compound | Inhibitory Rate in 1 μM (%) |
|---|---|
| Example 1 | 90 |
| Example 2 | 80 |
| Example 12 | 90 |
| Example 13 | 89 |
| Example 21 | 85 |
| Example 24 | 96 |
| Example 25 | 97 |
| Example 26 | 98 |
| Example 29 | 97 |
| Example 30 | 97 |
| Example 31 | 97 |
| Example 33 | 96 |
| Example 35 | 98 |
| Example 38 | 98 |
| Example 43 | 98 |
| Example 59 | 92 |
| Example 70 | 97 |
| Example 73 | 97 |
| Example 79 | 93 |
| Example 82 | 97 |
| Example 83 | 74 |
| Example 87 | 98 |
| Example 114 | 86 |
| Example 117 | 85 |
| Example 119 | 93 |
| Example 120 | 95 |
| Example 121 | 80 |
| Example 124 | 81 |
| Example 127 | 79 |
| Example 128 | 97 |
| Example 129 | 82 |
| Example 130 | 93 |
| Example 131 | 87 |
| Example 132 | 87 |
| Example 133 | 87 |
| Example 138 | 93 |
| Example 142 | 93 |
| Example 143 | 98 |
| Example 144 | 98 |
| Example 148 | 92 |
| Example 152 | 90 |
| Example 153 | 85 |
| Example 158 | 85 |
| Example 161 | 56 |
| Example 165 | 86 |
| Example 169 | 97 |
| Example 170 | 86 |
| Example 172 | 96 |
| Example 175 | 95 |
| Example 176 | 82 |
| Example 177 | 92 |
| Example 180 | 87 |
| Example 183 | 92 |
| Example 188 | 81 |
| Example 190 | 87 |
| Example 193 | 90 |
| Example 194 | 93 |
| Example 198 | 90 |
| Example 200 | 88 |
| Example 213 | 93 |
| Example 214 | 89 |
| Example 222 | 92 |
| Example 54 | 99 |
| Example 58 | 96 |
| Example 86 | 98 |
| Example 277 | 94 |
| Example 278 | 75 |
| Example 280 | 78 |
| Example 281 | 84 |
| Example 282 | 83 |
| Example 283 | 85 |
| Example 284 | 80 |
| Example 285 | 82 |
| Example 286 | 83 |
| Example 287 | 89 |
| Example 288 | 84 |
| Example 296 | 86 |
| Example 297 | 84 |
| Example 298 | 79 |
| Example 299 | 84 |
| Example 300 | 83 |
| Example 301 | 86 |
| Example 302 | 87 |
| Example 303 | 85 |
| Example 304 | 86 |
| Example 305 | 85 |
| Example 306 | 85 |
| Example 307 | 81 |
| Example 308 | 83 |
| Example 309 | 85 |
| Example 310 | 82 |
| Example 311 | 79 |
| Example 312 | 71 |
| Example 313 | 82 |
| Example 314 | 91 |
| Example 315 | 94 |
| Example 316 | 94 |
| Example 317 | 95 |
| Example 318 | 94 |
| Example 319 | 96 |
| Example 322 | 93 |
| Example 323 | 93 |

Experimental Example 4

Quantification Test of 24-HC

Animals used were 6-week-old female C57BL/6N mice (3 mice/group). A test compound was suspended in a 0.5% aqueous methylcellulose [133-14255 WAKO] solution (1 mg/mL). The body weight of the mice was measured, and the solution was forcibly administered orally and repeatedly once a day for 3 days. At 16 hours after the third administration, half of the brain was harvested, and the amount of 24-HC was measured.

The wet weight of the brain was measured, and the brain was homogenized with 4-fold amount of saline. This solution was used as a brain extract. The 24-HC in the brain extract was extracted with an acetonitrile solution (98% acetonitrile, 1.98% methanol, 0.02% formic acid), and quantified by HPLC. The average value of 24-HC amount was calculated and the results are shown in relative values with the control group as 100%. The results are shown in the following Table 3.

TABLE 3

| Test Compound | Decreasing Rate in 30 mg/kg (%) |
|---|---|
| Example 33 | 49 |
| Example 70 | 61 |
| Example 124 | 59 |
| Example 127 | 44 |
| Example 129 | 44 |
| Example 130 | 54 |
| Example 132 | 65 |
| Example 133 | 70 |
| Example 142 | 69 |

Experimental Example 5

Novel Object Recognition Test Using an APP Transgenic Mouse (Tg2576)

Animals used were 6-week-old Tg2576 mice and their wild-type mice (10 mice/group). A test compound was suspended in a 0.5% aqueous methyl cellulose [133-14255 WAKO] solution (3 mg/mL). The body weight of the mice was measured, and the solution was forcibly administered orally and repeatedly at 10 mL/kg once a day for 6 weeks. Then, a novel object recognition test was performed as follows. On the day before acquisition trial, the mice kept in the same cage were put in an observation box in which the illuminance was set to 300 lx, and habituated for 30 min. After the habituation, a compound was orally administered. On the next day, the mice were put, as an acquisition trial, in an observation box in which two same objects were placed, and the number and duration of contacts to the objects were measured for 5 min under 300 lx. A compound was orally administered after the measurement. The day after the acquisition trial, the one object was replaced with a novel object, and the number and duration of contacts to each of the object were measured for 5 min. A metal cylinder and ceramic triangular pyramid were used in this test. A control group (test compound-untreated group) and a control group in wild-type mice were used for comparison. The results are shown as the rate (%) of the number and duration of contacts to the novel object relative to the total number and duration of contacts to the objects. The results are shown in the following Table 4.

TABLE 4

| | | wild-type mice control group | APP transgenic mouse | |
| --- | --- | --- | --- | --- |
| | | | control group | Example 70 |
| exploration Rate (%) of Novel Object | number of contacts | 61.2 | 50.0 | 55.2 |
| | duration of contacts | 69.7 | 52.1 | 65.2 |

INDUSTRIAL APPLICABILITY

The compound of the present invention has a superior CH24H inhibitory action, which is useful as an agent for the prophylaxis or treatment of epilepsy, neurodegenerative disease (e.g., Alzheimer's disease, mild cognitive disorder, Huntington's disease, Parkinson's disease, multiple sclerosis, amyotrophic lateral sclerosis, traumatic brain injury, cerebral infarction, glaucoma and the like), schizophrenia and the like.

This application is based on patent applications No. 2012-270445 filed on Dec. 11, 2012 and No. 2013-210439 filed on Oct. 7, 2013 in Japan, the contents of which are encompassed in full herein.

The invention claimed is:

1. A compound or a salt thereof, which is selected from the group consisting of:
   (2R)-1-((1-(4-(4-methyl-1H-pyrazol-1-yl)pyridin-3-yl)piperidin-4-yl)carbonyl)pyrrolidine-2-carbonitrile or a salt thereof,
   (2R)-1-((1-(4-(4-chloro-1H-pyrazol-1-yl)pyridin-3-yl)piperidin-4-yl)carbonyl)pyrrolidine-2-carbonitrile or a salt thereof, and
   (2R)-4,4-difluoro-1-((1-(4-(4-methyl-1H-pyrazol-1-yl)pyridin-3-yl)piperidin-4-yl)carbonyl)pyrrolidine-2-carbonitrile or a salt thereof.

2. A compound or a salt thereof, which is (2R)-1-((1-(4-(4-methyl-1H-pyrazol-1-yl)pyridin-3-yl)piperidin-4-yl)carbonyl)pyrrolidine-2-carbonitrile or a salt thereof.

3. A compound or a salt thereof, which is (2R)-1-((1-(4-(4-chloro-1H-pyrazol-1-yl)pyridin-3-yl)piperidin-4-yl)carbonyl)pyrrolidine-2-carbonitrile or a salt thereof.

4. A compound or a salt thereof, which is (2R)-4,4-difluoro-1-((1-(4-(4-methyl-1H-pyrazol-1-yl)pyridin-3-yl)piperidin-4-yl)carbonyl)pyrrolidine-2-carbonitrile or a salt thereof.

5. A pharmaceutical composition comprising the compound or salt of claim 1, and a pharmacologically acceptable carrier.

6. A method for the treatment of Alzheimer's disease in a mammal, which comprises administering an effective amount of the compound or salt of claim 1 to the mammal.

7. A pharmaceutical composition comprising the compound or salt of claim 2, and a pharmacologically acceptable carrier.

8. A method for the treatment of Alzheimer's disease in a mammal, which comprises administering an effective amount of the compound or salt of claim 2 to the mammal.

9. A pharmaceutical composition comprising the compound or salt of claim 3, and a pharmacologically acceptable carrier.

10. A method for the treatment of Alzheimer's disease in a mammal, which comprises administering an effective amount of the compound or salt of claim 3 to the mammal.

11. A pharmaceutical composition comprising the compound or salt of claim 4, and a pharmacologically acceptable carrier.

12. A method for the treatment of Alzheimer's disease in a mammal, which comprises administering an effective amount of the compound or salt of claim 4 to the mammal.

\* \* \* \* \*